US012662464B2

(12) United States Patent
Che et al.

(10) Patent No.: US 12,662,464 B2
(45) Date of Patent: Jun. 23, 2026

(54) DEGRADERS OF CYCLIN-DEPENDENT KINASE 12 (CDK12) AND USES THEREOF

(71) Applicant: DANA-FARBER CANCER INSTITUTE, INC., Boston, MA (US)

(72) Inventors: Jianwei Che, Sharon, MA (US); Nathanael S. Gray, Stanford, CA (US); Tinghu Zhang, Brookline, MA (US); Baishan Jiang, Brookline, MA (US); Yang Gao, Boston, MA (US); Nicholas Paul Kwiatkowski, Brookline, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 1191 days.

(21) Appl. No.: 17/604,852

(22) PCT Filed: Apr. 23, 2020

(86) PCT No.: PCT/US2020/029483
§ 371 (c)(1),
(2) Date: Oct. 19, 2021

(87) PCT Pub. No.: WO2020/219650
PCT Pub. Date: Oct. 29, 2020

(65) Prior Publication Data

US 2022/0227734 A1 Jul. 21, 2022

Related U.S. Application Data

(60) Provisional application No. 62/837,331, filed on Apr. 23, 2019.

(51) Int. Cl.

| | |
|---|---|
| *C07D 401/14* | (2006.01) |
| *A61K 38/00* | (2006.01) |
| *A61K 45/06* | (2006.01) |
| *A61K 47/54* | (2017.01) |
| *C07D 417/14* | (2006.01) |

(52) U.S. Cl.
CPC ............ *C07D 401/14* (2013.01); *A61K 45/06* (2013.01); *A61K 47/555* (2017.08); *C07D 417/14* (2013.01); *A61K 38/00* (2013.01)

(58) Field of Classification Search
CPC .. C07D 401/14; C07D 417/14; A61K 47/555; A61K 45/06
See application file for complete search history.

(56) References Cited

U.S. PATENT DOCUMENTS

| | | | | |
|---|---|---|---|---|
| 9,694,084 | B2 * | 7/2017 | Bradner | A61K 47/54 |
| 10,730,862 | B2 * | 8/2020 | Crews | A61P 35/00 |
| 2017/0121321 | A1 | 5/2017 | Crews et al. | |

FOREIGN PATENT DOCUMENTS

| | | | | |
|---|---|---|---|---|
| CN | 109153675 | A | 1/2019 | |
| WO | 2015058126 | A1 | 4/2015 | |
| WO | WO-2015058163 | A2 * | 4/2015 | A61K 31/415 |
| WO | 2015154039 | A2 | 10/2015 | |
| WO | 2017185023 | A1 | 10/2017 | |
| WO | 2017185031 | A1 | 10/2017 | |
| WO | 2018013867 | A1 | 1/2018 | |
| WO | 2018098361 | A1 | 5/2018 | |
| WO | 2020023480 | A1 | 1/2020 | |

OTHER PUBLICATIONS

Greenleaf, Arno L. "Human CDK12 and CDK13, multi-tasking CTD kinases for the new millenium." Transcription 10, No. 2 (2019): 91-110 (Year: 2019).*
Chila , Rosaria, Federica Guffanti, and Giovanna Damia. "Role and therapeutic potential of CDK12 in human cancers." Cancer treatment reviews 50 (2016): 83-88 (Year: 2016).*
(Continued)

*Primary Examiner* — James H Alstrum-Acevedo
*Assistant Examiner* — Carolyn L. Ladd
(74) *Attorney, Agent, or Firm* — ArentFox Schiff LLP; Daniel W. Clarke; Shawn P. Foley

(57) ABSTRACT

Provided herein are bifunctional compounds with a moiety (e.g., lenalidomide, thalidomide) that is a binder of an E3 ubiquitin ligase (e.g., Cereblon) and another moiety that is a binder of a target protein (e.g., kinase (e.g., CDK (e.g., CDK9 and/or CDK12))) to induce degradation of the target protein CDK9 and/or CDK12. Also provided are pharmaceutical compositions comprising the bifunctional compounds, and methods of treating and/or preventing diseases (e.g., proliferative diseases, such as cancers (e.g., ovarian cancer, breast cancer, or prostate cancer))). Provided also are methods of inducing the degradation of the target protein (e.g., kinase (e.g., CDK (e.g., CDK9 and/or CDK12))), and methods of inducing apoptosis in a cell in a biological sample or subject by administering the bifunctional compound or composition described herein.

(I)

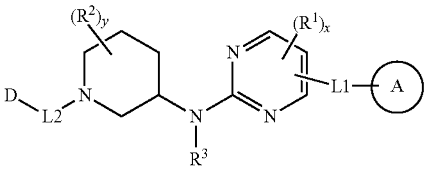

12 Claims, 5 Drawing Sheets

Specification includes a Sequence Listing.

(56) References Cited

OTHER PUBLICATIONS

Churcher, Ian. "Protac-induced protein degradation in drug discovery: breaking the rules or just making new ones?." Journal of medicinal chemistry 61, No. 2 (2018): 444-452 (Year: 2018).*
Mullard, Asher. "First targeted protein degrader hits the clinic." Nature reviews. Drug discovery (2019) (Year: 2019).*
Franco, Lia Carolina, FÃ¡ tima Morales, Silvia Boffo, and Antonio Giordano. "CDK9: A key player in cancer and other diseases." Journal of Cellular Biochemistry 119, No. 2 (2018): 1273-1284 (Year: 2018).*
Lui, Goldie YL, Carla Grandori, and Christopher J. Kemp. "CDK12: an emerging therapeutic target for cancer." Journal of clinical pathology 71, No. 11 (2018): 957-962 (Year: 2018).*
Neklesa, Taavi K., James D. Winkler, and Craig M. Crews. "Targeted protein degradation by PROTACs." Pharmacology & therapeutics 174 (2017): 138-144 (Year: 2017).*
Hanahan, Douglas, and Robert A. Weinberg. "The Hallmarks of Cancer." Cell 100, No. 1 (2000): 57-70 (Year: 2000).*
Scudellari, Megan. "The protein slayers." Nature 567, No. 7748 (2019): 298-300 (Year: 2019).*
Galbraith, Matthew D., Heather Bender, and JoaquÃn M. Espinosa. "Therapeutic targeting of transcriptional cyclin-dependent kinases." Transcription 10, No. 2 (2019): 118-136 (Year: 2019).*
Hellvard, Annelie, Lutz Zeitlmann, Ulrich Heiser, Astrid Kehlen, AndrÃ© Niestroj, Hans-Ulrich Demuth, Joanna Koziel, Nicolas Delaleu, Jan Potempa, and Piotr Mydel. "Inhibition of CDK9 as a therapeutic strategy for inflammatory arthritis." Scientific reports 6, No. 1 (2016): 31441 (Year: 2016).*
Henry, Kate L., Debra Kellner, Bekim Bajrami, John E. Anderson, Mercedes Beyna, Govinda Bhisetti, Tom Cameron et al. "CDK12-mediated transcriptional regulation of noncanonical NF-Î ºB components is essential for signaling." Science signaling 11, No. 541 (2018): eaam8216 (Year: 2018).*
Huang, Hai-Tsang, Dennis Dobrovolsky, Joshiawa Paulk, Guang Yang, Ellen L. Weisberg, Zainab M. Doctor, Dennis L. Buckley et al. "A chemoproteomic approach to query the degradable kinome using a multi-kinase degrader." Cell chemical biology 25, No. 1 ( 2018): 88-99. (Year: 2018).*
Taylor, Richard D., Malcolm MacCoss, and Alastair DG Lawson. "Rings in drugs: Miniperspective." Journal of medicinal chemistry 57, No. 14 (2014): 5845-5859. (Year: 2014).*
Meanwell, Nicholas A. "Synopsis of some recent tactical application of bioisosteres in drug design." Journal of medicinal chemistry 54, No. 8 (2011): 2529-2591. (Year: 2011).*
"Blood Cancer (Hematological Malignancies) Program." Penn Medicine Accessed Mar. 6, 2025. https://www.pennmedicine.org/cancer/navigating-cancer-care/programs-and-centers/hematological-malignancies-program. (Year: 2025).*
"Blood Cancers."Yale Medicine, Jun. 28, 2022. https://www.yalemedicine.org/conditions/blood-cancers#:~:text=Treatments%20for%20blood%20cancers%20also,consensus%20prior%20to%20starting%20therapy (Year: 2022).*
"Leukemia."MD Anderson Cancer Center. Accessed Mar. 6, 2025. https://www.mdanderson.org/cancer-types/leukemia.html (Year: 2025).*
Institute of Medicine (US) Roundtable; Yaffe S, editor. Rational Therapeutics for Infants and Children: Workshop Summary. Washington (DC): National Academies Press (US); 2000. 3, Pharmacokinetics and Pharmacodynamics in Children vs Adults. Available from: https://www.ncbi.nlm.nih.gov/books/NBK22550 (Year: 2000).*
Veal, G.J. and Boddy, A.V., Aug. 2012, Chemotherapy in newborns and preterm babies. In Seminars in Fetal and Neonatal Medicine (vol. 17, No. 4, pp. 243-248). WB Saunders) (Year: 2012).*
Pettersson, Mariell, and Craig M. Crews. "PROteolysis TArgeting Chimeras (PROTACs)-past, present and future." Drug Discovery Today: Technologies 31 (2019): 15-27) (Year: 2019).*
Valle-Reyes, S., Dobrovinskaya, O., Pelayo, R. and Schnoor, M., 2021. Acute lymphoblastic leukemia cell lines in immunology research. Trends in Immunology, 42(3), pp. 182-185. (Year: 2021).*
Singh, K., Kumari, S., Singh, B., Choubey, R. B., Mitra, D.K. and Rai, A.K., 2022. Jurkat T Cells are Immunophenotypically Distinct from T-Cell Acute Lymphoblastic Leukemia Cells Due to High-Level Surface Expression of CD5. Cancer Investigation, 40(8), pp. 675-679. (Year: 2022).*
Chennamadhavuni A, Iyengar V, Mukkamalla SKR, et al. Leukemia. [Updated Jan. 17, 2023]. In: StatPearls [Internet]. Treasure Island (FL): StatPearls Publishing; Jan. 2025-. Available from: https://www.ncbi.nlm.nih.gov/books/NBK560490/. (Year: 2023).*
Wilson, A et al. 2025. Jurkat T-cell lines exhibit marked genomic instability affecting karyotype, mutational profile, gene expression, immunophenotype and function. Scientific Reports, 15(1), p. 22426) (Year: 2025).*
Hughes, et al., "Molecular Recognition of Ternary Complexes: a New Dimension in the Structure-Guided Design of Chemical Degraders," Essays in Biochemistry, Nov. 8, 2017; vol. 61; Iss. 5; pp. 505-516.
Lai, et al., "Induced Protein Degradation: an Emerging Drug Discovery Paradigm," Nature Reviews Drug Discovery, Nov. 25, 2016; vol. 16, Iss. 2, pp. 101-114.
Moon, et al., "Chemically Induced Cellular Proteolysis: An Emerging Therapeutic Strategy for Undruggable Targets," Molecules and Cells, Nov. 7, 2018; vol. 41, Iss. 11, pp. 933-942.
Bian, et al., "Discovery of Wogonin-based PROTACs against CDK9 and capable of achieving antitumor activity," Bioorganic Chemistry, 81, 373-381 (2018).
Galbraith, et al., "Therapeutic targeting of transcriptional cyclin-dependent kinases," Transcription, 10, 2, 118-136 (2019).
Hu, et al., "Discovery of ERD-308 as a Highly Potent Proteolysis Targeting Chimera (PROTAC) Degrader of Estrogen Receptor (ER)," Journal of Medicinal Chemistry, 62, 3, 1420-1442 (2019).
Morales, et al., "Overview of CDK9 as a target in cancer research," Cell Cycle, 15, 4, 519-527 (2016).
Olson, et al., "Pharmacological perturbation of CDK9 using selective CDK9 inhibition or degradation," Nature Chemical Biology, 14, 2, 163-170 (2018).
Qin, et al., "Discovery of QCA570 as an Exceptionally Potent and Efficacious Proteolysis Targeting Chimera (PROTAC) Degrader of the Bromodomain and Extra-Terminal (BET) Proteins Capable of Inducing Complete and Durable Tumor Regression," Journal of Medicinal Chemistry, 61, 15, 6685-6704 (2018).
Raina, et al., "PROTAC-induced BET protein degradation as a therapy for castration-resistant prostate cancer," Proceedings of the National Academy of Sciences, 113, 26, 7124-7129 (2016).
Robb, et al., "Chemically induced degradation of CDK9 by a proteolysis targeting chimera (PROTAC)," Chemical Communications, 53, 54, 7577-7580 (2017).
Scheepstra, et al., "Bivalent Ligands for Protein Degradation in Drug Discovery," Computational and Structural Biotechnology Journal, 17, 160-176 (2019).
Tan, et al., "When Kinases Meet PROTACs," Chinese Journal of Chemistry, Zhongguo Kexueyuan, 36, 10, 971-977 (2018).
Xi, et al., 2019, "Small molecule PROTACs in targeted therapy: An emerging strategy to induce protein degradation," European Journal of Medicinal Chemistry, 174, 159-180 (2019).
Zeng, et al., "Targeting MYC dependency in ovarian cancer through inhibition of CDK7 and CDK12/13," Elife, 7, 39030-1 (2018).
Bekes, M. et al., "PROTAC targeted protein degraders: the past is prologue", Nature Reviews, 2022, vol. 21, pp. 181-200.
Bondeson, D. P. et al., "Lessons in PROTAC design from selective degradation with a promiscuous warhead", Cell Chem. Biol., 2018, vol. 25, No. 1, pp. 78-87.
Lai, A. C. et al., "Modular PROTAC Design for the Degradation of Oncogenic BCR-ABL", Angew. Chem. Int. Ed., 2016, vol. 55, pp. 807-810.
Li, X. et al., "Proteolysis-targeting chimera (PROTAC) for targeted protein degradation and cancer therapy", J. Hematol. Oncol., 2020, vol. 13, No. 50, 14 pages.
Lui, G. Y. L. et al., "CDK12: An emerging therapeutic target for cancer", J. Clin. Pathol., 2018, vol. 71, No. 11, pp. 957-962.

(56) References Cited

OTHER PUBLICATIONS

Richter, A. et al., "Cyclin-Dependent Kinase Inhibitors in Hematological Malignancies-Current Understanding, (Pre-) Clinical Application and Promising Approaches", Cancers, 2021, vol. 13, No. 2497, 18 pages.
Simpson, D. L. et al., "Killing of Human Myelomonocytic Leukemia and Lymphocytic Cell Lines by Actinobacillus actinomycetemcomitans Leukotoxin", Infection and Immunity, 1988, vol. 56, No. 5, pp. 1162-1166.
Tan, L. et al., "When Kinases Meet PROTACS", Chin. J. Chem., 2018, vol. 36, pp. 971-977.
Nandave, M. et al., "PROTAC-mediated protein degradation: A paradigm shift in cancer therapeutics", Springer, 2024, 400 pages.

* cited by examiner

SEQUENCE LISTING

<160> NUMBER OF SEQ ID NOS: 3

<210> SEQ ID NO 1
<211> LENGTH: 352
<212> TYPE: PRT
<213> ORGANISM: Homo sapiens

<400> SEQUENCE: 1

Met Glu Ser Gly Gly Arg Pro Ser Leu Cys Gln Phe Ile Leu Leu Gly
1 5 10 15

Thr Thr Ser Val Val Thr Ala Ala Leu Tyr Ser Val Tyr Arg Gln Lys
20 25 30

Ala Arg Val Ser Gln Glu Leu Lys Gly Ala Lys Lys Val His Leu Gly
35 40 45

Glu Asp Leu Lys Ser Ile Leu Ser Glu Ala Pro Gly Lys Cys Val Pro
50 55 60

Tyr Ala Val Ile Glu Gly Ala Val Arg Ser Val Lys Glu Thr Leu Asn
65 70 75 80

Ser Gln Phe Val Glu Asn Cys Lys Gly Val Ile Gln Arg Leu Thr Leu
85 90 95

Gln Glu His Lys Met Val Trp Asn Arg Thr Thr His Leu Trp Asn Asp
100 105 110

Cys Ser Lys Ile Ile His Gln Arg Thr Asn Thr Val Pro Phe Asp Leu
115 120 125

Val Pro His Glu Asp Gly Val Asp Val Ala Val Arg Val Leu Lys Pro
130 135 140

Leu Asp Ser Val Asp Leu Gly Leu Glu Thr Val Tyr Glu Lys Phe His
145 150 155 160

Pro Ser Ile Gln Ser Phe Thr Asp Val Ile Gly His Tyr Ile Ser Gly
165 170 175

Glu Arg Pro Lys Gly Ile Gln Glu Thr Glu Glu Met Leu Lys Val Gly
180 185 190

Ala Thr Leu Thr Gly Val Gly Glu Leu Val Leu Asp Asn Asn Ser Val
195 200 205

Arg Leu Gln Pro Pro Lys Gln Gly Met Gln Tyr Tyr Leu Ser Ser Gln
210 215 220

Asp Phe Asp Ser Leu Leu Gln Arg Gln Glu Ser Ser Val Arg Leu Trp
225 230 235 240

Lys Val Leu Ala Leu Val Phe Gly Phe Ala Thr Cys Ala Thr Leu Phe
245 250 255

Phe Ile Leu Arg Lys Gln Tyr Leu Gln Arg Gln Glu Arg Leu Arg Leu
260 265 270

Lys Gln Met Gln Glu Glu Phe Gln Glu His Glu Ala Gln Leu Leu Ser
275 280 285

Arg Ala Lys Pro Glu Asp Arg Glu Ser Leu Lys Ser Ala Cys Val Val
290 295 300

Cys Leu Ser Ser Phe Lys Ser Cys Val Phe Leu Glu Cys Gly His Val
305 310 315 320

Cys Ser Cys Thr Glu Cys Tyr Arg Ala Leu Pro Glu Pro Lys Lys Cys
325 330 335

-continued

```
Pro Ile Cys Arg Gln Ala Ile Thr Arg Val Ile Pro Pro Tyr Asn Ser
            340                 345                 350


<210> SEQ ID NO 2
<211> LENGTH: 923
<212> TYPE: PRT
<213> ORGANISM: Homo sapiens

<400> SEQUENCE: 2

Met Glu Glu Gly Asn Asn Asn Glu Glu Val Ile His Leu Asn Asn Phe
1               5                   10                  15

His Cys His Arg Gly Gln Glu Trp Ile Asn Leu Arg Asp Gly Pro Ile
            20                  25                  30

Thr Ile Ser Asp Ser Ser Asp Glu Glu Arg Ile Pro Met Leu Val Thr
        35                  40                  45

Pro Ala Pro Gln Gln His Glu Glu Glu Asp Leu Asp Asp Asp Val Ile
    50                  55                  60

Leu Thr Glu Thr Asn Lys Pro Gln Arg Ser Arg Pro Asn Leu Ile Lys
65                  70                  75                  80

Pro Ala Ala Gln Trp Gln Asp Leu Lys Arg Leu Gly Glu Glu Arg Pro
                85                  90                  95

Lys Lys Ser Arg Ala Ala Phe Glu Ser Asp Lys Ser Ser Tyr Phe Ser
            100                 105                 110

Val Cys Asn Asn Pro Leu Phe Asp Ser Gly Ala Gln Asp Asp Ser Glu
        115                 120                 125

Asp Asp Tyr Gly Glu Phe Leu Asp Leu Gly Pro Pro Gly Ile Ser Glu
    130                 135                 140

Phe Thr Lys Pro Ser Gly Gln Thr Glu Arg Glu Pro Lys Pro Gly Pro
145                 150                 155                 160

Ser His Asn Gln Ala Ala Asn Asp Ile Val Asn Pro Arg Ser Glu Gln
                165                 170                 175

Lys Val Ile Ile Leu Glu Glu Gly Ser Leu Leu Tyr Thr Glu Ser Asp
            180                 185                 190

Pro Leu Glu Thr Gln Asn Gln Ser Ser Glu Asp Ser Glu Thr Glu Leu
        195                 200                 205

Leu Ser Asn Leu Gly Glu Ser Ala Ala Leu Ala Asp Asp Gln Ala Ile
    210                 215                 220

Glu Glu Asp Cys Trp Leu Asp His Pro Tyr Phe Gln Ser Leu Asn Gln
225                 230                 235                 240

Gln Pro Arg Glu Ile Thr Asn Gln Val Val Pro Gln Glu Arg Gln Pro
                245                 250                 255

Glu Ala Glu Leu Gly Arg Leu Leu Phe Gln His Glu Phe Pro Gly Pro
            260                 265                 270

Ala Phe Pro Arg Pro Glu Pro Gln Gln Gly Gly Ile Ser Gly Pro Ser
        275                 280                 285

Ser Pro Gln Pro Ala His Pro Leu Gly Glu Phe Glu Asp Gln Gln Leu
    290                 295                 300

Ala Ser Asp Asp Glu Glu Pro Gly Pro Ala Phe Pro Met Gln Glu Ser
305                 310                 315                 320

Gln Glu Pro Asn Leu Glu Asn Ile Trp Gly Gln Glu Ala Ala Glu Val
                325                 330                 335

Asp Gln Glu Leu Val Glu Leu Leu Val Lys Glu Thr Glu Ala Arg Phe
            340                 345                 350

Pro Asp Val Ala Asn Gly Phe Ile Glu Glu Ile Ile His Phe Lys Asn
```

```
        355                 360                 365

Tyr Tyr Asp Leu Asn Val Leu Cys Asn Phe Leu Leu Glu Asn Pro Asp
    370                 375                 380

Tyr Pro Lys Arg Glu Asp Arg Ile Ile Ile Asn Pro Ser Ser Ser Leu
385                 390                 395                 400

Leu Ala Ser Gln Asp Glu Thr Lys Leu Pro Lys Ile Asp Phe Phe Asp
                405                 410                 415

Tyr Ser Lys Leu Thr Pro Leu Asp Gln Arg Cys Phe Ile Gln Ala Ala
            420                 425                 430

Asp Leu Leu Met Ala Asp Phe Lys Val Leu Ser Ser Gln Asp Ile Lys
        435                 440                 445

Trp Ala Leu His Glu Leu Lys Gly His Tyr Ala Ile Thr Arg Lys Ala
    450                 455                 460

Leu Ser Asp Ala Ile Lys Lys Trp Gln Glu Leu Ser Pro Glu Thr Ser
465                 470                 475                 480

Gly Lys Arg Lys Lys Arg Lys Gln Met Asn Gln Tyr Ser Tyr Ile Asp
                485                 490                 495

Phe Lys Phe Glu Gln Gly Asp Ile Lys Ile Glu Lys Arg Met Phe Phe
            500                 505                 510

Leu Glu Asn Lys Arg Arg His Cys Arg Ser Tyr Asp Arg Arg Ala Leu
        515                 520                 525

Leu Pro Ala Val Gln Gln Glu Gln Glu Phe Tyr Glu Gln Lys Ile Lys
    530                 535                 540

Glu Met Ala Glu His Glu Asp Phe Leu Leu Ala Leu Gln Met Asn Glu
545                 550                 555                 560

Glu Gln Tyr Gln Lys Asp Gly Gln Leu Ile Glu Cys Arg Cys Cys Tyr
                565                 570                 575

Gly Glu Phe Pro Phe Glu Glu Leu Thr Gln Cys Ala Asp Ala His Leu
            580                 585                 590

Phe Cys Lys Glu Cys Leu Ile Arg Tyr Ala Gln Glu Ala Val Phe Gly
        595                 600                 605

Ser Gly Lys Leu Glu Leu Ser Cys Met Glu Gly Ser Cys Thr Cys Ser
    610                 615                 620

Phe Pro Thr Ser Glu Leu Glu Lys Val Leu Pro Gln Thr Ile Leu Tyr
625                 630                 635                 640

Lys Tyr Tyr Glu Arg Lys Ala Glu Glu Glu Val Ala Ala Ala Tyr Ala
                645                 650                 655

Asp Glu Leu Val Arg Cys Pro Ser Cys Ser Phe Pro Ala Leu Leu Asp
            660                 665                 670

Ser Asp Val Lys Arg Phe Ser Cys Pro Asn Pro His Cys Arg Lys Glu
        675                 680                 685

Thr Cys Arg Lys Cys Gln Gly Leu Trp Lys Glu His Asn Gly Leu Thr
    690                 695                 700

Cys Glu Glu Leu Ala Glu Lys Asp Asp Ile Lys Tyr Arg Thr Ser Ile
705                 710                 715                 720

Glu Glu Lys Met Thr Ala Ala Arg Ile Arg Lys Cys His Lys Cys Gly
                725                 730                 735

Thr Gly Leu Ile Lys Ser Glu Gly Cys Asn Arg Met Ser Cys Arg Cys
            740                 745                 750

Gly Ala Gln Met Cys Tyr Leu Cys Arg Val Ser Ile Asn Gly Tyr Asp
        755                 760                 765

His Phe Cys Gln His Pro Arg Ser Pro Gly Ala Pro Cys Gln Glu Cys
    770                 775                 780
```

```
Ser Arg Cys Ser Leu Trp Thr Asp Pro Thr Glu Asp Asp Glu Lys Leu
785                 790                 795                 800

Ile Glu Glu Ile Gln Lys Glu Ala Glu Glu Glu Gln Lys Arg Lys Asn
                805                 810                 815

Gly Glu Asn Thr Phe Lys Arg Ile Gly Pro Pro Leu Glu Lys Pro Val
            820                 825                 830

Glu Lys Val Gln Arg Val Glu Ala Leu Pro Arg Pro Val Pro Gln Asn
        835                 840                 845

Leu Pro Gln Pro Gln Met Pro Pro Tyr Ala Phe Ala His Pro Pro Phe
    850                 855                 860

Pro Leu Pro Pro Val Arg Pro Val Phe Asn Asn Phe Pro Leu Asn Met
865                 870                 875                 880

Gly Pro Ile Pro Ala Pro Tyr Val Pro Pro Leu Pro Asn Val Arg Val
                885                 890                 895

Asn Tyr Asp Phe Gly Pro Ile His Met Pro Leu Glu His Asn Leu Pro
            900                 905                 910

Met His Phe Gly Pro Gln Pro Arg His Arg Phe
        915                 920


<210> SEQ ID NO 3
<211> LENGTH: 866
<212> TYPE: PRT
<213> ORGANISM: Homo sapiens

<400> SEQUENCE: 3

Met Glu Glu Gly Asn Asn Asn Glu Glu Val Ile His Leu Asn Asn Phe
1               5                   10                  15

His Cys His Arg Gly Gln Glu Trp Ile Asn Leu Arg Asp Gly Pro Ile
            20                  25                  30

Thr Ile Ser Asp Ser Ser Asp Glu Glu Arg Ile Pro Met Leu Val Thr
        35                  40                  45

Pro Ala Pro Gln Gln His Glu Glu Glu Asp Leu Asp Asp Asp Val Ile
    50                  55                  60

Leu Thr Glu Asp Asp Ser Glu Asp Asp Tyr Gly Glu Phe Leu Asp Leu
65                  70                  75                  80

Gly Pro Pro Gly Ile Ser Glu Phe Thr Lys Pro Ser Gly Gln Thr Glu
                85                  90                  95

Arg Glu Pro Lys Pro Gly Pro Ser His Asn Gln Ala Ala Asn Asp Ile
            100                 105                 110

Val Asn Pro Arg Ser Glu Gln Lys Val Ile Ile Leu Glu Glu Gly Ser
        115                 120                 125

Leu Leu Tyr Thr Glu Ser Asp Pro Leu Glu Thr Gln Asn Gln Ser Ser
    130                 135                 140

Glu Asp Ser Glu Thr Glu Leu Leu Ser Asn Leu Gly Glu Ser Ala Ala
145                 150                 155                 160

Leu Ala Asp Asp Gln Ala Ile Glu Glu Asp Cys Trp Leu Asp His Pro
                165                 170                 175

Tyr Phe Gln Ser Leu Asn Gln Gln Pro Arg Glu Ile Thr Asn Gln Val
            180                 185                 190

Val Pro Gln Glu Arg Gln Pro Glu Ala Glu Leu Gly Arg Leu Leu Phe
        195                 200                 205

Gln His Glu Phe Pro Gly Pro Ala Phe Pro Arg Pro Glu Pro Gln Gln
    210                 215                 220

Gly Gly Ile Ser Gly Pro Ser Ser Pro Gln Pro Ala His Pro Leu Gly
```

-continued

```
225                 230                 235                 240

Glu Phe Glu Asp Gln Gln Leu Ala Ser Asp Asp Glu Glu Pro Gly Pro
                245                 250                 255

Ala Phe Pro Met Gln Glu Ser Gln Glu Pro Asn Leu Glu Asn Ile Trp
            260                 265                 270

Gly Gln Glu Ala Ala Glu Val Asp Gln Glu Leu Val Glu Leu Leu Val
        275                 280                 285

Lys Glu Thr Glu Ala Arg Phe Pro Asp Val Ala Asn Gly Phe Ile Glu
    290                 295                 300

Glu Ile Ile His Phe Lys Asn Tyr Tyr Asp Leu Asn Val Leu Cys Asn
305                 310                 315                 320

Phe Leu Leu Glu Asn Pro Asp Tyr Pro Lys Arg Glu Asp Arg Ile Ile
                325                 330                 335

Ile Asn Pro Ser Ser Ser Leu Leu Ala Ser Gln Asp Glu Thr Lys Leu
            340                 345                 350

Pro Lys Ile Asp Phe Phe Asp Tyr Ser Lys Leu Thr Pro Leu Asp Gln
        355                 360                 365

Arg Cys Phe Ile Gln Ala Ala Asp Leu Leu Met Ala Asp Phe Lys Val
    370                 375                 380

Leu Ser Ser Gln Asp Ile Lys Trp Ala Leu His Glu Leu Lys Gly His
385                 390                 395                 400

Tyr Ala Ile Thr Arg Lys Ala Leu Ser Asp Ala Ile Lys Lys Trp Gln
                405                 410                 415

Glu Leu Ser Pro Glu Thr Ser Gly Lys Arg Lys Lys Arg Lys Gln Met
            420                 425                 430

Asn Gln Tyr Ser Tyr Ile Asp Phe Lys Phe Glu Gln Gly Asp Ile Lys
        435                 440                 445

Ile Glu Lys Arg Met Phe Phe Leu Glu Asn Lys Arg Arg His Cys Arg
    450                 455                 460

Ser Tyr Asp Arg Arg Ala Leu Leu Pro Ala Val Gln Gln Glu Gln Glu
465                 470                 475                 480

Phe Tyr Glu Gln Lys Ile Lys Glu Met Ala Glu His Glu Asp Phe Leu
                485                 490                 495

Leu Ala Leu Gln Met Asn Glu Glu Gln Tyr Gln Lys Asp Gly Gln Leu
            500                 505                 510

Ile Glu Cys Arg Cys Cys Tyr Gly Glu Phe Pro Phe Glu Glu Leu Thr
        515                 520                 525

Gln Cys Ala Asp Ala His Leu Phe Cys Lys Glu Cys Leu Ile Arg Tyr
    530                 535                 540

Ala Gln Glu Ala Val Phe Gly Ser Gly Lys Leu Glu Leu Ser Cys Met
545                 550                 555                 560

Glu Gly Ser Cys Thr Cys Ser Phe Pro Thr Ser Glu Leu Glu Lys Val
                565                 570                 575

Leu Pro Gln Thr Ile Leu Tyr Lys Tyr Tyr Glu Arg Lys Ala Glu Glu
            580                 585                 590

Glu Val Ala Ala Ala Tyr Ala Asp Glu Leu Val Arg Cys Pro Ser Cys
        595                 600                 605

Ser Phe Pro Ala Leu Leu Asp Ser Asp Val Lys Arg Phe Ser Cys Pro
    610                 615                 620

Asn Pro His Cys Arg Lys Glu Thr Cys Arg Lys Cys Gln Gly Leu Trp
625                 630                 635                 640

Lys Glu His Asn Gly Leu Thr Cys Glu Glu Leu Ala Glu Lys Asp Asp
                645                 650                 655
```

-continued

```
Ile Lys Tyr Arg Thr Ser Ile Glu Glu Lys Met Thr Ala Ala Arg Ile
            660                 665                 670

Arg Lys Cys His Lys Cys Gly Thr Gly Leu Ile Lys Ser Glu Gly Cys
        675                 680                 685

Asn Arg Met Ser Cys Arg Cys Gly Ala Gln Met Cys Tyr Leu Cys Arg
    690                 695                 700

Val Ser Ile Asn Gly Tyr Asp His Phe Cys Gln His Pro Arg Ser Pro
705                 710                 715                 720

Gly Ala Pro Cys Gln Glu Cys Ser Arg Cys Ser Leu Trp Thr Asp Pro
                725                 730                 735

Thr Glu Asp Asp Glu Lys Leu Ile Glu Glu Ile Gln Lys Glu Ala Glu
            740                 745                 750

Glu Glu Gln Lys Arg Lys Asn Gly Glu Asn Thr Phe Lys Arg Ile Gly
        755                 760                 765

Pro Pro Leu Glu Lys Pro Val Glu Lys Val Gln Arg Val Glu Ala Leu
    770                 775                 780

Pro Arg Pro Val Pro Gln Asn Leu Pro Gln Pro Gln Met Pro Pro Tyr
785                 790                 795                 800

Ala Phe Ala His Pro Pro Phe Pro Leu Pro Pro Val Arg Pro Val Phe
                805                 810                 815

Asn Asn Phe Pro Leu Asn Met Gly Pro Ile Pro Ala Pro Tyr Val Pro
            820                 825                 830

Pro Leu Pro Asn Val Arg Val Asn Tyr Asp Phe Gly Pro Ile His Met
        835                 840                 845

Pro Leu Glu His Asn Leu Pro Met His Phe Gly Pro Gln Pro Arg His
    850                 855                 860

Arg Phe
865
```

DEGRADERS OF CYCLIN-DEPENDENT KINASE 12 (CDK12) AND USES THEREOF

RELATED APPLICATIONS

This application is a national stage application, filed under 35 U.S.C. § 371, of International Application No. PCT/US2020/029483, filed Apr. 23, 2020, which claims the benefit of priority under 35 U.S.C. § 119 (e) to U.S. Provisional Application, U.S. Ser. No. 62/837,331, filed Apr. 23, 2019, each of which is incorporated herein by reference in its entirety.

GOVERNMENT SUPPORT

This invention was made with government support under grant number PO1 CA154303 awarded by the National Institutes of Health. The government has certain rights in the invention.

BACKGROUND OF THE INVENTION

Recently, a new therapeutic strategy to reduce and/or eliminate proteins associated with certain pathological states, PROTAC® (proteolysis targeting chimeras; e.g., see U.S. patent application U.S. Ser. No. 14/792,414, filed Jul. 6, 2015; U.S. Ser. No. 14/707,930, filed May 8, 2015, which is incorporated herein by reference), was developed by creating bifunctional compounds that recruit E3 ubiquitin ligase to a target protein, which subsequently induce ubiquitination and proteasome-mediated degradation of the target protein. E3 ubiquitin ligases are proteins that, in combination with an E2 ubiquitin-conjugating enzyme, promote the attachment of ubiquitin to a lysine of a target protein via an isopeptide bond (e.g., an amide bond that is not present on the main chain of a protein). The ubiquitination of the protein then results in the degradation of the target protein by the proteasome.

Cyclin-dependent kinase 12 (CDK12) and Cyclin-dependent kinase 13 (CDK13) are elongation regulators of RNA polymerase II-mediated transcription through phosphorylation of the C-terminal domain (CTD) domain of RNA polymerase II. CDK12 and CDK13 play a critical role in mediating genome stability. However, the detailed mechanism is not clear, and the exact site of phosphorylation on CTD by CDK12 is still controversial. A genome-wide screening also identified CDK12/cyclin K playing a critical role in mediating genome stability via regulation of expression of DDR genes. The deletion of CDK12/cyclin K severely impaired the expression of several critical regulators of genome stability, such as BRCA1, ATR, FANCI and FANCD2 proteins, in cells. Again, the precise of contribution of CDK12, especially its kinase activity, to this process needs to be unveiled. Deletion of CDK12 and CDK13 impairs the expression of several critical regulators of genome stability. Mutations of CDK12 were identified in a variety of cancers including ovarian cancer, breast cancer, and prostate cancer, and these alterations on CDK12 sensitized these tumors to DNA damaging agents, such as cisplatin and its derivatives, and inhibitors of DNA repair, such as PARP inhibitors. Thus, CDK12 is a potential therapeutic target of drug for treating cancers and other diseases. Exemplary CDK12 inhibitor THZ531 has been disclosed as binding to a non-canonical cysteine 1039 which sits outside of the ATP pocket. A reversible CDK12 inhibitor showing good selectivity over other CDK's (e.g., CDK2, CDK4, CDK9) has also been reported. However, as CDK13 shares the same kinase domain sequence with CDK12, the two currently reported CDK12 inhibitors also show potent inhibition activity against CDK13. Therefore, development of small molecules selectively targeting CDK12 while sparing other targets (e.g., CDK13) is of particular interest.

Therefore, there is a need to identify compounds that effectively promote the degradation of target proteins e.g., (CDK12, CDK9, found to be associated with certain pathological states, including proliferative diseases, such as cancer). In particular, compounds that can take advantage of cellular machinery involved in protein homeostasis (e.g., ubiquitination and proteasome degradation) to target the degradation of certain proteins may find use as therapeutic agents. There is a need for compounds that both target a protein (e.g., kinase (e.g., CDK (e.g., CDK9, CDK12))), and also bind E3 ubiquitin ligase, thereby inducing proteasome degradation of the target protein (e.g., kinase (e.g., CDK (e.g., CDK9, CDK12))).

SUMMARY OF THE INVENTION

The present disclosure stems from the recognition that a bifunctional molecule that includes an E3 ubiquitin ligase binding moiety that is based on an imide drug (e.g., lenalidomide, thalidomide, VHL ligand) and also includes a binder and/or inhibitor of a target protein (e.g., kinase (e.g., CDK (e.g., CDK9 and/or CDK12))) may induce proteasome degradation of the target protein (e.g., kinase (e.g., CDK (e.g., CDK9 and/or CDK12))). The disclosure therefore provides new compounds, compositions, and methods for the treatment of various diseases (e.g., proliferative diseases, such as cancers (e.g., ovarian cancer, breast cancer, or prostate cancer)) associated with the target protein (e.g., kinase (e.g., CDK (e.g., CDK9, CDK12))) based on this discovery. In contrast to conventional CDK12 inhibitors which target both CDK12 and CDK13, the bifunctional compounds described herein rapidly degrade the target protein (e.g., kinase (e.g., CDK (e.g., CDK9 and/or CDK12))) to low levels, blocking transcription, and inducing apoptosis in a quicker and more selective manner. The invention therefore provides a new therapeutic strategy for treating various diseases and conditions, particularly those associated with a target protein (e.g., kinase (e.g., CDK (e.g., CDK9 and/or CDK12))).

Described herein are bifunctional compounds of Formula (I). The compounds described herein include a component that binds to the target protein (e.g., kinase (e.g., CDK (e.g., CDK9, CDK12))) and a component that binds an E3 ubiquitin ligase (e.g., lenalidomide, thalidomide) and therefore may be useful in promoting and/or inducing the degradation of the target protein (e.g., kinase (e.g., CDK (e.g., CDK9, CDK12))). The compounds may be useful in treating and/or preventing disease and conditions, such as a proliferative disease (e.g., cancers) associated with the target protein (e.g., kinase (e.g., CDK (e.g., CDK9, CDK12))) in a subject in need thereof. Also provided are pharmaceutical compositions and kits including a compound described herein.

In one aspect, the present disclosure provides compounds of Formula (I):

(I)

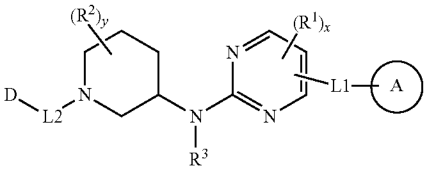, and pharmaceutically acceptable salts, solvates, hydrates, polymorphs, co-crystals, tautomers, stereoisomers, isotopically labeled derivatives, and prodrugs thereof, wherein $R^1$, $R^2$, $R^3$, x, y, L1, L2, D, and Ring

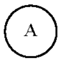

are as defined herein.

In Formula (I), D is a E3 ubiquitin ligase binding moiety. In certain embodiments, D is derived from an immunomodulatory imide drug. In certain embodiments, D is derived from lenalidomide. In certain embodiments, D is derived from thalidomide. In certain embodiments, D is an E3 ubiquitin ligase binding moiety, wherein D is of Formulae (IA), (IB), or a compound based on a ligand that binds to von Hippel-Lindau (a "VHL ligand"). In certain embodiments, D is derived from a VHL ligand.

In certain embodiments, D is of Formula (IA):

(IA)

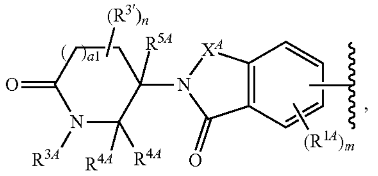

wherein $R^{1A}$, $R^{3A}$, $R^{4A}$, $R^{5A}$, $R^{3'}$, $X^A$, a1, m, and n are as defined herein.

In certain embodiments, D is of Formula (IB):

(IB)

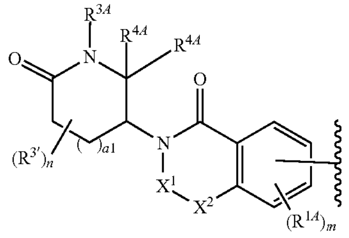

wherein $R^{1A}$, $R^{3A}$, $R^{4A}$, $R^{3'}$, $X^1$, $X^2$, a1, m, and n are as defined herein.

In certain embodiments, D is of formula:

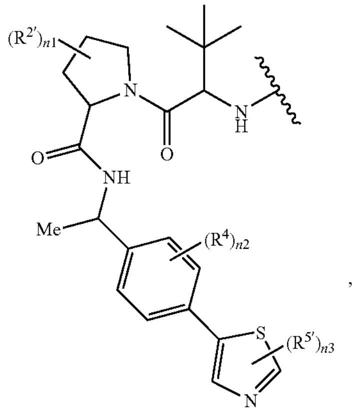

wherein $R^{2'}$, $R^{4'}$, $R^{5'}$, n1', n2', and n3' are as defined herein.

Exemplary compounds of Formula (I) include, but are not limited to:

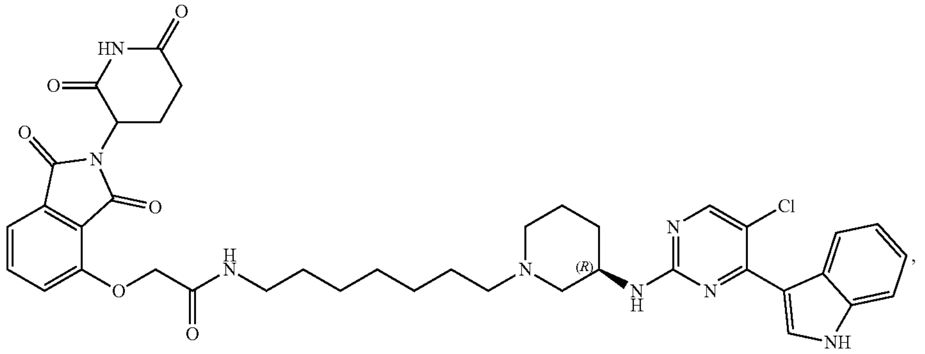

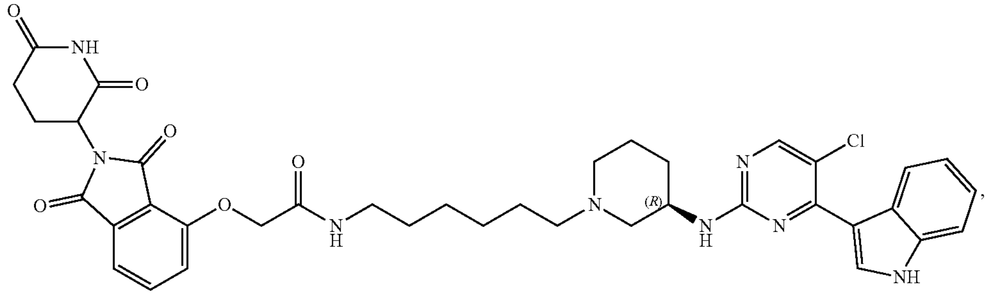

-continued
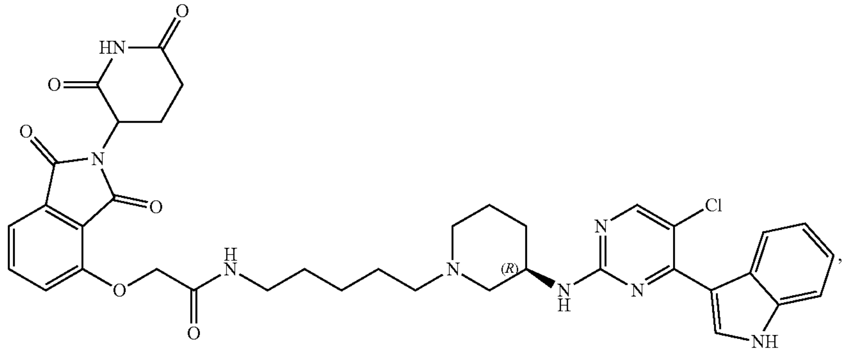
,
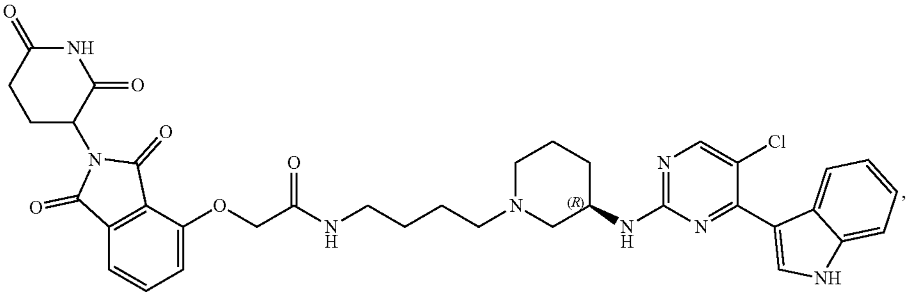
,
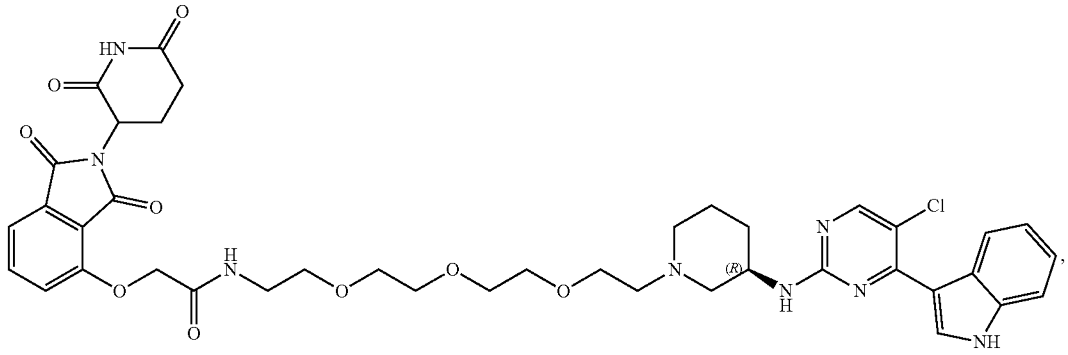
,
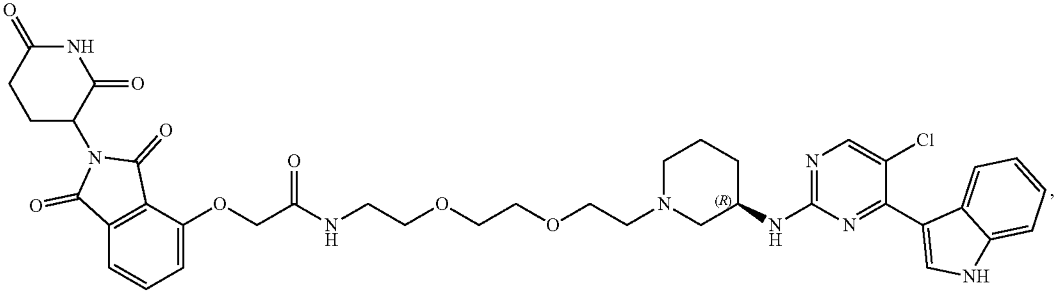
,
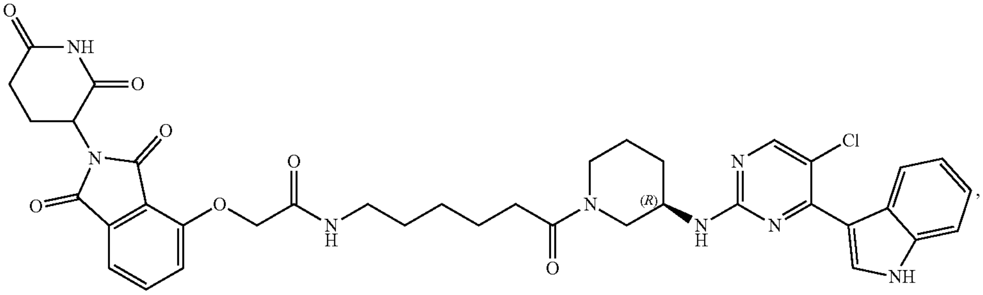
,

-continued
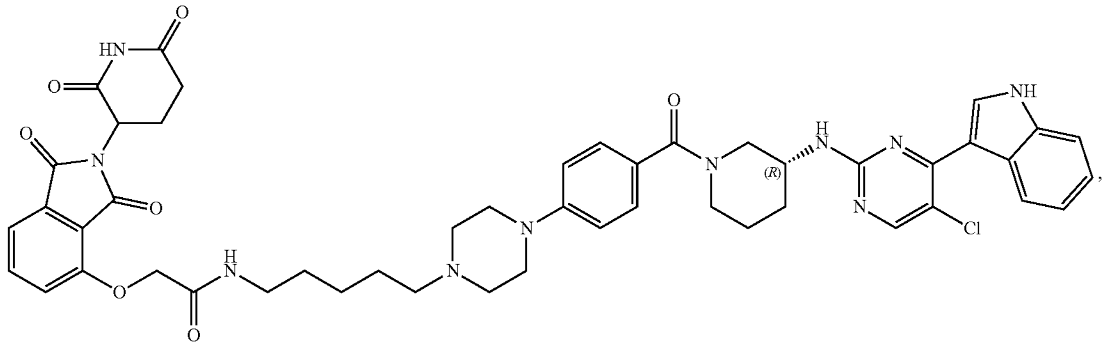
,
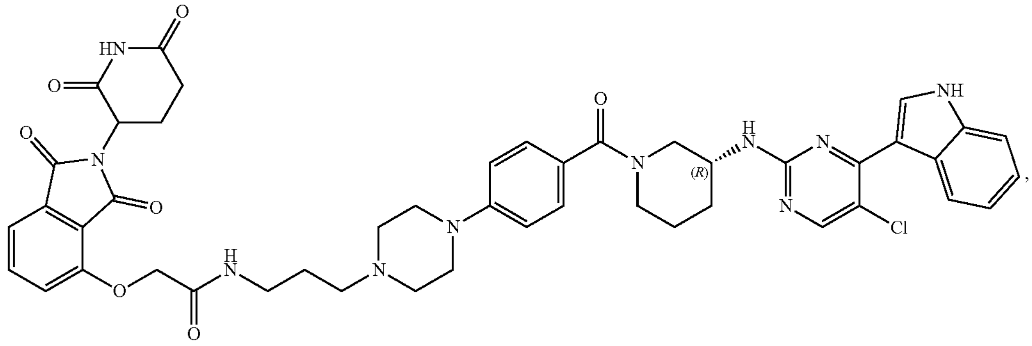
,
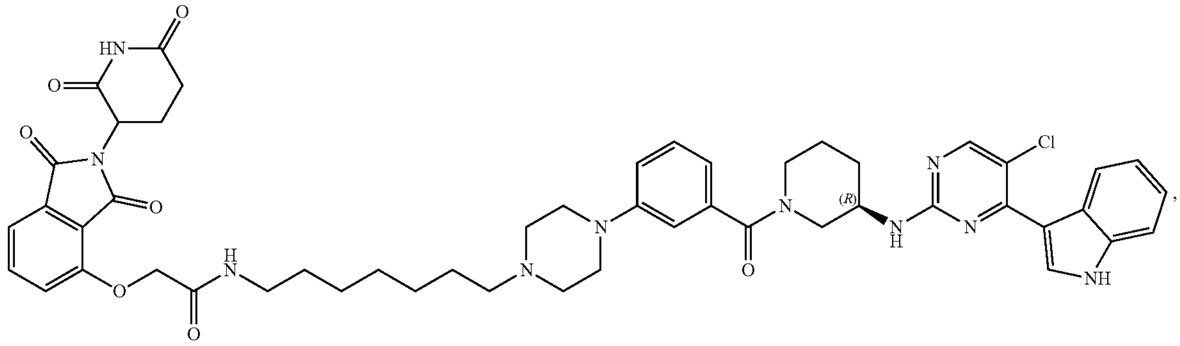
,
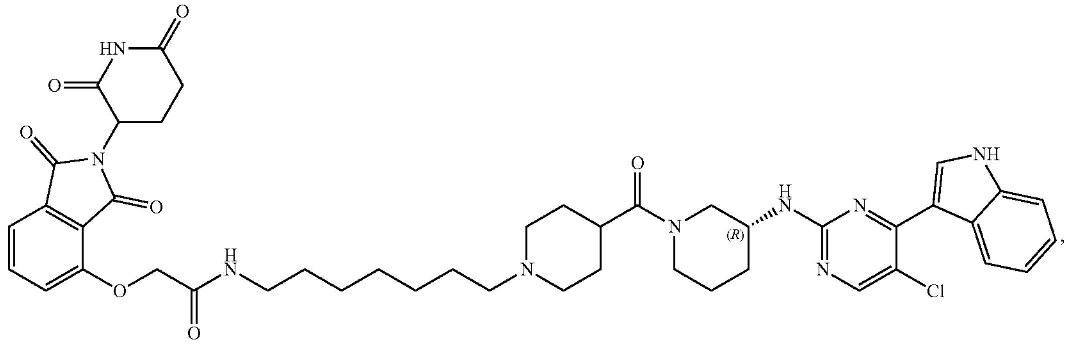
,
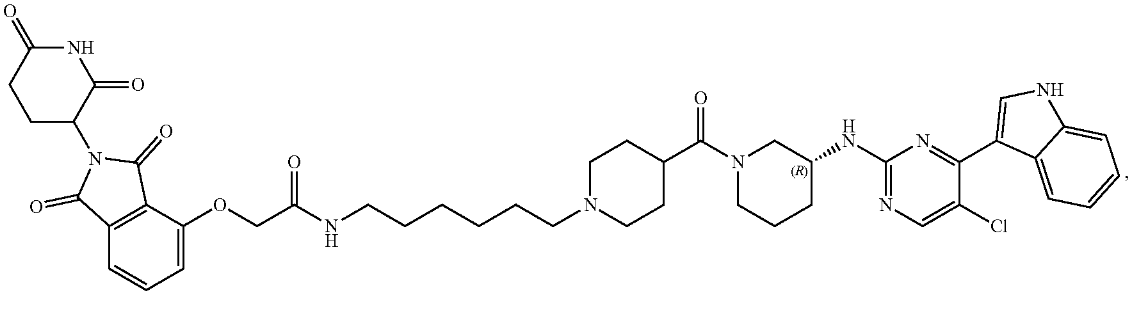
,

-continued
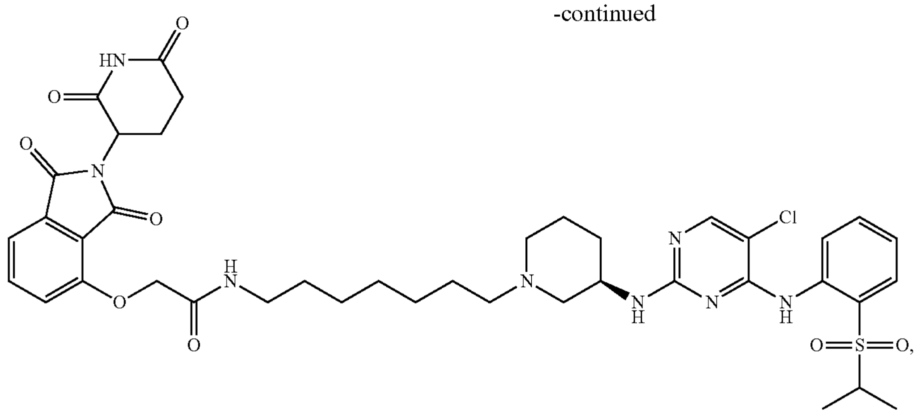
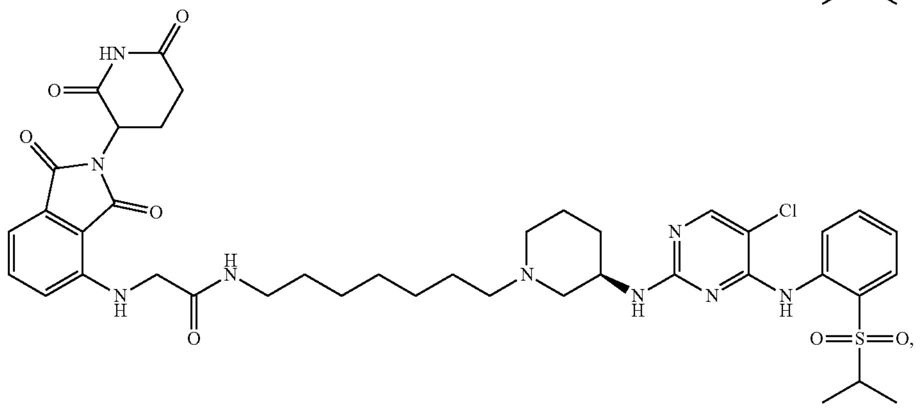
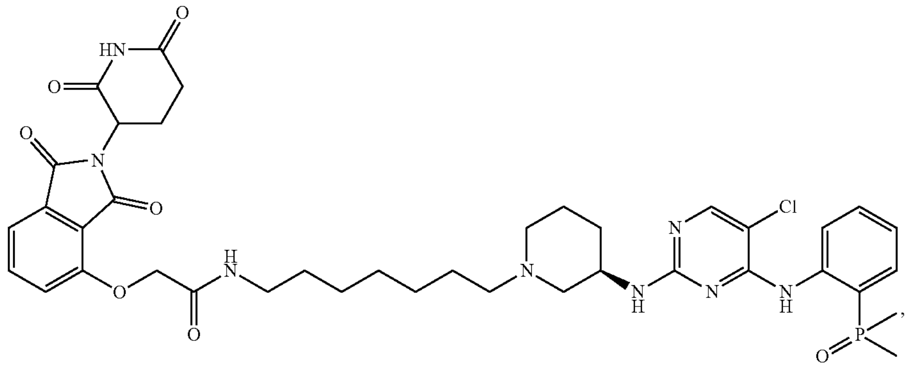
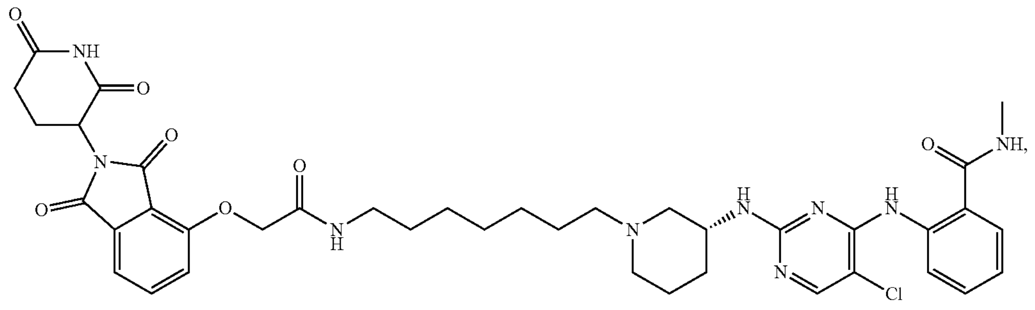

-continued
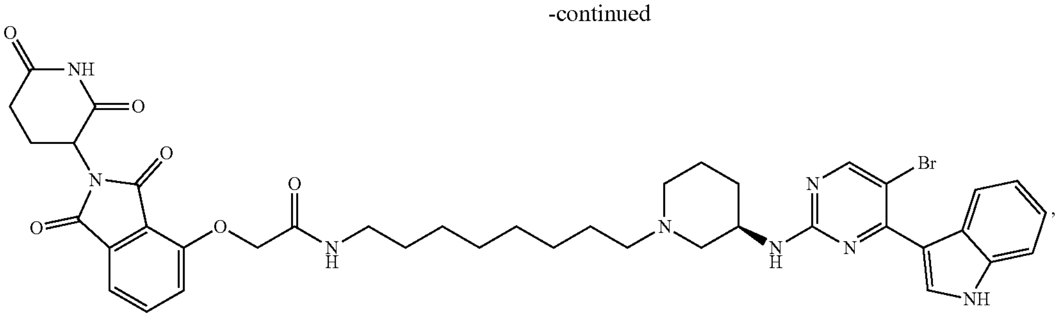
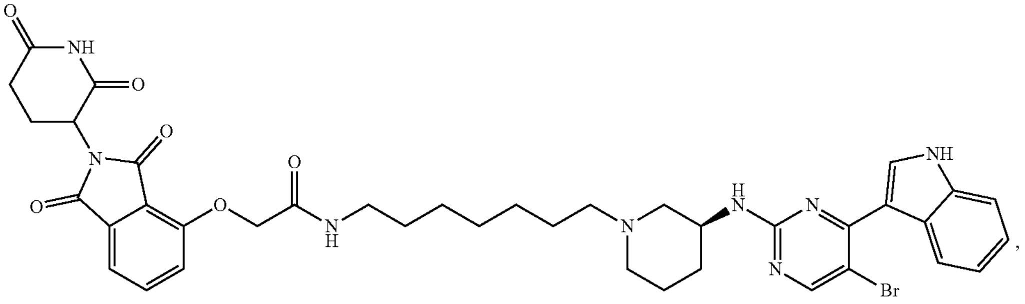
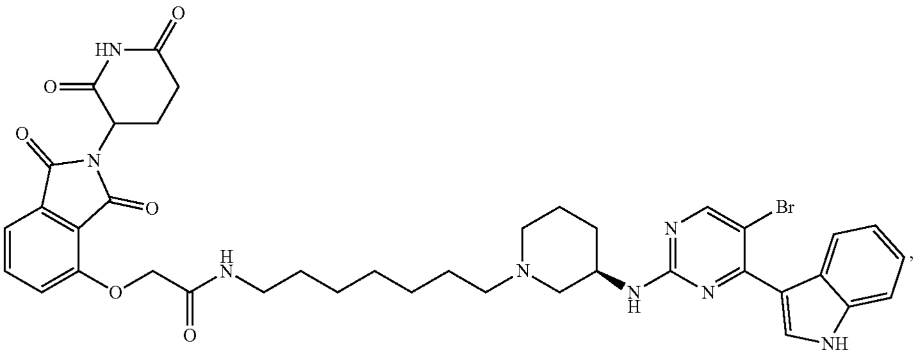
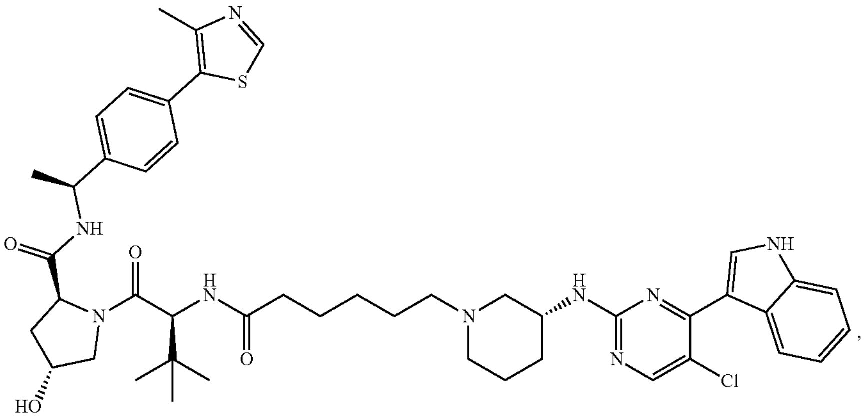
and pharmaceutically acceptable salts, solvates, hydrates, polymorphs, co-crystals, tautomers, stereoisomers, isotopically labeled derivatives, and prodrugs thereof.

Additional exemplary compounds of Formula (I) include, but are not limited to:

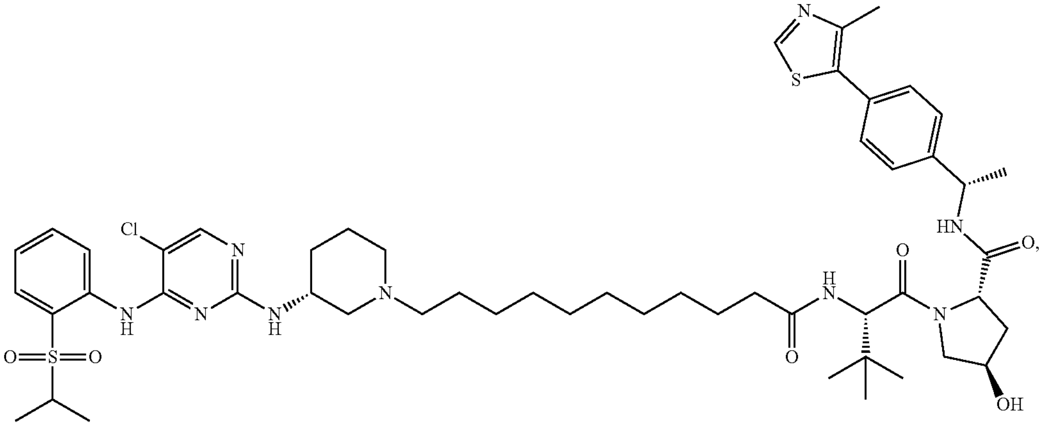

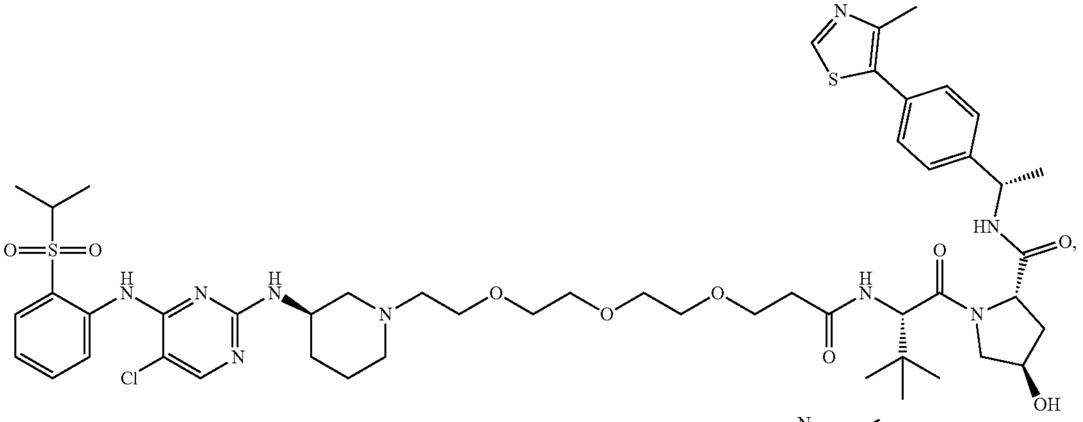

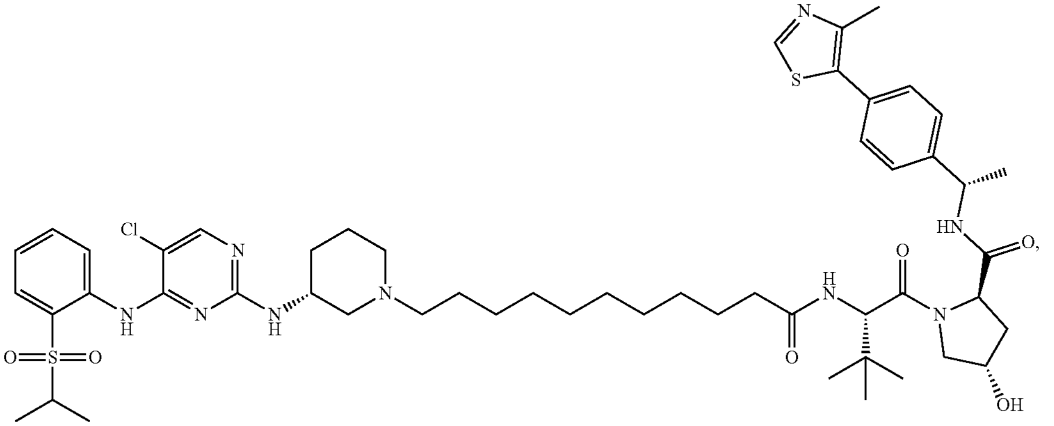

and pharmaceutically acceptable salts, solvates, hydrates, polymorphs, co-crystals, tautomers, stereoisomers, isotopically labeled derivatives, and prodrugs thereof.

In another aspect, described herein are pharmaceutical compositions including a compound described herein, and optionally a pharmaceutically acceptable excipient. In certain embodiments, a pharmaceutical composition described herein includes a therapeutically or prophylactically effective amount of a compound described herein. The pharmaceutical compositions may be useful in inducing the degradation of the target protein (e.g., kinase (e.g., CDK (e.g., CDK9, CDK12))) in a subject or cell, in treating a disease (e.g., a proliferative disease (e.g., ovarian cancer, breast cancer, or prostate cancer)) in a subject in need thereof, or in preventing a disease in a subject in need thereof. In certain embodiments, the compound being administered or used induces the degradation of target protein (e.g., kinase (e.g., CDK (e.g., CDK9, CDK12))) in a subject or cell, in treating a disease (e.g., a proliferative disease (e.g., ovarian cancer, breast cancer, or prostate cancer)) in a subject in need thereof, or in preventing a disease in a subject in need thereof.

In still another aspect, described herein are kits including a container with a compound or pharmaceutical composition described herein. A kit described herein may include a single dose or multiple doses of the compound or pharmaceutical composition. The described kits may be useful in inducing the degradation of the target protein (e.g., kinase (e.g., CDK (e.g., CDK9, CDK12))). In certain embodiments, a kit described herein further includes instructions for using the compound or pharmaceutical composition included in the kit.

In certain embodiments, the compound being administered or used induces the degradation of the target protein (e.g., kinase (e.g., CDK (e.g., CDK9, CDK12))).

Another aspect of the present disclosure relates to methods of treating a disease in a subject in need thereof, the methods comprising administering to the subject a therapeutically effective amount of a compound or pharmaceutical composition described herein. In another aspect, the present disclosure provides methods of preventing a disease in a subject in need thereof, the methods comprises administering to the subject a prophylactically effective amount of a compound or pharmaceutical composition described herein.

In yet another aspect, the present disclosure provides compounds and pharmaceutical compositions described herein for use in a method of the disclosure (e.g., a method of inducing the degradation of the target protein (e.g., kinase (e.g., CDK (e.g., CDK9, CDK12))), a method of inducing apoptosis in a cell of a subject, a method of treating and/or preventing a disease (e.g., a proliferative disease (e.g., ovarian cancer, breast cancer, or prostate cancer)).

Definitions

Definitions of specific functional groups and chemical terms are described in more detail below. The chemical elements are identified in accordance with the Periodic Table of the Elements, CAS version, *Handbook of Chemistry and Physics,* 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry,* 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer, or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The invention additionally encompasses compounds described herein as individual isomers substantially free of other isomers, and alternatively, as mixtures of various isomers.

When a range of values is listed, it is intended to encompass each value and sub-range within the range. For example, "$C_{1-6}$" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

"Hydrocarbon chain" refers to a substituted or unsubstituted divalent alkyl, alkenyl, or alkynyl group. A hydrocarbon chain includes at least one chain, each node ("carbon unit") of which including at least one carbon atom, between the two radicals of the hydrocarbon chain. For example, hydrocarbon chain $-C^AH(C^BH_2C^CH_3)-$ includes only one carbon unit $C^A$. The term "$C_x$ hydrocarbon chain," wherein x is a positive integer, refers to a hydrocarbon chain that includes x number of carbon unit(s) between the two radicals of the hydrocarbon chain. If there is more than one possible value of x, the smallest possible value of x is used for the definition of the hydrocarbon chain. For example, $-CH(C_2H_5)-$ is a $C_1$ hydrocarbon chain, and

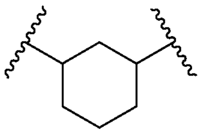

is a $C_3$ hydrocarbon chain. When a range of values is used, e.g., a $C_{1-6}$ hydrocarbon chain, the meaning of the range is as described herein. A hydrocarbon chain may be saturated (e.g., $-(CH_2)_4-$). A hydrocarbon chain may also be unsaturated and include one or more C=C and/or C≡C bonds anywhere in the hydrocarbon chain. For instance, $-CH{=}CH-(CH_2)_2-$, $-CH_2-C{\equiv}C-CH_2-$, and $-C{\equiv}C-CH{=}CH-$ are all examples of a unsubstituted and unsaturated hydrocarbon chain. In certain embodiments, the hydrocarbon chain is unsubstituted (e.g., $-(CH_2)_4-$). In certain embodiments, the hydrocarbon chain is substituted (e.g., $-CH(C_2H_5)-$ and $-CF_2-$). Any two substituents on the hydrocarbon chain may be joined to form an optionally substituted carbocyclyl, optionally substituted heterocyclyl, optionally substituted aryl, or optionally substituted heteroaryl ring. For instance,

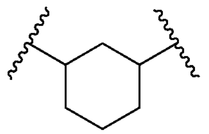 [SMILES: *C1CCCC(*)C1]
,
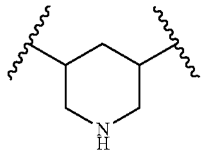
,
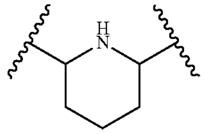
,
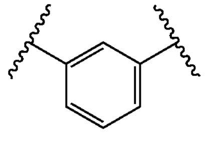
,

-continued

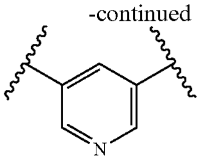

, and

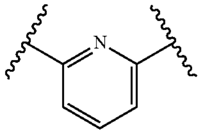

are all examples of a hydrocarbon chain. In contrast, in certain embodiments

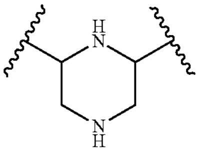

and

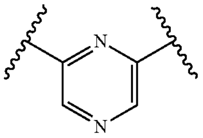

are not within the scope of the hydrocarbon chains described herein.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and $_{ww}$ero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from the group consisting of nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from the group consisting of nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from the group consisting of nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from the group consisting of nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, aziridinyl, oxiranyl, and thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from the group consisting of nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from the group consisting of nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from the group consisting of nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from the group consisting of nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Partially unsaturated" refers to a group that includes at least one double or triple bond. A "partially unsaturated" ring system is further intended to encompass rings having multiple sites of unsaturation but is not intended to include aromatic groups (e.g., aryl or heteroaryl groups) as defined herein. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups are further referred to using the suffix -ene, e.g., alkylene, alkenylene, alkynylene, carbocyclylene, heterocyclylene, arylene, and heteroarylene.

The term "optionally substituted" refers to substituted or unsubstituted.

Alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, $—NO_2$, $—N_3$, $—SO_2H$, $—SO_3H$, —OH, $—OR^{aa}$, $—ON(R^{bb})_2$, $—N(R^{bb})_2$, $—N(R^{bb})_3+X^-$, $—N(OR^{cc})R^{bb}$, —SH, $—SR^{aa}$, $—SSR^{cc}$, $—C(═O)R^{aa}$, $—CO_2H$, —CHO, $—C(OR^{cc})_2$, $—CO_2R^{aa}$, $—OC(═O)R^{aa}$, $—OCO_2R^{aa}$, $—C(═O)N(R^{bb})_2$, $—OC(═O)N(R^{bb})_2$, $—NR^{bb}C(═O)R^{aa}$, $—NR^{bb}CO_2R^{aa}$, $—NR^{bb}C(═O)N(R^{bb})_2$, $—C(═NR^{bb})R^{aa}$, $—C(═NR^{bb})OR^{aa}$, $—OC(═NR^{bb})R^{aa}$, $—OC(═NR^{bb})OR^{aa}$, $—C(═NR^{bb})N(R^{bb})_2$, $—OC(═NR^{bb})N(R^{bb})_2$, $—NR^{bb}C(═NR^{bb})N(R^{bb})_2$, $—C(═O)NR^{bb}SO_2R^{aa}$, $—NR^{bb}SO_2R^{aa}$, $—SO_2N(R^{bb})_2$, $—SO_2R^{aa}$, $—SO_2OR^{aa}$, $—OSO_2R^{aa}$, $—S(═O)R^{aa}$, $—OS(═O)R^{aa}$, $—Si(R^{aa})_3$, $—OSi(R^{aa})_3—C(═S)N(R^{bb})_2$, $—C(═O)SR^{aa}$, $—C(═S)SR^{aa}$, $—SC(═S)SR^{aa}$, $—SC(═O)SR^{aa}$, $—OC(═O)SR^{aa}$, $—SC(═O)OR^{aa}$, $—SC(═O)R^{aa}$, $—P(═O)(R^{aa})_2$, $—P(═O)(OR^{cc})_2$, $—OP(═O)(R^{aa})_2$, $—OP(═O)(OR^{cc})_2$, $—P(═O)(N(R^{bb})_2)_2$, $—OP(═O)(N(R^{bb})_2)_2$, $—NR^{bb}P(═O)(R^{aa})_2$, $—NR^{bb}P(═O)(OR^{cc})_2$, $—NR^{bb}P(═O)(N(R^{bb})_2)_2$, $—P(R^{cc})_2$, $—P(OR^{cc})_2$, $—P(R^{cc})_3{}^+X^-$, $—P(OR^{cc})_3{}^+X^-$, $—P(R^{cc})_4$, $—P(OR^{cc})_4$, $—OP(R^{cc})_2$, $—OP(R^{cc})_3{}^+X^-$, $—OP(OR^{cc})_2$, $—OP(OR^{cc})_3{}^+X^-$, $—OP(R^{aa})_4$, $—OP(OR^{cc})_4$, $—B(R^{cc})_2$, $—B(OR^{cc})_2$, $—BR^{aa}(OR^{cc})$, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

or two geminal hydrogens on a carbon atom are replaced with the group ═O, ═S, $═NN(R^{bb})_2$, $═NNR^{bb}C(═O)R^{aa}$, $═NNR^{bb}C(═O)OR^{aa}$, $═NNR^{bb}S(═O)_2R^{aa}$, $═NR^{bb}$, or $═NOR^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, $—OR^{aa}$, $—N(R^{cc})_2$, —CN, $—C(═O)R^{aa}$, $—C(═O)N(R^{cc})_2$, $—CO_2R^{aa}$, $—SO_2R^{aa}$, $—C(═NR^{cc})OR^{aa}$, $—C(═NR^{cc})N(R^{cc})_2$, $—SO_2N(R^{cc})_2$, $—SO_2R^{cc}$, $—SO_2OR^{cc}$, $—SOR^{aa}$, $—C(═S)N(R^{cc})_2$, $—C(═O)SR^{cc}$, $—C(═S)SR^{cc}$, $—P(═O)(R^{aa})_2$, $—P(═O)(OR^{cc})_2$, $—P(═O)(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, $—NO_2$, $—N_3$, $—SO_2H$, $—SO_3H$, —OH, $—OR^{ee}$, $—ON(R^{ff})_2$, $—N(R^{ff})_2$, $—N(R^{ff})_3{}^+X^-$, $—N(OR^{ee})R^{ff}$, —SH, $—SR^{ee}$, $—SSR^{ee}$, $—C(═O)R^{ee}$, $—CO_2H$, $—CO_2R^{ee}$, $—OC(═O)R^{ee}$, $—OCO_2R^{ee}$, $—C(═O)N(R^{ff})_2$, $—OC(═O)N(R^{ff})_2$, $—NR^{ff}C(═O)R^{ee}$, $—NR^{ff}CO_2R^{ee}$, $—NR^{ff}C(═O)N(R^{ff})_2$, $—C(═NR^{ff})OR^{ee}$, $—OC(═NR^{ff})R^{ee}$, $—OC(═NR^{ff})OR^{ee}$, $—C(═NR^{ff})N(R^{ff})_2$, $—OC(═NR^{ff})N(R^{ff})_2$, $—NR^{ff}C(═NR^{ff})N(R^{ff})_2$, $—NR^{ff}SO_2R^{ee}$, $—SO_2N(R^{ff})_2$, $—SO_2R^{ee}$, $—SO_2OR^{ee}$, $—OSO_2R^{ee}$, $—S(═O)R^{ee}$, $—Si(R^{ee})_3$, $—OSi(R^{ee})_3$, $—C(═S)N(R^{ff})_2$, $—C(═O)SR^{ee}$, $—C(═S)SR^{ee}$, $—SC(═S)SR^{ee}$, $—P(═O)(OR^{ee})_2$, $—P(═O)(R^{ee})_2$, $—OP(═O)(R^{ee})_2$, $—OP(═O)(OR^{ee})_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form ═O or ═S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —$NO_2$, —$N_3$, —$SO_2H$, —$SO_3H$, —OH, —$OC_{1-6}$ alkyl, —ON($C_{1-6}$ alkyl)$_2$, —N($C_{1-6}$ alkyl)$_2$, —N($C_{1-6}$ alkyl)$_3^+X^-$, —NH($C_{1-6}$ alkyl)$_2^+X^-$, —$NH_2$($C_{1-6}$ alkyl) $^+X^-$, —$NH_3^+X^-$, —N($OC_{1-6}$ alkyl)($C_{1-6}$ alkyl), —N(OH($C_{1-6}$ alkyl), —NH(OH), —SH, —$SC_{1-6}$ alkyl, —SS($C_{1-6}$ alkyl), —C(═O)$C_{1-6}$ alkyl), —$CO_2H$, —$CO_2$($C_{1-6}$ alkyl), —OC(═O($C_{1-6}$ alkyl), —$CO_2$($C_{1-6}$ alkyl), —C(═O)$NH_2$, —C(═O)N($C_{1-6}$ alkyl)$_2$, —OC(═O)NH($C_{1-6}$ alkyl), —NHC(═O)($C_{1-6}$ alkyl), —N($C_{1-6}$ alkyl)C(═O)($C_{1-6}$ alkyl), —$NHCO_2$($C_{1-6}$ alkyl), —NHC(═O)N($C_{1-6}$ alkyl)$_2$, —NHC(═O)NH($C_{1-6}$ alkyl), —NHC(═O)$NH_2$, —C(═NH)O($C_{1-6}$ alkyl), —OC(═NH)($C_{1-6}$ alkyl), —OC(═NH)$OC_{1-6}$ alkyl, —C(═NH)N($C_{1-6}$ alkyl)$_2$, —C(═NH)NH($C_{1-6}$ alkyl), —C(═NH)$NH_2$, —OC(═NH)N($C_{1-6}$ alkyl)$_2$, —OC(NH)NH($C_{1-6}$ alkyl), —OC(NH)$NH_2$, —NHC(NH)N($C_{1-6}$ alkyl)$_2$, —NHC(═NH)$NH_2$, —$NHSO_2$($C_{1-6}$ alkyl), —$SO_2N$($C_{1-6}$ alkyl)$_2$, —$SO_2NH$($C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —Si($C_{1-6}$ alkyl)$_3$, —OSi($C_{1-6}$ alkyl)$_3$—C(═S)N($C_{1-6}$ alkyl)$_2$, C(═S)NH($C_{1-6}$ alkyl), C(═S)$NH_2$, —C(═O)S($C_{1-6}$ alkyl), —C(═S)$SC_{1-6}$ alkyl, —SC(═S)$SC_{1-6}$ alkyl, —P(═O)($OC_{1-6}$ alkyl)$_2$, —P(═O)($C_{1-6}$ alkyl)$_2$, —OP(═O)($C_{1-6}$ alkyl)$_2$, —OP(═O)($OC_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form ═O or ═S; wherein $X^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4]^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$. $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

The term "acyl" refers to a group having the general formula —C(═O)$R^{X1}$, —C(═O)O$R^{X1}$, —C(═O)—C(═O)$R^{X1}$, —C(═O)S$R^{X1}$, —C(═O)N($R^{X1}$)$_2$, —C(═S)$R^{X1}$, —C(═S)N($R^{X1}$)$_2$, and —C(═S)S($R^{X1}$), —C(═N$R^{X1}$)$R^{X1}$, —C(═N$R^{X1}$)O$R^{X1}$, —C(═N$R^{X1}$)S$R^{X1}$, and —C(═N$R^{X1}$)N($R^{X1}$)$_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—$CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

"Alkoxy" or "alkoxyl" refers to a radical of the formula: —O-alkyl.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —O$R^{aa}$, —N($R^{cc}$)$_2$, —CN, —C(═O)$R^{aa}$, —C(═O)N($R^{cc}$)$_2$, —$CO_2R^{aa}$, —$SO_2R^{aa}$, —C(═N$R^{bb}$)$R^{aa}$, —C(═N$R^{cc}$)O$R^{aa}$, —C(═N$R^{cc}$)N($R^{cc}$)$_2$, —$SO_2$N($R^{cc}$)$_2$, —$SO_2R^{cc}$, —$SO_2OR^{cc}$, —SO$R^{aa}$, —C(═S)N($R^{cc}$)$_2$, —C(═O)S$R^{cc}$, —C(═S)S$R^{cc}$, —P(═O)(O$R^{cc}$)$_2$, —P(═O)($R^{aa}$)$_2$, —P(═O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on a nitrogen atom is a nitrogen protecting group (also referred to as an amino protecting group). Nitrogen protecting groups include, but are not limited to, —OH, —$OR^{aa}$, —$N(R^{cc})_2$, —C(═O)$R^{aa}$, —C(═O)$N(R^{cc})_2$, —$CO_2R^{aa}$, —$SO_2R^{aa}$, —C(═$NR^{cc}$)$R^{aa}$, —C(═$NR^{cc}$)$OR^{aa}$, —C(═$NR^{cc}$)$N(R^{cc})_2$, —$SO_2N(R^{cc})_2$, —$SO_2R^{cc}$, —$SO_2OR^{cc}$, —$SOR^{aa}$, —C(═S)$N(R^{cc})_2$, —C(═O)$SR^{cc}$, —C(═S)$SR^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

For example, nitrogen protecting groups such as amide groups (e.g., —C(═O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, 0-nitrocinnamide, N-acetylmethionine derivative, o-nitrobenzamide, and o-(benzoyloxymethyl)benzamide.

Nitrogen protecting groups such as carbamate groups (e.g., —C(═O)$OR^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(═O)$_2R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N—[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —C(═O)$SR^{aa}$, —C(═O)$R^{aa}$, —$CO_2R^{aa}$, —C(═O)N$(R^{bb})_2$, —C(═$NR^{bb}$)$R^{aa}$, —C(═$NR^{bb}$)$OR^{aa}$, —C(═$NR^{bb}$)N$(R^{bb})_2$, —S(═O)$R^{aa}$, —$SO_2R^{aa}$, —$Si(R^{aa})_3$, —P$(R^{aa})_2$, —$P(R^{aa})_3{}^+X^-$, —$P(OR^{cc})_2$, —$P(OR^{cc})_3{}^+X^-$, —P(═O)$(R^{aa})_2$, —P(═O)$(OR^{cc})_2$, and —P(═O)(N$(R^{bb})_2)_2$, wherein $^+X^-$, $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —C(═O)$SR^{aa}$, —C(═O)$R^{aa}$, —$CO_2R^{aa}$, —C(═O)N$(R^{aa})_2$, —C(═$NR^{bb}$)$R^{aa}$, —C(═$NR^{bb}$)$OR^{aa}$, —C(═$NR^{bb}$)N$(R^{bb})_2$, —S(═O)$R^{aa}$, —$SO_2R^{aa}$, —$Si(R^{aa})_3$, —$P(R^{aa})_2$, —$P(R^{aa})_3{}^+X^-$, —$P(OR^{cc})_2$, —$P(OR^{cc})_3{}^+X^-$, —P(═O)$(R^{aa})_2$, —P(═O)$(OR^{cc})_2$, and —P(═O)(N$(R^{bb})_2)_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

As used herein, a "leaving group" (LG) is an art-understood term referring to a molecular fragment that departs with a pair of electrons in a heterolytic bond cleavage, wherein the molecular fragment is an anion or neutral molecule. As used herein, a leaving group can be an atom or a group capable of being displaced by a nucleophile. See, for example, Smith, *March Advanced Organic Chemistry* 6th ed. (501-502). Exemplary leaving groups include, but are not limited to, halo (e.g., chloro, bromo, iodo) and activated substituted hydroxyl groups (e.g., —OC(═O)$SR^{aa}$, —OC(═O)$R^{aa}$, —$OCO_2R^{aa}$, —OC(═O)N$(R^{bb})_2$, —OC(═$NR^{bb}$)$R^{aa}$, —OC(═$NR^{bb}$)$OR^{aa}$, —OC(═$NR^{bb}$)N$(R^{bb})_2$, —OS(═O)$R^{aa}$, —$OSO_2R^{aa}$, —$OP(R^{aa})_2$, —OP$(R^{aa})_3$, —OP(═O)$_2R^{aa}$, —OP(═O)$(R^{aa})_2$, —OP(═O)$(OR^{cc})_2$, —OP(═O)$_2$N$(R^{bb})_2$, and —OP(═O)$(NR^{bb})_2$, wherein $R^{aa}$, $R^{bb}$, and $R^{cc}$ are as defined herein). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, amines, ammonia, alcohols, ether moieties, sulfur-containing moieties, thioether moieties, zinc halides, magnesium moieties, diazonium salts, and copper moieties.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of Formula (I) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R \cdot x\ H_2O$, wherein R is the compound and wherein x is a number greater than 0. A given compound may form more than one type of hydrates, including, e.g., monohydrates (x is 1), lower hydrates (x is a number greater than 0 and smaller than 1, e.g., hemihydrates ($R \cdot 0.5H_2O$)), and polyhydrates (x is a number greater than 1, e.g., dihydrates ($R \cdot 2H_2O$) and hexahydrates ($R \cdot 6H_2O$)).

The term "tautomers" refer to compounds that are interchangeable forms of a particular compound structure, and that vary in the displacement of hydrogen atoms and electrons. Thus, two structures may be in equilibrium through the movement of a electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refer to compounds, including derivatives of the compounds of Formula (I), which have cleavable groups and become by solvolysis or under physiological conditions the compounds of Formula (I) which are pharmaceutically active in vivo. Such examples include, but are not limited to, ester derivatives and the like. Other derivatives of the compounds of this invention have activity in both their acid and acid derivative forms, but in the acid sensitive form often offers advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of this invention are particular prodrugs. In some cases it is desirable to prepare double ester type prodrugs such as (acyloxy) alkyl esters or ((alkoxycarbonyl)oxy)alkylesters. $C_{1-8}$ alkyl, $C_{2-8}$ alkenyl, $C_{2-8}$ alkynyl, aryl, $C_{7-12}$ substituted aryl, and $C_{7-12}$ arylalkyl esters of the compounds of Formula (I) may be preferred.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal.

The terms "administer," "administering," or "administration," refers to implanting, absorbing, ingesting, injecting, inhaling, or otherwise introducing an inventive compound, or a pharmaceutical composition thereof.

The terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

The terms "condition," "disease," and "disorder" are used interchangeably.

An "effective amount" of a compound of Formula (I) refers to an amount sufficient to elicit the desired biological response, i.e., treating the condition. As will be appreciated by those of ordinary skill in this art, the effective amount of a compound of Formula (I) may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of an inventive compound may reduce the tumor burden or stop the growth or spread of a tumor.

A "therapeutically effective amount" of a compound of Formula (I) is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces, or avoids symptoms or causes of the condition, or enhances the therapeutic efficacy of another therapeutic agent.

A "prophylactically effective amount" of a compound of Formula (I) is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, autoinflammatory diseases, and autoimmune diseases.

The terms "neoplasm" and "tumor" are used interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites.

The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a malignant neoplasm (*Stedman's Medical Dictionary,* 25th ed.; Hensyl ed.; Williams & Wilkins: Philadelphia, 1990). Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; eye cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrinetumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "angiogenesis" refers to the formation and the growth of new blood vessels. Normal angiogenesis occurs in the healthy body of a subject for healing wounds and for restoring blood flow to tissues after injury. The healthy body controls angiogenesis through a number of means, e.g., angiogenesis-stimulating growth factors and angiogenesis inhibitors. Many disease states, such as cancer, diabetic blindness, age-related macular degeneration, rheumatoid arthritis, and psoriasis, are characterized by abnormal (i.e., increased or excessive) angiogenesis. Abnormal or pathological angiogenesis refers to angiogenesis greater than that in a normal body, especially angiogenesis in an adult not related to normal angiogenesis (e.g., menstruation or wound healing). Abnormal angiogenesis can provide new blood vessels that feed diseased tissues and/or destroy normal tissues, and in the case of cancer, the new vessels can allow tumor cells to escape into the circulation and lodge in other organs (tumor metastases). In certain embodiments, the angiogenesis is pathological angiogenesis.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments, or organelles (such as obtained by lysing cells and separating the components thereof by centrifugation or otherwise). Other examples of biological samples include blood, serum, urine, semen, fecal matter, cerebrospinal fluid, interstitial fluid, mucus, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. Biological samples also include those biological samples that are transgenic, such as a transgenic oocyte, sperm cell, blastocyst, embryo, fetus, donor cell, or cell nucleus, or cells or cell lines derived from biological samples.

The term "tissue" refers to any biological tissue of a subject (including a group of cells, a body part, or an organ) or a part thereof, including blood and/or lymph vessels, which is the object to which a compound, particle, and/or composition of the invention is delivered. A tissue may be an abnormal or unhealthy tissue, which may need to be treated. A tissue may also be a normal or healthy tissue that is under a higher than normal risk of becoming abnormal or unhealthy, which may need to be prevented. In certain embodiments, the tissue is the central nervous system. In certain embodiments, the tissue is the brain.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces, or avoids symptoms, signs, or causes of the condition, and/or enhances the therapeutic efficacy of another therapeutic agent. In certain embodiments, a therapeutically effective amount is an amount sufficient for binding a target (e.g., kinase (e.g., CDK (e.g., CDK9, CDK12))). In certain embodiments, a therapeutically effective amount is an amount sufficient for treating a proliferative disease (e.g., cancer). In certain embodiments, a therapeutically effective amount is an amount sufficient for binding a target protein (e.g., kinase (e.g., CDK (e.g., CDK9, CDK12))) and/or inducing the degradation of the target (e.g., kinase (e.g., CDK (e.g., CDK9, CDK12))).

A "prophylactically effective amount" of a compound described herein is an amount sufficient to prevent a condition, or one or more signs or symptoms associated with the condition, or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is an amount sufficient for binding a target (e.g., kinase (e.g., CDK (e.g., CDK9, CDK12))) and/or inducing the degradation of the target (e.g., kinase (e.g., CDK (e.g., CDK9, CDK12))). In certain embodiments, a prophylactically effective amount is an amount sufficient for treating a disease (e.g., proliferative disease (e.g., ovarian cancer, breast cancer, or prostate cancer)).

In certain embodiments, a prophylactically effective amount is an amount sufficient for binding a target (e.g., kinase (e.g., CDK (e.g., CDK9, CDK12))) and/or inducing the degradation of the target (e.g., kinase (e.g., CDK (e.g., CDK9, CDK12))), and treating and/or preventing a disease (e.g., proliferative disease (e.g., ovarian cancer, breast cancer, or prostate cancer)).

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary,* 25th ed.; Hensyl ed.; Williams & Wilkins: Philadelphia, 1990. Exemplary cancers include, but are not limited to, hematological malignancies. Additional exemplary cancers include, but are not limited to, lung cancer (e.g., bronchogenic carcinoma, small cell lung cancer (SCLC), non-small cell lung cancer (NSCLC), adenocarcinoma of the lung); kidney cancer (e.g., nephroblastoma, a.k.a. Wilms' tumor, renal cell carcinoma); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

A "protein," "peptide," or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

The term "therapeutic agent" refers to any substance having therapeutic properties that produce a desired, usually beneficial, effect. For example, therapeutic agents may treat, ameliorate, and/or prevent disease. Therapeutic agents, as disclosed herein, may be biologics or small molecule therapeutics.

The term "E3 ubiquitin ligase" or "E3 ligase" refers to any protein that recruits an E2 ubiquitin-conjugating enzyme that has been loaded with ubiquitin, recognizes a protein substrate, and assists or directly catalyzes the transfer of ubiquitin from the E2 protein to the protein substrate. For E3 ubiquitin ligase, an exemplary sequence from GenBank:

ACH72645.1 (*Homo sapiens*) is:

(SEQ ID NO: 1)

MESGGRPSLC QFILLGTTSV VTAALYSVYR QKARVSQELK

GAKKVHLGED LKSILSEAPG KCVPYAVIEG AVRSVKETLN

SQFVENCKGV IQRLTLQEHK MVWNRTTHLW NDCSKIIHQR

TNTVPFDLVP HEDGVDVAVR VLKPLDSVDL GLETVYEKFH

PSIQSFTDVI GHYISGERPK GIQETEEMLK VGATLTGVGE

LVLDNNSVRL QPPKQGMQYY LSSQDFDSLL QRQESSVRLW

KVLALVFGFA TCATLFFILR KQYLQRQERL RLKQMQEEFQ

EHEAQLLSRA KPEDRESLKS ACVVCLSSFK SCVFLECGHV

CSCTECYRAL PEPKKCPICR QAITRVIPPY NS.

For E3 ubiquitin ligase, another exemplary sequence from GenBank: AAP47175.1 (*Homo sapiens*) is:

(SEQ ID NO: 2)

MEEGNNNEEV IHLNNFHCHR GQEWINLRDG PITISDSSDE

ERIPMLVTPA PQQHEEEDLD DDVILTETNK PQRSRPNLIK

PAAQWQDLKR LGEERPKKSR AAFESDKSSY FSVCNNPLFD

SGAQDDSEDD YGEFLDLGPP GISEFTKPSG QTEREPKPGP

SHNQAANDIV NPRSEQKVII LEEGSLLYTE SDPLETQNQS

SEDSETELLS NLGESAALAD DQAIEEDCWL DHPYFQSLNQ

QPREITNQVV PQERQPEAEL GRLLFQHEFP GPAFPRPEPQ

QGGISGPSSP QPAHPLGEFE DQQLASDDEE PGPAFPMQES

QEPNLENIWG QEAAEVDQEL VELLVKETEA RFPDVANGFI

EEIIHFKNYY DLNVLCNFLL ENPDYPKRED RIIINPSSSL

LASQDETKLP KIDFFDYSKL TPLDQRCFIQ AADLLMADFK

VLSSQDIKWA LHELKGHYAI TRKALSDAIK KWQELSPETS

GKRKKRKQMN QYSYIDFKFE QGDIKIEKRM FFLENKRRHC

RSYDRRALLP AVQQEQEFYE QKIKEMAEHE DFLLALQMNE

EQYQKDGQLI ECRCCYGEFP FEELTQCADA HLFCKECLIR

YAQEAVFGSG KLELSCMEGS CTCSFPTSEL EKVLPQTILY

KYYERKAEEE VAAAYADELV RCPSCSFPAL LDSDVKRFSC

PNPHCRKETC RKCQGLWKEH NGLTCEELAE KDDIKYRTSI

EEKMTAARIR KCHKCGTGLI KSEGCNRMSC RCGAQMCYLC

RVSINGYDHF CQHPRSPGAP CQECSRCSLW TDPTEDDEKL

IEEIQKEAEE EQKRKNGENT FKRIGPPLEK PVEKVQRVEA

LPRPVPQNLP QPQMPPYAFA HPPFPLPPVR PVFNNFPLNM

GPIPAPYVPP LPNVRVNYDF GPIHMPLEHN LPMHFGPQPR

HRF.

-continued

For E3 ubiquitin ligase, another exemplary sequence from GenBank: AAP47174.1 (*Homo sapiens*) is:

(SEQ ID NO: 3)

MEEGNNNEEV IHLNNFHCHR GQEWINLRDG PITISDSSDE

ERIPMLVTPA PQQHEEEDLD DDVILTEDDS EDDYGEFLDL

GPPGISEFTK PSGQTEREPK PGPSHNQAAN DIVNPRSEQK

VIILEEGSLL YTESDPLETQ NQSSEDSETE LLSNLGESAA

LADDQAIEED CWLDHPYFQS LNQQPREITN QVVPQERQPE

AELGRLLFQH EFPGPAFPRP EPQQGGISGP SSPQPAHPLG

EFEDQQLASD DEEPGPAFPM QESQEPNLEN IWGQEAAEVD

QELVELLVKE TEARFPDVAN GFIEEIIHFK NYYDLNVLCN

FLLENPDYPK REDRIIINPS SSLLASQDET KLPKIDFFDY

SKLTPLDQRC FIQAADLLMA DFKVLSSQDI KWALHELKGH

YAITRKALSD AIKKWQELSP ETSGKRKKRK QMNQYSYIDF

KFEQGDIKIE KRMFFLENKR RHCRSYDRRA LLPAVQQEQE

FYEQKIKEMA EHEDFLLALQ MNEEQYQKDG QLIECRCCYG

EFPFEELTQC ADAHLFCKEC LIRYAQEAVF GSGKLELSCM

EGSCTCSFPT SELEKVLPQT ILYKYYERKA EEEVAAAYAD

ELVRCPSCSF PALLDSDVKR FSCPNPHCRK ETCRKCQGLW

KEHNGLTCEE LAEKDDIKYR TSIEEKMTAA RIRKCHKCGT

GLIKSEGCNR MSCRCGAQMC YLCRVSINGY DHFCQHPRSP

GAPCQECSRC SLWTDPTEDD EKLIEEIQKE AEEEQKRKNG

ENTFKRIGPP LEKPVEKVQR VEALPRPVPQ NLPQPQMPPY

AFAHPPFPLP PVRPVFNNFP LNMGPIPAPY VPPLPNVRVN

YDFGPIHMPL EHNLPMHFGP QPRHRF.

The term "binder" refers to a compound that binds to a protein. The binder binds to a protein with a $K_d$ of less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

The term "proteasome" refers to a protease complex for carrying out degradation of proteins. Specifically, the proteasome is a multisubunit enzyme complex, which can also play a key role regulating proteins that control cell-cycle progression and apoptosis. The proteasome conducts proteolysis of selected proteins.

The term "CDK" refers to a cyclin-dependent kinase. CDK's are a family of protein serine or threonine kinases, where the activity of these kinases is based on association with a non-catalytic regulatory subunit called a cyclin. CDK's are involved in the control of the cell cycle. Examples of CDK's include, but are not limited to, CDK9, CDK12, and CDK13. Other examples of CDK include, but are not limited to, CDK2, CDK4, CDK13, CDK14, CDK15, CDK16, CDK17, and CDK18. The process of eukaryotic cell division may be broadly divided into a series of sequential phases termed G1, S, G2, and M. Correct progression through the various phases of the cell cycle has been shown to be critically dependent upon the spatial and temporal regulation of a family of proteins known as cyclin dependent kinases (CDK's) and a diverse set of their cognate protein partners termed cyclins. CDK's are $CDCl_2$ (also known as CDK1) homologous serine-threonine kinase proteins that are able to utilize ATP as a substrate in the phosphorylation of diverse polypeptides in a sequence-dependent context. Cyclins are a family of proteins characterized by a homology region, containing approximately 100 amino acids, termed the "cyclin box" which is used in binding to, and defining selectivity for, specific CDK partner proteins. Modulation of the expression levels, degradation rates, protein levels, and activity levels of various CDK's and cyclins throughout the cell cycle leads to the cyclical formation of a series of CDK/cyclin complexes, in which the CDK's are enzymatically active. The formation of these complexes controls passage through discrete cell cycle checkpoints and thereby enables the process of cell division to continue. Failure to satisfy the prerequisite biochemical criteria at a given cell cycle checkpoint, e.g., failure to form a required CDK/cyclin complex, can lead to cell cycle arrest and/or cellular apoptosis. Aberrant cellular proliferation can often be attributed to loss of correct cell cycle control. Inhibition of CDK enzymatic activity therefore provides a means by which abnormally dividing cells can have their division arrested and/or be killed. The diversity of CDK's, CDK complexes, and their critical roles in mediating the cell cycle, provides a broad spectrum of potential therapeutic targets selected on the basis of a defined biochemical rationale.

(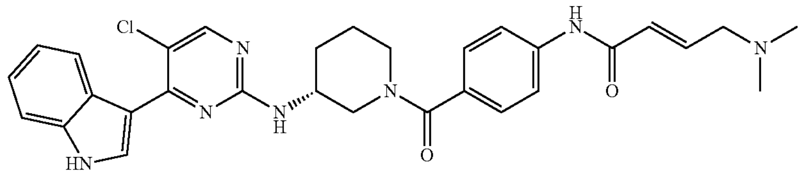).

Figure 1:
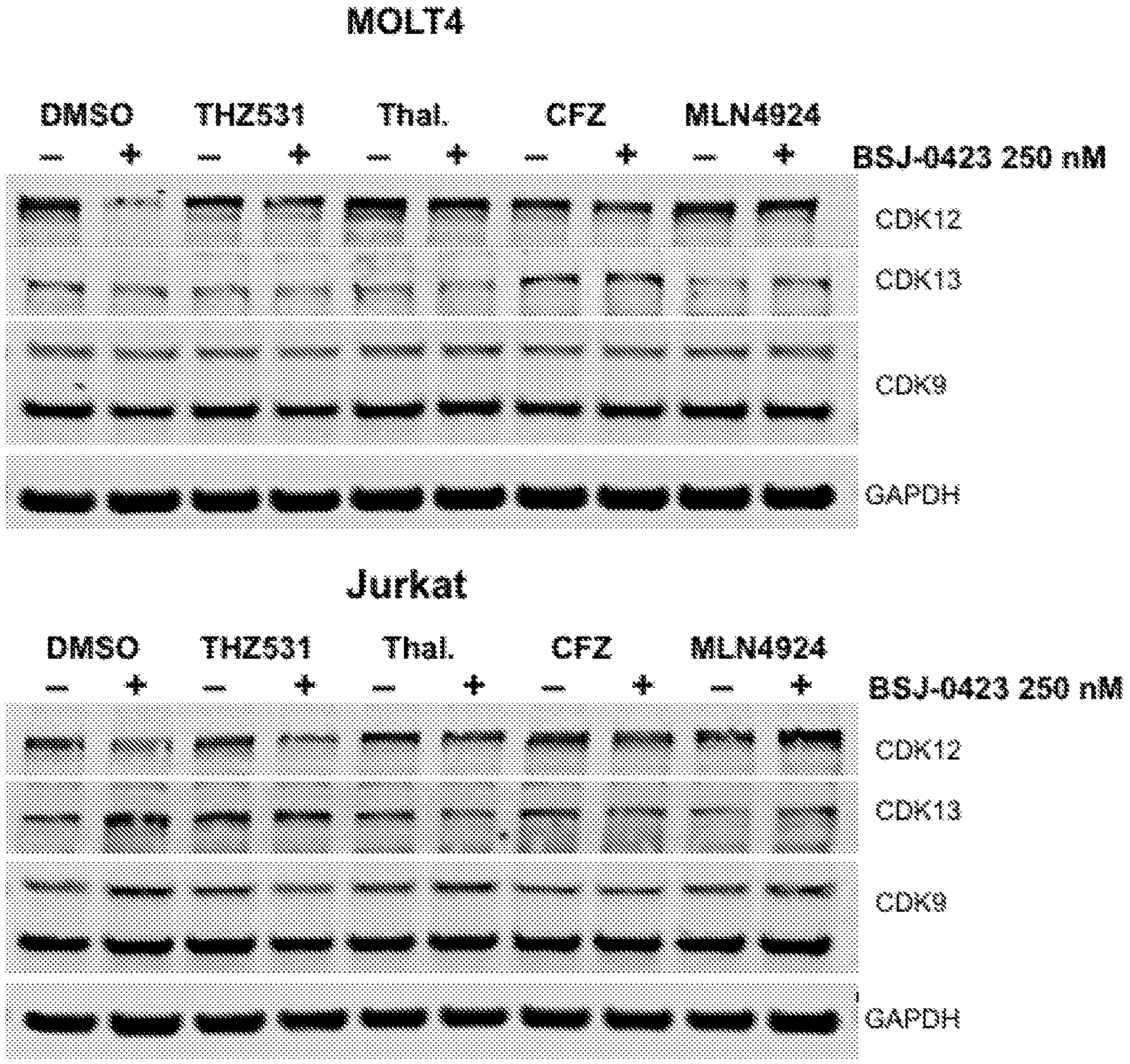
FIGS. 1-3 show the degradation rescued by pre-treatment with Carlfilzomib and exemplary CDK12 irreversible inhibitor, THZ-5-31

FIG. 1 shows the levels of CDK12, CDK13, and CDK9 as well as GAPDH in T-cell Acute Lymphoblastic Leukemia (T-ALL) cells that are Jurkat (human T-lymphocyte cells) and Molt 4 cells (human Acute Lymphoblastic Leukemia cells). The degradation of CDK12, CDK13, CDK9 was rescued by 2 hour pre-treatment with exemplary CDK12 inhibitor THZ-5-31, exemplary protease inhibitor Carfilzomib (CFZ), thalidomide (Thal.) and MLN4924 (inhibitor of NEDD8-Activating Enzyme (NAE)) at the indicated concentrations before treatment with exemplary CDK12 inhibitor BSJ-0423 (BSJ-04-023) at 250 nM for 6 hours. BSJ-04-023 is of formula:

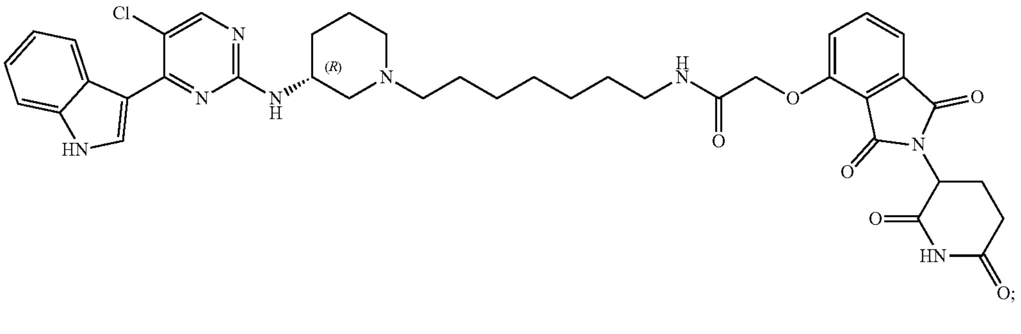

and of formula:

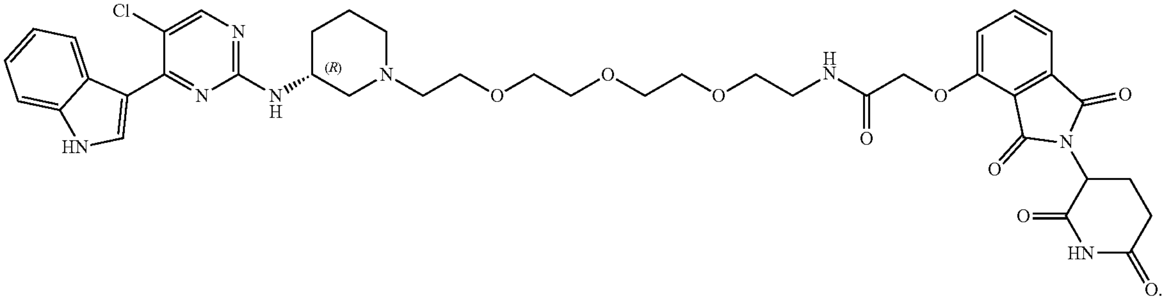

Figure 2:
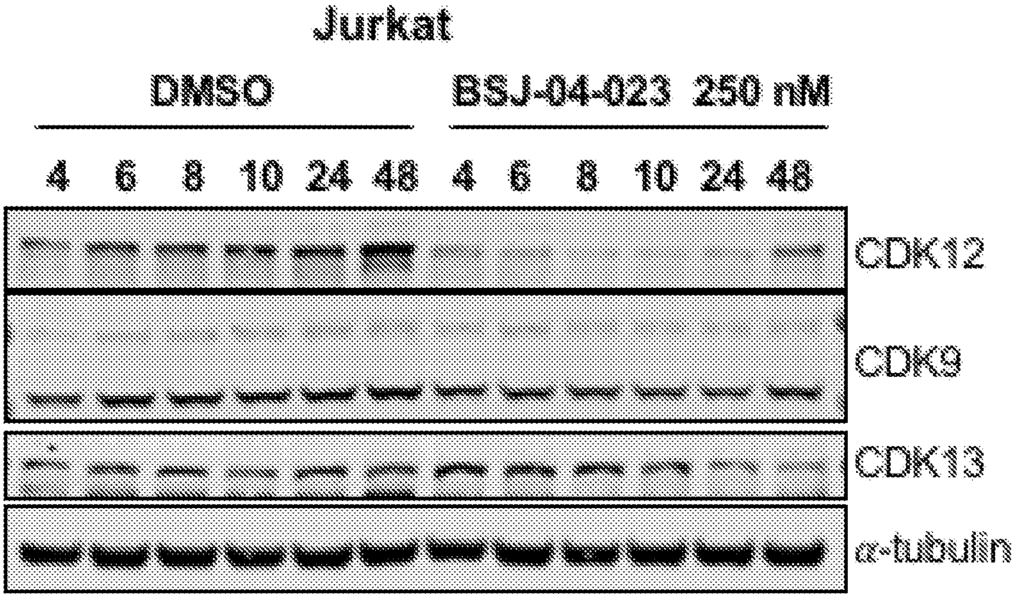

FIG. 2 shows the levels of CDK12, CDK13, and CDK9 as well as GAPDH in T-ALL Jurkat cells. Cells treated with DMSO or exemplary CDK12 degrader BSJ-0423 (BSJ-04-023) at 250 nM were collected and examined with Western blots at the indicated time points.

Figure 3:
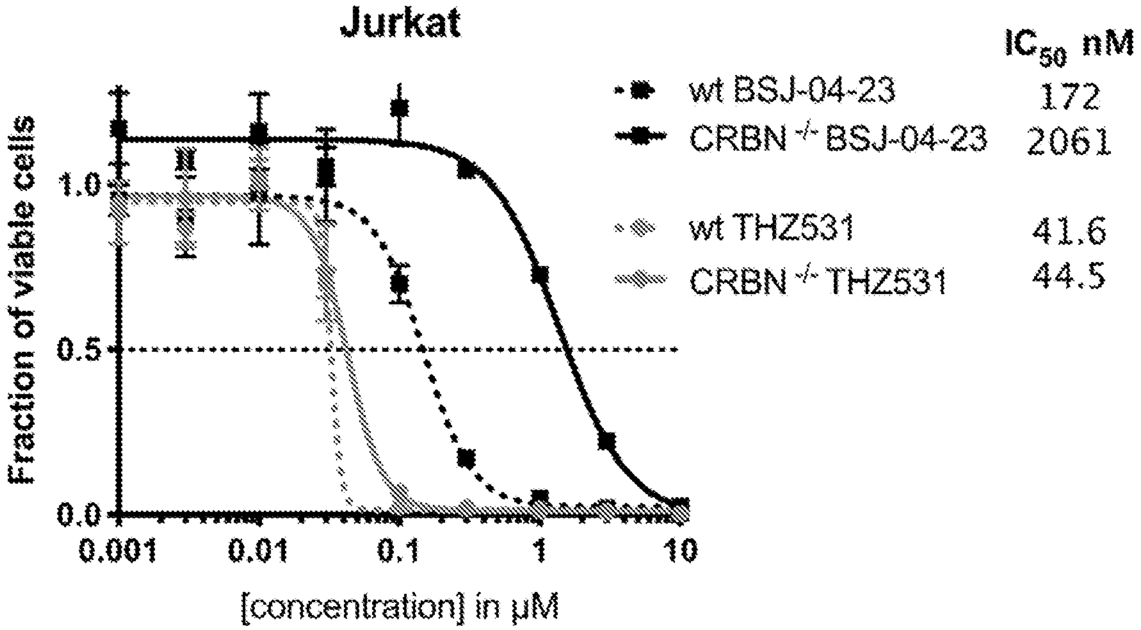

FIG. 3 shows the dose-dependent inhibitory antiproliferation activity ($IC_{50}$) after treatment with exemplary CDK12 inhibitor THZ-5-31, and CDK12 degrader BSJ-04-023 at the indicated concentrations in T-ALL Jurkat cells with CRBN knockout (—/—) and without CRBN knockout (wt). CRBN knockout imparts ~10× resistance to BSJ-0423, but not THZ-5-31, which demonstrates the activity of BSJ-04-023 in Jurkat cells (wt) is CRBN dependent.

Figure 4A:
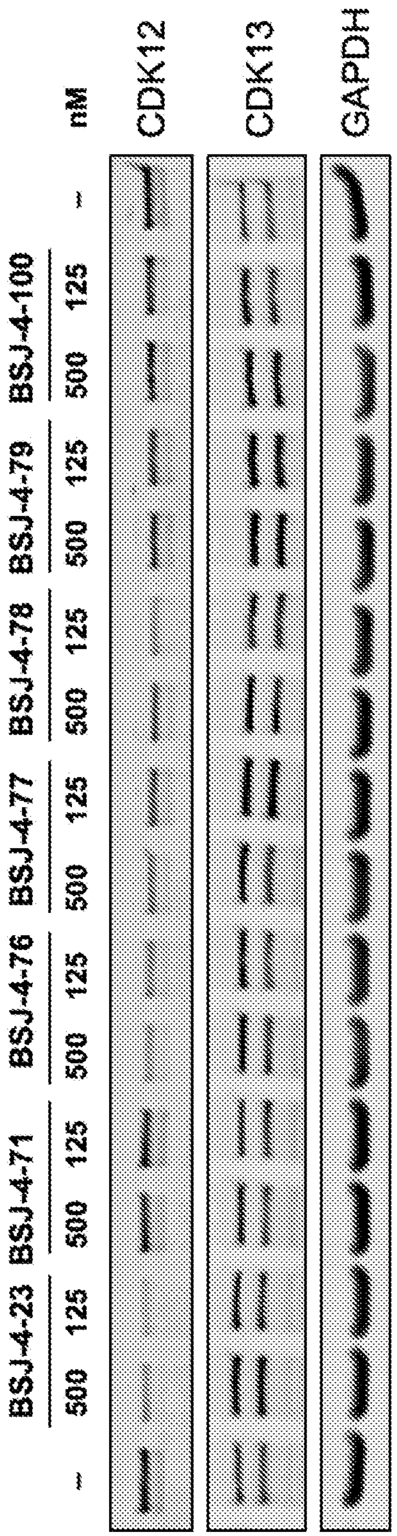

FIG. 4A shows the levels of CDK12 and CDK13, as well as GAPDH in T-cell Acute Lymphoblastic Leukemia (T-ALL) cells that are Jurkat (human T-lymphocyte cells). Cells treated with DMSO or with the CDK12 degraders BSJ-04-023, BSJ-04-071, BSJ-04-076, BSJ-04-077, BSJ-04-078, BSJ-04-079, and BSJ-04-100 at the indicated concentrations were collected and examined with Western blots at 6 hours.

Figure 4B:
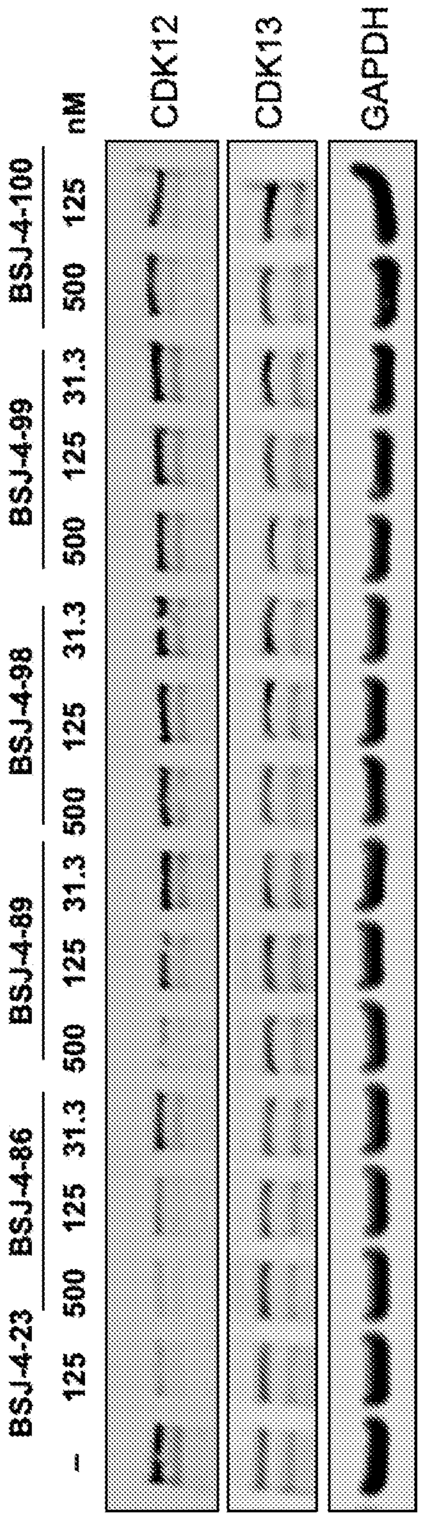

FIG. 4B shows the levels of CDK12 and CDK13, as well as GAPDH in T-cell Acute Lymphoblastic Leukemia (T-ALL) cells that are Jurkat (human T-lymphocyte cells). Cells treated with DMSO or with the CDK12 degraders BSJ-04-023, BSJ-04-086, BSJ-04-089, BSJ-04-098, BSJ-04-099, and BSJ-04-100 at the indicated concentrations were collected and examined with Western blots at 6 hours.

DETAILED DESCRIPTION OF CERTAIN EMBODIMENTS OF THE INVENTION

The bifunctional compounds described herein interact with a target (e.g., a kinase, e.g., CDK, such as CDK9, CDK12) and an E3 ubiquitin ligase (e.g., Cereblon). As described herein, without wishing to be bound by any particular theory, the therapeutic effect may be the result of degradation, modulation, inhibition, or binding of a target (e.g., kinase (e.g., CDK (e.g., CDK9, CDK12))) by a compound described herein. The therapeutic effect may be a result of the bifunctional compound, which includes a binder of an E3 ubiquitin ligase (e.g., Cereblon) and a binder of a target (e.g., kinase (e.g., CDK (e.g., CDK9, CDK12))), thereby inducing the degradation of the target protein. The compounds may be used to induce degradation of the target (e.g., kinase (e.g., CDK (e.g., CDK9, CDK12))), for treating and/or preventing diseases (e.g., proliferative diseases, such as cancers (e.g., ovarian cancer, breast cancer, or prostate cancer)), for treating and/or preventing diseases associated with the target (e.g., a kinase (e.g., CDK (e.g., CDK9, CDK12))), and/or inducing apoptosis in a cell in a biological sample or subject.

In one aspect, disclosed are compounds of Formula (I):

(I)

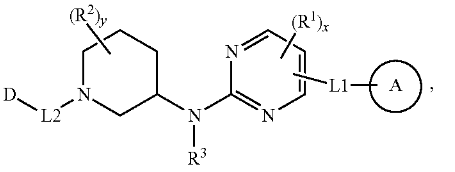

or a pharmaceutically acceptable salt, co-crystal, tautomer, stereoisomer, solvate, hydrate, polymorph, isotopically enriched derivative, or prodrug thereof, wherein:

each instance of $R^1$ is independently halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$OR^{D1}$, —$N(R^{D1a})_2$, or —$SR^{D1}$; wherein $R^{D1}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, or a sulfur protecting group when attached to a sulfur atom;

wherein each occurrence of $R^{D1a}$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; or optionally two instances of $R^{D1a}$ are taken together with their intervening atoms to form a substituted or unsubstituted heterocyclic or substituted or unsubstituted heteroaryl ring;

each instance of $R^2$ is independently halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —CN, —$OR^{D1}$, —$N(R^{D1a})_2$, or —$SR^{D1}$;

$R^3$ is hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each instance of $R^X$ is independently halogen, optionally substituted acyl, optionally substituted alkyl, or a nitrogen protecting group;

each instance of $R^Y$ is independently halogen, optionally substituted acyl, optionally substituted alkyl, —$SO_2R^{Y1}$, —$P(=O)(R^{Y2})_2$, —$OR^{Y1}$; or —$N(R^{Y2})_2$;

$R^{Y1}$ is hydrogen, acyl, optionally substituted alkyl, or an oxygen protecting group when attached to a oxygen atom;

each instance of $R^{Y2}$ is independently hydrogen, optionally substituted acyl, optionally substituted alkyl, or a nitrogen protecting group when attached to a nitrogen atom;

w is 0, 1, 2, 3, 4, 5, or 6;

w1 is 0, 1, 2, 3, 4, or 5;

x is 0, 1, or 2;

y is 0, 1, 2, 3, 4, 5, 6, 7, 8, or 9;

L1 is a bond, optionally substituted alkylene, —$NR^A$—, —O—, or —S—; wherein $R^A$ is hydrogen, optionally substituted acyl, optionally substituted alkyl, or a nitrogen protecting group;

L2 is a linker;

Ring A is of formula:

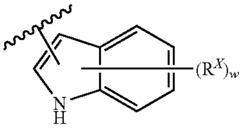

or

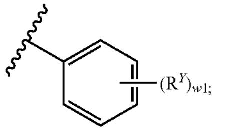

and

D is an E3 ubiquitin ligase binding moiety.

Group D

In certain embodiments, D is an E3 ubiquitin ligase binding moiety. D includes all moieties that bind, or can bind, any E3 ubiquitin ligase. For example, in certain embodiments, D is capable of binding an E3 ubiquitin ligase, such as Cereblon. In certain embodiments, D is capable of binding to multiple different E3 ubiquitin ligases. In certain embodiments, D binds to Cereblon. In certain embodiments, D is based on an immunomodulatory imide drug. In certain embodiments, D is derived from lenalidomide. In certain embodiments, D is derived from thalidomide.

Human Cereblon (CRBN) is a protein of 442 amino acids with an apparent molecular weight of ~51 kDa (GenBank: AAH17419). (For the CRBN protein sequence see: Higgins et al., *Neurology.* 2004, 63, 1927-31. For additional information related to the CRBN structure, see Hartmann et al., *PLoS One.* 2015, 10, e0128342.) Human CRBN contains the N-terminal part (237-amino acids from 81 to 317) of ATP-dependent Lon protease domain without the conserved Walker A and Walker B motifs, 11 casein kinase II phosphorylation sites, 4 protein kinase C phosphorylation sites, 1 N-linked glycosylation site, and 2 myristoylation sites. CRBN is widely expressed in testis, spleen, prostate, liver, pancreas, placenta, kidney, lung, skeletal muscle, ovary, small intestine, peripheral blood leukocyte, colon, brain, and retina. CRBN is located in the cytoplasm, nucleus, and peripheral membrane. (Chang et al., *Int. J. Biochem. Mol. Biol.* 2011, 2, 287-94.)

Cereblon is an E3 ubiquitin ligase, and it forms an E3 ubiquitin ligase complex with damaged DNA binding protein 1 (DDB1), Cullin-4A (CUL4A), and regulator of cullins 1 (ROC1). This complex ubiquitinates a number of other proteins. Through a mechanism which has not been completely elucidated, Cereblon ubiquitination of target proteins results in increased levels of fibroblast growth factor 8 (FGF8) and fibroblast growth factor 10 (FGF10). FGF8, in turn, regulates a number of developmental processes, such as limb and auditory vesicle formation.

In certain embodiments, D is a modulator, binder, inhibitor, or ligand of Cereblon. In certain embodiments, D is a modulator of Cereblon. In certain embodiments, D is a binder of Cereblon. In certain embodiments, D is an inhibitor of Cereblon. In certain embodiments, D is a ligand of Cereblon. In certain embodiments, D is any modulator, binder, inhibitor, or ligand of Cereblon disclosed in U.S. patent application U.S. Ser. No. 14/792,414, filed Jul. 6, 2015, U.S. patent application U.S. Ser. No. 14/707,930, filed May 8, 2015, and International Patent Application, PCT/US2013/054663, filed Aug. 13, 2013, each of which is incorporated herein by reference. In certain embodiments, D has a binding affinity (K) to Cereblon of about 1-10 μM. In certain embodiments, D has a $K_d$ to Cereblon of about 3 μM. In certain embodiments, D has a binding affinity ($K_d$) to Cereblon as disclosed in U.S. patent application U.S. Ser. No. 14/792,414, filed Jul. 6, 2015.

In certain embodiments, D is a modulator, binder, inhibitor, or ligand of a Cereblon variant. In certain embodiments, D is a modulator, binder, inhibitor, or ligand of a Cereblon isoform.

In certain embodiments, D comprises an optionally substituted heteroaryl ring. In certain embodiments, D comprises an optionally substituted fused bicyclic heteroaryl ring. In certain embodiments, D comprises an optionally substituted fused bicyclic heteroaryl ring and a heterocyclic ring. In certain embodiments, D comprises an optionally substituted fused bicyclic heteroaryl ring and a heterocyclic ring, where the heterocyclic ring contains at least one nitrogen. In certain embodiments, D comprises an optionally substituted fused bicyclic heteroaryl ring and a heterocyclic ring, where the fused bicyclic heteroaryl ring and heterocyclic ring each contain at least one nitrogen. In certain embodiments, D comprises an optionally substituted fused bicyclic heteroaryl ring and a heterocyclic ring, where the fused bicyclic heteroaryl ring and heterocyclic ring each contain one nitrogen. In certain embodiments, D comprises an optionally substituted phthalimido group, or an analogue or derivative thereof. In certain embodiments, D comprises an optionally substituted phthalimido-glutarimide group, or an analogue or derivative thereof.

In certain embodiments, D is of Formula (E-I):

(E-I)

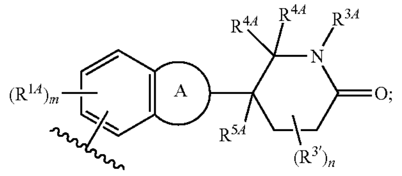

wherein:

Ring A is a substituted or unsubstituted heterocyclyl, or substituted or unsubstituted heteroaryl ring;

each $R^{1A}$ is, independently, halogen, —OH, $C_1$-$C_6$ alkyl, or $C_1$-$C_6$ alkoxy;

each $R^{3A}$ is, independently, H or $C_1$-$C_3$ alkyl;

each $R^{3'}$ is, independently, $C_1$-$C_3$ alkyl;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, $C_1$-$C_3$ alkyl, F, or Cl;

m is 0, 1, 2, or 3; and n is 1 or 2.

In certain embodiments, Formula (E-I) is derived from an immunomodulatory imide drug (e.g., derived from lenalidomide or thalidomide). In certain embodiments, Formula (E-I) is of Formula (IA) or Formula (IB). In certain embodiments, the compounds of Formula (IA) or Formula (IB) are optionally further substituted.

In certain embodiments, D is of Formula (IA):

(IA)

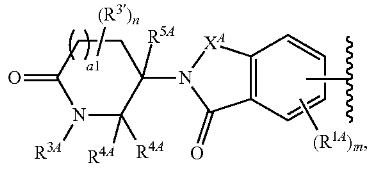

wherein:

$X^A$ is C(O) or $C(R^{3A})_2$;

each $R^{1A}$ is independently halogen, —OH. $C_1$-$C_6$ alkyl, or $C_1$-$C_6$ alkoxy;

$R^{3A}$ is H or $C_1$-$C_3$ alkyl;

each $R^{3'}$ is independently $C_1$-$C_3$ alkyl;

each $R^{4A}$ is independently H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, $C_1$-$C_3$ alkyl, or halogen;

m is 0, 1, 2, or 3;

n is 0, 1 or 2; and a1 is 0 or 1.

In certain embodiments, D is of Formula (IA-a):

(IA-a)

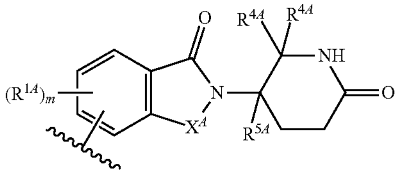

wherein:

$X^A$ is C(O) or $C(R^{3A})_2$;

each $R^{1A}$ is, independently, halogen, —OH, $C_1$-$C_6$ alkyl, or $C_1$-$C_6$ alkoxy;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, $C_1$-$C_3$ alkyl, F, or Cl; and m is 0, 1, 2, or 3.

In certain embodiments, D is of Formula (IA-b):

(IA-b)

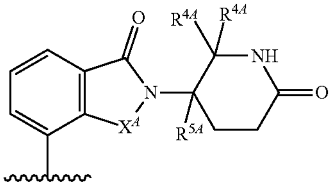

wherein:

$X^A$ is C(O) or $C(R^{3A})$;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O; and $R^{5A}$ is H, $C_1$-$C_3$ alkyl, F, or Cl.

In certain embodiments, D is of Formula (IA-c):

(IA-c)

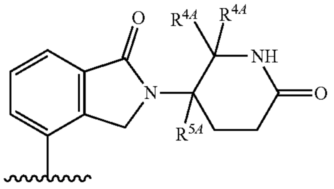

wherein:

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O; and $R^{5A}$ is H, $C_1$-$C_3$ alkyl, F, or Cl.

In certain embodiments, D is of Formula (IA-d):

(IA-d)

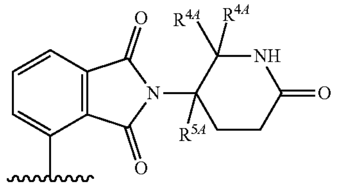

wherein:

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O; and $R^{5A}$ is H, $C_1$-$C_3$ alkyl, F, or Cl.

In certain embodiments, D is of Formula (IB):

(IB)

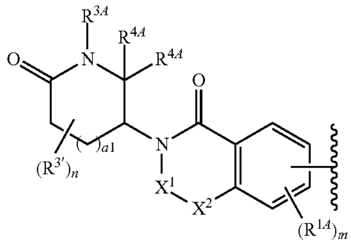

wherein:

—$X^1$—$X^2$— is $C(R^{3A})$═N or $C(R_{3A})_2$—$C(R^{3A})_2$;

each $R^{1A}$ is independently halogen, —OH, $C_1$-$C_6$ alkyl, or $C_1$-$C_6$ alkoxy;

$R^{3A}$ is H or $C_1$-$C_3$ alkyl;

each $R^{3'}$ is independently $C_1$-$C_3$ alkyl;

each $R^{4A}$ is independently H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, $C_1$-$C_3$ alkyl, or halogen;

m is 0, 1, 2, or 3;

n is 0, 1, or 2; and a1 is 0 or 1.

In certain embodiments, D is of Formula (IB-a):

(IB-a)

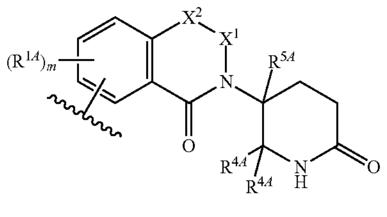

wherein:

$X^1$—$X^2$ is $C(R^{3A})$═N or $C(R^{3A})_2$—$C(R^{3A})_2$;

each $R^{1A}$ is, independently, halogen, —OH, $C_1$-$C_6$ alkyl, or $C_1$-$C_6$ alkoxy;

each $R^{3A}$ is, independently, H or $C_1$-$C_3$ alkyl;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, $C_1$-$C_3$ alkyl, F, or Cl; and m is 0, 1, 2, or 3.

In certain embodiments, D is of Formula (IB-b):

(IB-b)

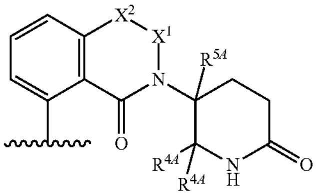

wherein:

$X^1$—$X^2$ is $C(R^{3A})$═N or $C(R^{3A})_2$—$C(R^{3A})_2$;

each $R^{3A}$ is, independently, H or $C_1$-$C_3$ alkyl;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O; and $R^{5A}$ is H, $C_1$-$C_3$ alkyl, F, or Cl.

In certain embodiments, D is of Formula (IB-c):

(IB-c)

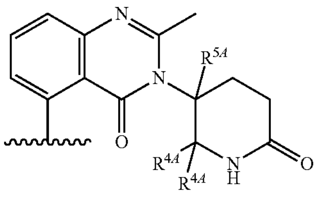

wherein:

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O; and $R^{5A}$ is H, $C_1$-$C_3$ alkyl, F, or Cl.

Formulae (IA), (IA-a), and (IA-b) include substituent $X^A$. In certain embodiments, $X^A$ is C(O). In certain embodiments, $X^A$ is $C(R^{3A})_2$.

Formulae (IA), (IA-a), and (IA-b) include substituents —$X^1$—$X^2$. In certain embodiments, —$X^1$—$X^2$— is $C(R^{3A})$═N. In certain embodiments, —$X^1$—$X^2$— is C(H)═N. In certain embodiments, —$X^1$—$X^2$— is $C(C_1$-$C_3$ alkyl)═N. In certain embodiments, —$X^1$—$X^2$— is $C(R_{3A})_2$—$C(R^{3A})_2$. In certain embodiments, —$X^1$—$X^2$— is $C(H)_2$—$C(H)_2$. In certain embodiments, —$X^1$—$X^2$— is $C(H)_2$—$C(C_1$-$C_3$ alkyl$)_2$. In certain embodiments, —$X^1$—$X^2$— is $C(H)_2$—C $(C_1$-$C_3$ alkyl$)_2$. In certain embodiments, —$X^1$—$X^{2-}$ is $C(H)_2$—$C(C_1$-$C_3$ alkyl$)_2$. In certain embodiments, —$X^1$—$X^{2-}$ is $C(C_1$-$C_3$ alkyl$)_2$-$C(C_1$-$C_3$ alkyl$)_2$.

In certain embodiments, D is a compound based on a ligand that binds to von Hippel-Lindau (a "VHL ligand"). In certain embodiments, D is derived from a VHL ligand.

In certain embodiments, D is of the formula:

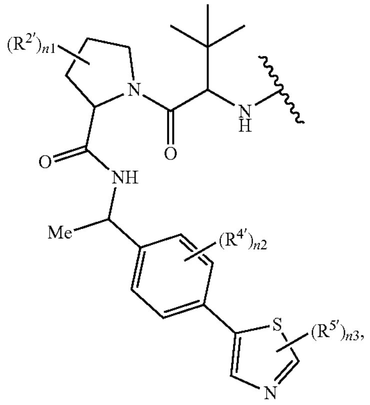

wherein:

each $R^{2'}$ is independently halogen, —OH, $C_1$-$C_6$ alkyl, or $C_1$-$C_6$ alkoxy;

each $R^{4'}$ is independently halogen, —OH, $C_1$-$C_6$ alkyl, or $C_1$-$C_6$ alkoxy;

each $R^{5'}$ is independently halogen, —OH, $C_1$-$C_6$ alkyl, or $C_1$-$C_6$ alkoxy;

n1' is 0, 1, 2, 3, 4, 5, or 6;

n2' is 0, 1, 2, 3, or 4; and n3' is 0, 1, or 2.

In certain embodiments, D has zero instances of $R^{2'}$. In certain embodiments, D has one or more instances of $R^{2'}$. In certain embodiments, n1' is 0. In certain embodiments, n1' is 1. In certain embodiments, n1' is 2. In certain embodiments, n1' is 3. In certain embodiments, n1' is 4. In certain embodiments, n1' is 5. In certain embodiments, n1' is 6. In certain embodiments, each instance of $R^{2'}$ is independently halogen, —OH, $C_1$-$C_6$ alkyl, or $C_1$-$C_6$ alkoxy. In certain embodiments, at least one instance of $R^{2'}$ is halogen (e.g., F, Cl, Br, or I). In certain embodiments, at least one instance of $R^{2'}$ is —OH. In certain embodiments, at least one instance of $R^{2'}$ is unsubstituted $C_1$-$C_6$ alkyl (e.g., unsubstituted methyl, unsubstituted ethyl, or unsubstituted n-propyl). In certain embodiments, at least one instance of $R^{2'}$ is $C_1$-$C_6$ alkoxy (e.g., —O(unsubstituted $C_1$-$C_6$ alkyl)). In certain embodiments, at least one instance of $R^{2'}$ is —O(Me). In certain embodiments, at least one instance of $R^{2'}$ is —O(Et). In certain embodiments, at least one instance of $R^{2'}$ is —O(n-propyl). In certain embodiments, at least one instance of $R^{2'}$ is —O(isopropyl). In certain embodiments, at least one instance of $R^{2'}$ is —O(n-butyl).

In certain embodiments, D has zero instances of $R^{4'}$. In certain embodiments, D has one or more instances of $R^{4'}$. In certain embodiments, n2' is 0. In certain embodiments, n2' is 1. In certain embodiments, n2' is 2. In certain embodiments, n2' is 3. In certain embodiments, n2' is 4. In certain embodiments, each instance of $R^{4'}$ is independently halogen, —OH, $C_1$-$C_6$alkyl, or $C_1$-$C_6$ alkoxy. In certain embodiments, at least one instance of $R^{4'}$ is halogen (e.g., F, Cl, Br, or I). In certain embodiments, at least one instance of $R^{2'}$ is —OH. In certain embodiments, at least one instance of $R^{4'}$ is unsubstituted $C_1$-$C_6$ alkyl (e.g., unsubstituted methyl, unsubstituted ethyl, or unsubstituted n-propyl). In certain embodiments, at least one instance of $R^{4'}$ is $C_1$-$C_6$alkoxy (e.g., —O(unsubstituted $C_1$-$C_6$alkyl)). In certain embodiments, at least one instance of $R^{4'}$ is —O(Me). In certain embodiments, at least one instance of $R^{4'}$ is —O(Et). In certain embodiments, at least one instance of $R^{4'}$ is —O(n-propyl). In certain embodiments, at least one instance of $R^{4'}$ is —O(isopropyl). In certain embodiments, at least one instance of $R^{4'}$ is —O(n-butyl).

In certain embodiments, D has zero instances of $R^{5'}$. In certain embodiments, D has one or more instances of $R^{5'}$. In certain embodiments, n3' is 0. In certain embodiments, n3' is 1. In certain embodiments, n3' is 2. In certain embodiments, n3' is 3. In certain embodiments, each instance of $R^{5'}$ is independently halogen, —OH, $C_1$-$C_6$ alkyl, or $C_1$-$C_6$ alkoxy. In certain embodiments, at least one instance of $R^{5'}$ is halogen (e.g., F, Cl, Br, or I). In certain embodiments, at least one instance of $R^{5'}$ is —OH. In certain embodiments, at least one instance of $R^{5'}$ is $C_1$-$C_6$ alkyl. In certain embodiments, at least one instance of $R^{5'}$ is unsubstituted $C_1$-$C_6$ alkyl (e.g., unsubstituted methyl, unsubstituted ethyl, or unsubstituted n-propyl). In certain embodiments, at least one instance of $R^{5'}$ is unsubstituted methyl. In certain embodiments, at least one instance of $R^{5'}$ is unsubstituted ethyl. In certain embodiments, at least one instance of $R^{5'}$ is unsubstituted n-propyl. In certain embodiments, at least one instance of $R^{5'}$ is $C_1$-$C_6$alkoxy (e.g., —O(unsubstituted $C_1$-$C_6$alkyl)). In certain embodiments, at least one instance of $R^{5'}$ is —O(Me). In certain embodiments, at least one instance of $R^{5'}$ is —O(Et). In certain embodiments, at least one instance of $R^{5'}$ is —O(n-propyl). In certain embodiments, at least one instance of $R^{5'}$ is —O(isopropyl). In certain embodiments, at least one instance of $R^{5'}$ is —O(n-butyl).

In certain embodiments, D is of the formula:

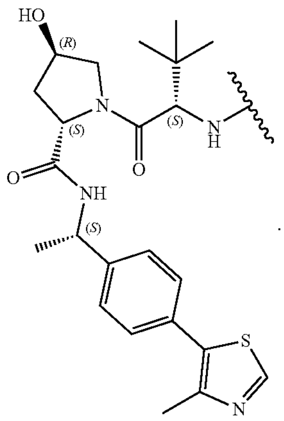
.

In certain embodiments, D is of the formula:

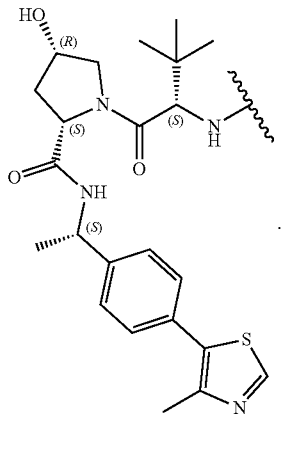

Ring A

Formula (I) includes Ring A. In certain embodiments, Ring A is of formula:

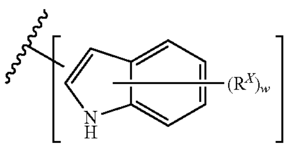

or

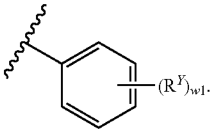

In certain embodiments, Ring A is of formula:

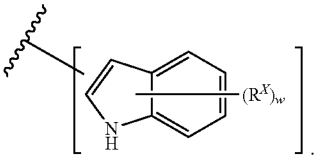

In certain embodiments, Ring A is of formula:

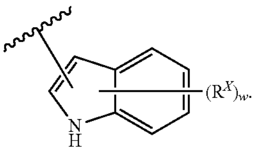

In certain embodiments, on Ring A, there are zero instances of substituent $R^X$. In certain embodiments, on Ring A, there are one or more instances of substituent $R^X$. In certain embodiments, w is 0. In certain embodiments, w is 1. In certain embodiments, w is 2. In certain embodiments, w is 3. In certain embodiments, w is 4. In certain embodiments, w is 5. In certain embodiments, w is 6. In certain embodiments, at least one instance of RX is halogen (e.g., F, Cl, Br, or I). In certain embodiments, at least one instance of RX is optionally substituted acyl (e.g., —C(=O)Me). In certain embodiments, at least one instance of $R^X$ is optionally substituted alkyl (e.g., substituted or unsubstituted $C_{1-6}$ alkyl) (e.g., optionally substituted methyl, optionally substituted ethyl, or optionally substituted propyl)). In certain embodiments, at least one instance of $R^X$ is optionally substituted $C_{1-6}$ alkyl. In certain embodiments, at least one instance of $R^X$ is optionally substituted methyl. In certain embodiments, at least one instance of $R^X$ is optionally substituted optionally substituted ethyl. In certain embodiments, at least one instance of $R^X$ is optionally substituted n-propyl. In certain embodiments, at least one instance of $R^X$ is optionally substituted isopropyl. In certain embodiments, at least one instance of $R^X$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, Ring A is of formula:

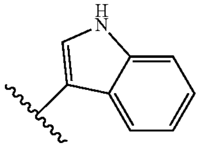,
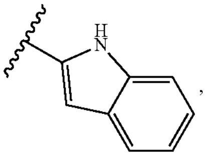,
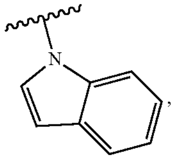,
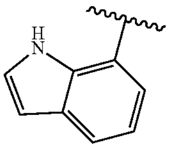,
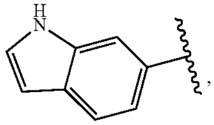,
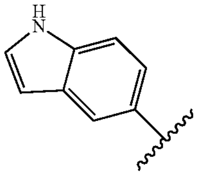,
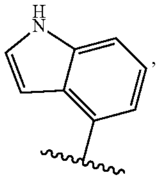,
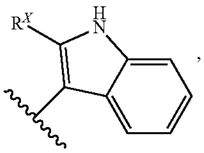,
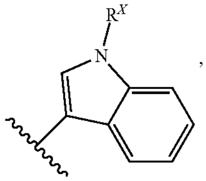,
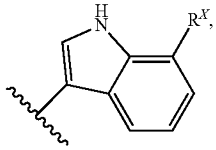,
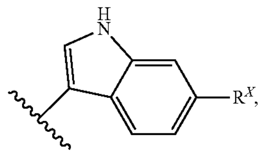,
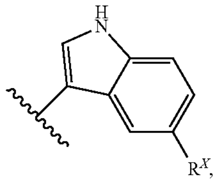, or
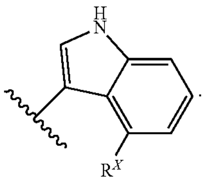.

In certain embodiments, Ring A is of formula:

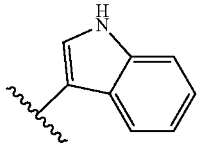,

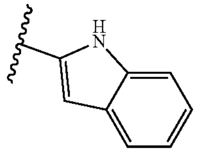,

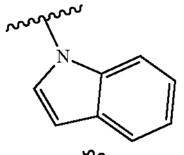,

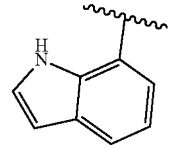,

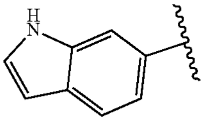,

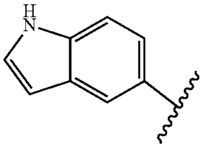, or

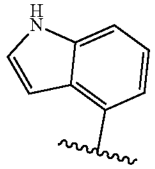.

In certain embodiments, Ring A is of formula:

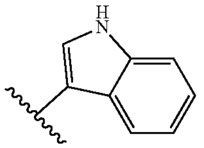.

In certain embodiments, Ring A is of formula

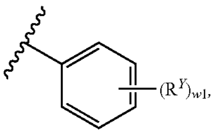

wherein each instance of $R^Y$ is independently halogen, optionally substituted acyl, optionally substituted alkyl, —$SO_2R^{Y1}$, —P(═O)($R^{Y2}$)$_2$, —$OR^{Y1}$; or —N($R^{Y2}$)$_2$; $R^{Y1}$ is hydrogen, acyl, optionally substituted alkyl, or an oxygen protecting group when attached to a oxygen atom; each instance of $R^{Y2}$ is independently hydrogen, optionally substituted acyl, optionally substituted alkyl, or a nitrogen protecting group when attached to a nitrogen atom; and w1 is 0, 1, 2, 3, 4, or 5. In certain embodiments, on Ring A, there are zero instances of substituent $R^Y$. In certain embodiments, on Ring A, there are one or more instances of substituent $R^Y$. In certain embodiments, w1 is 0. In certain embodiments, w1 is 1. In certain embodiments, w1 is 2. In certain embodiments, w1 is 3. In certain embodiments, w1 is 4. In certain embodiments, w1 is 5. In certain embodiments, Ring A is of formula:

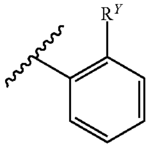, 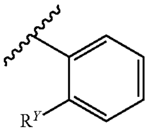, 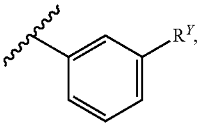

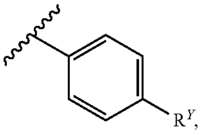 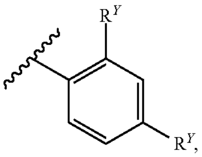

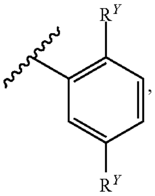, 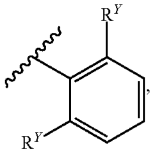, 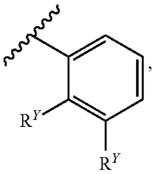,

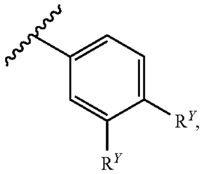 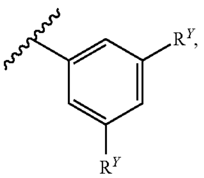 or

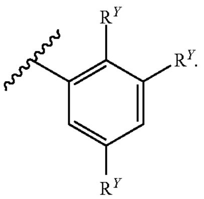

In certain embodiments, Ring A is of formula:

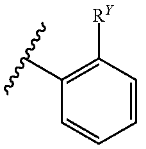,

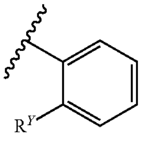,

-continued

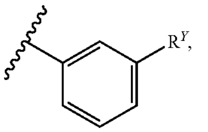

or

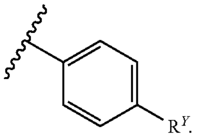

In certain embodiments, at least one instance of $R^Y$ is halogen (e.g., F, Cl, Br, or I). In certain embodiments, at least one instance of $R^Y$ is optionally substituted acyl (e.g., —C(═O)Me). In certain embodiments, at least one instance of $R^Y$ is optionally substituted alkyl (e.g., substituted or unsubstituted $C_{1-6}$ alkyl) (e.g., optionally substituted methyl, optionally substituted ethyl, or optionally substituted propyl)). In certain embodiments, at least one instance of $R^Y$ is optionally substituted $C_{1-6}$ alkyl. In certain embodiments, at least one instance of $R^Y$ is optionally substituted methyl. In certain embodiments, at least one instance of $R^X$ is optionally substituted optionally substituted ethyl. In certain embodiments, at least one instance of $R^Y$ is optionally substituted n-propyl. In certain embodiments, at least one instance of $R^Y$ is optionally substituted isopropyl. In certain embodiments, at least one instance of $R^Y$ is optionally substituted acyl, optionally substituted alkyl, $—SO_2R^{Y1}$, $—P(═O)(R^{Y2})_2$, $—OR^{Y1}$; or $—N(R^{Y2})_2$; $R^{Y1}$ is hydrogen, acyl, optionally substituted alkyl, or an oxygen protecting group when attached to a oxygen atom; each instance of $R^{Y2}$ is independently hydrogen, optionally substituted acyl, optionally substituted alkyl, or a nitrogen protecting group when attached to a nitrogen atom. In certain embodiments, at least one instance of $R^Y$ is optionally substituted acyl, $—SO_2R^{Y1}$, $—P(═O)(R^{Y2})_2$, $—OR^{Y1}$; or $—N(R^{Y2})_2$. In certain embodiments, at least one instance of $R^Y$ is optionally substituted acyl (e.g., —C(═O)Me). In certain embodiments, at least one instance of $R^Y$ is $—C(═O)N(R^{y3})_2$, wherein each instance of $R^{y3}$ is independently hydrogen or optionally substituted alkyl. In certain embodiments, at least one instance of $R^Y$ is $—C(═O)NH(R^{y3})$, wherein $R^{y3}$ is optionally substituted alkyl. In certain embodiments, at least one instance of $R^Y$ is —C(═O)NH(optionally substituted $C_1$-$C_6$alkyl). In certain embodiments, at least one instance of $R^Y$ is —C(═O)NH(Me). In certain embodiments, at least one instance of $R^Y$ is $—SO_2R^{Y1}$, where $R^{Y1}$ is hydrogen, acyl, or optionally substituted alkyl. In certain embodiments, at least one instance of $R^Y$ is $—SO_2R^{Y1}$, wherein $R^{Y1}$ is optionally substituted $C_1$-$C_6$ alkyl. In certain embodiments, at least one instance of $R^Y$ is $—SO_2R^{Y1}$, wherein $R^{Y1}$ is optionally substituted methyl, optionally substituted ethyl, optionally substituted n-propyl, optionally substituted isopropyl, optionally substituted n-butyl, optionally substituted isobutyl, or optionally substituted n-pentyl. In certain embodiments, at least one instance of $R^Y$ is $—SO_2R^{Y1}$, wherein $R^{Y1}$ is optionally substituted isopropyl. In certain embodiments, at least one instance of $R^Y$ is

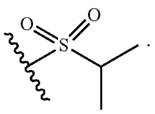 [SMILES: *S(=O)(=O)C(C)C]

In certain embodiments, at least one instance of $R^Y$ is $—P(═O)(R^{Y2})_2$, wherein each instance of $R^{Y2}$ is independently optionally substituted alkyl. In certain embodiments, at least one instance of $R^Y$ is $—P(═O)(R^{Y2})_2$, wherein each instance of $R^{Y2}$ is unsubstituted $C_1$-$C_6$alkyl. In certain embodiments, at least one instance of $R^Y$ is $—P(═O)(R^{Y2})_2$, wherein each instance of $R^{Y2}$ is optionally substituted $C_1$-$C_6$ alkyl. In certain embodiments, at least one instance of $R^Y$ is $—P(═O)(R^{Y2})_2$, wherein each instance of $R^{Y2}$ is independently optionally substituted methyl, optionally substituted ethyl, optionally substituted n-propyl, optionally substituted isopropyl, optionally substituted n-butyl, optionally substituted isobutyl, or optionally substituted n-pentyl. In certain embodiments, at least one instance of $R^Y$ is $—P(═O)(R^{Y2})_2$, wherein each instance of $R^{Y2}$ is optionally substituted methyl. In certain embodiments, at least one instance of $R^Y$ is

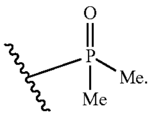 [SMILES: *P(C)(C)=O]

In certain embodiments, at least one instance of $R^Y$ is $—OR^{Y1}$ or $—N(R^{Y2})_2$; wherein $R^{Y1}$ is hydrogen, acyl, optionally substituted alkyl, or an oxygen protecting group when attached to a oxygen atom; each instance of $R^{Y2}$ is independently hydrogen, optionally substituted acyl, optionally substituted alkyl, or a nitrogen protecting group when attached to a nitrogen atom. In certain embodiments, at least one instance of $R^Y$ is $—OR^{Y1}$ (e.g., —OH or —O(optionally substituted $C_1$-$C_6$ alkyl)). In certain embodiments, at least one instance of $R^Y$ is $—N(R^{Y2})_2$ (e.g., $—NH_2$, $—NMe_2$)).

In certain embodiments, $R^{Y1}$ is hydrogen, acyl, optionally substituted alkyl, or an oxygen protecting group when attached to an oxygen atom. In certain embodiments, $R^{Y1}$ is hydrogen. In certain embodiments, $R^{Y1}$ is acyl (e.g., —C(═O)Me). In certain embodiments, $R^{Y1}$ is optionally substituted alkyl (e.g., substituted or unsubstituted $C_{1-6}$ alkyl) (e.g., optionally substituted methyl, optionally substituted ethyl, or optionally substituted propyl)). In certain embodiments, $R^{Y1}$ is an oxygen protecting group (e.g., methyl, methoxylmethyl (MOM), trimethylsilyl (TMS), triethylsilyl (TES), triisopropylsilyl (TIPS), dimethylisopropylsilyl (IPDMS), diethylisopropylsilyl (DEIPS), dimethylthexylsilyl, tbutyldimethylsilyl (TBDMS), t-butyldiphenylsilyl (TBDPS), methanesulfonate (mesylate), benzylsulfonate, or tosylate (Ts)). In certain embodiments, each instance of $R^{Y2}$ is independently hydrogen, optionally substituted acyl, optionally substituted alkyl, or a nitrogen protecting group when attached to a nitrogen atom. In certain embodiments, at least one instance of $R^{Y2}$ is hydrogen. In certain embodiments, at least one instance of $R^{Y2}$ is acyl (e.g., —C(═O)Me). In certain embodiments, at least one instance of $R^{Y2}$ is optionally substituted alkyl (e.g., substituted or unsubstituted $C_{1-6}$ alkyl) (e.g., optionally substituted methyl, optionally substituted ethyl, or optionally substituted propyl)). In certain embodiments, at least one instance of $R^{Y2}$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

In certain embodiments, Ring A is of formula:

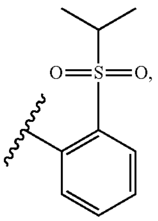

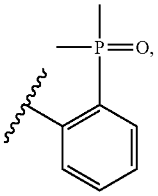

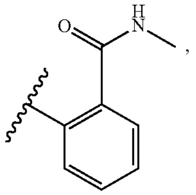

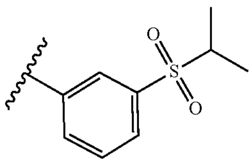

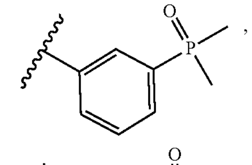

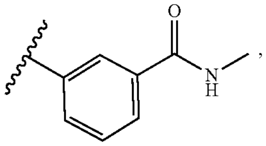

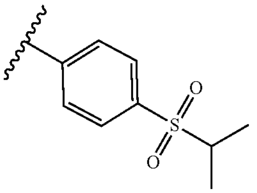

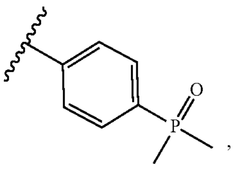

or

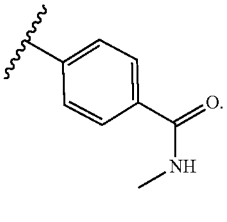

In certain embodiments, Ring A is of formula:

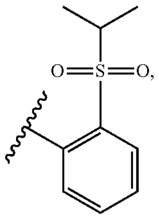

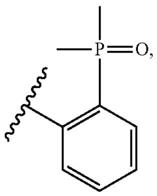

or

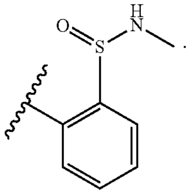

Linkers L1 and L2

Linker L1 connects the pyrimidine of Formula (I) and Ring A. In certain embodiments, L1 is a bond. In certain embodiments, L1 is optionally substituted alkylene. In certain embodiments, L1 is optionally substituted $C_{1-6}$ alkylene. In certain embodiments, L1 is unsubstituted $C_{1-6}$ alkylene. In certain embodiments, L1 is unsubstituted $C_{2-6}$ alkylene. In certain embodiments, L1 is unsubstituted $C_{1-6}$ alkylene. In certain embodiments, L1 is unsubstituted $C_{4-6}$ alkylene. In certain embodiments, L1 is —$CH_2$—. In certain embodiments, L1 is —$NR^A$—, —O—, or —S—; wherein $R^A$ is hydrogen, optionally substituted acyl, optionally substituted alkyl, or a nitrogen protecting group. In certain embodiments, L1 is —$NR^A$—, wherein $R^A$ is hydrogen, optionally substituted acyl, optionally substituted alkyl, or a nitrogen protecting group. In certain embodiments, L1 is —NH—. In certain embodiments, L1 is —N(optionally substituted alkyl)- (e.g., —N(optionally substituted $C_{1-6}$ alkyl)-). In certain embodiments, L1 is —O—. In certain embodiments, L1 is —S—. In certain embodiments, L1 is —NH—, —O—, or —S—.

In Formula (I), L2 is a divalent moiety linking the group D to the piperidine moiety of Formula (I). In Formula (I), L2 is a divalent moiety. In certain embodiments, L2 is a substituted or unsubstituted $C_{1-50}$ hydrocarbon chain as the shortest path between D and the piperidine moiety of Formula (I), optionally wherein one or more chain atoms of the hydrocarbon chain are independently replaced with —C(═O)—, —O—, —$NR^b$—, —S—, or a cyclic moiety, wherein $R^b$ is independently hydrogen, substituted or unsubstituted $C_{1-6}$ alkyl, or a nitrogen protecting group. In certain embodiments, L2 is a substituted or unsubstituted $C_{1-30}$ hydrocarbon chain, optionally wherein one or more chain atoms of the hydrocarbon chain are independently replaced with —C(═O)—, —O—, —$NR^b$—, —S—, or a cyclic moiety, wherein $R^b$ is independently hydrogen, substituted or unsubstituted $C_{1-6}$ alkyl, or a nitrogen protecting group. In certain embodiments, L2 is an unsubstituted $C_{1-30}$ hydrocarbon chain, optionally wherein one or more chain atoms of the hydrocarbon chain are independently replaced with —C(═O)—, —O—, —$NR^b$—, —S—, or a cyclic moiety, wherein $R^b$ is independently hydrogen, substituted or unsubstituted $C_{1-6}$ alkyl, or a nitrogen protecting group. In certain embodiments, L2 is a substituted or unsubstituted $C_{1-24}$ hydrocarbon chain, optionally wherein one or more chain atoms of the hydrocarbon chain are independently replaced with —C(═O)—, —O—, —$NR^b$—, —S—, or a cyclic moiety, wherein $R^b$ is independently hydrogen, substituted or unsubstituted $C_{1-6}$ alkyl, or a nitrogen protecting group. In certain embodiments, L2 is an unsubstituted $C_{1-24}$ hydrocarbon chain, optionally wherein one or more chain atoms of the hydrocarbon chain are independently replaced with —C(═O)—, —O—, —$NR^b$—, —S—, or a cyclic moiety, wherein $R^b$ is independently hydrogen, substituted or unsubstituted $C_{1-6}$ alkyl, or a nitrogen protecting group. In certain embodiments, L2 is a substituted or unsubstituted $C_{1-20}$ hydrocarbon chain, optionally wherein one or more chain atoms of the hydrocarbon chain are independently replaced with —C(═O)—, —O—, —$NR^b$—, —S—, or a cyclic moiety, wherein $R^b$ is independently hydrogen, substituted or unsubstituted $C_{1-6}$ alkyl, or a nitrogen protecting group. In certain embodiments, L2 is an unsubstituted $C_{1-20}$ hydrocarbon chain, optionally wherein one or more chain atoms of the hydrocarbon chain are independently replaced with —C(═O)—, —O—, —$NR^b$—, —S—, or a cyclic moiety, wherein $R^b$ is independently hydrogen, substituted or unsubstituted $C_{1-6}$ alkyl, or a nitrogen protecting group. In certain embodiments, at least one chain atom of the hydrocarbon chain of L2 is independently replaced with —O—. In certain embodiments, L2 is any "L0" group or "Linker" group recited in U.S. patent application, U.S.S.N. 1407,930, filed May 8, 2015, which is incorporated herein by reference. In certain embodiments, L2 is any "L" group recited in U.S. patent application, U.S.S.N. 14n92,414, filed Jul. 6, 2015, which is incorporated herein by reference.

In certain embodiments, the chain of linker L2 comprises up to 50 consecutive covalently bonded atoms in length as the shortest path between D and the piperidine moiety of Formula (I), excluding hydrogen atoms and substituents. In certain embodiments, the chain of linker L2 comprises up to 50 consecutive covalently bonded atoms in length, excluding hydrogen atoms and substituents. In certain embodiments, L2 comprises up to 46 consecutive covalently bonded atoms in length, excluding hydrogen atoms and substituents. In certain embodiments, L2 comprises up to 45 consecutive covalently bonded atoms in length, excluding hydrogen atoms and substituents. In certain embodiments, L2 comprises up to 40 consecutive covalently bonded atoms in length, excluding hydrogen atoms and substituents. In certain embodiments, L2 comprises up to 35 consecutive covalently bonded atoms in length, excluding hydrogen atoms and substituents. In certain embodiments, L2 comprises up to 32 consecutive covalently bonded atoms in length, excluding hydrogen atoms and substituents. In certain embodiments, L2 comprises up to 30 consecutive covalently bonded atoms in length, excluding hydrogen atoms and substituents. In certain embodiments, L2 comprises up to 25 consecutive covalently bonded atoms in length, excluding hydrogen atoms and substituents. In certain embodiments, L2 comprises up to 25 consecutive covalently bonded atoms in length, excluding hydrogen atoms and substituents. In certain embodiments, L2 comprises up to 23 consecutive covalently bonded atoms in length, excluding hydrogen atoms and substituents. In certain embodiments, L2 comprises up to 20 consecutive covalently bonded atoms in length, excluding hydrogen atoms and substituents. In certain embodiments, L2 comprises up to 14 consecutive covalently bonded atoms in length, excluding hydrogen atoms and substituents. In certain embodiments, L2 comprises up to 15 consecutive covalently bonded atoms in length, excluding hydrogen atoms and substituents. In certain embodiments, L2 comprises up to 12 consecutive covalently bonded atoms in length, excluding hydrogen atoms and substituents. In certain embodiments, L2 comprises up to 11 consecutive covalently bonded atoms in length, excluding hydrogen atoms and substituents. In certain embodiments, L2 comprises up to 10 consecutive covalently bonded atoms in length, excluding hydrogen atoms and substituents. In certain embodiments, L2 comprises up to 9 consecutive covalently bonded atoms in length, excluding hydrogen atoms and substituents. In certain embodiments, L2 comprises up to 8 consecutive covalently bonded atoms in length, excluding hydrogen atoms and substituents. In certain embodiments, L2 comprises up to 7 consecutive covalently bonded atoms in length, excluding hydrogen atoms and substituents. In certain embodiments, L2 comprises up to 6 consecutive covalently bonded atoms in length, excluding hydrogen atoms and substituents. In certain embodiments, L2 comprises up to 5 consecutive covalently bonded atoms in length, excluding hydrogen atoms and substituents. In certain embodiments, L2 comprises up to 3 consecutive covalently bonded atoms in length, excluding hydrogen atoms and substituents.

In certain embodiments, any of the atoms in L2 can be substituted. In certain embodiments, none of the atoms in the linker L2 are substituted. In certain embodiments, none of the carbon atoms in the linker are substituted.

In certain embodiments, L2 is a linker that contains an asymmetric carbon/stereocenter, i.e., an $sp^3$ hybridized carbon atom bearing 4 different groups attached thereto. In certain embodiments, the compound comprising such an L2 group is enantiomerically enriched or substantially enantiomerically enriched. In certain embodiments, the compound comprising such an L2 group is enantiomerically pure. In certain embodiments, the compound comprising such an L2 group is racemic.

In certain embodiments, L2 comprises substituted or unsubstituted carbocyclylene, substituted or unsubstituted heterocyclylene, substituted or unsubstituted arylene, substituted or unsubstituted heteroarylene, or substituted or unsubstituted heteroalkylene, or combinations thereof. In certain embodiments, L2 is substituted or unsubstituted carbocyclylene, substituted or unsubstituted heterocyclylene, substituted or unsubstituted arylene, substituted or unsubstituted heteroarylene, or substituted or unsubstituted heteroalkylene. In certain embodiments, L2 is a linker selected from the group consisting of the following divalent moieties: substituted and unsubstituted alkylene, substituted and unsubstituted alkenylene, substituted and unsubstituted alkynylene, substituted and unsubstituted heteroalkylene, substituted and unsubstituted heteroalkenylene, substituted and unsubstituted heteroalkynylene, substituted and unsubstituted heterocyclylene, substituted and unsubstituted carbocyclylene, substituted and unsubstituted arylene, substituted and unsubstituted heteroarylene, and combinations thereof.

Reference to L2 being a combination of at least two instances of the divalent moieties described herein refers to a linker consisting of at least one instance of a first divalent moiety and at least one instance of a second divalent moiety, wherein the first and second divalent moieties are the same or different and are within the scope of the divalent moieties described herein, and the instances of the first and second divalent moieties are consecutive covalently attached to each other. For example, when L2 is a combination of alkylene and heteroalkylene linkers -alkylene-heteroalkylene-, -alkylene-(heteroalkylene)$_2$-, and -heteroalkylene-alkylene-heteroalkylene- are all within the scope of L, wherein each instance of alkylene in any one of the linkers may be the same or different, and each instance of heteroalkylene in any one of the linkers may be the same or different.

In certain embodiments, L2 comprises at least one instance of substituted or unsubstituted alkylene, e.g., substituted or unsubstituted $C_{1-6}$alkylene, substituted or unsubstituted $C_{1-2}$alkylene, substituted or unsubstituted $C_{2-3}$alkylene, substituted or unsubstituted $C_{3-4}$alkylene, substituted or unsubstituted $C_{4-5}$alkylene, substituted or unsubstituted $C_{1-6}$alkylene, substituted or unsubstituted $C_{3-6}$alkylene, or substituted or unsubstituted $C_{4-6}$alkylene. Exemplary alkylene groups include unsubstituted alkylene groups such as methylene ($—CH_2—$), ethylene ($—(CH_2)_2—$), n-propylene ($—(CH_2)_3—$), n-butylene ($—(CH_2)_4—$), n-pentylene ($—(CH_2)_5—$), and n-hexylene ($—(CH_2)_6—$).

In certain embodiments, L2 comprises at least one instance of substituted or unsubstituted alkenylene, e.g., substituted or unsubstituted $C_{2-6}$alkenylene, substituted or unsubstituted $C_{2-3}$alkenylene, substituted or unsubstituted $C_{3-4}$alkenylene, substituted or unsubstituted $C_{4-5}$alkenylene, or substituted or unsubstituted $C_{5-6}$alkenylene.

In certain embodiments, L2 comprises at least one instance of substituted or unsubstituted alkynylene, e.g., substituted or unsubstituted $C_{2-6}$alkynylene, substituted or unsubstituted $C_{2-3}$alkynylene, substituted or unsubstituted $C_{3-4}$alkynylene, substituted or unsubstituted $C_{4-5}$alkynylene, or substituted or unsubstituted $C_{5-6}$alkynylene.

In certain embodiments, L2 comprises at least one instance of substituted or unsubstituted heteroalkylene, e.g., substituted or unsubstituted hetero$C_{1-6}$alkylene, substituted or unsubstituted hetero$C_{1-2}$alkylene, substituted or unsubstituted hetero$C_{2-3}$alkylene, substituted or unsubstituted hetero$C_{3-4}$alkylene, substituted or unsubstituted hetero$C_{4-5}$ alkylene, or substituted or unsubstituted hetero$C_{5-6}$alkylene. Exemplary heteroalkylene groups include unsubstituted heteroalkylene groups, such as $—(CH_2)_2—O(CH_2)_2—$, $—OCH_2—$, $—CH_2O—$, $—O(CH_2)_2—$, $—(CH_2)_2O—$, $—O(CH_2)_3—$, $—(CH_2)_3O—$, $—O(CH_2)_4—$, $—(CH_2)_4O—$, $—O(CH_2)_5—$, $—(CH_2)_5O—$, $—O(CH_2)_6—$, and $—O(CH_2)_6O—$, and amide groups (e.g., —NH—C(═O)— and —C(═O)NH—).

In certain embodiments, L2 comprises at least one instance of substituted or unsubstituted heteroalkenylene, e.g., substituted or unsubstituted hetero$C_{2-6}$alkenylene, substituted or unsubstituted hetero$C_{2-3}$alkenylene, substituted or unsubstituted hetero$C_{3-4}$ alkenylene, substituted or unsubstituted hetero$C_{4-5}$alkenylene, or substituted or unsubstituted hetero$C_{5-6}$alkenylene.

In certain embodiments, L2 comprises at least one instance of substituted or unsubstituted heteroalkynylene, e.g., substituted or unsubstituted hetero$C_{2-6}$alkynylene, substituted or unsubstituted hetero$C_{2-3}$alkynylene, substituted or unsubstituted hetero$C_{3-4}$ alkynylene, substituted or unsubstituted hetero$C_{4-5}$alkynylene, or substituted or unsubstituted hetero$C_{5-6}$alkynylene.

In certain embodiments, L2 comprises at least one instance of substituted or unsubstituted carbocyclylene, e.g., substituted or unsubstituted $C_{3-6}$carbocyclylene, substituted or unsubstituted $C_{3-4}$carbocyclylene, substituted or unsubstituted $C_{4-5}$ carbocyclylene, or substituted or unsubstituted $C_{5-6}$ carbocyclylene.

In certain embodiments, L2 comprises at least one instance of substituted or unsubstituted heterocyclylene, e.g., substituted or unsubstituted 3-6 membered heterocyclylene, substituted or unsubstituted 3-4 membered heterocyclylene, substituted or unsubstituted 4-5 membered heterocyclylene, or substituted or unsubstituted 5-6 membered heterocyclylene. In certain embodiments, at least one chain atom of the hydrocarbon chain of L2 is independently replaced with a 5-8 membered heterocyclyl group with 1-4 ring heteroatoms selected from the group consisting of nitrogen, oxygen, and sulfur. In certain embodiments, at least one chain atom of the hydrocarbon chain of L2 is independently replaced with a six-membered heterocyclyl group with 1-3 ring heteroatoms selected from the group consisting of nitrogen and oxygen. In certain embodiments, at least one chain atom of the hydrocarbon chain of L2 is independently replaced with piperidine or piperazine. In certain embodiments, at least one chain atom of the hydrocarbon chain of L2 is independently replaced with piperidine. In certain embodiments, at least one chain atom of the hydrocarbon chain of L2 is independently replaced with piperazine. In certain embodiments, at least one chain atom of the hydrocarbon chain of L2 is independently replaced with morpholine.

In certain embodiments, L2 comprises at least one instance of substituted or unsubstituted arylene, e.g., substituted or unsubstituted phenylene. In certain embodiments, at least one chain atom of the hydrocarbon chain of L2 is independently replaced with an optionally substituted phenyl group. In certain embodiments, L2 comprises at least one instance of substituted or unsubstituted heteroarylene, e.g., substituted or unsubstituted 5- to 6-membered heteroarylene.

In certain embodiments, L2 is an unsubstituted hydrocarbon chain, optionally wherein one or more chain atoms of the hydrocarbon chain are independently replaced with $—NR^b—$, and each instance of $R^b$ is independently hydrogen, substituted or unsubstituted $C_{1-6}$ alkyl, or a nitrogen protecting group, or optionally two instances of $R^b$ are taken together with their intervening atoms to form a substituted or unsubstituted heterocyclic or substituted or unsubstituted heteroaryl ring. In certain embodiments, at least one instance of $R^b$ is hydrogen. In certain embodiments, at least one instance of $R^b$ is substituted or unsubstituted $C_{1-6}$ alkyl (e.g., substituted or unsubstituted methyl or ethyl). In certain embodiments, at least one instance of $R^b$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

In certain embodiments, L2 is an optionally substituted $C_145$ hydrocarbon chain as the shortest path between D and the piperidine moiety of Formula (I), excluding hydrogen atoms and substituents, optionally wherein one or more chain atoms of the hydrocarbon chain are independently replaced with —C(═O)—, —O—, $—NR^b—$, —S—, or a cyclic moiety, wherein $R^b$ is independently hydrogen, substituted or unsubstituted $C_{1-6}$ alkyl, or a nitrogen protecting group. In certain embodiments, L2 is an unsubstituted $C_{1-45}$ hydrocarbon chain as the shortest path between D and the piperidine moiety of Formula (I), excluding hydrogen atoms and substituents, optionally wherein one or more chain atoms of the hydrocarbon chain are independently replaced with —C(═O)—, —O—, $—NR^b—$, —S—, or a cyclic moiety, wherein $R^b$ is independently hydrogen, substituted or unsubstituted $C_{1-6}$ alkyl, or a nitrogen protecting group. In certain embodiments, L2 is an optionally substituted $C_{1-24}$ hydrocarbon chain as the shortest path between D and the piperidine moiety of Formula (I), excluding hydrogen atoms and substituents, optionally wherein one or more chain atoms of the hydrocarbon chain are independently replaced with —C(═O)—, —O—, $—NR^b—$, —S—, or a cyclic moiety, wherein $R^b$ is independently hydrogen, substituted or unsubstituted $C_{1-6}$ alkyl, or a nitrogen protecting group. In certain embodiments, L2 is an unsubstituted $C_{1-24}$ hydrocarbon chain as the shortest path between D and the piperidine moiety of Formula (I), excluding hydrogen atoms and substituents, optionally wherein one or more chain atoms of the hydrocarbon chain are independently replaced with —C(═O)—, —O—, —$NR^b$—, —S—, or a cyclic moiety, wherein $R^b$ is independently hydrogen, substituted or unsubstituted $C_{1-6}$ alkyl, or a nitrogen protecting group. In certain embodiments, L2 is an optionally substituted $C_{1-20}$ hydrocarbon chain as the shortest path between D and the piperidine moiety of Formula (I), excluding hydrogen atoms and substituents, optionally wherein one or more chain atoms of the hydrocarbon chain are independently replaced with —C(═O)—, —O—, —$NR^b$—, —S—, or a cyclic moiety, wherein $R^b$ is independently hydrogen, substituted or unsubstituted $C_{1-6}$ alkyl, or a nitrogen protecting group. In certain embodiments, L2 is an unsubstituted $C_{1-20}$ hydrocarbon chain as the shortest path between D and the piperidine moiety of Formula (I), excluding hydrogen atoms and substituents, optionally wherein one or more chain atoms of the hydrocarbon chain are independently replaced with —C(═O)—, —O—, —$NR^b$—, —S—, or a cyclic moiety, wherein $R^b$ is independently hydrogen, substituted or unsubstituted $C_{1-6}$ alkyl, or a nitrogen protecting group. In certain embodiments, L2 is an optionally substituted $C_{1-30}$ hydrocarbon chain, wherein one or more chain atoms of the hydrocarbon chain are independently replaced with —O— or —$NR^b$—. In certain embodiments, L2 is an unsubstituted $C_{1-30}$ hydrocarbon chain, wherein one or more chain atoms of the hydrocarbon chain are independently replaced with —O— or —$NR^b$—. In certain embodiments, L2 is an unsubstituted $C_{1-30}$ hydrocarbon chain, wherein at least one chain atom of the hydrocarbon chain is independently replaced with —O—. In certain embodiments, L2 is an unsubstituted $C_{1-26}$ hydrocarbon chain, wherein one or more chain atoms of the hydrocarbon chain are independently replaced with —C(═O)—, —O—, or —$NR^b$—. In certain embodiments, L2 is an unsubstituted $C_{1-20}$ hydrocarbon chain, wherein one or more chain atoms of the hydrocarbon chain are independently replaced with —O—. In certain embodiments, L2 is an unsubstituted $C_{1-26}$ hydrocarbon chain, wherein one or more chain atoms of the hydrocarbon chain are independently replaced with —C(═O)—, —O—, or —$NR^b$—. In certain embodiments, L2 is an unsubstituted $C_{5-26}$ hydrocarbon chain, wherein one or more chain atoms of the hydrocarbon chain are independently replaced with —O—. In certain embodiments, L2 is an unsubstituted $C_{5-20}$ hydrocarbon chain, wherein one or more chain atoms of the hydrocarbon chain are independently replaced with —C(═O)—, —O—, or —$NR^b$—. In certain embodiments, L2 is an unsubstituted $C_{5-20}$ hydrocarbon chain, wherein one or more chain atoms of the hydrocarbon chain are independently replaced with —O—, or —$NR^b$—. In certain embodiments, L2 is an unsubstituted $C_{5-15}$ hydrocarbon chain, wherein one or more chain atoms of the hydrocarbon chain are independently replaced with —C(═O)—, —O—, or —$NR^b$—. In certain embodiments, L2 is an unsubstituted $C_{15-20}$ hydrocarbon chain, wherein one or more chain atoms of the hydrocarbon chain are independently replaced with —C(═O)—, —O—, or —$NR^b$—. In certain embodiments, L2 is an unsubstituted $C_{20-25}$ hydrocarbon chain, wherein one or more chain atoms of the hydrocarbon chain are independently replaced with —C(═O)—, —O—, or —$NR^b$—. In certain embodiments, L2 is a substituted or unsubstituted $C_{1-45}$ hydrocarbon chain. In certain embodiments, L2 is a substituted or unsubstituted $C_{5-40}$ hydrocarbon chain. In certain embodiments, one or more chain atoms of the hydrocarbon chain of L2 are independently replaced with —C(═O)—, —O—, —S—, —$NR^b$—, —N═, or ═N—. In certain embodiments, one or more chain atoms of the hydrocarbon chain of L2 are independently replaced with —C(═O)—, —O—, or —$NR^b$—, wherein $R^b$ is independently hydrogen, substituted or unsubstituted $C_{1-6}$ alkyl, or a nitrogen protecting group. In certain embodiments, L2 is an unsubstituted $C_{1-26}$ hydrocarbon chain, wherein at least one chain atom of the hydrocarbon chain is independently replaced with —O—.

In certain embodiments, L2 is an all-carbon, substituted or unsubstituted $C_{1-45}$ hydrocarbon chain as the shortest path between D and the piperidine moiety of Formula (I), excluding hydrogen atoms and substituents. In certain embodiments, L2 is an all-carbon, substituted or unsubstituted $C_{1-30}$ hydrocarbon chain as the shortest path between D and the piperidine moiety of Formula (I), excluding hydrogen atoms and substituents. In certain embodiments, L2 is an all-carbon, substituted or unsubstituted $C_{1-26}$ hydrocarbon chain as the shortest path between D and the piperidine moiety of Formula (I), excluding hydrogen atoms and substituents. In certain embodiments, L2 is an all-carbon, substituted or unsubstituted $C_{1-24}$ hydrocarbon chain as the shortest path between D and the piperidine moiety of Formula (I), excluding hydrogen atoms and substituents. In certain embodiments, L2 is an all-carbon, substituted or unsubstituted $C_{1-20}$ hydrocarbon chain as the shortest path between D and the piperidine moiety of Formula (I), excluding hydrogen atoms and substituents. In certain embodiments, L2 is an all-carbon, substituted or unsubstituted $C_{1-20}$ hydrocarbon chain as the shortest path between D and the piperidine moiety of Formula (I), excluding hydrogen atoms and substituents.

In certain embodiments, L2 is a bond.

In certain embodiments, L2 includes the moiety

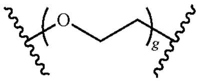, wherein g is 1, 2, 3, 4, 5, or 6. In certain embodiments, g is 1. In certain embodiments, g is 2. In certain embodiments, g is 3. In certain embodiments, g is 4. In certain embodiments, g is 5. In certain embodiments, g is 6.

In certain embodiments, L2 includes the moiety —NHC(═O)—.

In certain embodiments, L2 includes the moiety —NH—.

In certain embodiments, L2 is of the formula:

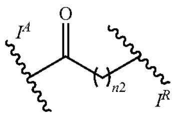, 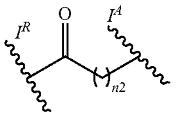,

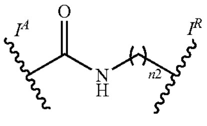, 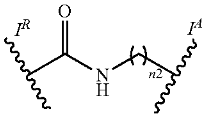,

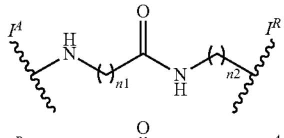,

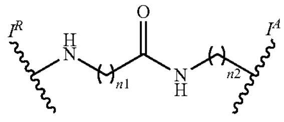,

-continued
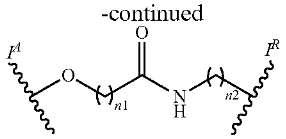
,
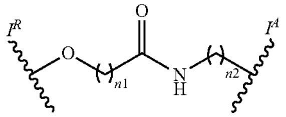
,
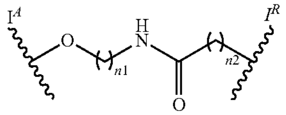
,
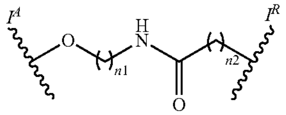
,
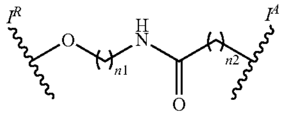
,
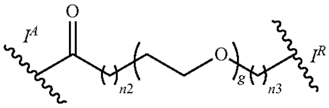
,
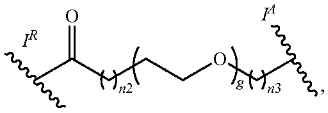
,
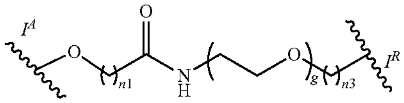
,
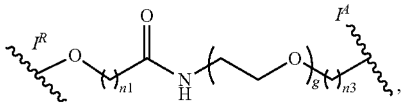
,
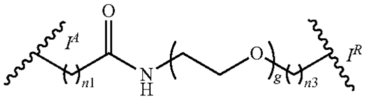
,
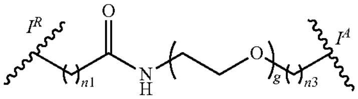
,
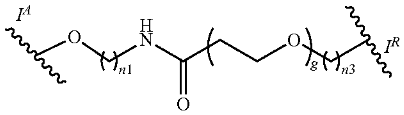
,
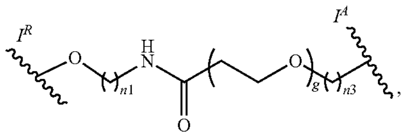
,
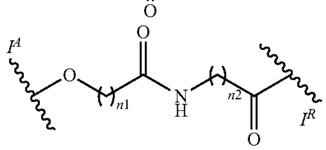
,
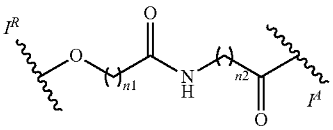
,
-continued
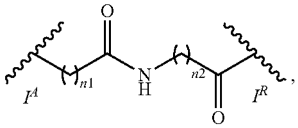
,
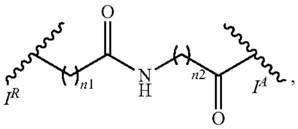
,
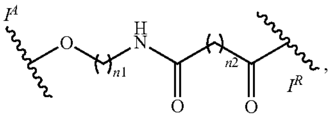
,
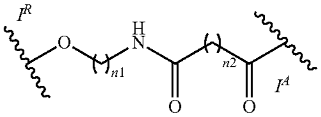
,
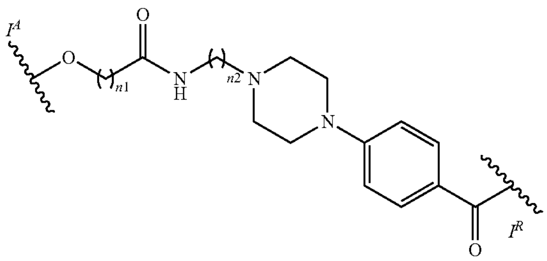
,
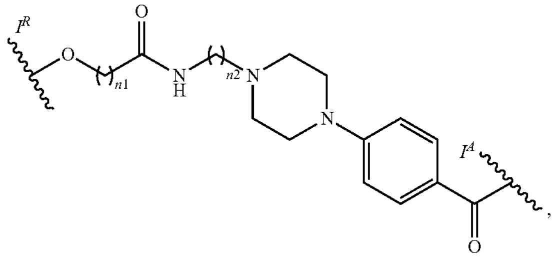
,
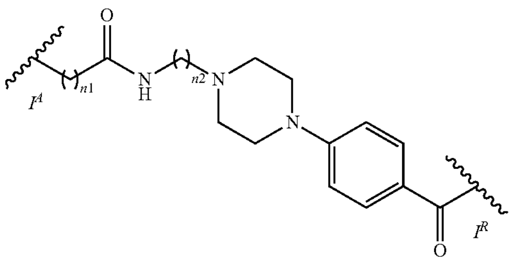
,
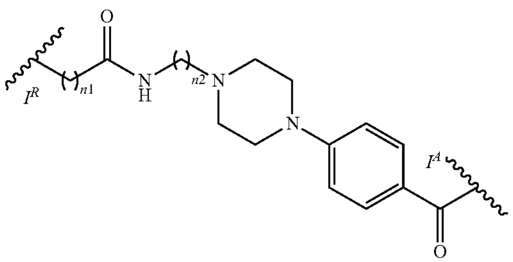
, -continued
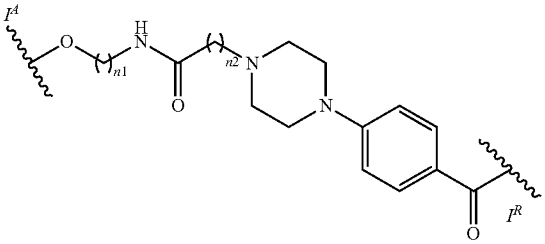
,
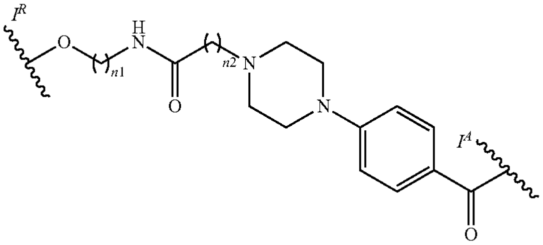
,
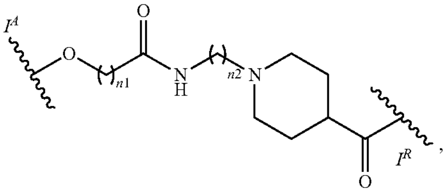
,
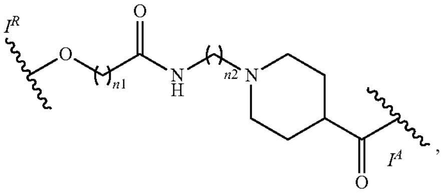
,
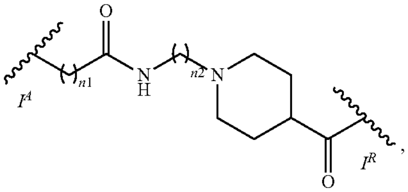
,
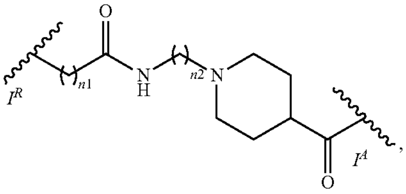
,
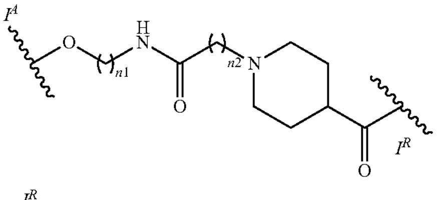
, or
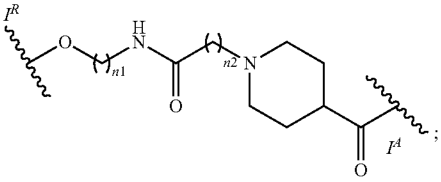
;
wherein $l^R$ indicates the point of attachment to D, and $l^A$ indicates the point of attachment to the moiety of formula
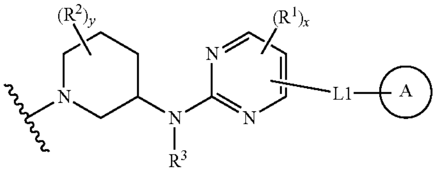
;
n1 is 1, 2, 3, 4, 5, or 6; n2 is 0, 1, 2, 3, 4, 5, 6, 7, 8, 9, or 10; n3 is 1, 2, 3, 4, 5, or 6; and g is 1, 2, 3, 4, 5, or 6. In certain embodiments, L2 is of the formula:
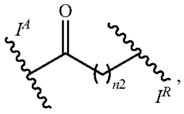
,
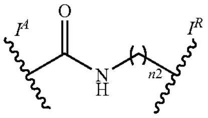
,
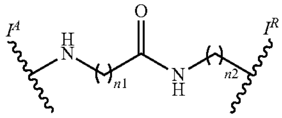
,
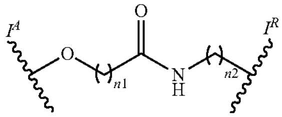
,
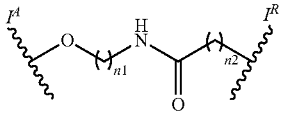
,
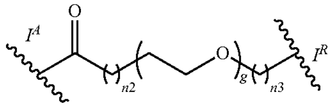
,
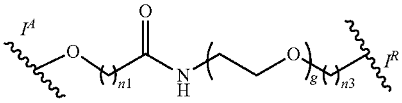
,
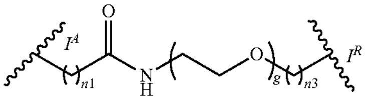
,
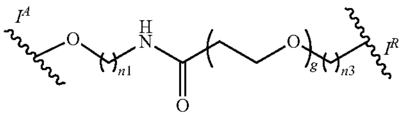
,
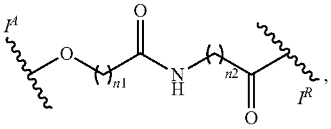
,
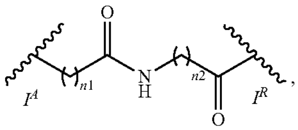
,
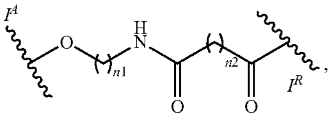
, -continued
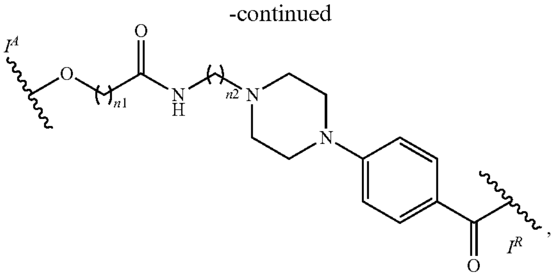
,
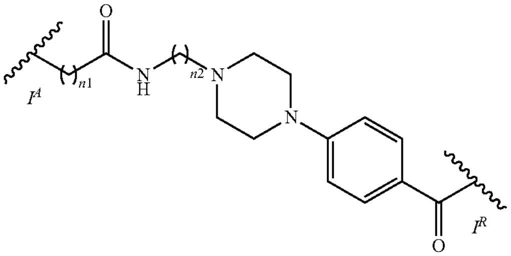
,
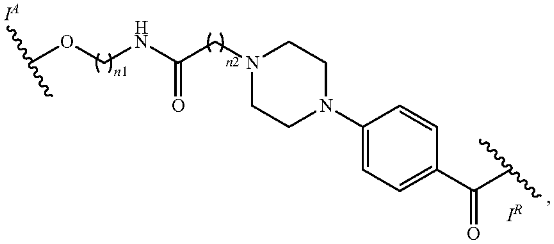
,
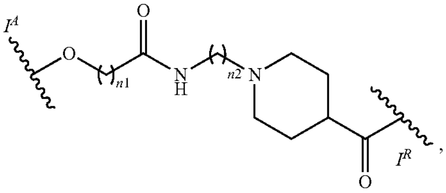
,
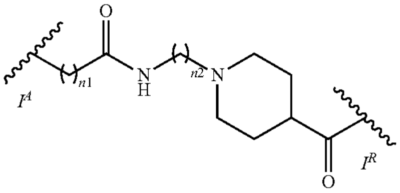
, or
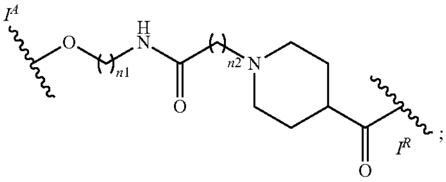
;
wherein $l^R$ indicates the point of attachment to D, and $l^A$ indicates the point of attachment to the moiety of formula
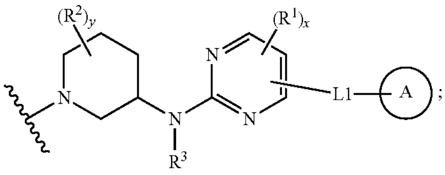
;
n1 is 1, 2, 3, 4, 5, or 6; n2 is 0, 1, 2, 3, 4, 5, 6, 7, 8, 9, or 10; n3 is 1, 2, 3, 4, 5, or 6; and g is 1, 2, 3, 4, 5, or 6. In certain embodiments, L2 is of the formula:
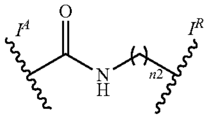
,
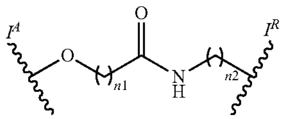
,
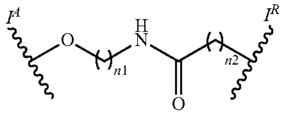
,
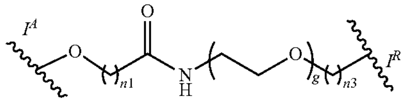
,
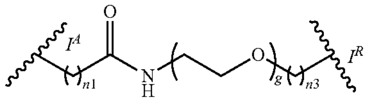
,
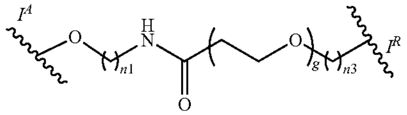
,
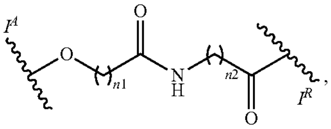
,
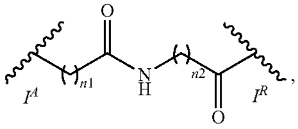
,
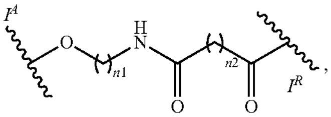
,
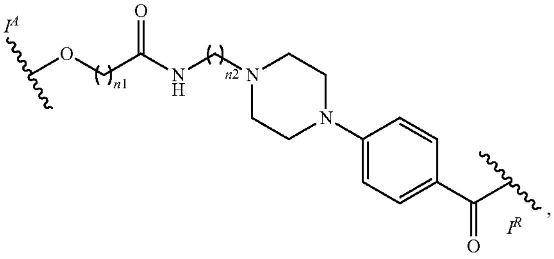
,
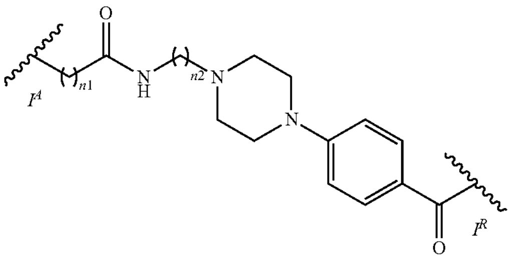
, -continued

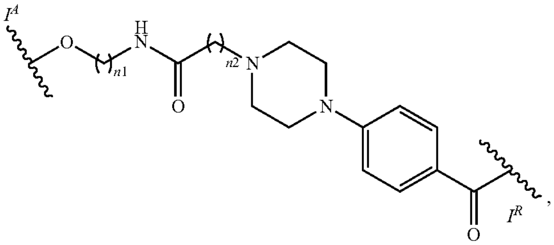,

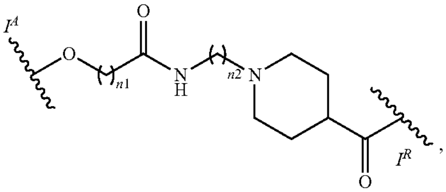,

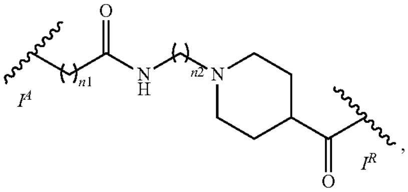, or

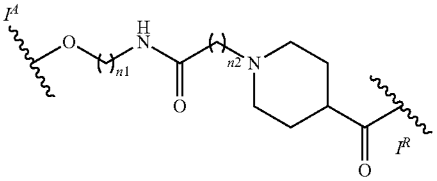;

wherein $l^R$ indicates the point of attachment to D, and $l^A$ indicates the point of attachment to the moiety of formula

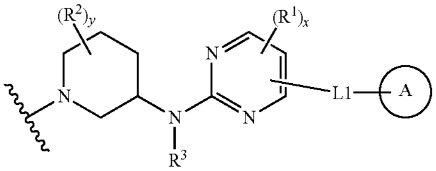;

n1 is 1, 2, 3, 4, 5, or 6; n2 is 1, 2, 3, 4, 5, 6, 7, 8, 9, or 10; n3 is 1, 2, 3, 4, 5, or 6; and g is 1, 2, 3, 4, 5, or 6. In certain embodiments, n1 is 1. In certain embodiments, n1 is 2. In certain embodiments, n1 is 3. In certain embodiments, n1 is 4. In certain embodiments, n1 is 5. In certain embodiments, n1 is 6. In certain embodiments, n2 is 0. In certain embodiments, n2 is 1. In certain embodiments, n2 is 2. In certain embodiments, n2 is 3. In certain embodiments, n2 is 4. In certain embodiments, n2 is 5. In certain embodiments, n2 is 6. In certain embodiments, n2 is 7. In certain embodiments, n2 is 8. In certain embodiments, n2 is 9. In certain embodiments, n2 is 10. In certain embodiments, n3 is 1. In certain embodiments, n3 is 2. In certain embodiments, n3 is 3. In certain embodiments, n3 is 4. In certain embodiments, n3 is 5. In certain embodiments, n3 is 6. In certain embodiments, g is 1. In certain embodiments, g is 2. In certain embodiments, g is 3. In certain embodiments, g is 4. In certain embodiments, g is 5. In certain embodiments, g is 6.

In certain embodiments, L2 is of the formula:

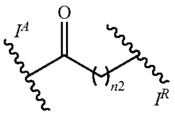, 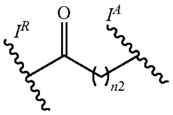,

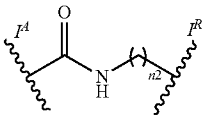, 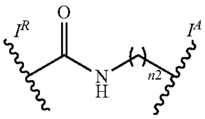,

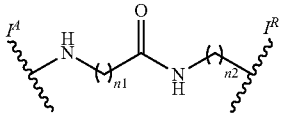,

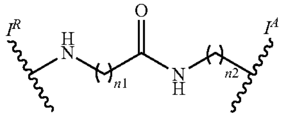,

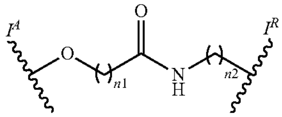,

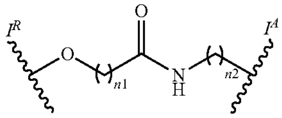,

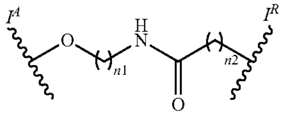,

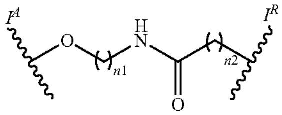,

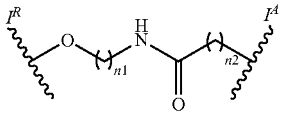,

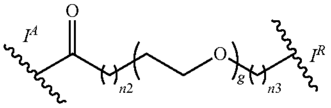,

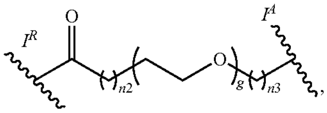,

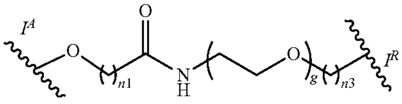,

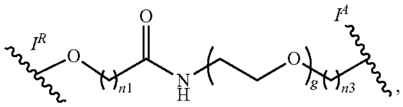,

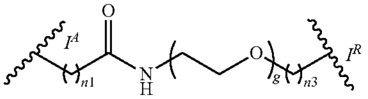,

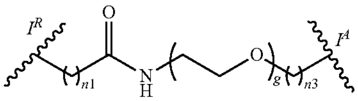,

-continued
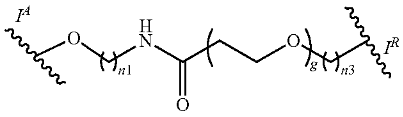,
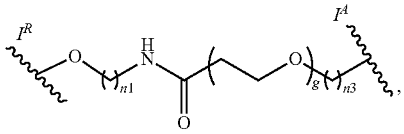,
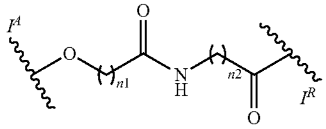,
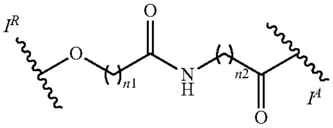,
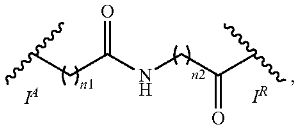,
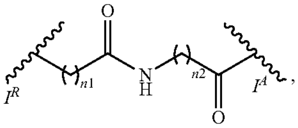,
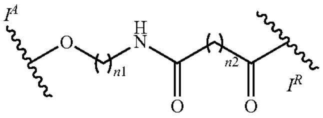,
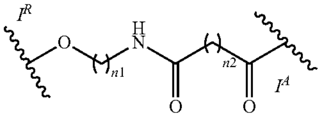,
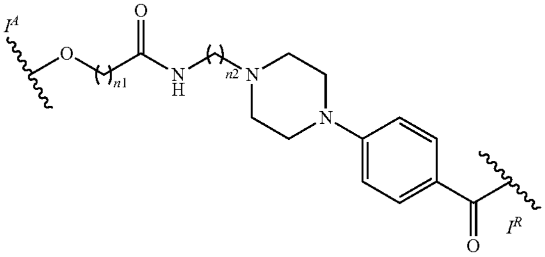,
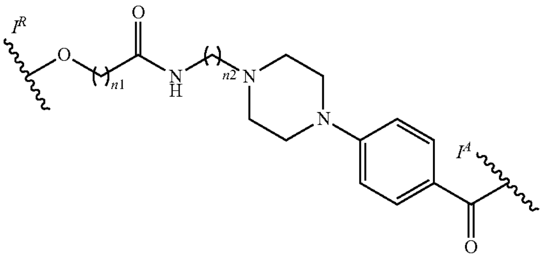,
-continued
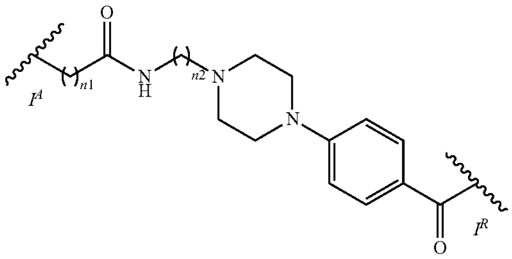,
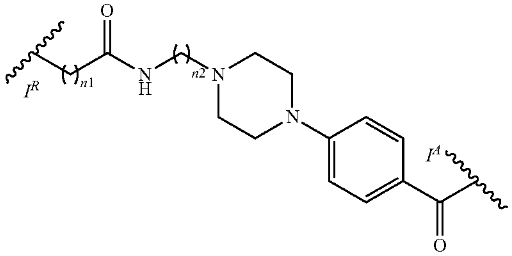,
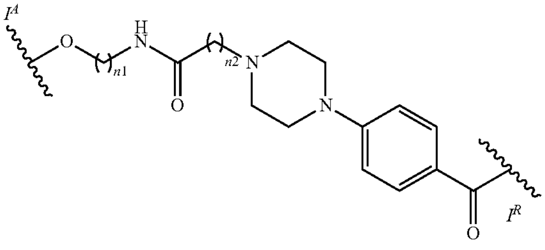,
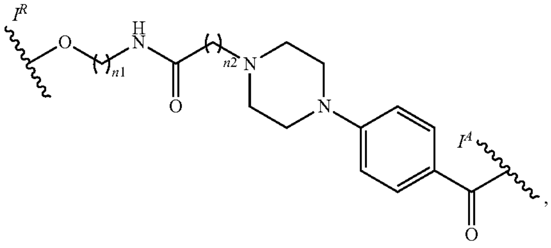,
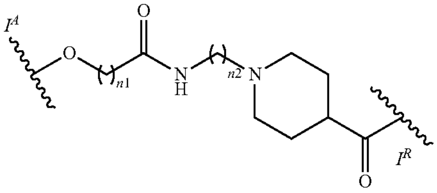,
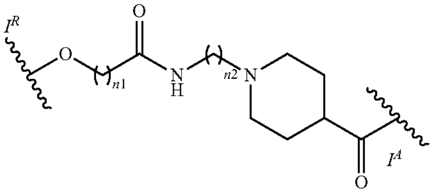,
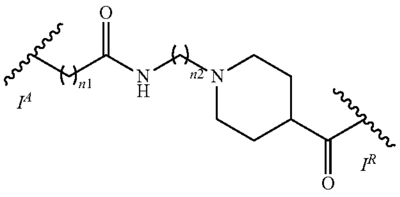, -continued
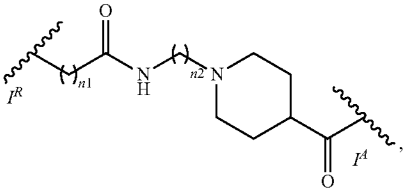
,
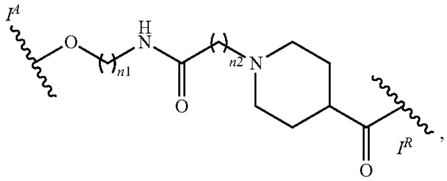
, or
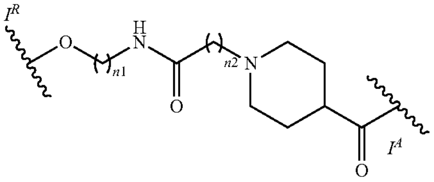
;
In certain embodiments, L2 is of the formula:
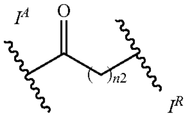
,
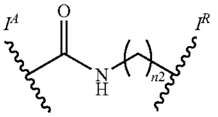
,
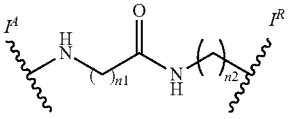
,
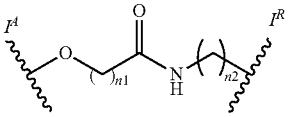
,
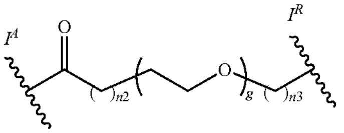
,
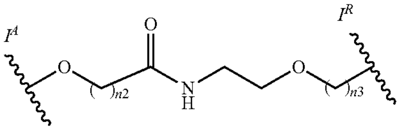
,
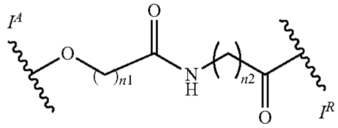
,
-continued
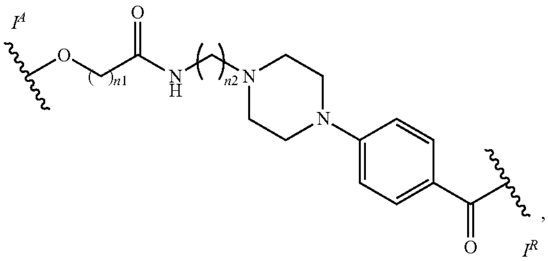
, or
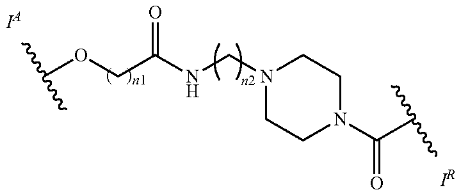
.
In certain embodiments, L2 is of the formula:
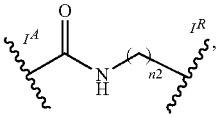
,
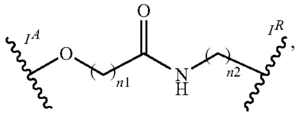
,
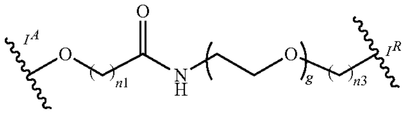
,
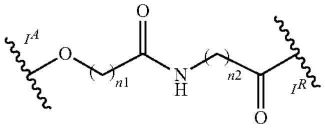
,
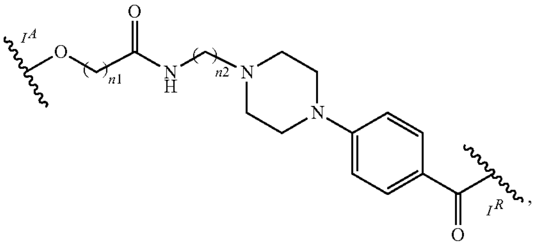
, or
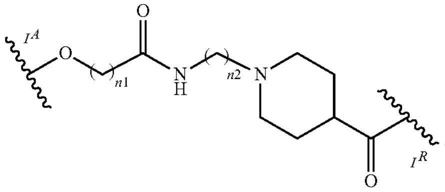
.
In certain embodiments, L2 is of the formula:
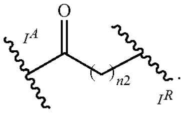
.

In certain embodiments, L2 is of the formula:

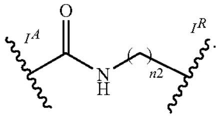

In certain embodiments, L2 is of the formula:

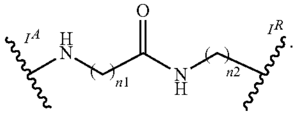

In certain embodiments, L2 is of the formula:

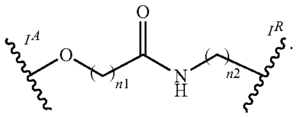

In certain embodiments, L2 is of the formula

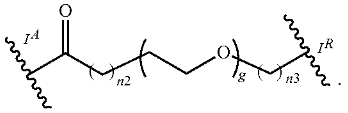

In certain embodiments, L2 is of the formula

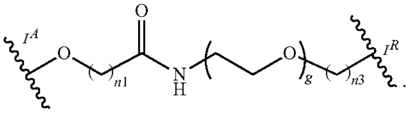

In certain embodiments, L2 is of the formula

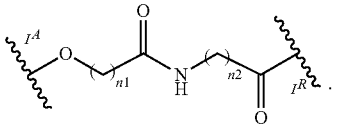

In certain embodiments, L2 is of the formula

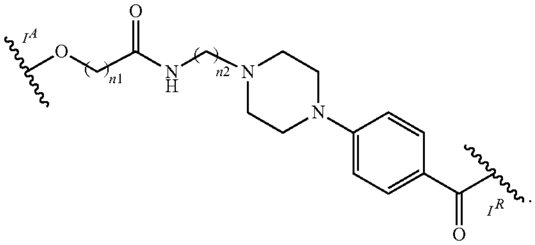

In certain embodiments, L2 is of the formula

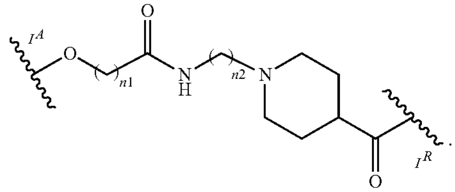

In certain embodiments, L2 is of the formula:

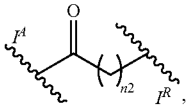

,

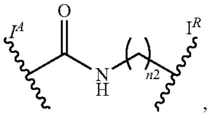

,

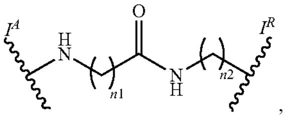

,

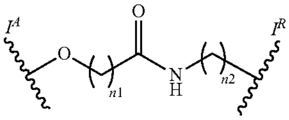

,

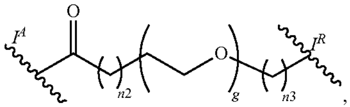

,

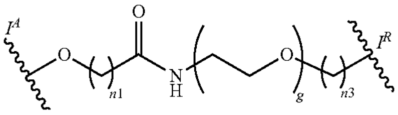

,

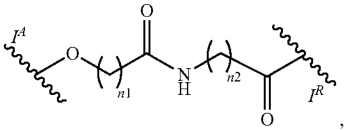

,

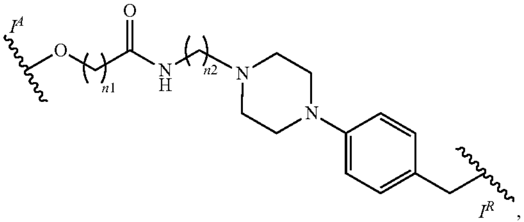

, or

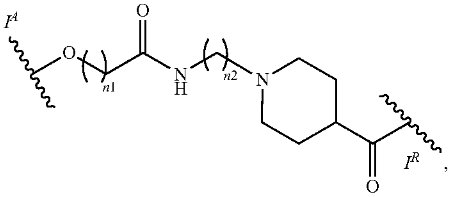

, wherein: n1 is 0 or 1; n2 is 0, 1, 2, 3, 4, 5, 6, 7, or 8; n3 or 2; and g is 2 or 3. In certain embodiments, L2 is of the formula:

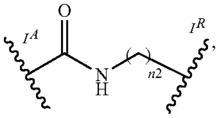, 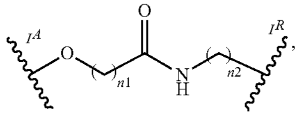,

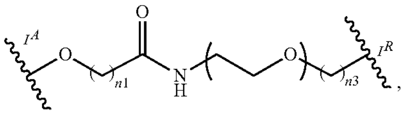,

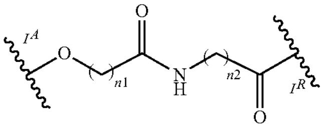,

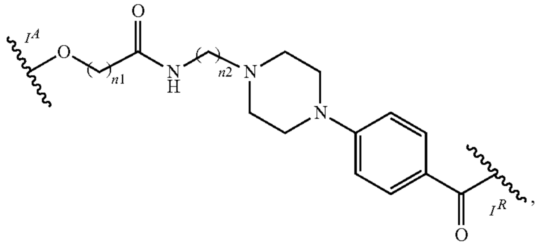, or

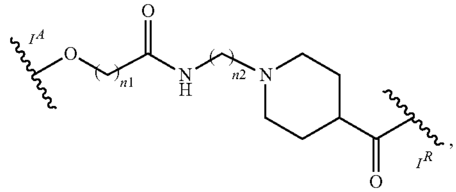, wherein: n1 is 1; n2 is 3, 4, 5, 6, 7, or 8; n3 is 1 or 2; and g is 2 or 3. In certain embodiments, n1 is 1. In certain embodiments, n1 is 2. In certain embodiments, n2 is 1. In certain embodiments, n2 is 2. In certain embodiments, n2 is 3. In certain embodiments, n2 is 4. In certain embodiments, n2 is 5. In certain embodiments, n2 is 6. In certain embodiments, n2 is 7. In certain embodiments, n2 is 8. In certain embodiments, n3 is 1. In certain embodiments, n3 is 2. In certain embodiments, n3 is 3. In certain embodiments, g is 1. In certain embodiments, g is 2. In certain embodiments, g is 3. In certain embodiments, g is 4.

In certain embodiments L2 is of the formula:

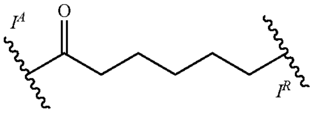,

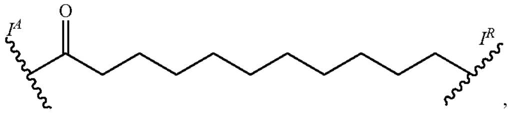,

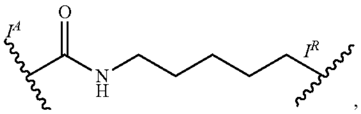,

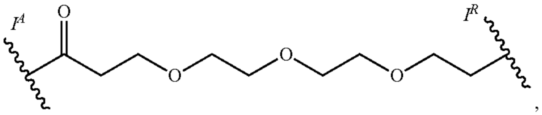,

-continued

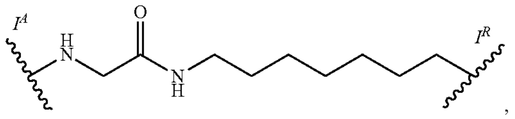,

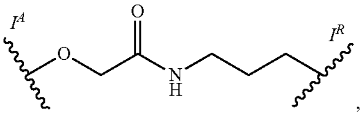,

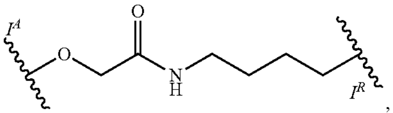,

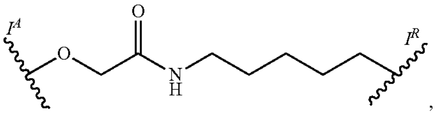,

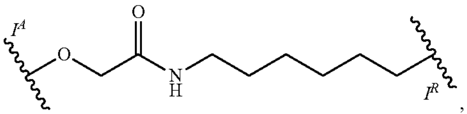,

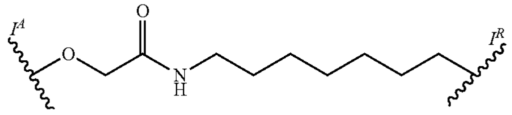,

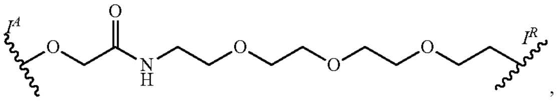,

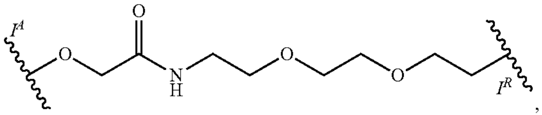,

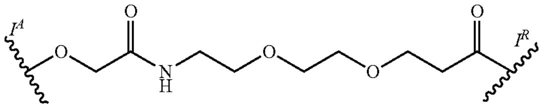,

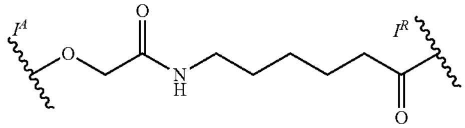,

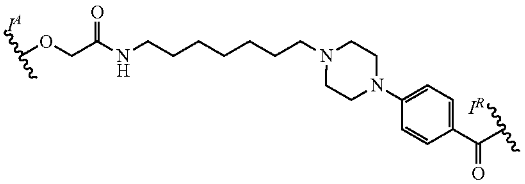,

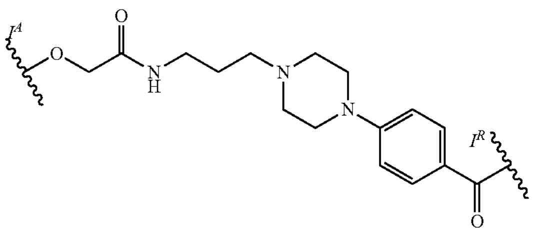,

-continued

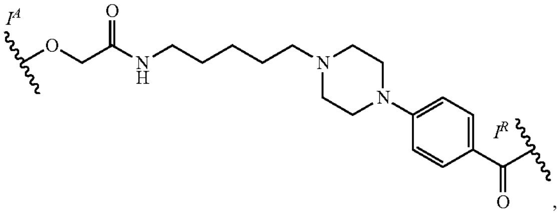

,

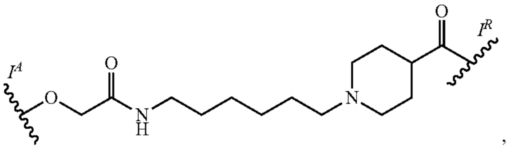

, or

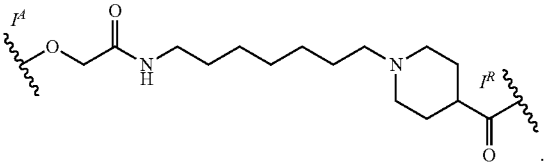

.

In certain embodiments, L2 is of the formula:

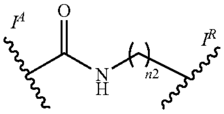

,

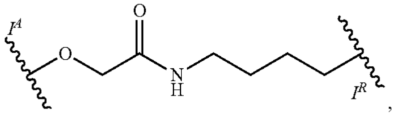

,

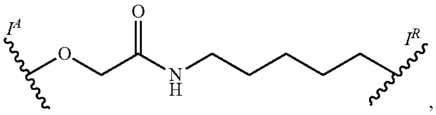

,

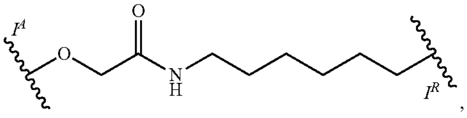

,

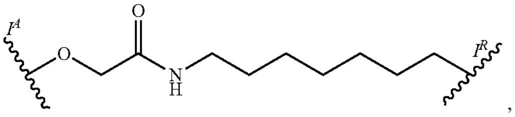

,

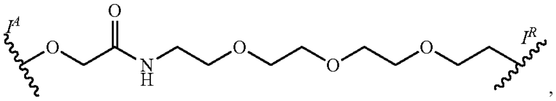

,

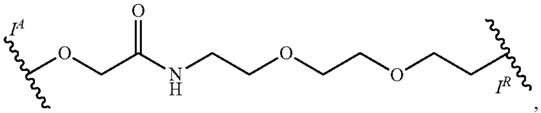

,

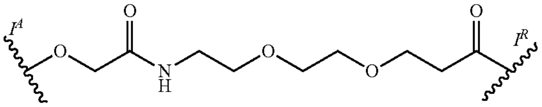

,

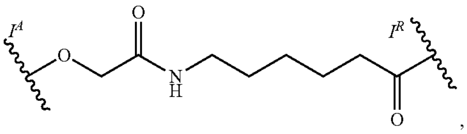

,

-continued

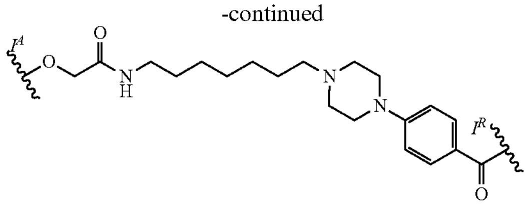

,

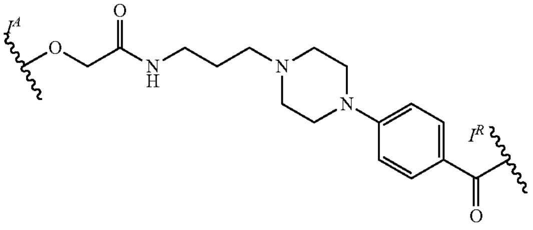

,

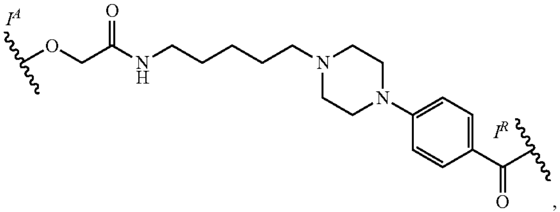

,

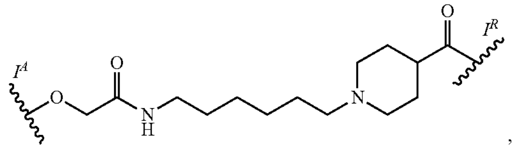

, or

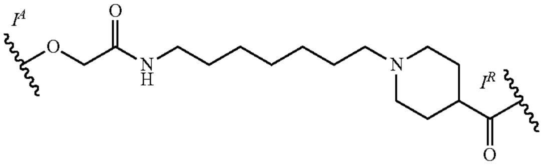

.

Substituents $R^1$, $R^2$, and $R^3$

Formula (I) includes zero or more instances of substituent $R^1$ on the pyrimidine ring. In certain embodiments, Formula (I) includes one instance of substituent $R^1$ on the pyrimidine ring. In certain embodiments, x is 0. In certain embodiments, x is 1. In certain embodiments, x is 2. In certain embodiments, x is 3. In certain embodiments, x is 4. In certain embodiments, x is 5. In certain embodiments, x is 6. In certain embodiments, at least one instance of $R^1$ is halogen (e.g., F, Cl, Br, or I). In certain embodiments, at least one instance of $R^1$ is Cl. In certain embodiments, at least one instance of $R^1$ is —Br. In certain embodiments, at least one instance of $R^1$ is —F. In certain embodiments, at least one instance of $R^1$ is —I. In certain embodiments, at least one instance of $R^1$ is optionally substituted acyl (e.g., —C(=O)Me). In certain embodiments, at least one instance of $R^1$ is optionally substituted alkyl (e.g., substituted or unsubstituted $C_{1-6}$ alkyl). In certain embodiments, at least one instance of $R^1$ is optionally substituted $C_{1-6}$ alkyl.

In certain embodiments, at least one instance of $R^1$ is substituted or unsubstituted methyl. In certain embodiments, at least one instance of $R^1$ is substituted methyl. In certain embodiments, at least one instance of $R^1$ is —$CF_3$. In certain embodiments, at least one instance of $R^1$ is unsubstituted methyl. In certain embodiments, at least one instance of $R^1$ is substituted or unsubstituted ethyl. In certain embodiments, at least one instance of $R^1$ is substituted or unsubstituted propyl. In certain embodiments, at least one instance of $R^1$ is optionally substituted alkenyl (e.g., substituted or unsubstituted $C_{2-6}$ alkenyl). In certain embodiments, at least one instance of $R^1$ is optionally substituted alkynyl (e.g., substituted or unsubstituted $C_{2-6}$ alkynyl). In certain embodiments, at least one instance of $R^1$ is optionally substituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^1$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^1$ is optionally substituted aryl (e.g., substituted or unsubstituted, 6- to 10-membered aryl). In certain embodiments, at least one instance of $R^1$ is benzyl. In certain embodiments, at least one instance of $R^1$ is substituted or unsubstituted phenyl. In certain embodiments, at least one instance of $R^1$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^1$ is —CN. In certain embodiments, at least one instance of $R^1$ is —$OR^{D1}$ (e.g., —OH or —OMe). In certain embodiments, at least one instance of $R^1$ is —$N(R^{D1a})_2$ (e.g., —$NMe_2$). In certain embodiments, at least one instance of $R^1$ is —$SR^{D1}$ (e.g., —SMe).

In certain embodiments, at least one instance of $R^1$ is —$OR^{D1}$, —$N(R^{D1a})_2$, or —$SR^{D1}$, and $R^{D1}$ is as defined herein. In certain embodiments, $R^{D1}$ is hydrogen. In certain embodiments, $R^{D1}$ is optionally substituted acyl (e.g., —C(═O)Me). In certain embodiments, $R^{D1}$ is optionally substituted alkyl (e.g., substituted or unsubstituted $C_{1-6}$ alkyl). In certain embodiments, $R^{D1}$ is substituted or unsubstituted methyl. In certain embodiments, $R^{D1}$ is substituted or unsubstituted ethyl. In certain embodiments, $R^{D1}$ is substituted or unsubstituted propyl. In certain embodiments, $R^{D1}$ is optionally substituted alkenyl (e.g., substituted or unsubstituted $C_{2-6}$ alkenyl). In certain embodiments, $R^{D1}$ is optionally substituted alkynyl (e.g., substituted or unsubstituted $C_{2-6}$ alkynyl). In certain embodiments, $R^{D1}$ is optionally substituted carbocyclyl (e.g., substituted or unsubstituted, 3- to 7-membered, monocyclic carbocyclyl comprising zero, one, or two double bonds in the carbocyclic ring system). In certain embodiments, $R^{D1}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{D1}$ is optionally substituted aryl (e.g., substituted or unsubstituted, 6- to 10-membered aryl). In certain embodiments, $R^{D1}$ is benzyl. In certain embodiments, $R^{D1}$ is optionally substituted phenyl. In certain embodiments, $R^{D1}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{D1}$ is an oxygen protecting group when attached to an oxygen atom. In certain embodiments, $R^{D1}$ is a sulfur protecting group when attached to a sulfur atom.

In certain embodiments, at least one instance of $R^{D1a}$ is hydrogen. In certain embodiments, at least one instance of $R^{D1a}$ is optionally substituted acyl (e.g., —C(═O)Me). In certain embodiments, at least one $R^{D1a}$ is optionally substituted alkyl (e.g., substituted or unsubstituted $C_{1-6}$ alkyl). In certain embodiments, at least one instance of $R^{D1a}$ is substituted or unsubstituted methyl. In certain embodiments, at least one instance of $R^{D1a}$ is substituted or unsubstituted ethyl. In certain embodiments, at least one instance of $R^{D1a}$ is substituted or unsubstituted propyl. In certain embodiments, at least one instance of $R^{D1a}$ is optionally substituted alkenyl (e.g., substituted or unsubstituted $C_{2-6}$ alkenyl). In certain embodiments, at least one instance of $R^{D1a}$ is optionally substituted alkynyl (e.g., substituted or unsubstituted $C_{2-6}$ alkynyl). In certain embodiments, at least one instance of $R^{D1a}$ is optionally substituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{D1a}$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{D1a}$ is optionally substituted aryl (e.g., substituted or unsubstituted, 6- to 10-membered aryl). In certain embodiments, at least one instance of $R^{D1a}$ is benzyl. In certain embodiments, at least one instance of $R^{D1a}$ is optionally substituted phenyl. In certain embodiments, at least one instance of $R^{D1a}$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^{D1a}$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, two instances of $R^{D1a}$ are taken together with their intervening atoms to form a substituted or unsubstituted heterocyclic ring (e.g., substituted or unsubstituted, 5- to 10-membered monocyclic or bicyclic heterocyclic ring, wherein one or two atoms in the heterocyclic ring are independently nitrogen, oxygen, or sulfur) or substituted or unsubstituted heteroaryl ring (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, the pyrimidine ring of Formula (I) is of formula:

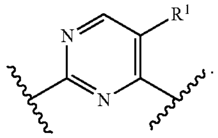

In certain embodiments, the pyrimidine ring of Formula (I) is of formula:

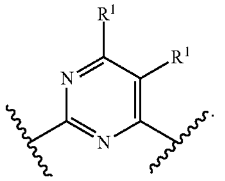

In certain embodiments, the pyrimidine ring of Formula (I) is of formula:

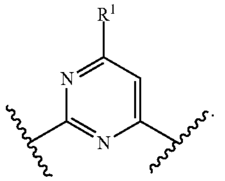

Formula (I) includes zero or more instances of substituent $R^2$ on the piperidine ring. In certain embodiments, Formula (I) includes zero instances of substituent $R^2$ on the piperidine ring. In certain embodiments, y is 0. In certain embodiments, y is 1. In certain embodiments, y is 2. In certain embodiments, y is 3. In certain embodiments, y is 4. In certain embodiments, n1 is 5. In certain embodiments, y is 6. In certain embodiments, y is 1. In certain embodiments, y is 2. In certain embodiments, y is 3. In certain embodiments, y is 4. In certain embodiments, y is 5. In certain embodiments, y is 6. In certain embodiments, y is 7. In certain embodiments, y is 8. In certain embodiments, y is 9. In certain embodiments, at least one instance of $R^2$ is halogen (e.g., F, Cl, Br, or I). In certain embodiments, at least one instance of $R^2$ is Cl. In certain embodiments, at least one instance of $R^2$ is optionally substituted acyl (e.g., —C(=O)Me). In certain embodiments, at least one instance of $R^2$ is optionally substituted alkyl (e.g., substituted or unsubstituted $C_{1-6}$ alkyl). In certain embodiments, at least one instance of $R^2$ is optionally substituted $C_{1-6}$ alkyl. In certain embodiments, at least one instance of $R^2$ is substituted or unsubstituted methyl. In certain embodiments, at least one instance of $R^2$ is substituted methyl. In certain embodiments, at least one instance of $R^2$ is —$CF_3$. In certain embodiments, at least one instance of $R^2$ is unsubstituted methyl. In certain embodiments, at least one instance of $R^2$ is substituted or unsubstituted ethyl. In certain embodiments, at least one instance of $R^2$ is substituted or unsubstituted propyl. In certain embodiments, at least one instance of $R^2$ is optionally substituted alkenyl (e.g., substituted or unsubstituted $C_{2-6}$ alkenyl). In certain embodiments, at least one instance of $R^2$ is optionally substituted alkynyl (e.g., substituted or unsubstituted $C_{2-6}$ alkynyl). In certain embodiments, at least one instance of $R^2$ is optionally substituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^2$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^2$ is optionally substituted aryl (e.g., substituted or unsubstituted, 6- to 10-membered aryl). In certain embodiments, at least one instance of $R^2$ is benzyl. In certain embodiments, at least one instance of $R^2$ is substituted or unsubstituted phenyl. In certain embodiments, at least one instance of $R^2$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^2$ is —CN. In certain embodiments, at least one instance of $R^2$ is —$OR^{D1}$ (e.g., —OH or —OMe). In certain embodiments, at least one instance of $R^2$ is —$N(R^{D1a})_2$ (e.g., —$NMe_2$). In certain embodiments, at least one instance of $R^2$ is —$SR^{D1}$ (e.g., —SMe). In certain embodiments, the piperidine ring of Formula (I) is of formula:

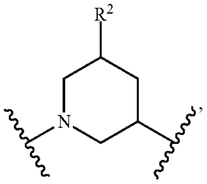 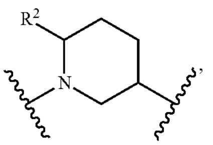 or

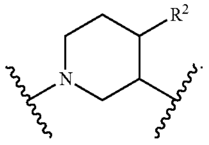

In certain embodiments, the piperidine ring of Formula (I) is of formula:

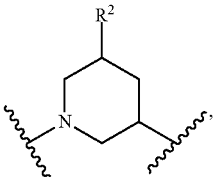 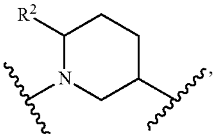 or

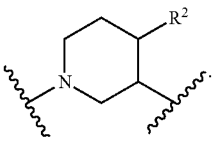

Formula (I) includes substituent $R^3$. In certain embodiments, $R^3$ is hydrogen. In certain embodiments, $R^2$ is halogen (e.g., F, Cl, Br, or I). In certain embodiments, $R^3$ is optionally substituted acyl (e.g., —C(=O)Me). In certain embodiments, $R^3$ is optionally substituted alkyl (e.g., substituted or unsubstituted $C_{1-6}$ alkyl). In certain embodiments, $R^3$ is optionally substituted $C_{1-6}$ alkyl. In certain embodiments, $R^3$ is substituted or unsubstituted methyl. In certain embodiments, $R^3$ is substituted or unsubstituted ethyl. In certain embodiments, $R^3$ is unsubstituted ethyl. In certain embodiments, $R^3$ is substituted or unsubstituted propyl. In certain embodiments, $R^3$ is unsubstituted n-propyl. In certain embodiments, $R^3$ is unsubstituted methyl or isopropyl. In certain embodiments, $R^3$ is optionally substituted alkenyl (e.g., substituted or unsubstituted $C_{2-6}$ alkenyl). In certain embodiments, $R^3$ is optionally substituted alkynyl (e.g., substituted or unsubstituted $C_{2-6}$ alkynyl). In certain embodiments, $R^3$ is optionally substituted carbocyclyl (e.g., substituted or unsubstituted, 3- to 7-membered, monocyclic carbocyclyl comprising zero, one, or two double bonds in the carbocyclic ring system). In certain embodiments, $R^3$ is optionally substituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^3$ is optionally substituted aryl (e.g., substituted or unsubstituted, 6- to 10-membered aryl). In certain embodiments, $R^3$ is benzyl. In certain embodiments, $R^3$ is substituted or unsubstituted phenyl. In certain embodiments, $R^3$ is unsubstituted phenyl. In certain embodiments, $R^3$ is optionally substituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^3$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

In certain embodiments, L1 is a bond, Ring A is of formula:

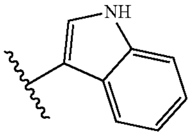
,

L2 is an unsubstituted $C_{1-24}$ hydrocarbon chain, optionally wherein one or more chain atoms of the hydrocarbon chain are independently replaced with —C(═O)—, —O—, —$NR^b$—, —S—, or a cyclic moiety, wherein $R^b$ is independently hydrogen, substituted or unsubstituted $C_{1-6}$ alkyl, or a nitrogen protecting group, at least one instance of $R^1$ is halogen, $R^3$ is hydrogen or optionally substituted $C_{1-6}$ alkyl, y is 0, x is 1, and D is of the formula:

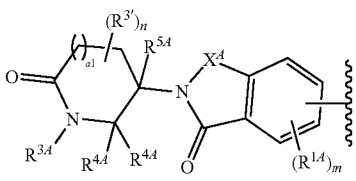

(IA), wherein $X^A$, $R^{1A}$, $R^{3A}$, $R^{3'}$, $R^{4A}$, $R^{5A}$, m, n, and a1 are as defined herein. In certain embodiments, L1 is a bond, Ring A is of formula:

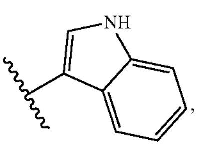 [SMILES: *c1c[nH]c2ccccc12]
,
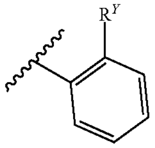
,

-continued

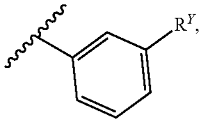
or
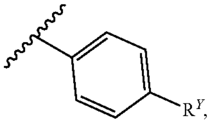

L2 is of the formula:

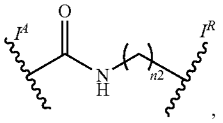
,
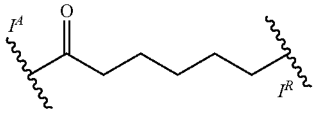
,
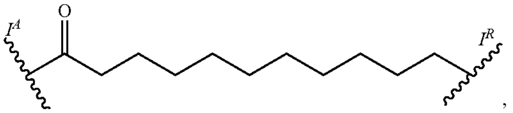
,
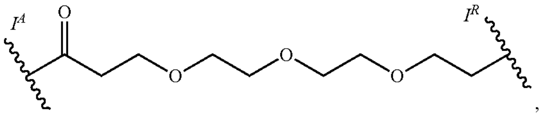
,
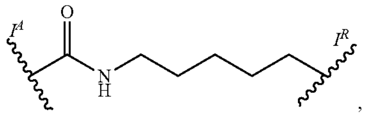
,
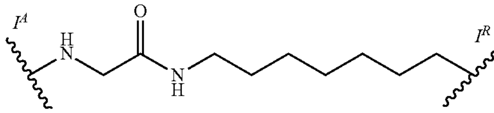
,
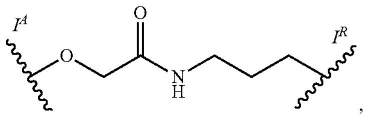
,
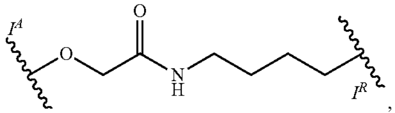
,
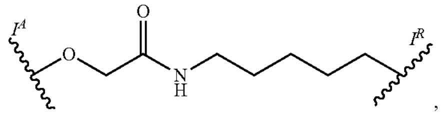
,
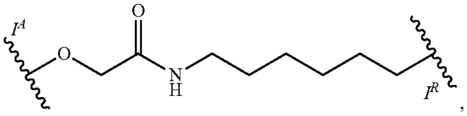
,
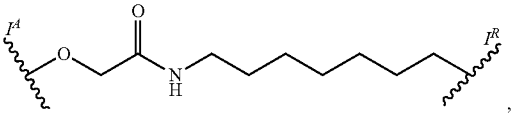
,
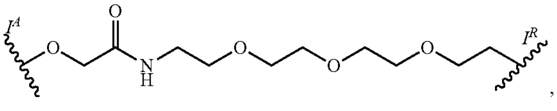
, -continued
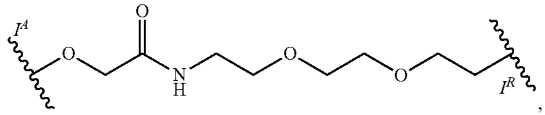
,
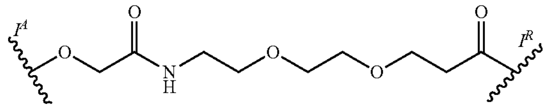
,
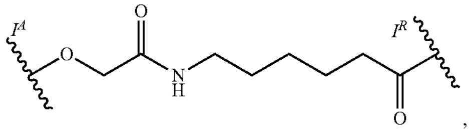
,
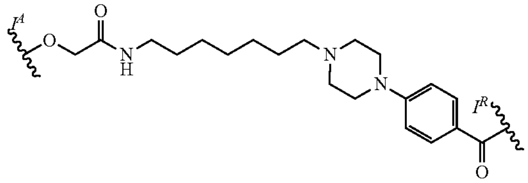
,
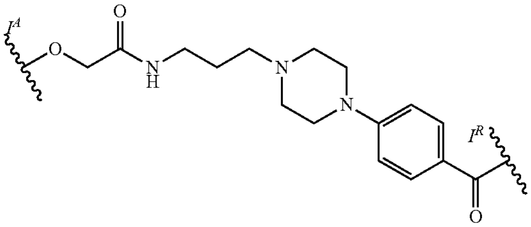
,
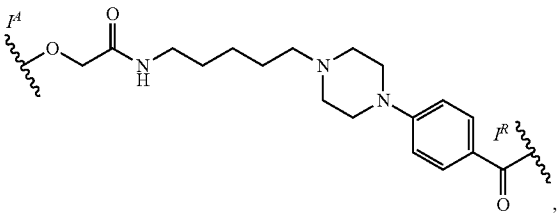
,
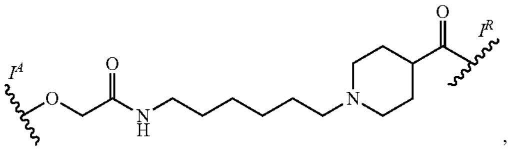
, or
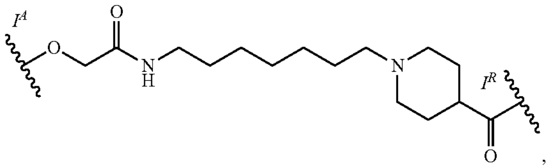
,
$R^3$ is halogen, $R^3$ is hydrogen, y is 0, x is 1, and D is of the formula:
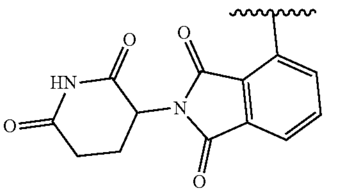
or
-continued
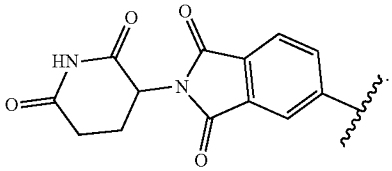
.
In certain embodiments, L1 is a bond, Ring A is of formula:
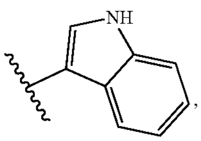 [SMILES: *c1c[nH]c2ccccc12]
,
L2 is of
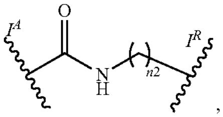
,
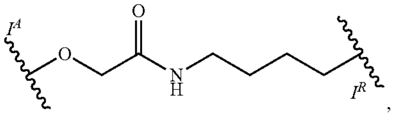
,
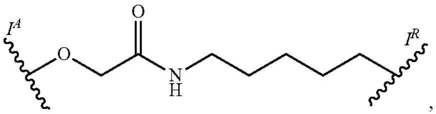
,
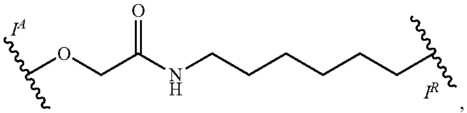
,
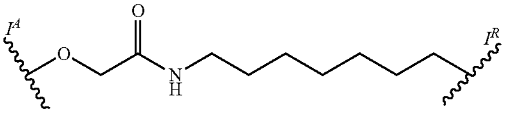
,
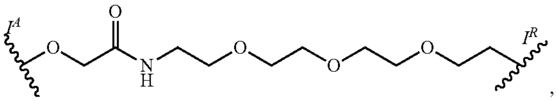
,
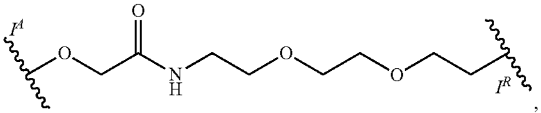
,
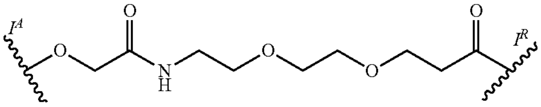
,
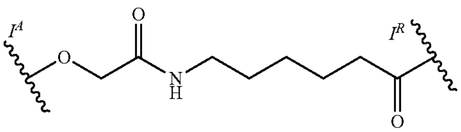
, -continued

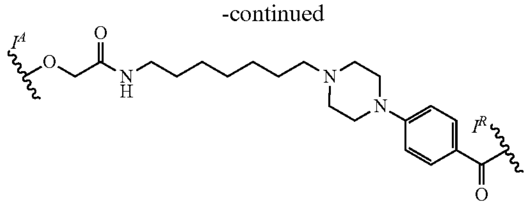

,

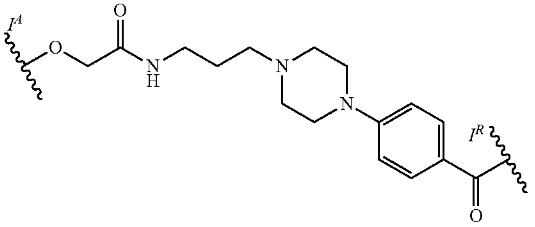

,

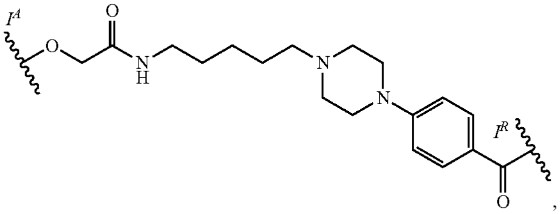

,

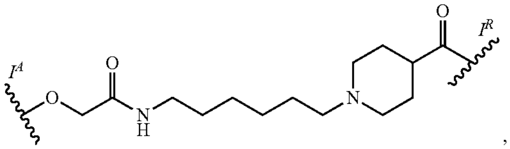

, or

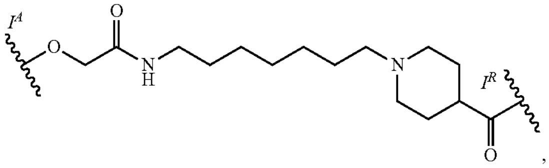

, $R^3$ is halogen, $R^3$ is hydrogen, y is 0, x is 1, and D is of the formula:

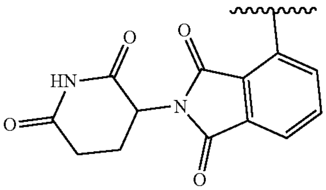

or

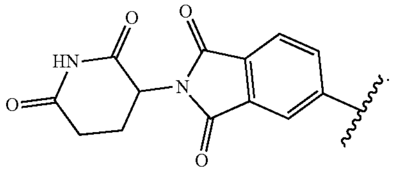

In certain embodiments, L1 is a bond, Ring A is of formula:

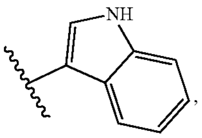 [SMILES: *c1c[nH]c2ccccc12]

L2 is an unsubstituted $C_{1-24}$ hydrocarbon chain, optionally wherein one or more chain atoms of the hydrocarbon chain are independently replaced with —C(=O)—, —O—, —$NR^b$—, —S—, or a cyclic moiety, wherein $R^b$ is independently hydrogen, substituted or unsubstituted $C_{1-6}$ alkyl, or a nitrogen protecting group, at least one instance of $R^1$ is halogen, $R^3$ is hydrogen or optionally substituted $C_{1-6}$ alkyl, y is 0, x is 1, and D is of the formula:

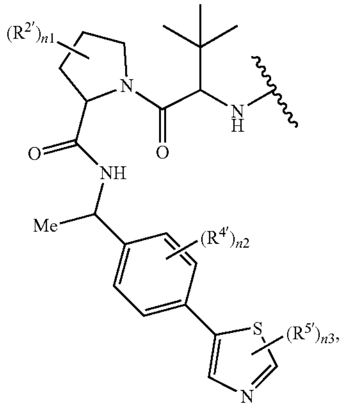

wherein $R^{2'}$, $R^{4'}$, $R^{5'}$, n1, n2, and n3 are as defined herein. In certain embodiments, L1 is a bond, Ring A is of formula:

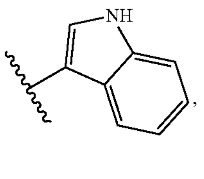

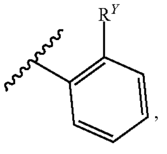

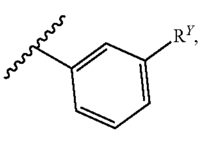

or

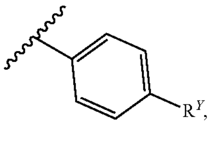

L2 is of the formula:

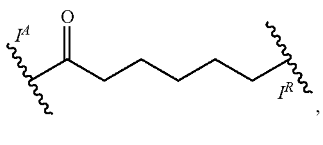

,

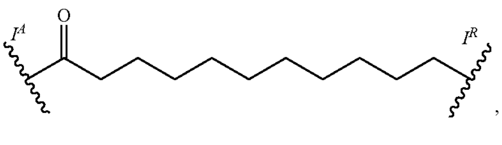

,

-continued
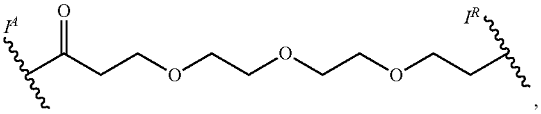, 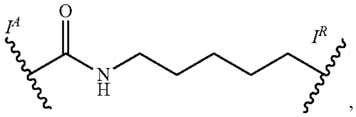,
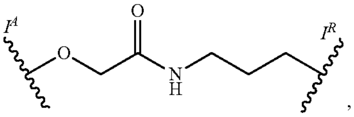, 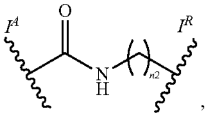, 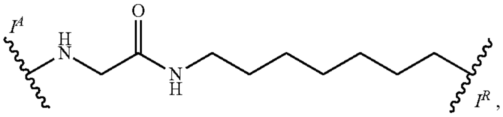,
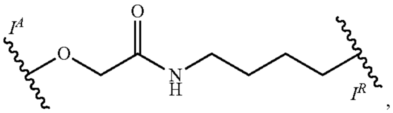, 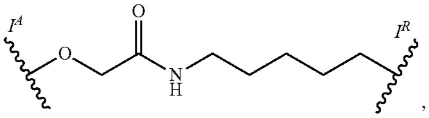,
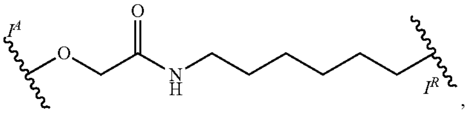, 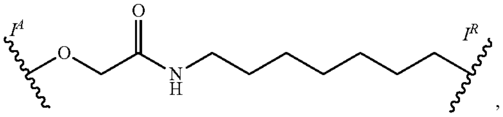,
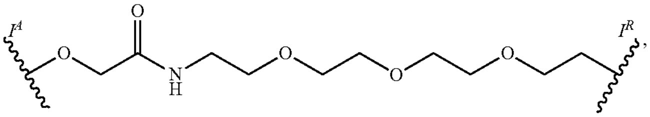,
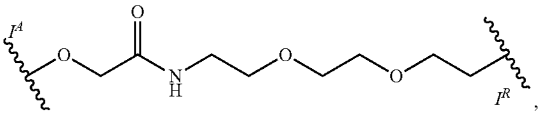, 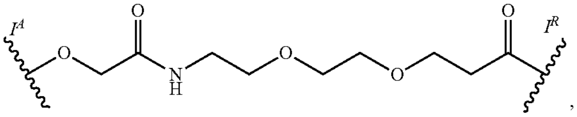,
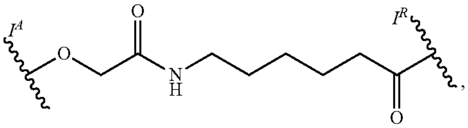,
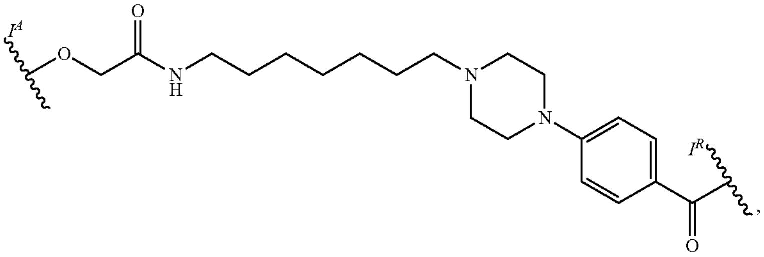,
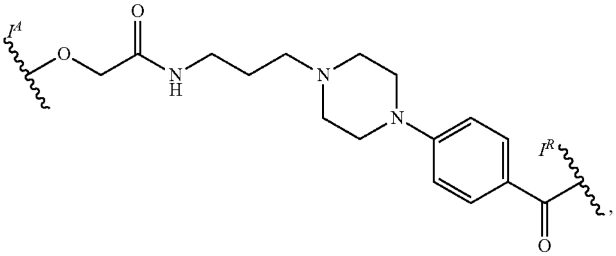,
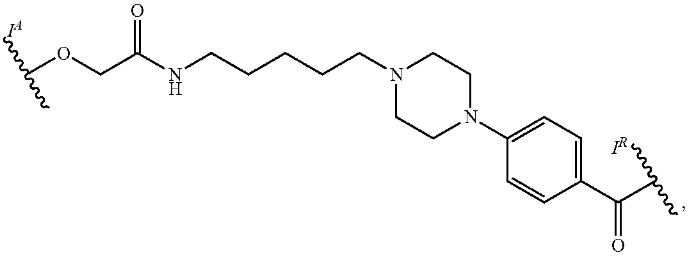, -continued
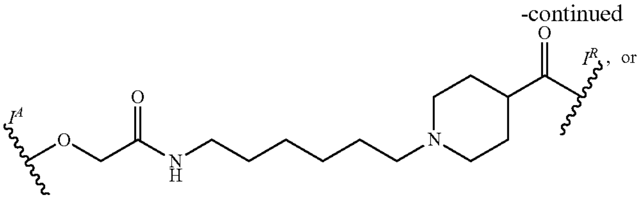
or
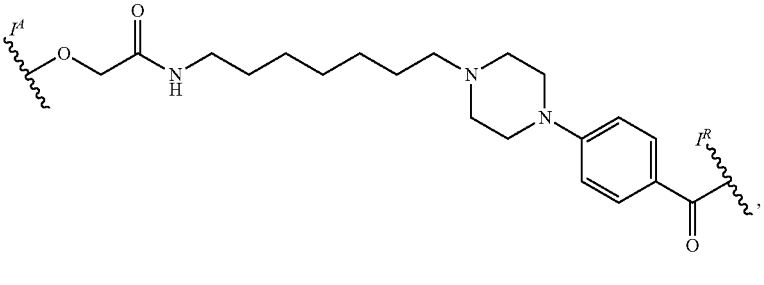
,
$R^3$ is halogen, $R^3$ is hydrogen, y is 0, x is 1, and D is of the formula:
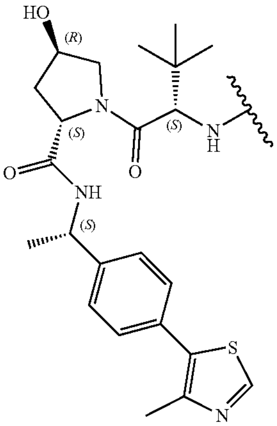
or
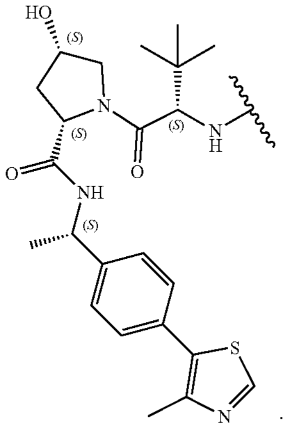
.
In certain embodiments, L1 is a bond, Ring A is of formula:
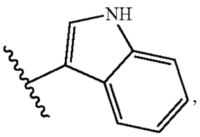 [SMILES: *c1c[nH]c2ccccc12]
,
L2 is of the formula:
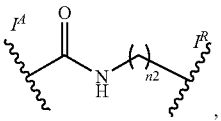
,
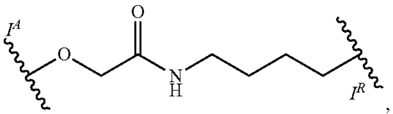
,
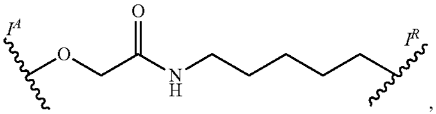
,
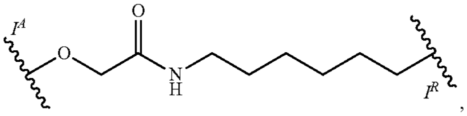
,
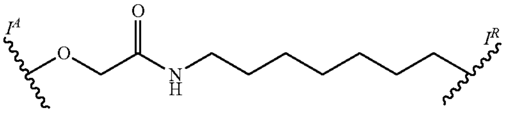
,
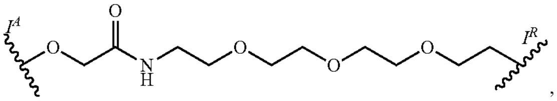
,
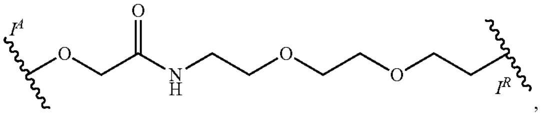
, -continued

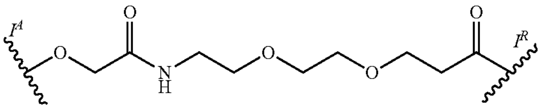

,

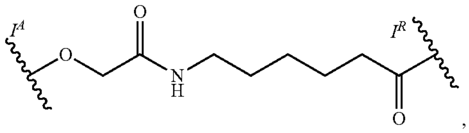

,

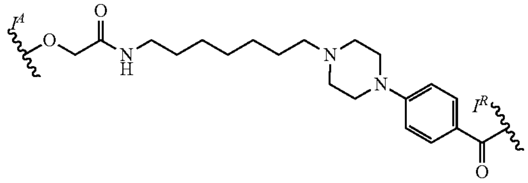

,

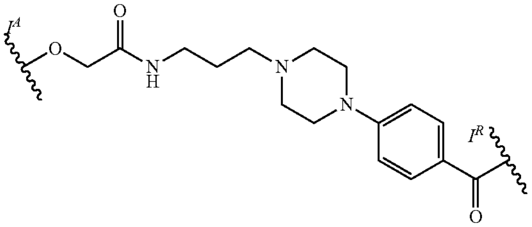

,

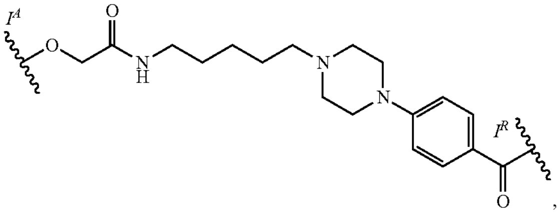

,

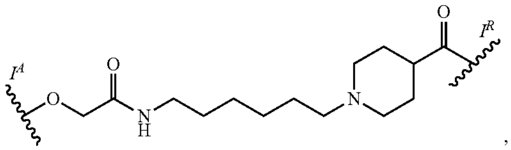

, or

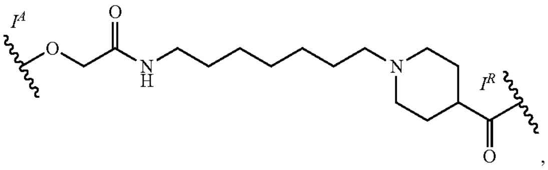

, $R^3$ is halogen, $R^3$ is hydrogen, y is 0, x is 1, and D is of the formula:

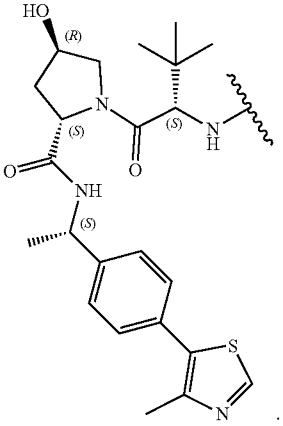

.

In certain embodiments, the compound of Formula (I) is of the formula:

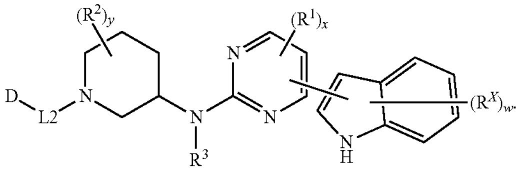

or a pharmaceutically acceptable salt, co-crystal, tautomer, stereoisomer, solvate, hydrate, polymorph, isotopically enriched derivative, or prodrug thereof.

In certain embodiments, the compound of Formula (I) is of the formula:

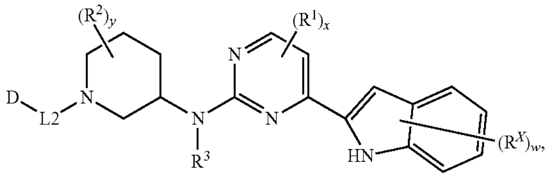

or a pharmaceutically acceptable salt, co-crystal, tautomer, stereoisomer, solvate, hydrate, polymorph, isotopically enriched derivative, or prodrug thereof.

In certain embodiments, the compound of Formula (I) is of the formula:

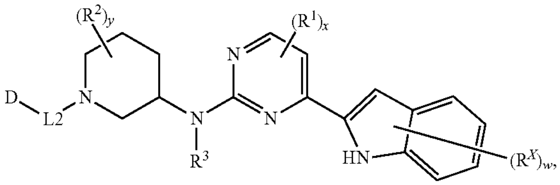

or a pharmaceutically acceptable salt, co-crystal, tautomer, stereoisomer, solvate, hydrate, polymorph, isotopically enriched derivative, or prodrug thereof; wherein D is of the formula:

(IA)

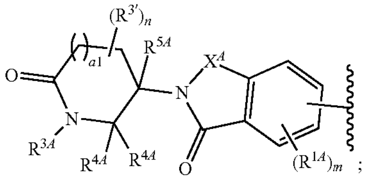
;

and L2 is of the formula:

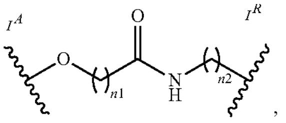
,

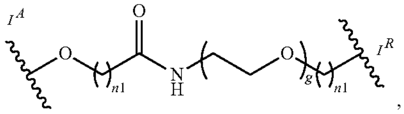
,

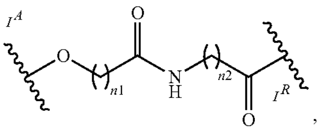
,

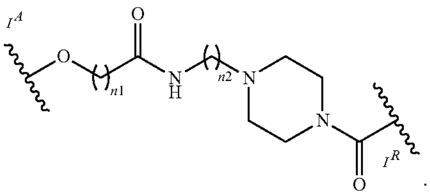
.

In certain embodiments, the compound of Formula (I) is of the formula:

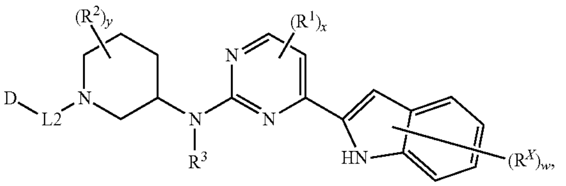

or a pharmaceutically acceptable salt, co-crystal, tautomer, stereoisomer, solvate, hydrate, polymorph, isotopically enriched derivative, or prodrug thereof; wherein D is of the formula:

(IA)

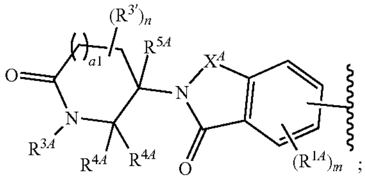
;

and L2 is of the formula:

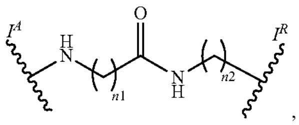
,

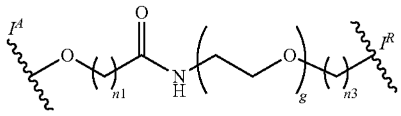
,

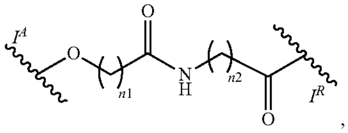
,

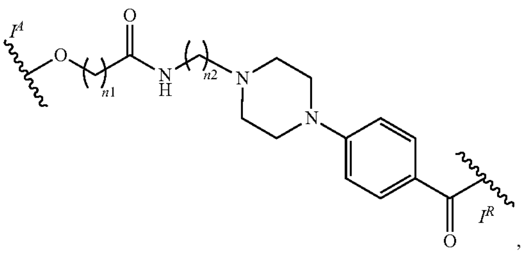
, or

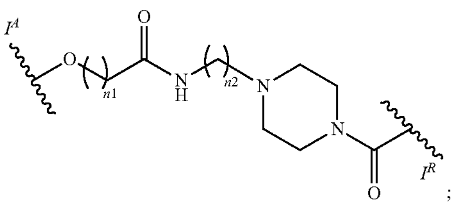
;

n1 is 1; n2 is 3, 4, 5, 6, 7, or 8; n3 is 1 or 2; and g is 2 or 3.

In certain embodiments, the compound of Formula (I) is of the formula:

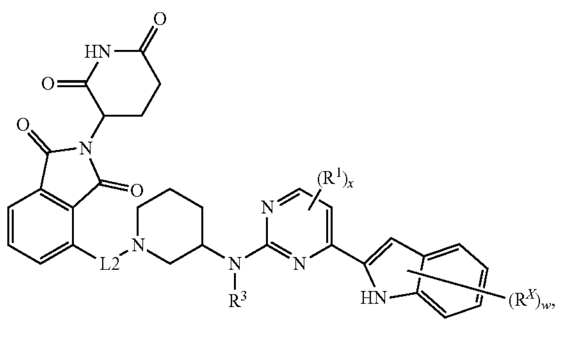

or a pharmaceutically acceptable salt, co-crystal, tautomer, stereoisomer, solvate, hydrate, polymorph, isotopically enriched derivative, or prodrug thereof.

In certain embodiments, the compound of Formula (I) is of the formula:

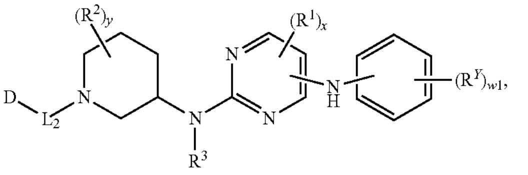

or a pharmaceutically acceptable salt, co-crystal, tautomer, stereoisomer, solvate, hydrate, polymorph, isotopically enriched derivative, or prodrug thereof.

In certain embodiments, the compound of Formula (I) is of the formula:

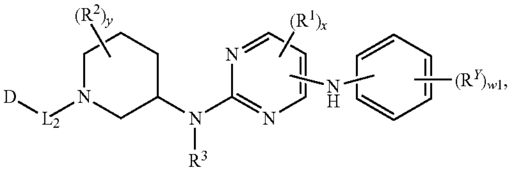

or a pharmaceutically acceptable salt, co-crystal, tautomer, stereoisomer, solvate, hydrate, polymorph, isotopically enriched derivative, or prodrug thereof; wherein D is of the formula:

(IA)

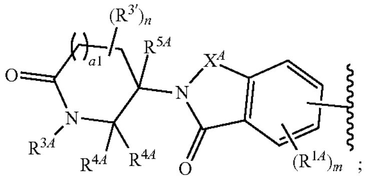

;

and

L2 is of the formula:

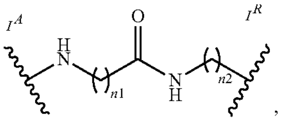

,

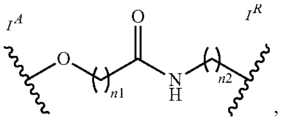

,

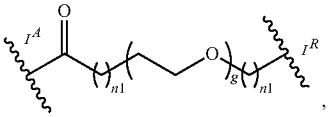

,

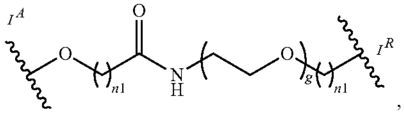

,

-continued

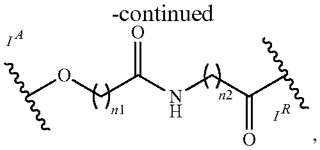

,

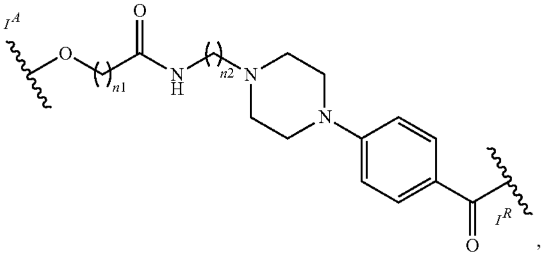

, or

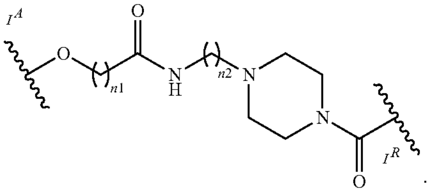

.

n1 is 0 or 1; n2 is 0, 1, 3, 4, 5, 6, 7, or 8; n3 is 1 or 2; and g is 2 or 3.

In certain embodiments, the compound of Formula (I) is of the formula:

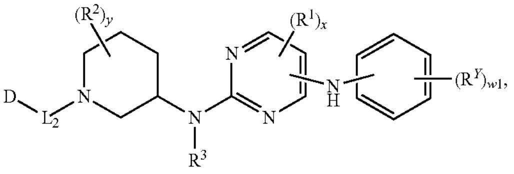

or a pharmaceutically acceptable salt, co-crystal, tautomer, stereoisomer, solvate, hydrate, polymorph, isotopically enriched derivative, or prodrug thereof; wherein D is of the formula:

(IA)

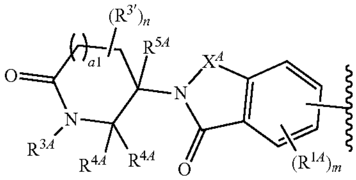

;

and L2 is of the formula:

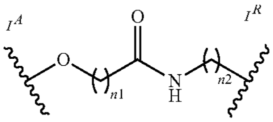

,

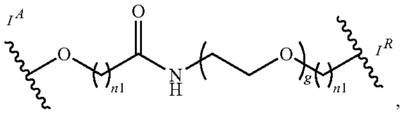

,

-continued

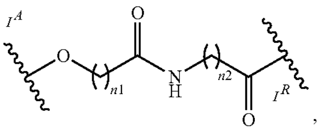

,

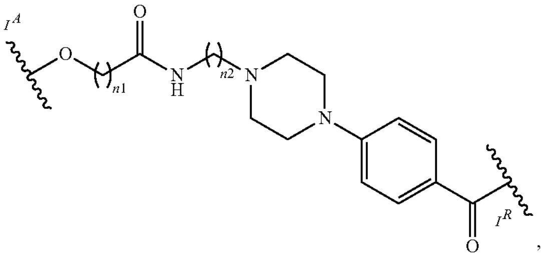

, or

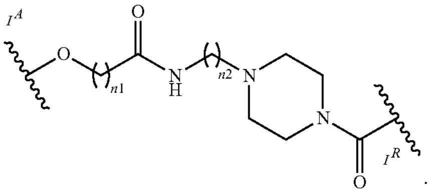

.

n1 is 1; n2 is 3, 4, 5, 6, 7, or 8; n3 is 1 or 2; and g is 2 or 3.

In certain embodiments, the compound of Formula (I) is of the formula:

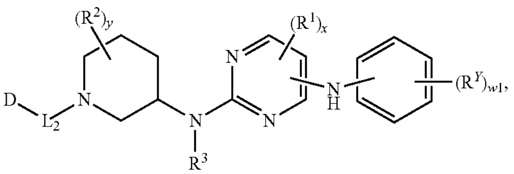

or a pharmaceutically acceptable salt, co-crystal, tautomer, stereoisomer, solvate, hydrate, polymorph, isotopically enriched derivative, or prodrug thereof.

In certain embodiments, the compound of Formula (I) is of the formula:

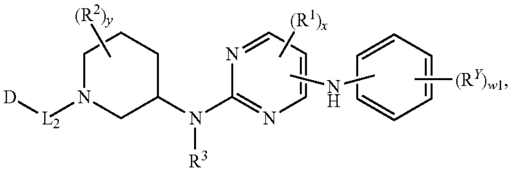

or a pharmaceutically acceptable salt, co-crystal, tautomer, stereoisomer, solvate, hydrate, polymorph, isotopically enriched derivative, or prodrug thereof;

wherein D is of the formula:

(IA)

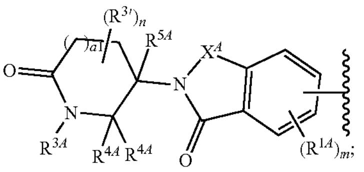

and

L2 is of the formula:

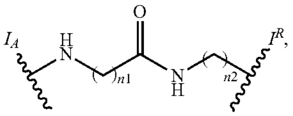

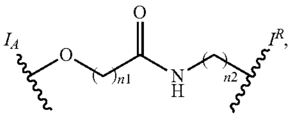

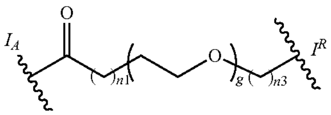

,

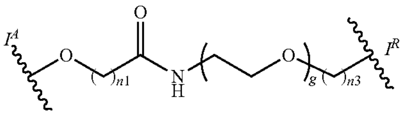

,

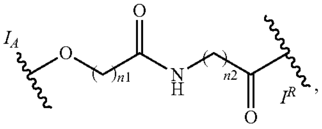

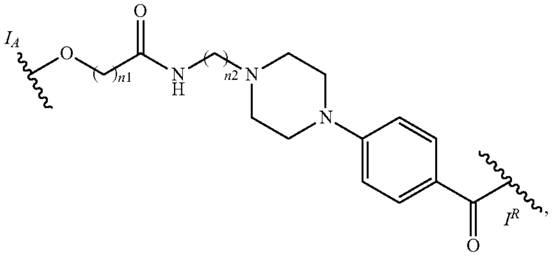

or

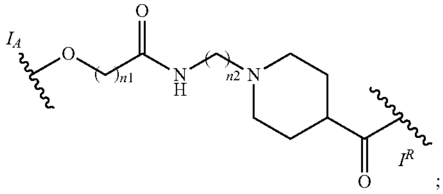

;

n1 is 0 or 1; n2 is 0, 1, 3, 4, 5, 6, 7, or 8; n3 is 1 or 2; and g is 2 or 3.

In certain embodiments, the compound of Formula (I) is of the formula:

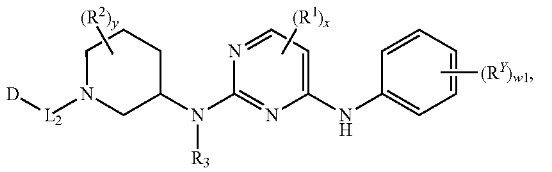

or a pharmaceutically acceptable salt, co-crystal, tautomer, stereoisomer, solvate, hydrate, polymorph, isotopically enriched derivative, or prodrug thereof;

wherein D is of the formula:

(IA)

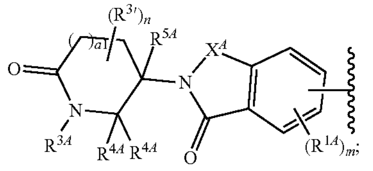

and

L2 is of the formula:

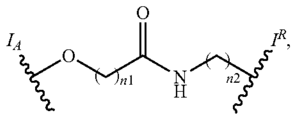

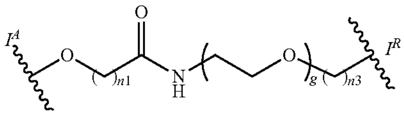

,

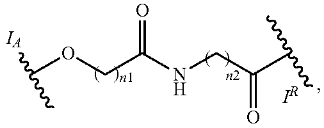

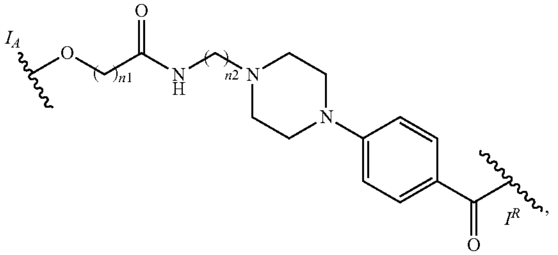

or

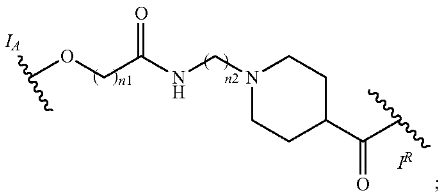

;

n1 is 1; n2 is 3, 4, 5, 6, 7, or 8; n3 is 1 or 2; and g is 2 or 3.

In certain embodiments, the compound of Formula (I) is of the formula:

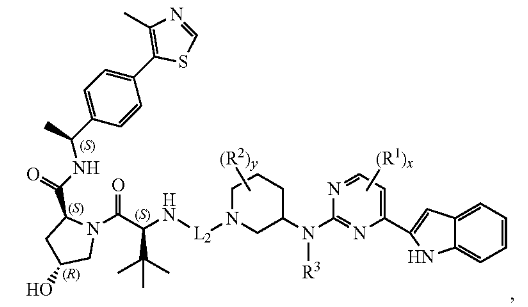

,

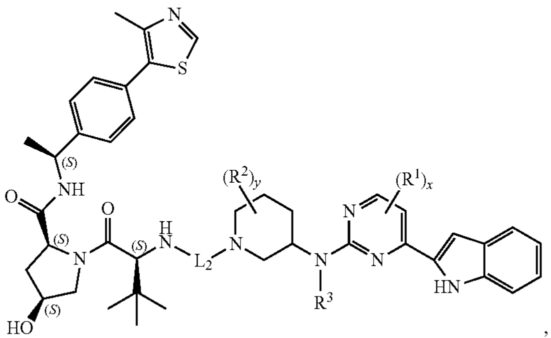

, or a pharmaceutically acceptable salt, co-crystal, tautomer, stereoisomer, solvate, hydrate, polymorph, isotopically enriched derivative, or prodrug thereof. In certain embodiments, the compound of Formula (I) is of the formula:

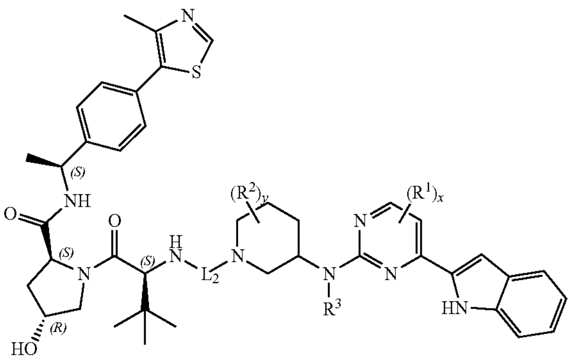

, or a pharmaceutically acceptable salt, co-crystal, tautomer, stereoisomer, solvate, hydrate, polymorph, isotopically enriched derivative, or prodrug thereof.

In certain embodiments, the compound of Formula (I) is of the formula:
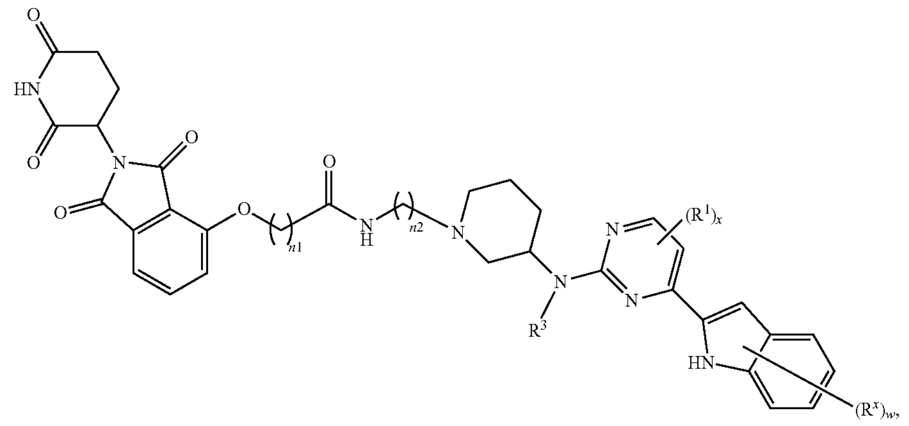
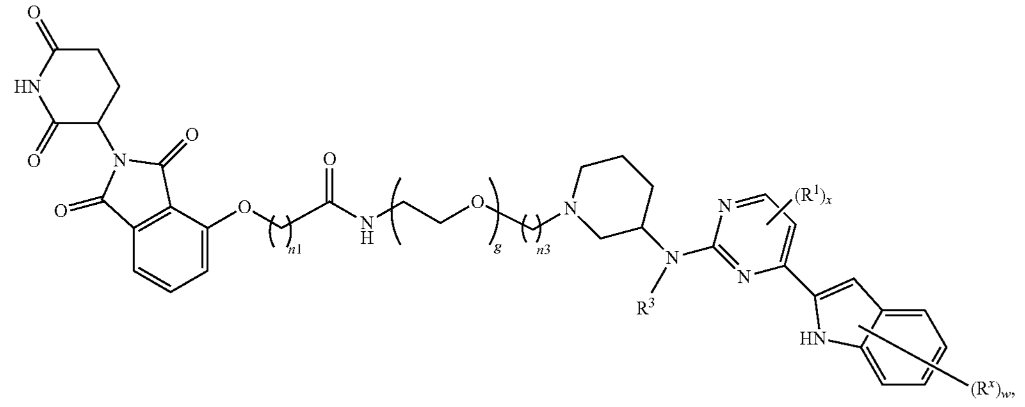
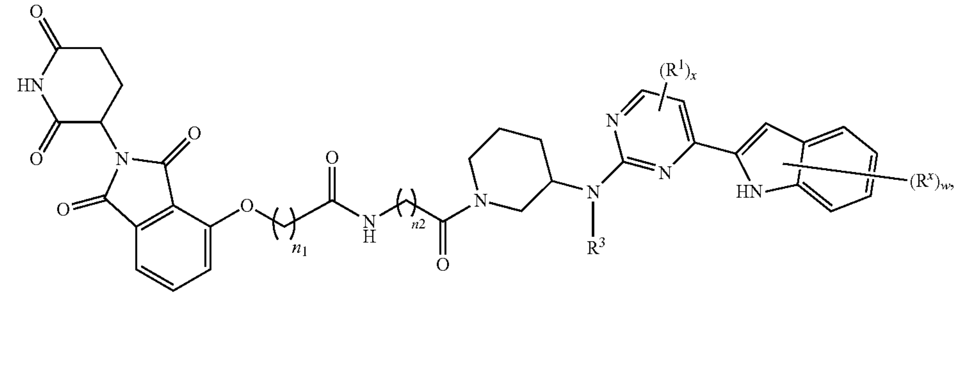
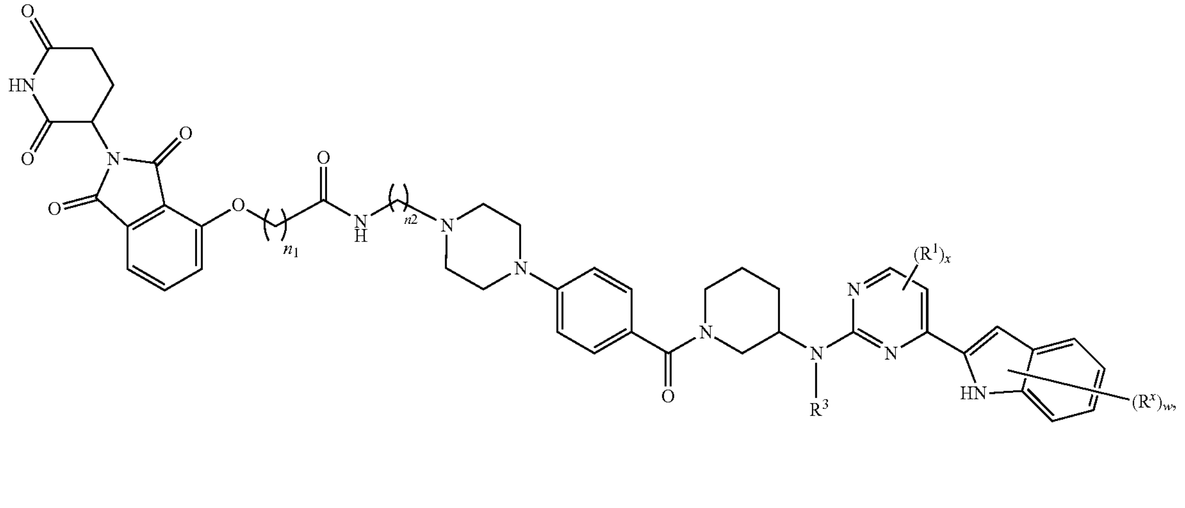

-continued

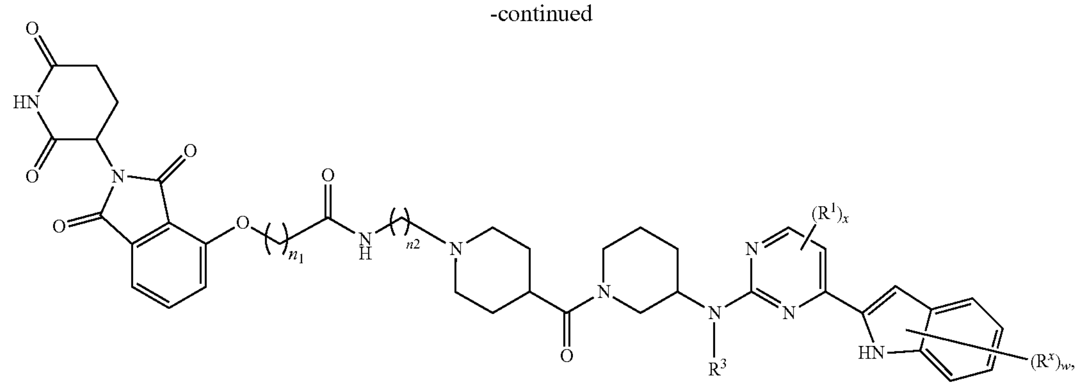

or a pharmaceutically acceptable salt, co-crystal, tautomer, stereoisomer, solvate, hydrate, polymorph, isotopically enriched derivative, or prodrug thereof.

In certain embodiments, the compound of Formula (I) is of the formula:

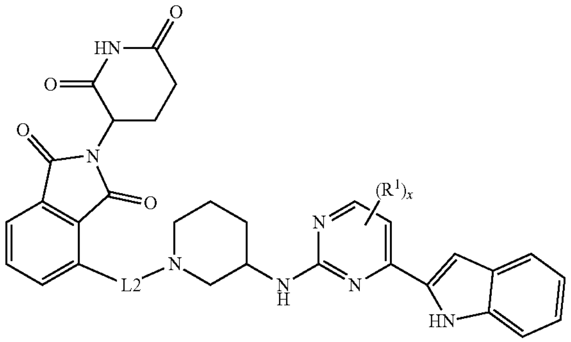

, or a pharmaceutically acceptable salt, co-crystal, tautomer, stereoisomer, solvate, hydrate, polymorph, isotopically enriched derivative, or prodrug thereof.

In certain embodiments, the compound of Formula (I) is of the formula:

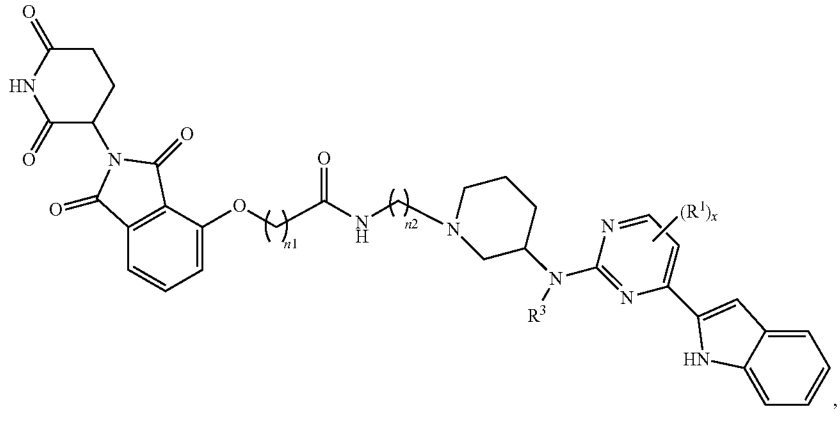

,

-continued
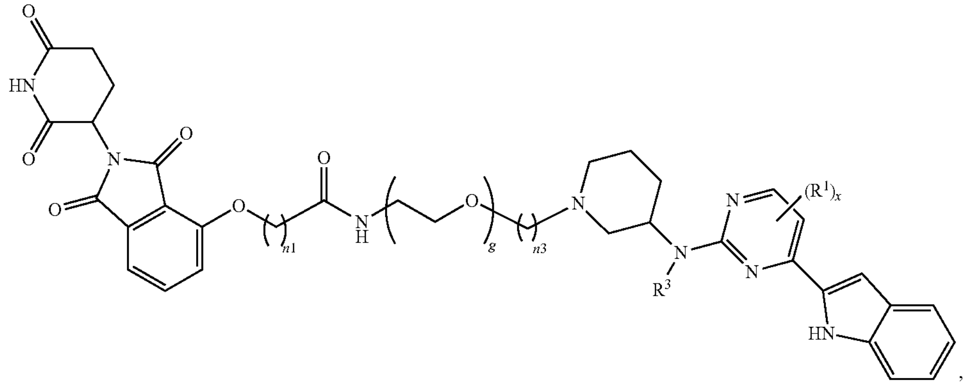
,
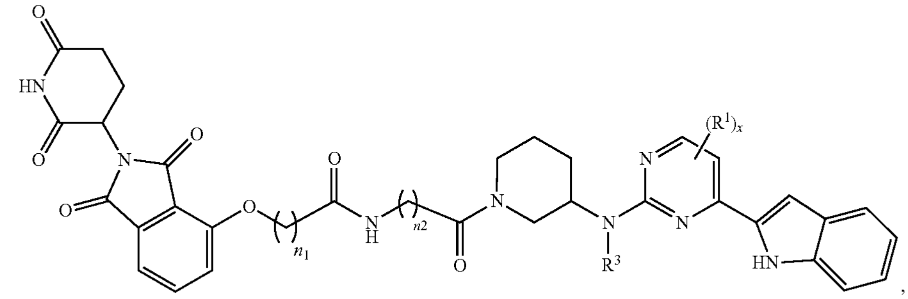
,
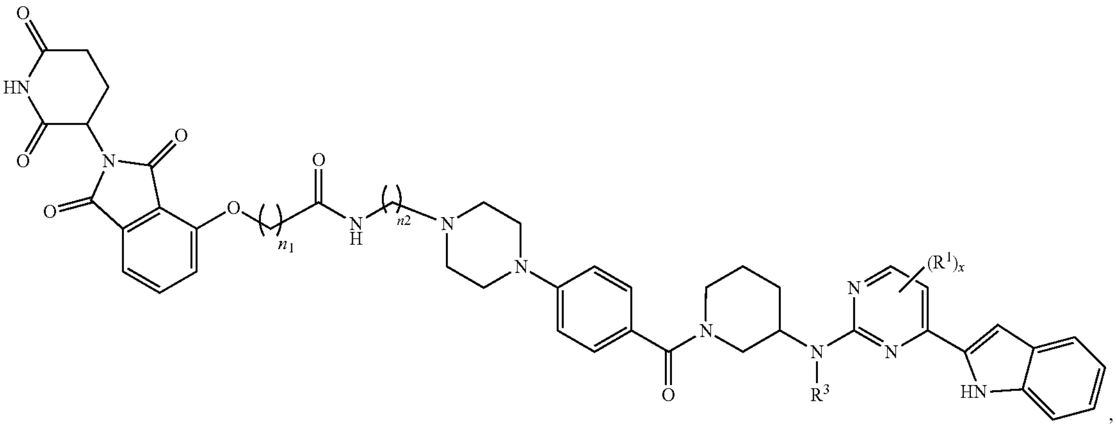
,
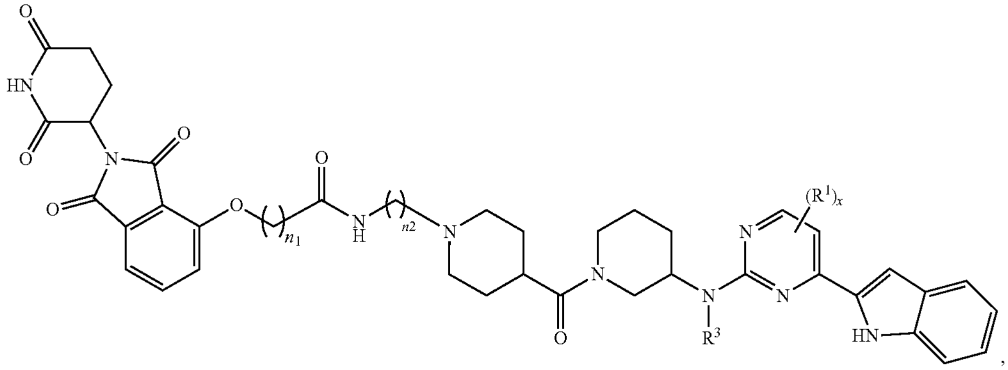
, or a pharmaceutically acceptable salt, co-crystal, tautomer, stereoisomer, solvate, hydrate, polymorph, isotopically enriched derivative, or prodrug thereof.

In certain embodiments, the compound of Formula (I) is of the formula:

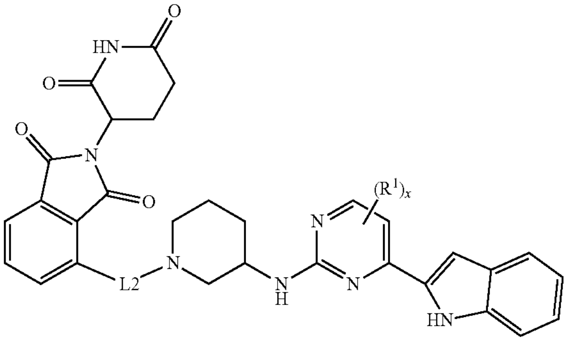

, or a pharmaceutically acceptable salt, co-crystal, tautomer, stereoisomer, solvate, hydrate, polymorph, isotopically enriched derivative, or prodrug thereof.

wherein $R^1$ is halogen or optionally substituted $C_{1-6}$ alkyl;

L2 is of the formula:

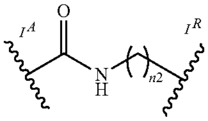

,

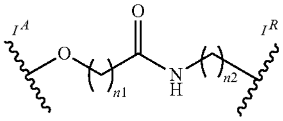

,

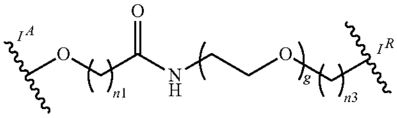

,

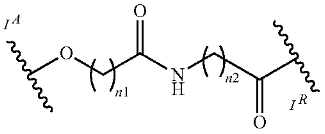

,

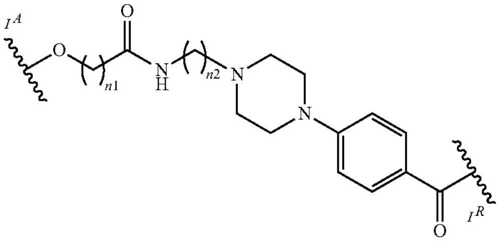

, or

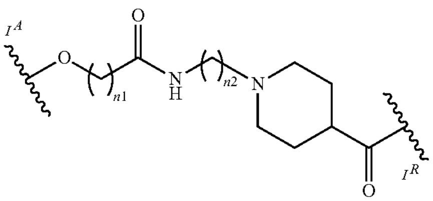

.

In certain embodiments, the compound of Formula (I) is of the formula:

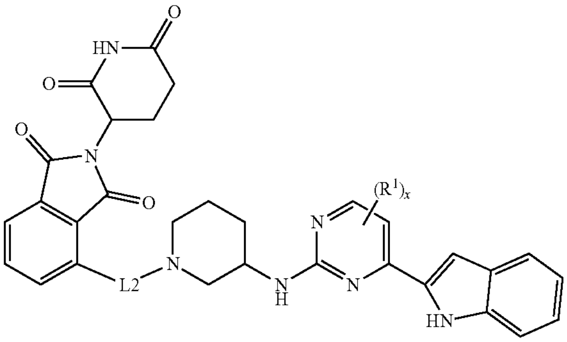

, or a pharmaceutically acceptable salt, co-crystal, tautomer, stereoisomer, solvate, hydrate, polymorph, isotopically enriched derivative, or prodrug thereof.

wherein $R^1$ is halogen or optionally substituted $C_{1-6}$ alkyl;

L2 is of the formula:

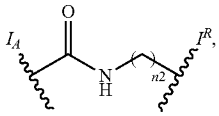

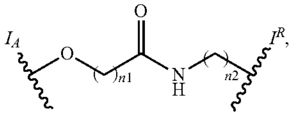

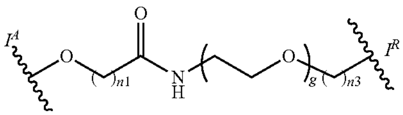

,

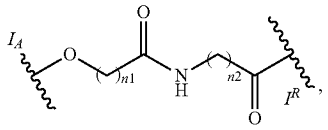

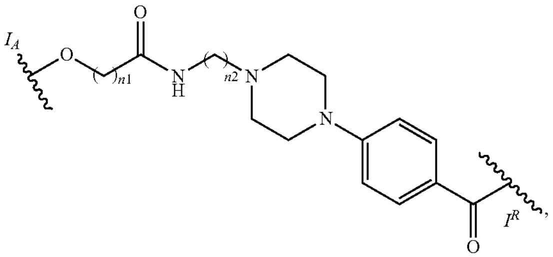

or

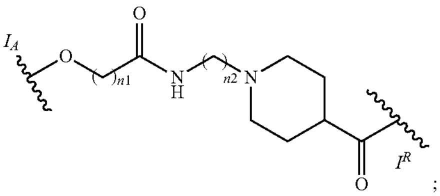

;

n1 is 1; n2 is 3, 4, 5, 6, 7, or 8; n3 is 1 or 2; and g is 2 or 3.

In certain embodiments, the compound of Formula (I) is of the formula:
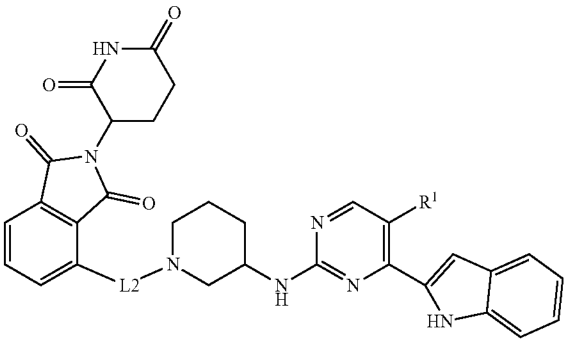
,
or a pharmaceutically acceptable salt, co-crystal, tautomer, stereoisomer, solvate, hydrate, polymorph, isotopically enriched derivative, or prodrug thereof.
In certain embodiments, the compound of Formula (I) is of the formula:
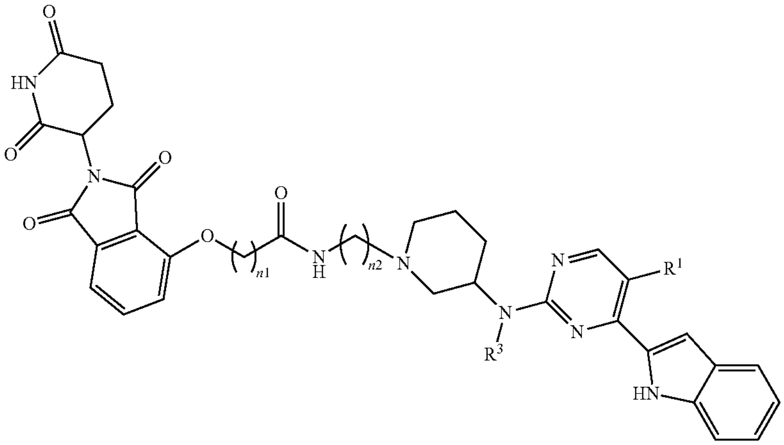
,
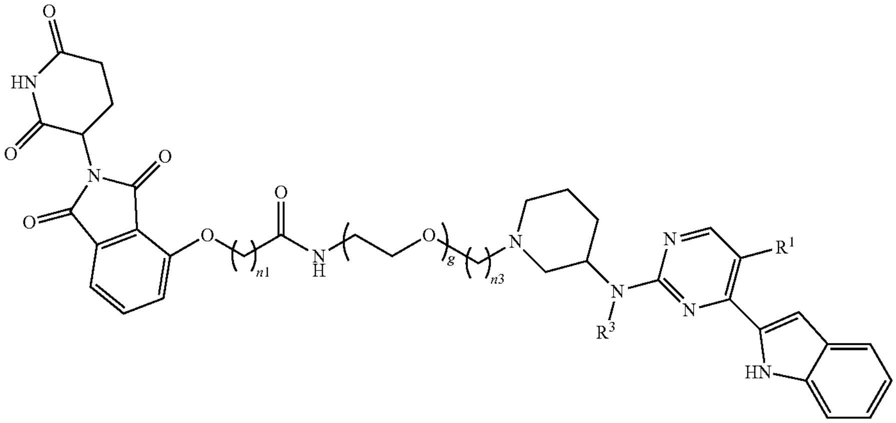
,
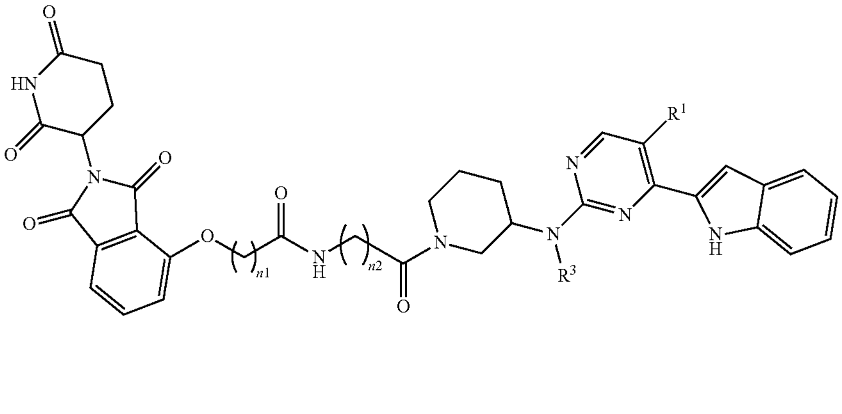
, -continued

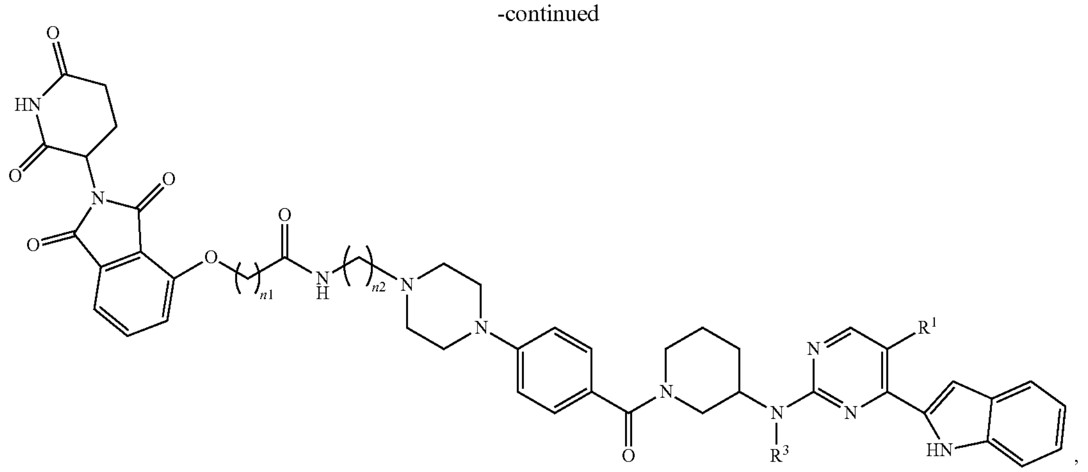

,

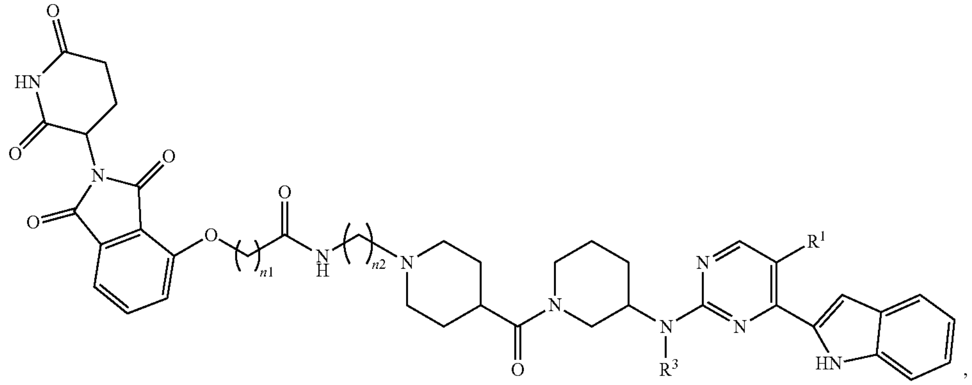

, or a pharmaceutically acceptable salt, co-crystal, tautomer, stereoisomer, solvate, hydrate, polymorph, isotopically enriched derivative, or prodrug thereof.

In certain embodiments, the compound of Formula (I) is of the formula:

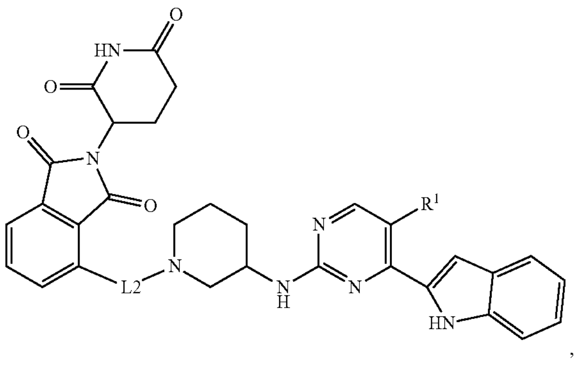

, or a pharmaceutically acceptable salt, co-crystal, tautomer, stereoisomer, solvate, hydrate, polymorph, isotopically enriched derivative, or prodrug thereof;

wherein L2 is of the formula:

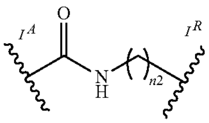

,

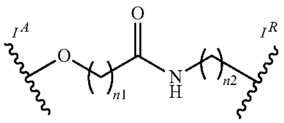

,

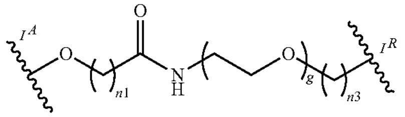

,

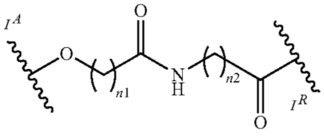

,

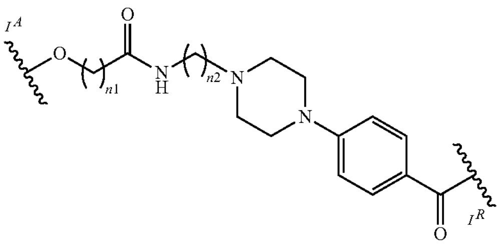

, or

-continued

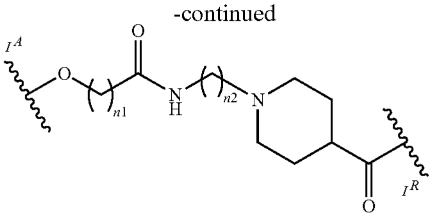

.

In certain embodiments, the compound of Formula (I) is of the formula:

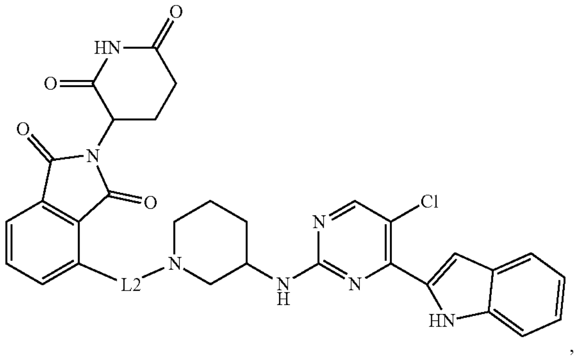

, or a pharmaceutically acceptable salt, co-crystal, tautomer, stereoisomer, solvate, hydrate, polymorph, isotopically enriched derivative, or prodrug thereof.

In certain embodiments, the compound of Formula (I) is of the formula:

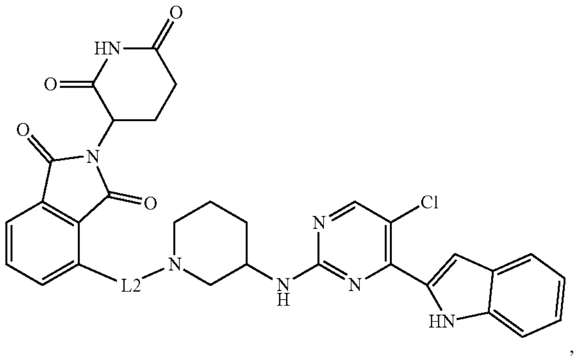

, or a pharmaceutically acceptable salt, co-crystal, tautomer, stereoisomer, solvate, hydrate, polymorph, isotopically enriched derivative, or prodrug thereof.

wherein L2 is of the formula:

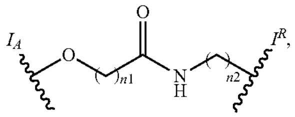

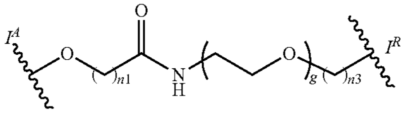

,

-continued

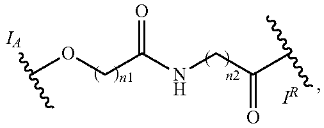

,

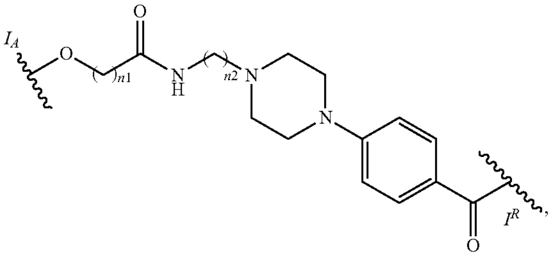

, or

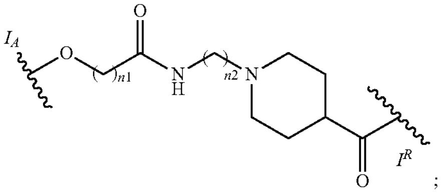

;

In certain embodiments, the compound of Formula (I) is of the formula:

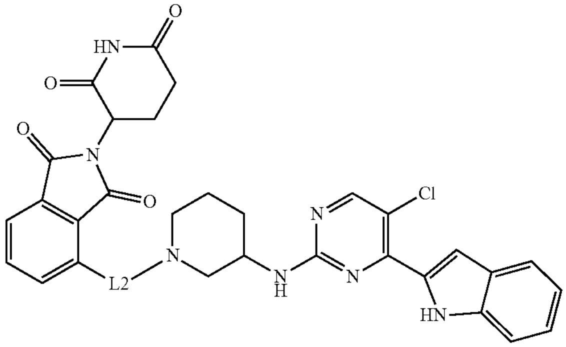

, or a pharmaceutically acceptable salt, co-crystal, tautomer, stereoisomer, solvate, hydrate, polymorph, isotopically enriched derivative, or prodrug thereof, wherein L2 is of the formula:

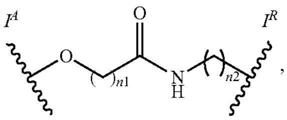

,

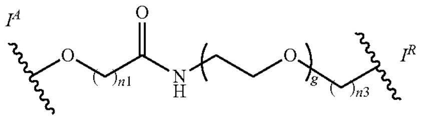

,

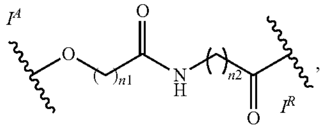

,

-continued

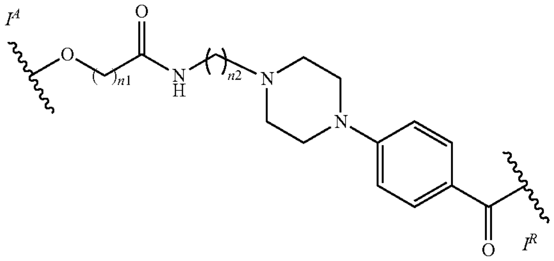, or

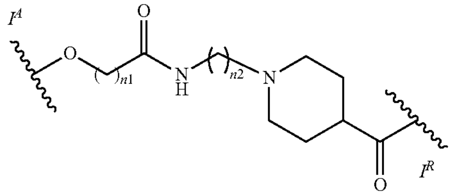;

n1 is 1; n2 is 3, 4, 5, 6, 7, or 8; n3 is 1 or 2; and g is 2 or 3.

In certain embodiments, the compound of Formula (I) is of the formula:

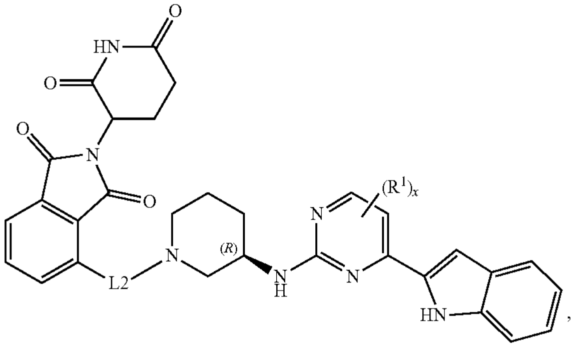, or

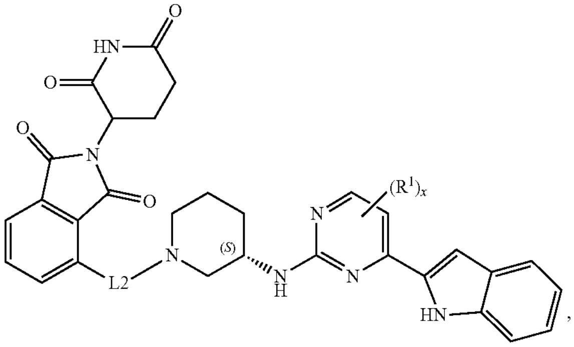, or a pharmaceutically acceptable salt, co-crystal, tautomer, stereoisomer, solvate, hydrate, polymorph, isotopically enriched derivative, or prodrug thereof.

In certain embodiments, the compound of Formula (I) is of the formula:

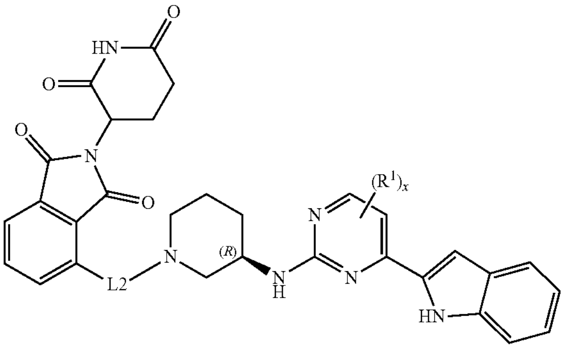, or

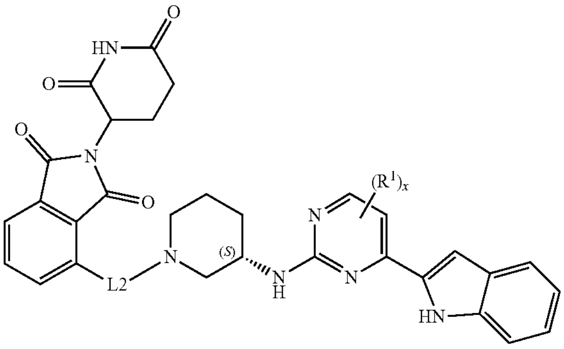, or a pharmaceutically acceptable salt, co-crystal, tautomer, stereoisomer, solvate, hydrate, polymorph, isotopically enriched derivative, or prodrug thereof, wherein $R^1$ is halogen or optionally substituted $C_{1-6}$ alkyl; and L2 is of the formula:

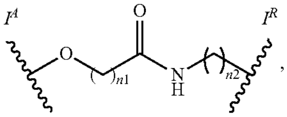,

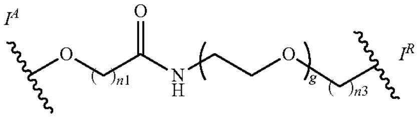,

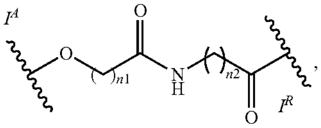,

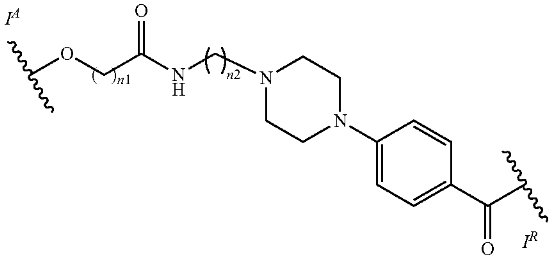,

-continued or

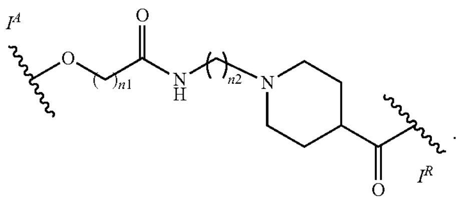

.

In certain embodiments, the compound of Formula (I) is of the formula:

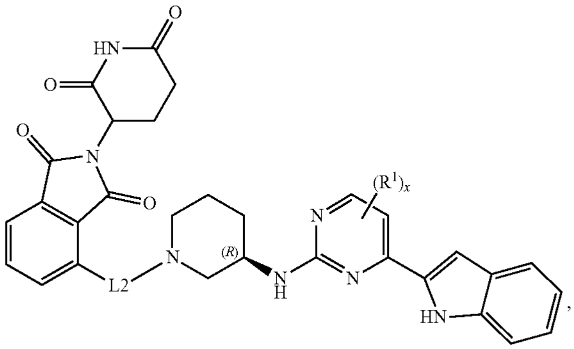

, or

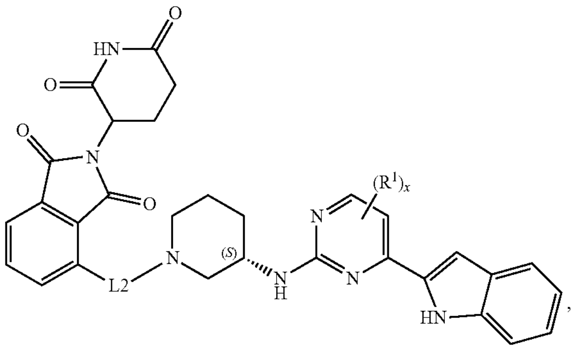

, or a pharmaceutically acceptable salt, co-crystal, tautomer, stereoisomer, solvate, hydrate, polymorph, isotopically enriched derivative, or prodrug thereof, wherein $R^1$ is halogen or optionally substituted $C_{1-6}$ alkyl; and L2 is of the formula:

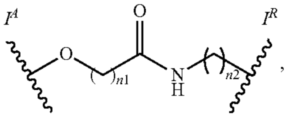

,

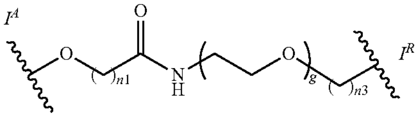

,

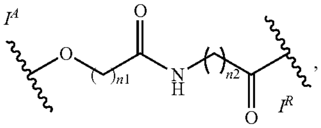

,

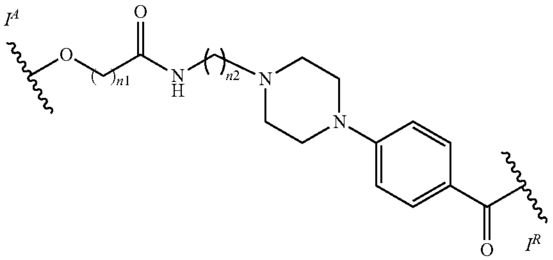

, or

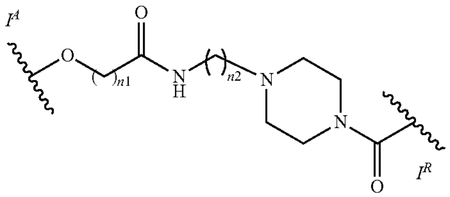

;

n1 is 1; n2 is 3, 4, 5, 6, 7, or 8; n3 is 1 or 2; and g is 2 or 3.

In certain embodiments, the compound of Formula (I) is of the formula:

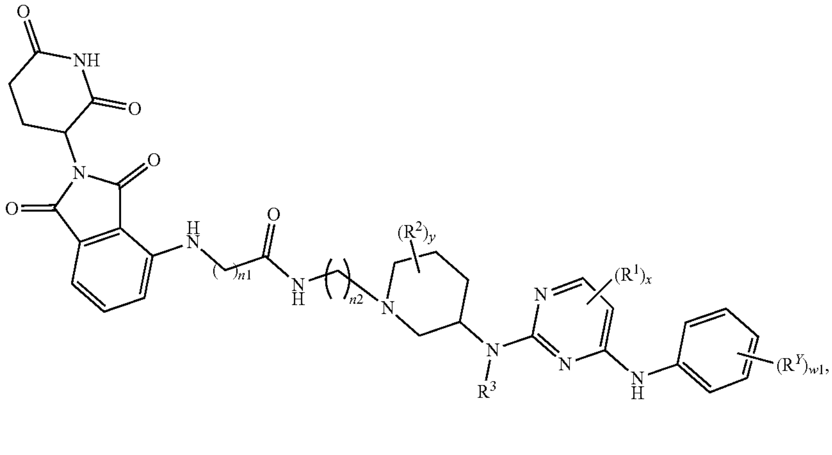

,

-continued

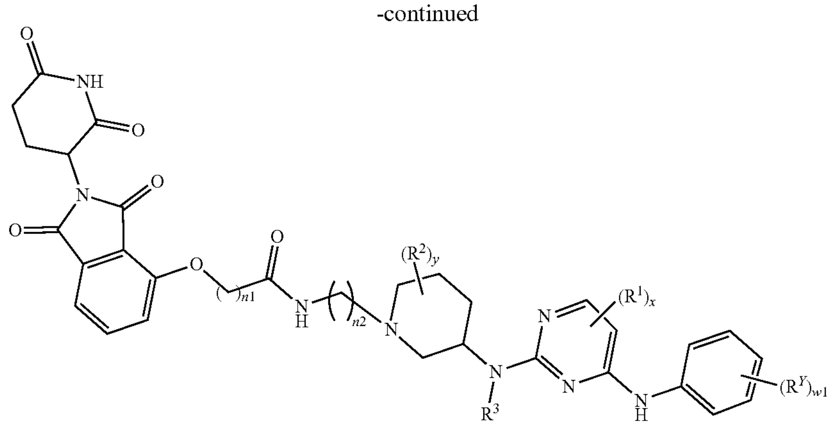

or a pharmaceutically acceptable salt, co-crystal, tautomer, stereoisomer, solvate, hydrate, polymorph, isotopically enriched derivative, or prodrug thereof, wherein n1 is 0 or 1; n2 is 0, 1, 3, 4, 5, 6, 7, or 8; n3 is 1 or 2; and g is 2 or 3.

In certain embodiments, the compound of Formula (I) is of the formula:

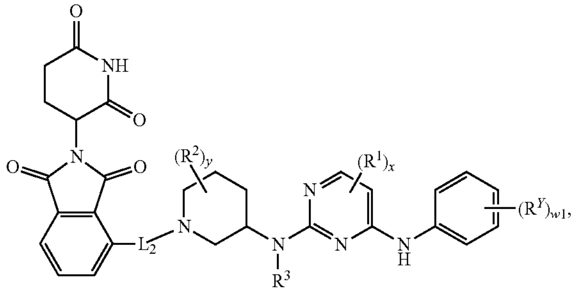

or a pharmaceutically acceptable salt, co-crystal, tautomer, stereoisomer, solvate, hydrate, polymorph, isotopically enriched derivative, or prodrug thereof.

In certain embodiments, the compound of Formula (I) is of the formula:

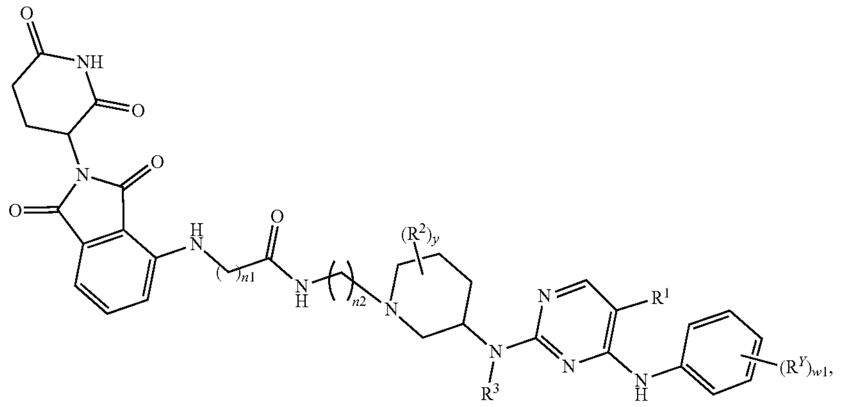

-continued

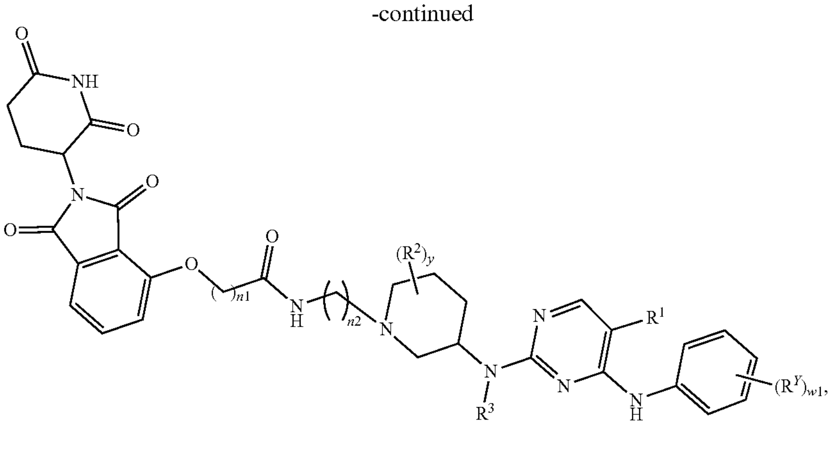

or a pharmaceutically acceptable salt, co-crystal, tautomer, stereoisomer, solvate, hydrate, polymorph, isotopically enriched derivative, or prodrug thereof.

In certain embodiments, the compound of Formula (I) is of the formula:

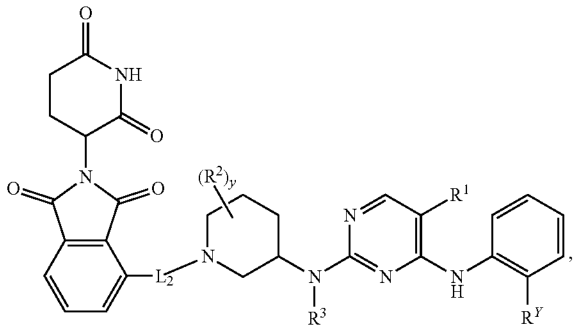

or a pharmaceutically acceptable salt, co-crystal, tautomer, stereoisomer, solvate, hydrate, polymorph, isotopically enriched derivative, or prodrug thereof.

In certain embodiments, the compound of Formula (I) is of the formula:

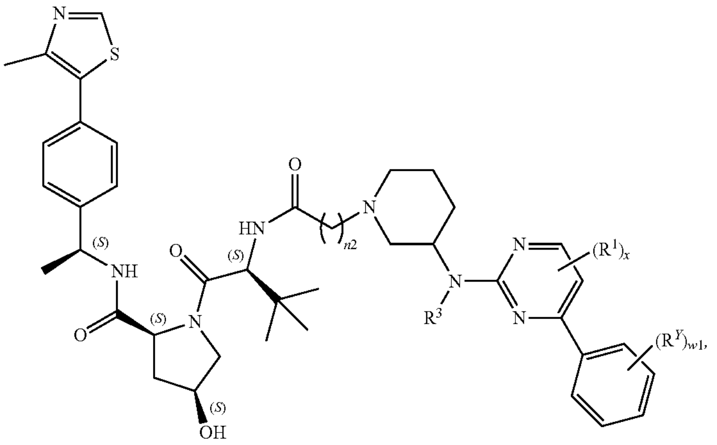

-continued
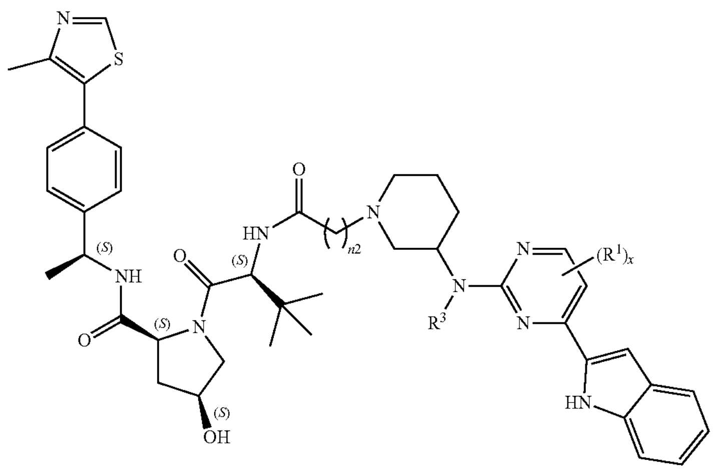
,
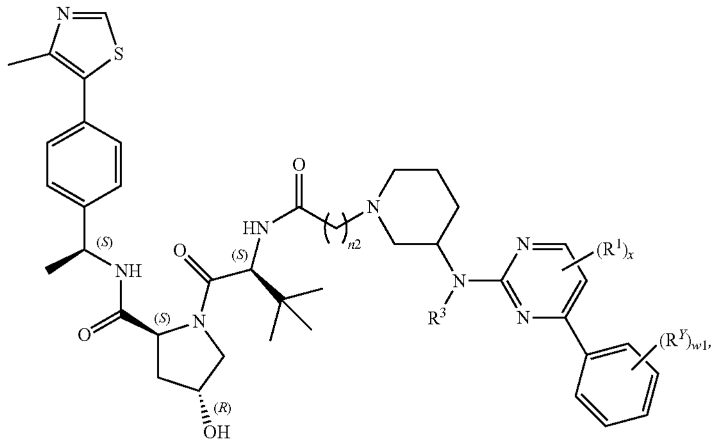
,
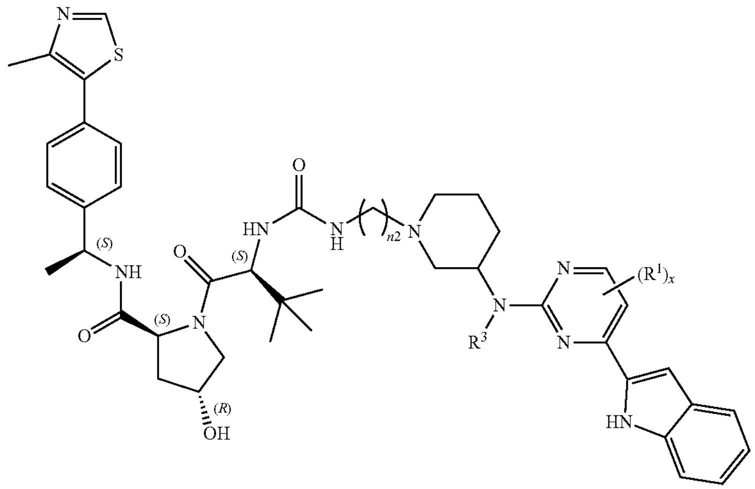
,

-continued
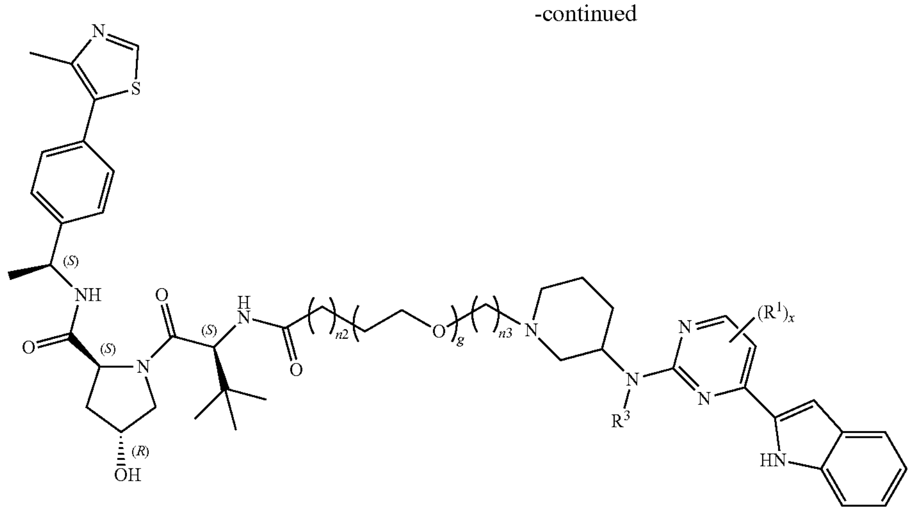
,
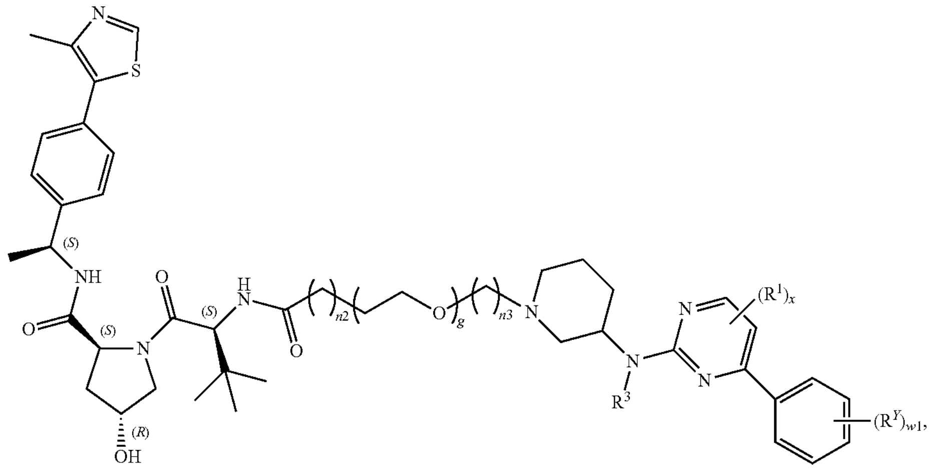
,
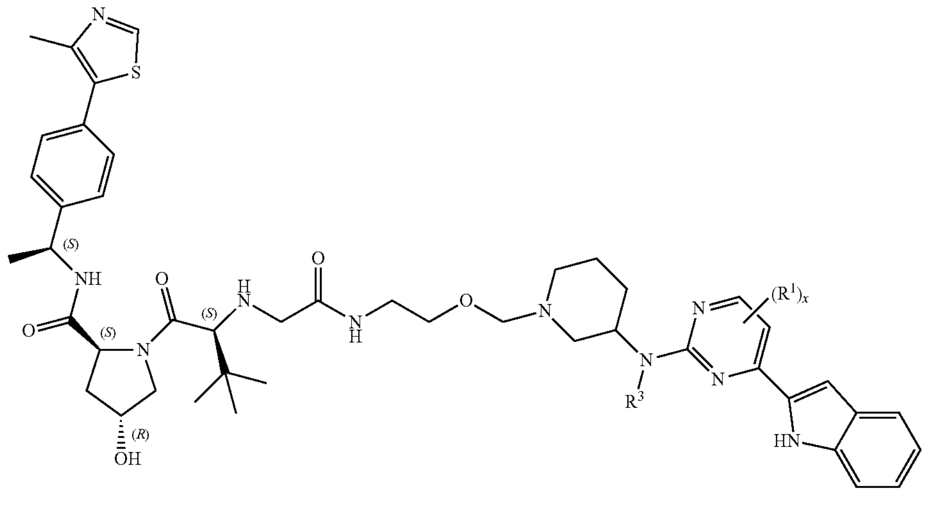
,

-continued
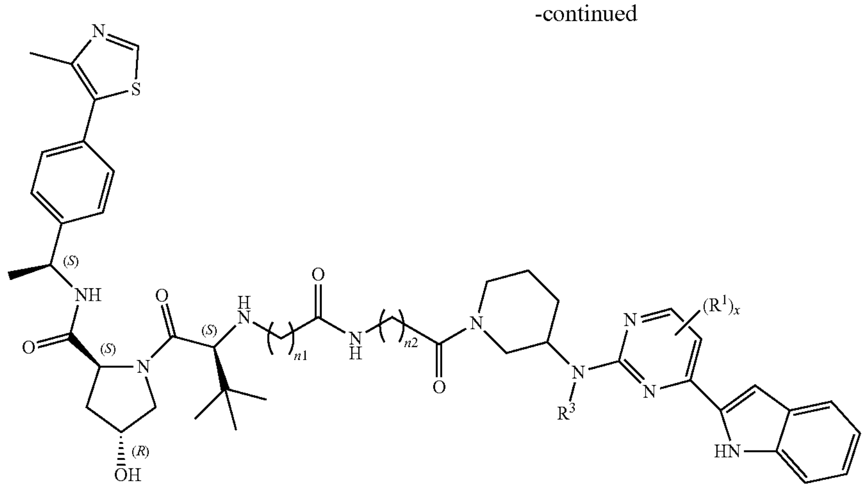
,
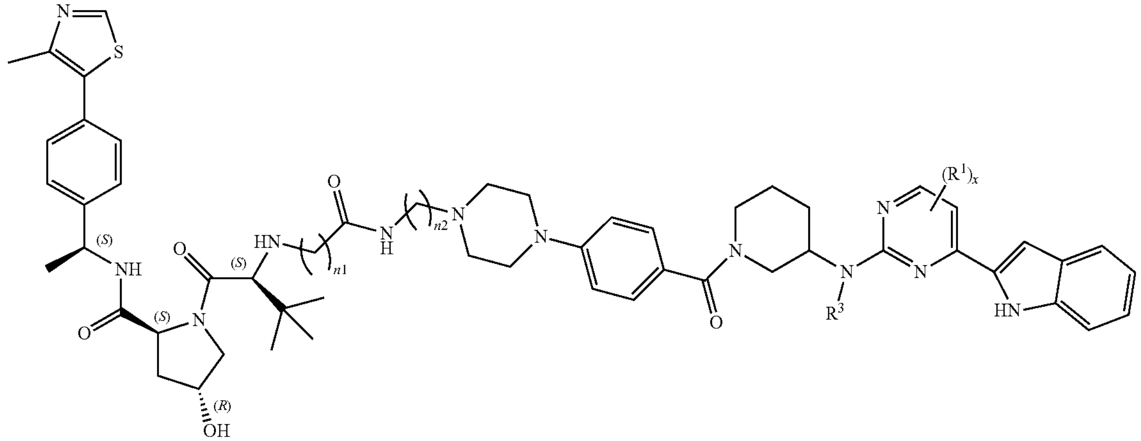
,
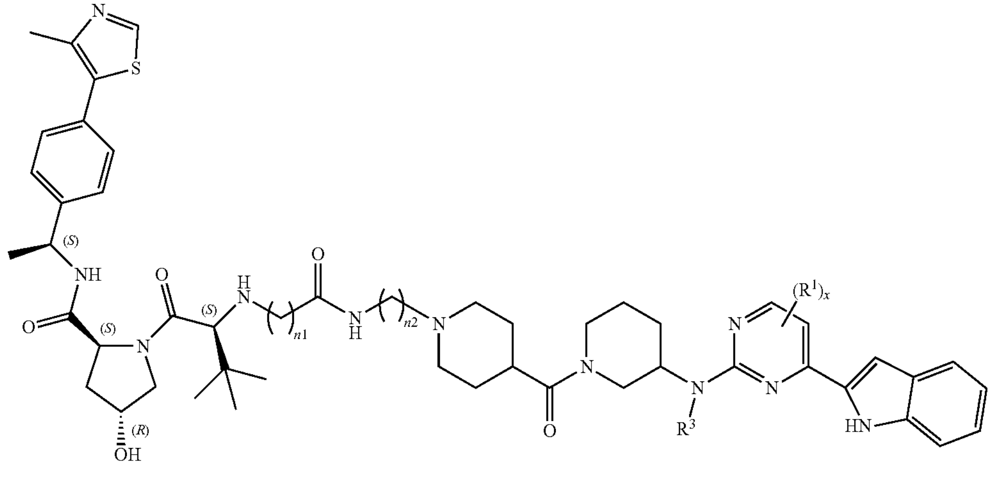
,

-continued
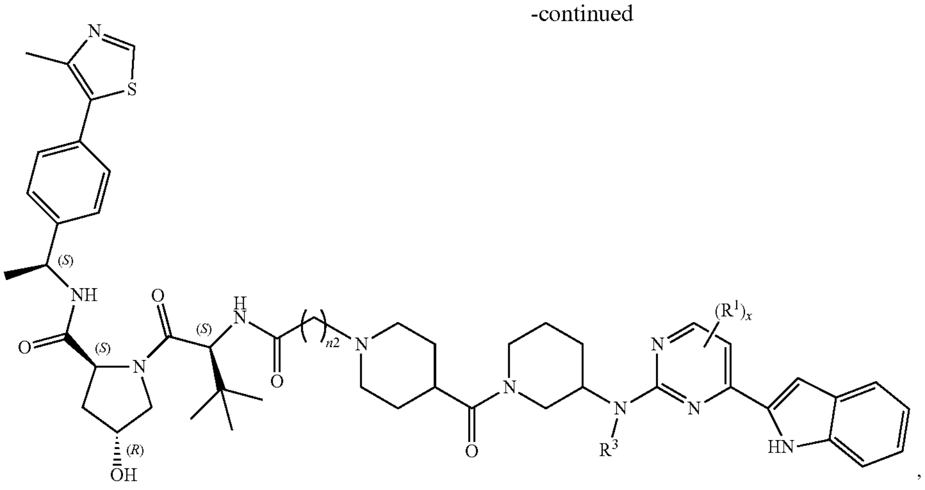
or a pharmaceutically acceptable salt, co-crystal, tautomer, stereoisomer, solvate, hydrate, polymorph, isotopically enriched derivative, or prodrug thereof.
In certain embodiments, the compound of Formula (I) is of the formula:
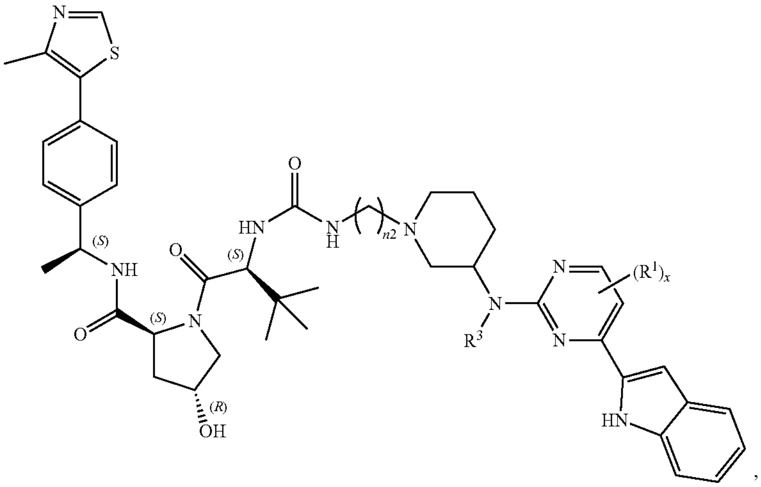
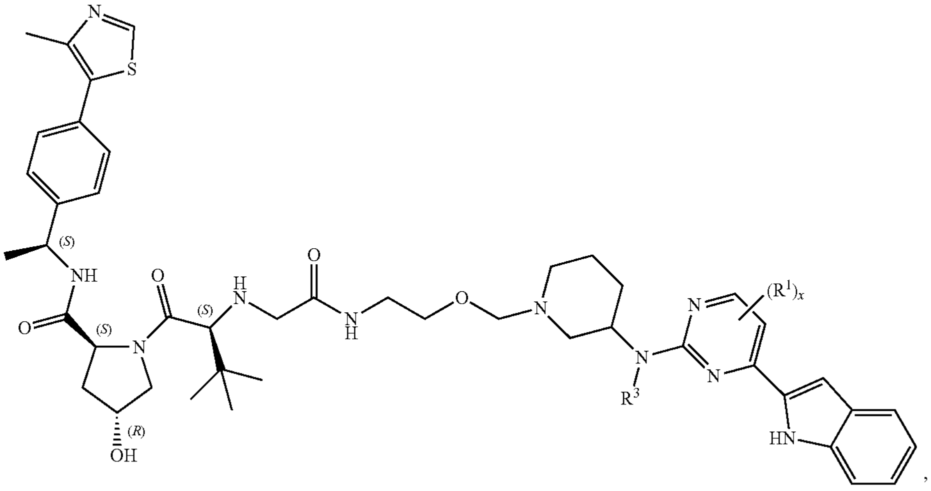

-continued
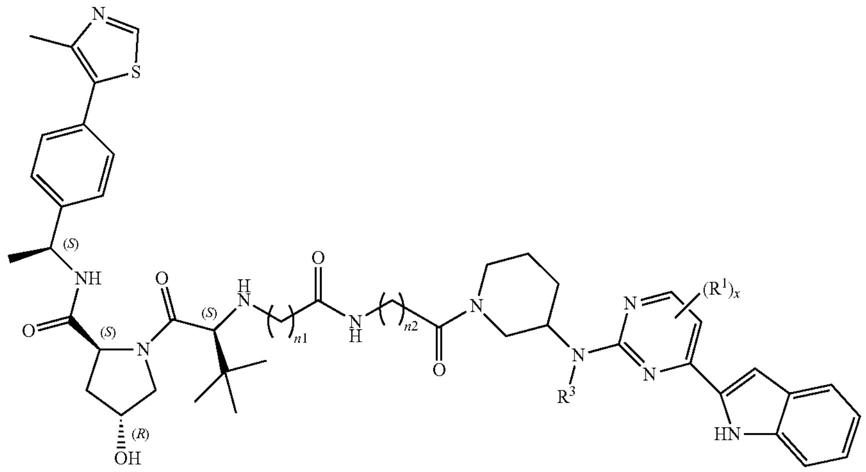
,
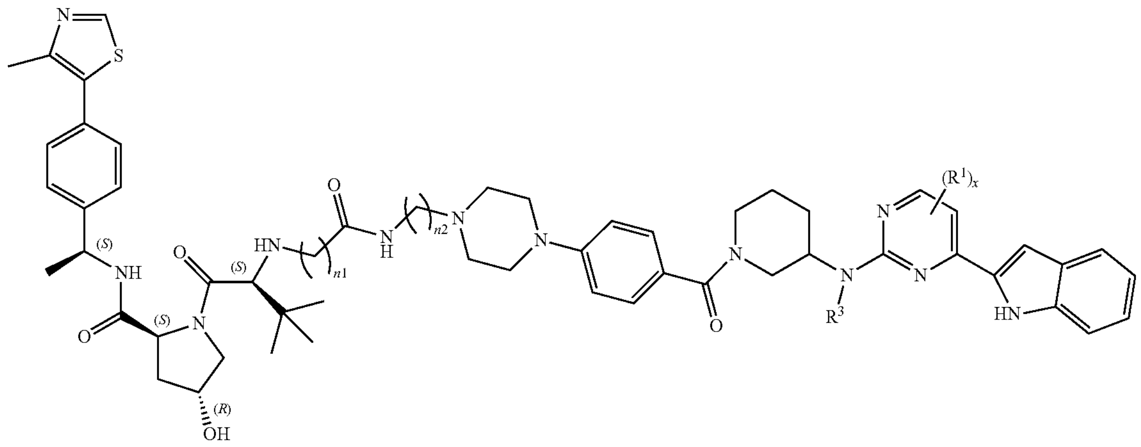
,
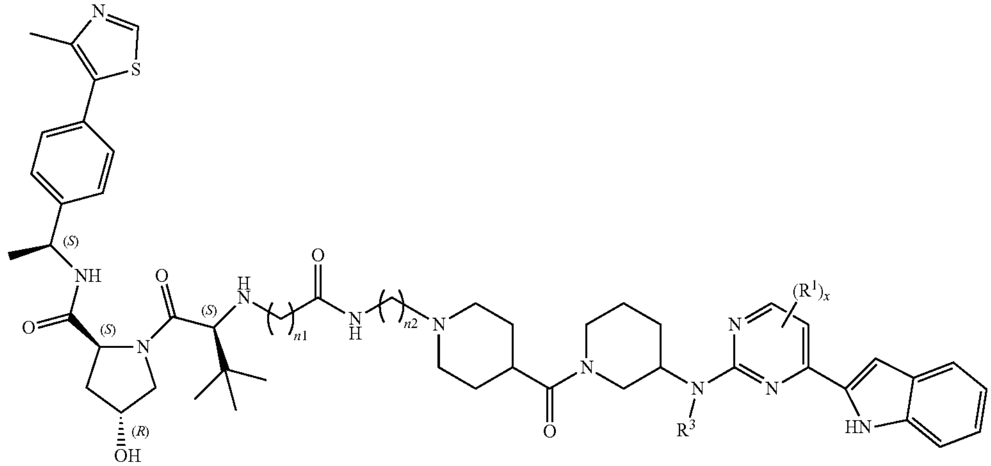
, or a pharmaceutically acceptable salt, co-crystal, tautomer, stereoisomer, solvate, hydrate, polymorph, isotopically enriched derivative, or prodrug thereof.

In certain embodiments, the compound of Formula (I) is of the formula:

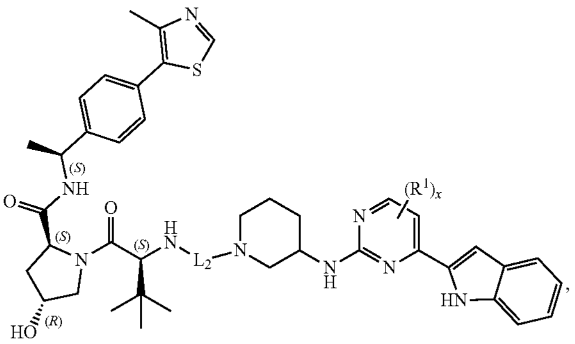

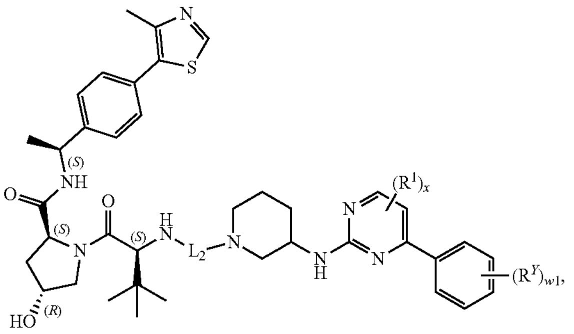

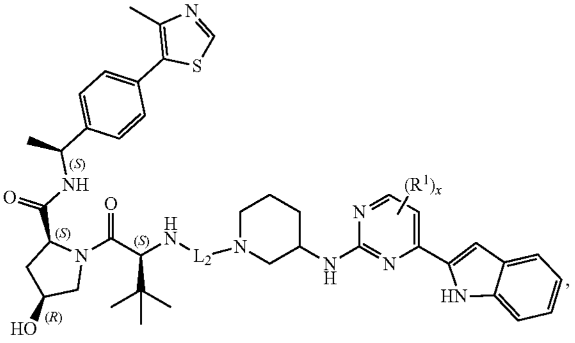

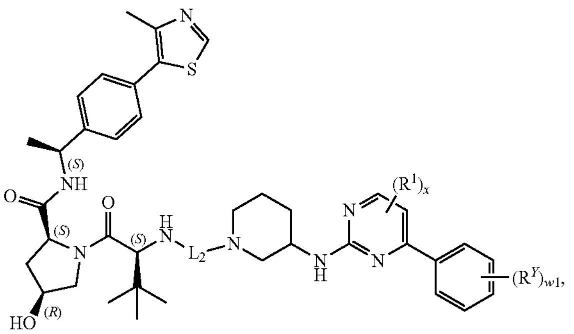

or a pharmaceutically acceptable salt, co-crystal, tautomer, stereoisomer, solvate, hydrate, polymorph, isotopically enriched derivative, or prodrug thereof.

wherein $R^1$ is halogen or optionally substituted $C_{1-6}$ alkyl; and

L2 is of the formula:

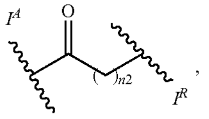

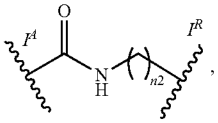

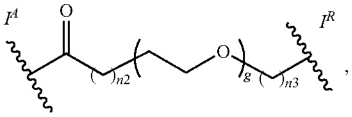

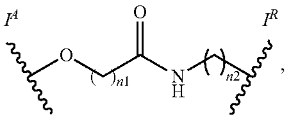

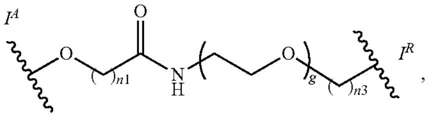

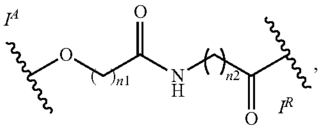

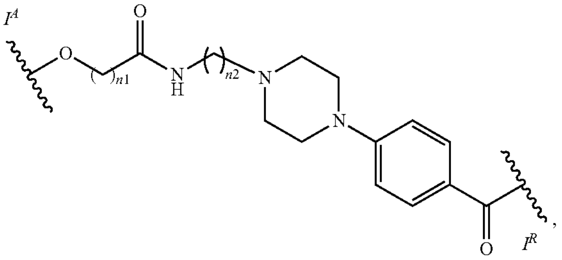

or

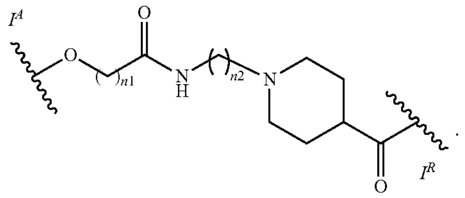

In certain embodiments, the compound of Formula (I) is of the formula:

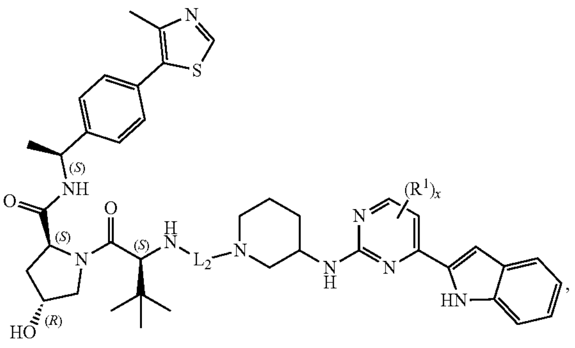

or a pharmaceutically acceptable salt, co-crystal, tautomer, stereoisomer, solvate, hydrate, polymorph, isotopically enriched derivative, or prodrug thereof.
wherein $R^1$ is halogen or optionally substituted $C_{1-6}$ alkyl; L2 is of the formula:
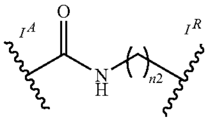
,
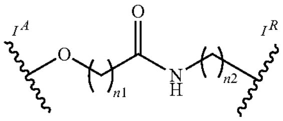
,
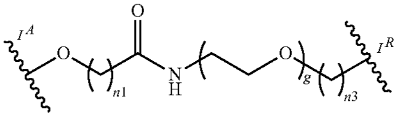
,
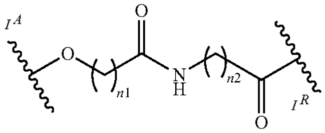
,
-continued
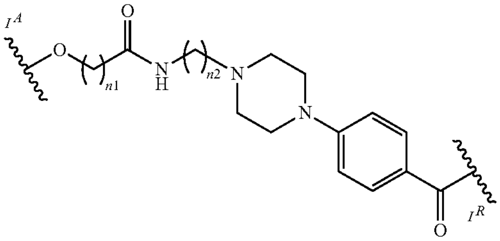
, or
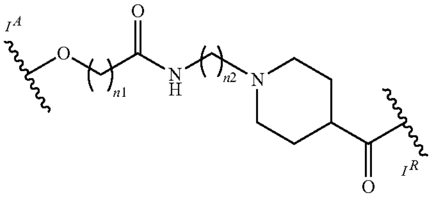
.
In certain embodiments, the compound of Formula (I) is of the formula:
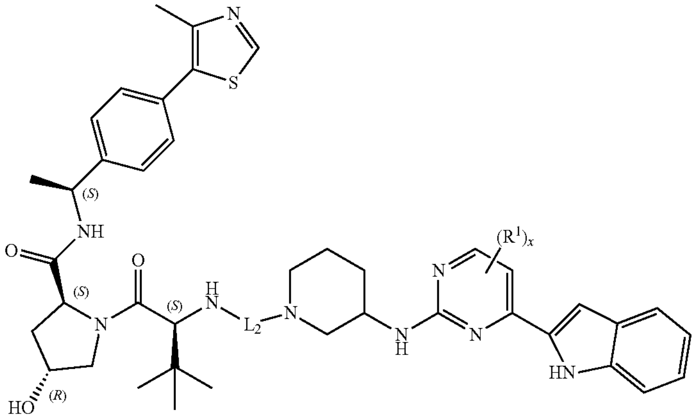
,
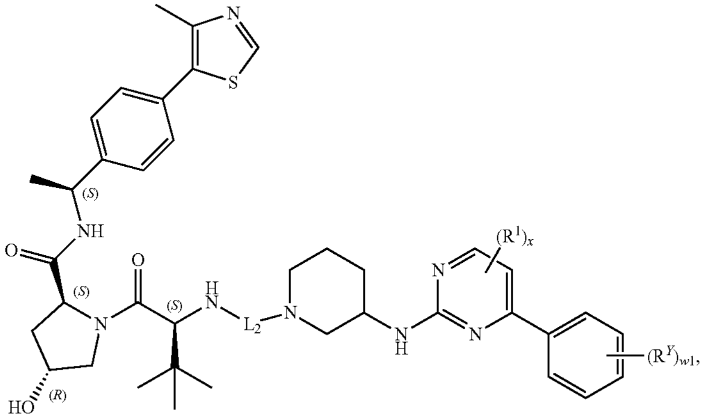

-continued
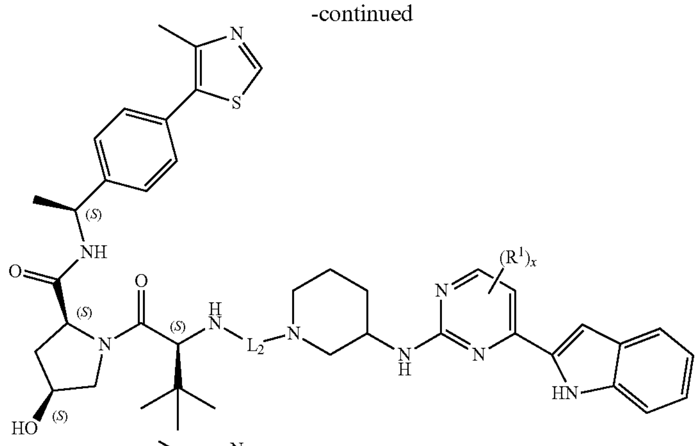
,
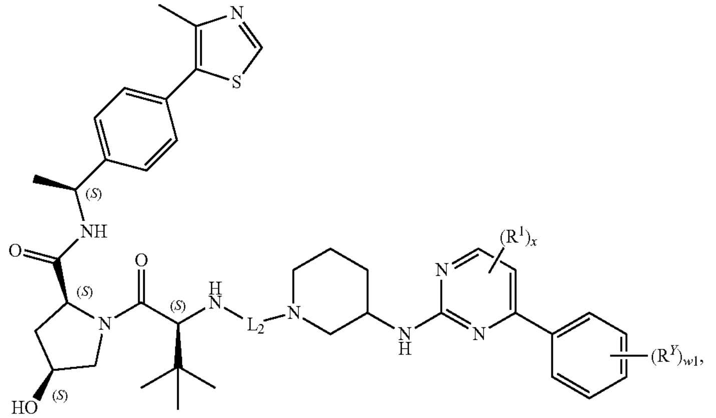
or a pharmaceutically acceptable salt, co-crystal, tautomer, stereoisomer, solvate, hydrate, polymorph, isotopically enriched derivative, or prodrug thereof.
wherein $R^1$ is halogen or optionally substituted $C_{1-6}$ alkyl;
L2 is of the formula:
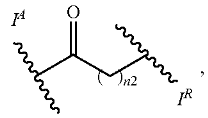
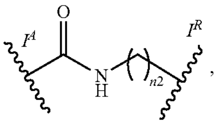
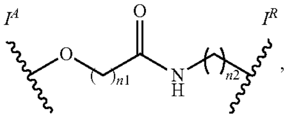
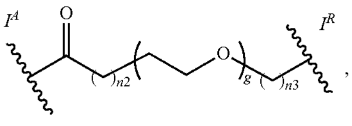
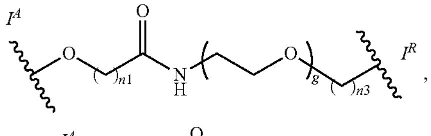
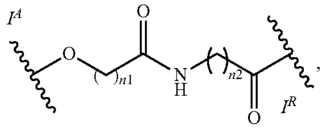
-continued
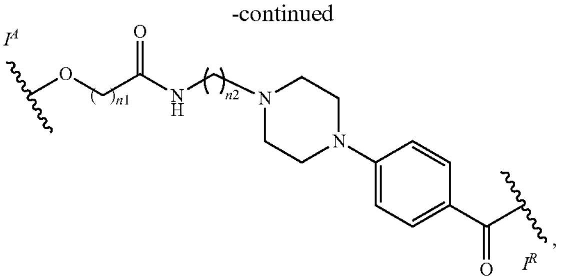
or
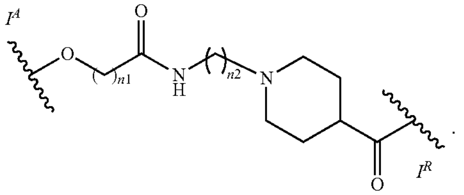
n1 is 1; n2 is 0, 1, 2, 3, 4, 5, 6, 7, 8, 9, or 10; n3 is 1 or 2; and g is 2 or 3.

In certain embodiments, the compound of Formula (I) is of the formula:

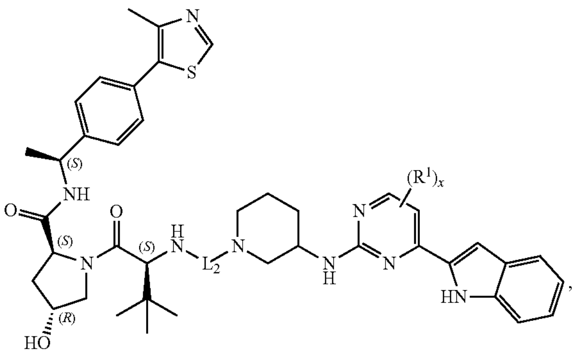

or a pharmaceutically acceptable salt, co-crystal, tautomer, stereoisomer, solvate, hydrate, polymorph, isotopically enriched derivative, or prodrug thereof.

wherein $R^1$ is halogen or optionally substituted $C_{1-6}$ alkyl;

L2 is of the formula:

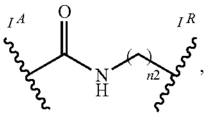

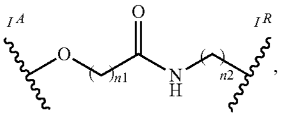

-continued

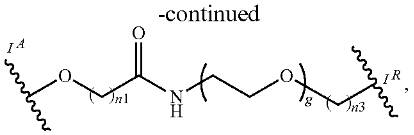

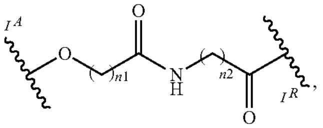

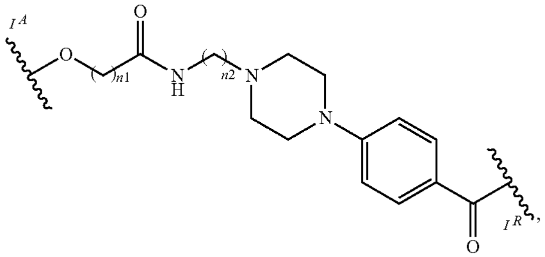

or

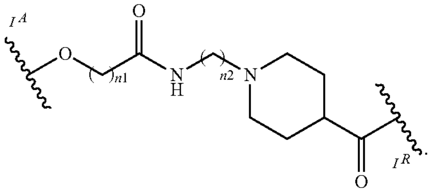

n1 is 1; n2 is 3, 4, 5, 6, 7, or 8; n3 is 1 or 2; and g is 2 or 3.

In certain embodiments, the compound of Formula (I) is of the formula:

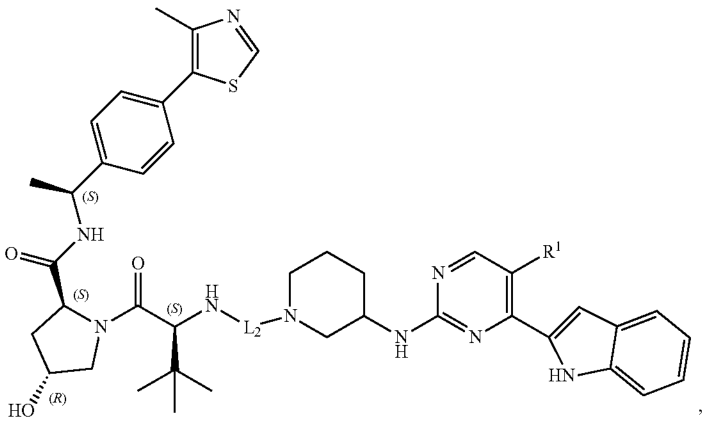

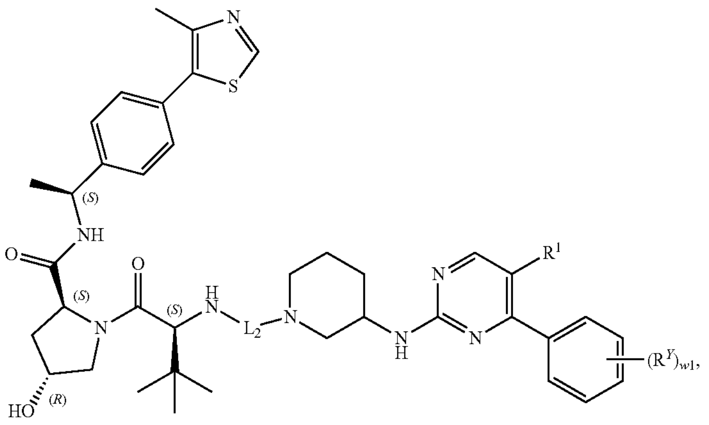

-continued

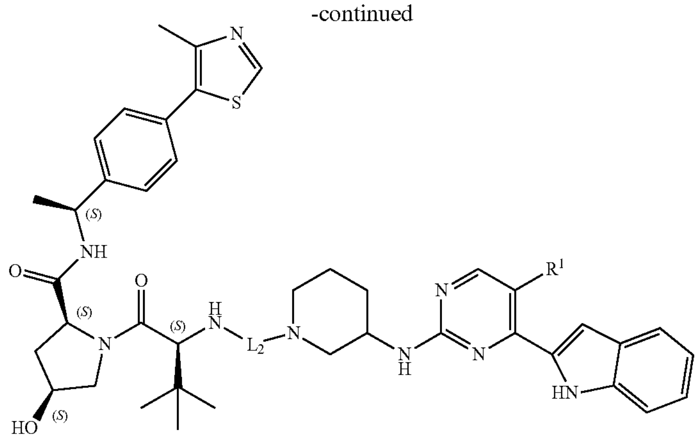

,

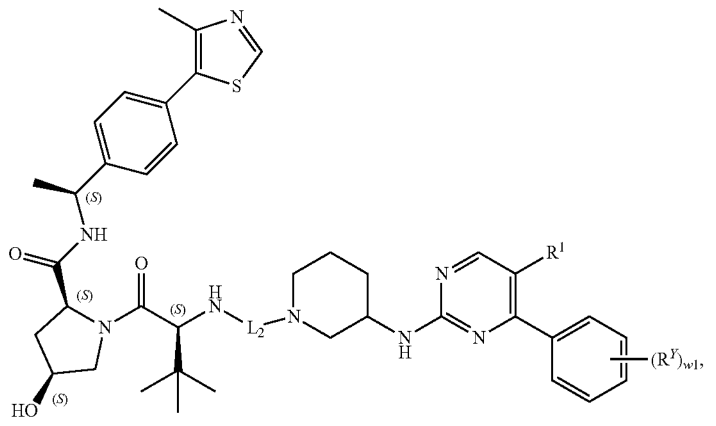

or a pharmaceutically acceptable salt, co-crystal, tautomer, stereoisomer, solvate, hydrate, polymorph, isotopically enriched derivative, or prodrug thereof.

In certain embodiments, the compound of Formula (I) is of the formula:

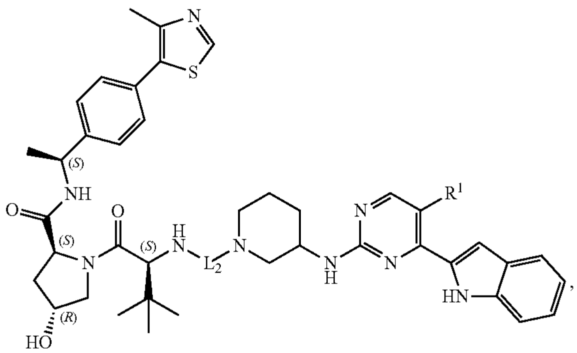

or a pharmaceutically acceptable salt, co-crystal, tautomer, stereoisomer, solvate, hydrate, polymorph, isotopically enriched derivative, or prodrug thereof.

In certain embodiments, the compound of Formula (I) is of the formula:
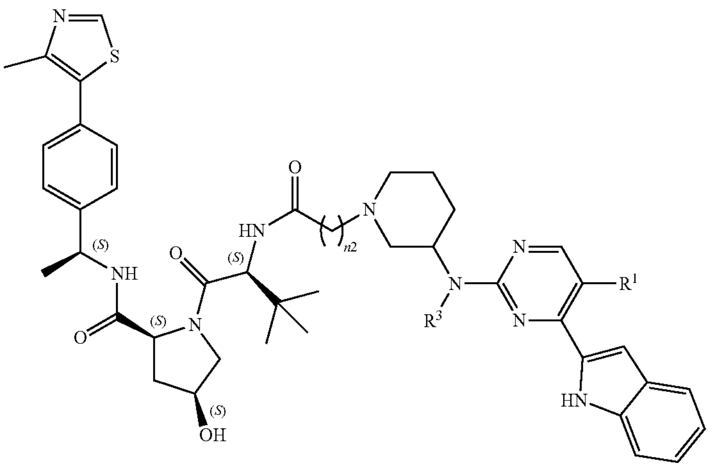
,
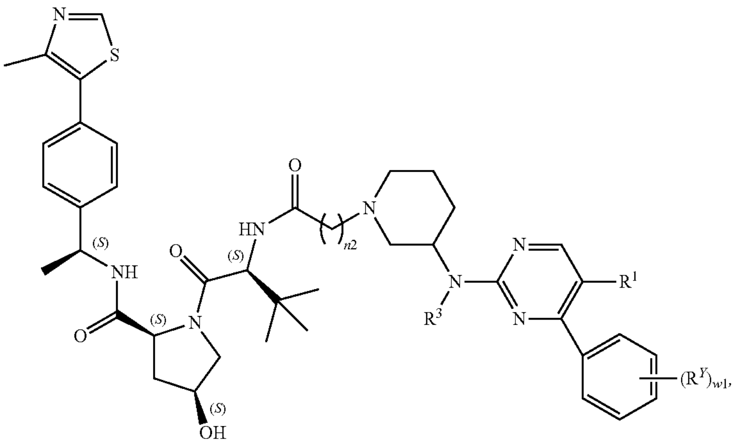
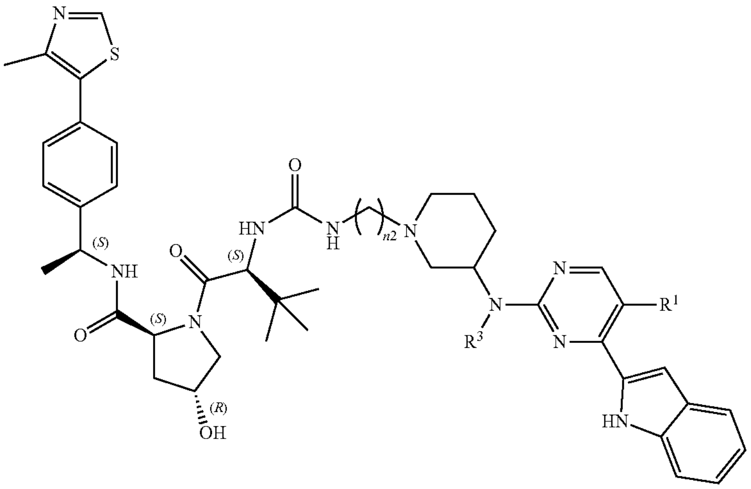
, -continued
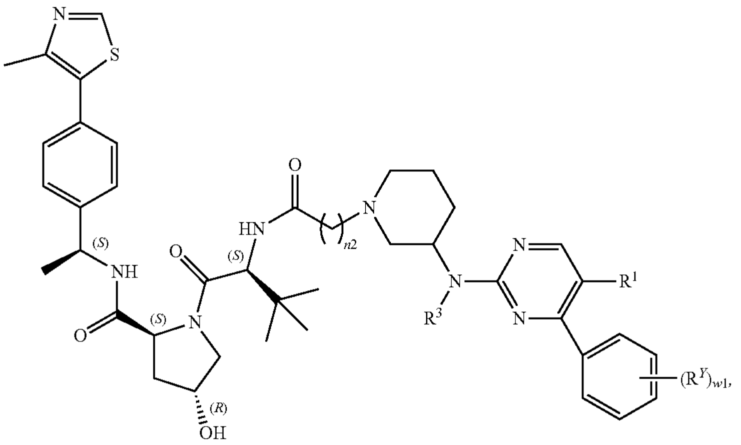
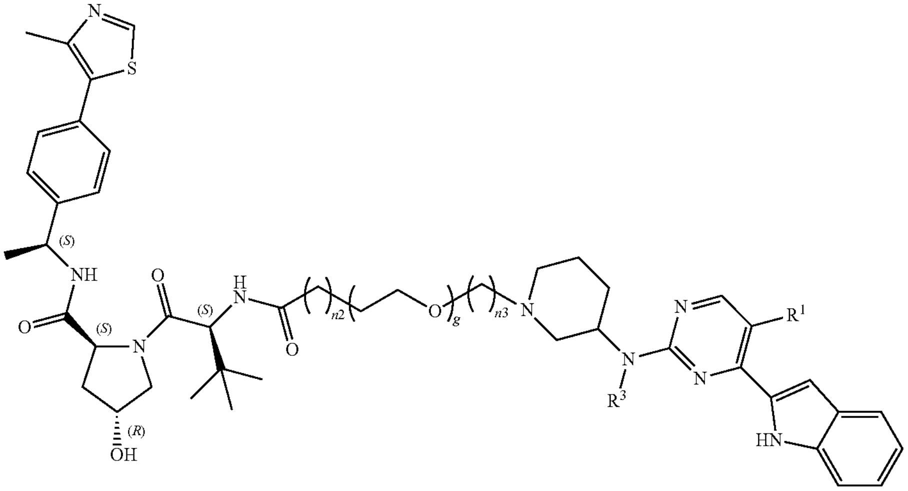
,
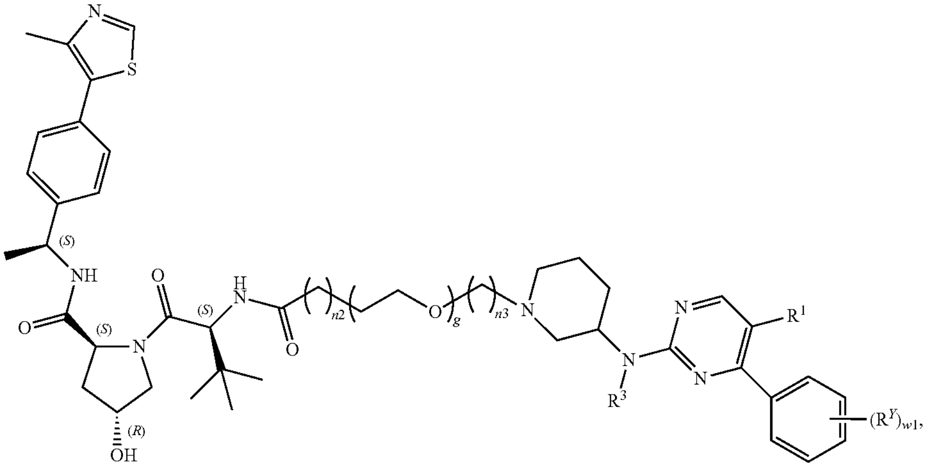

-continued
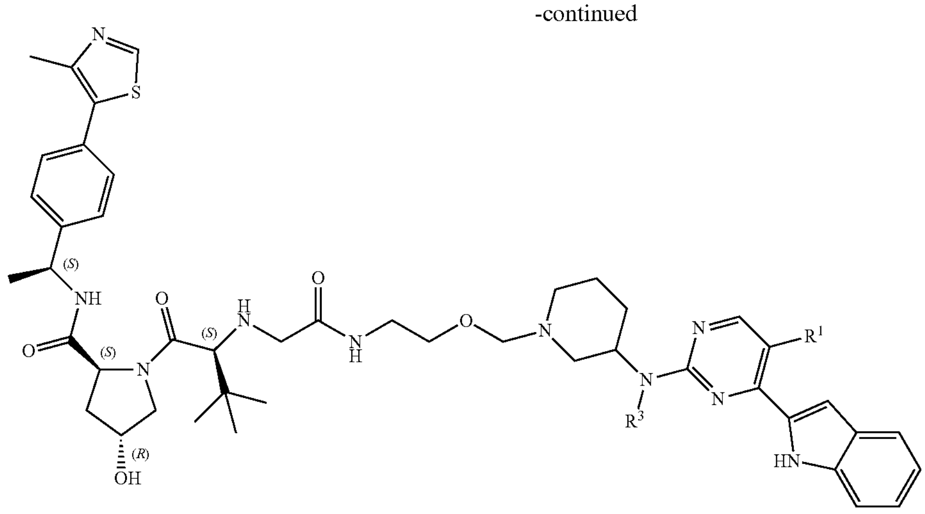
,
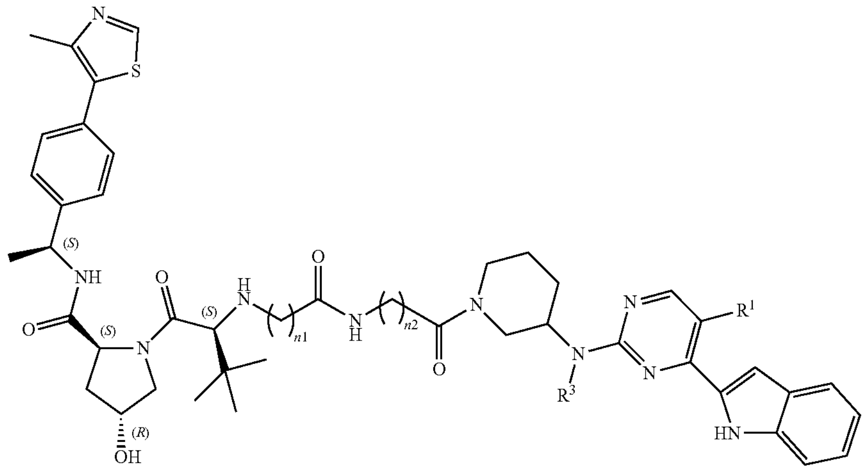
,
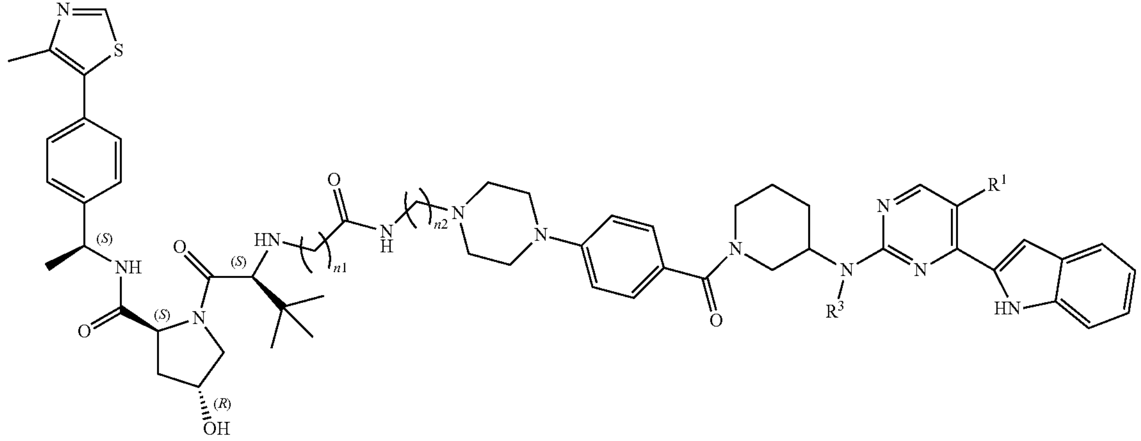
,

-continued
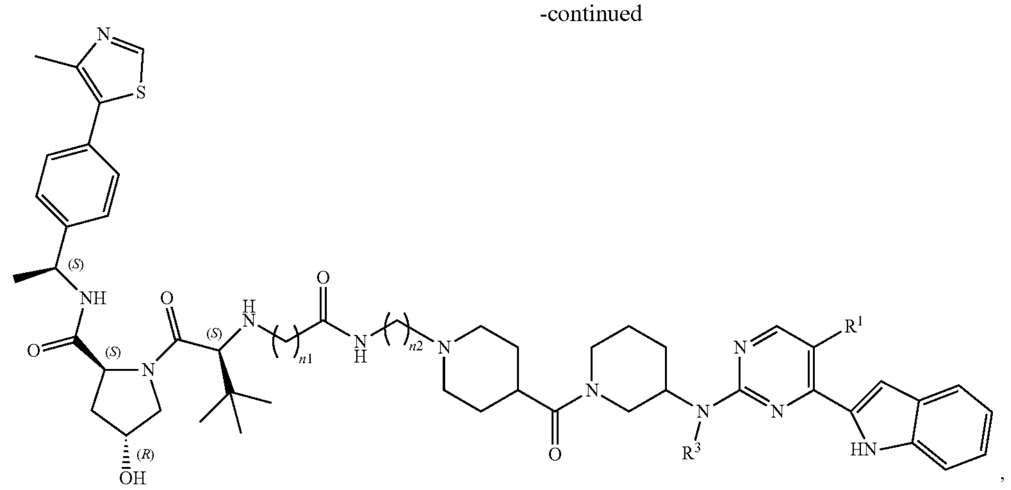
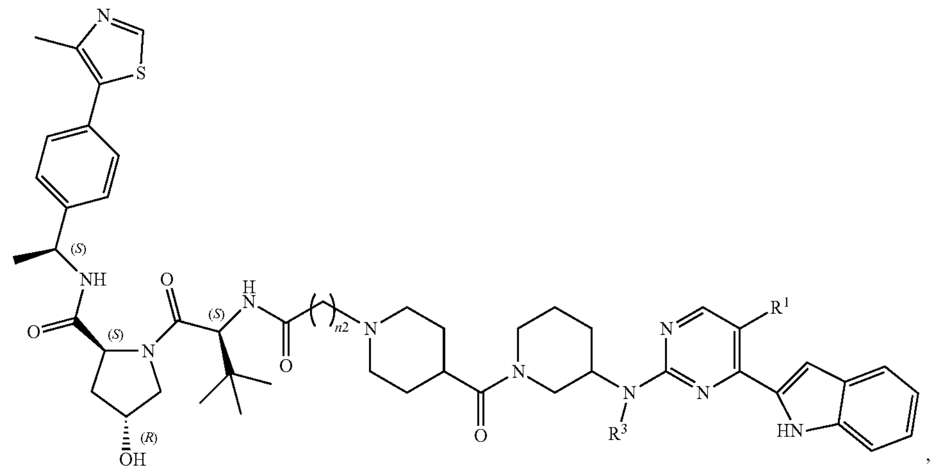
or a pharmaceutically acceptable salt, co-crystal, tautomer, stereoisomer, solvate, hydrate, polymorph, isotopically enriched derivative, or prodrug thereof.
In certain embodiments, the compound of Formula (I) is of the formula:
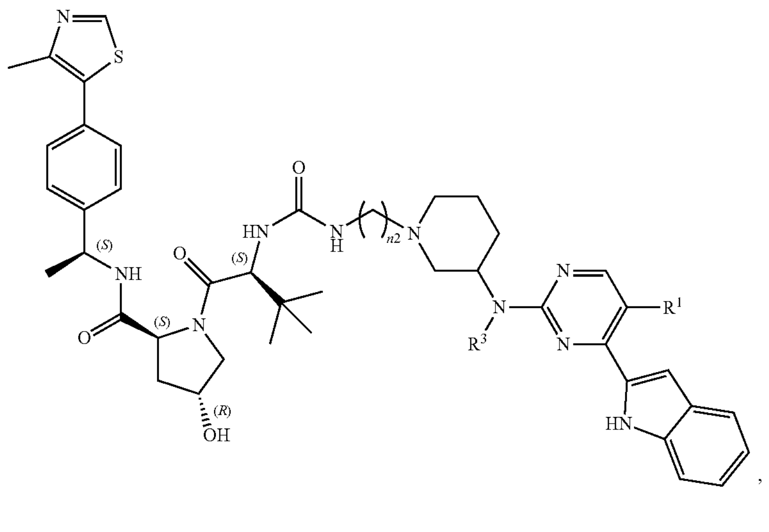

-continued
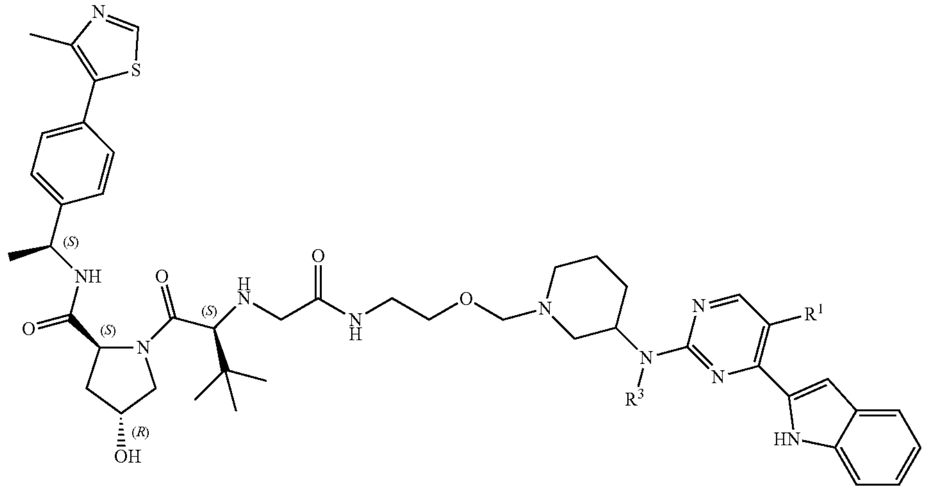
,
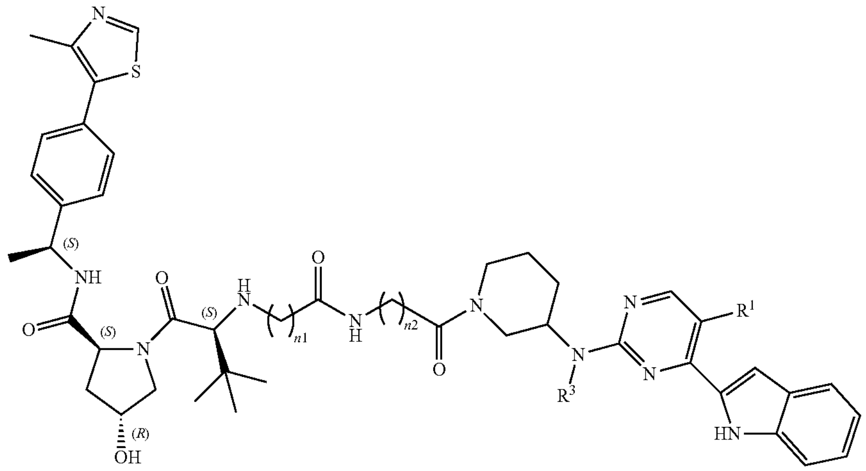
,
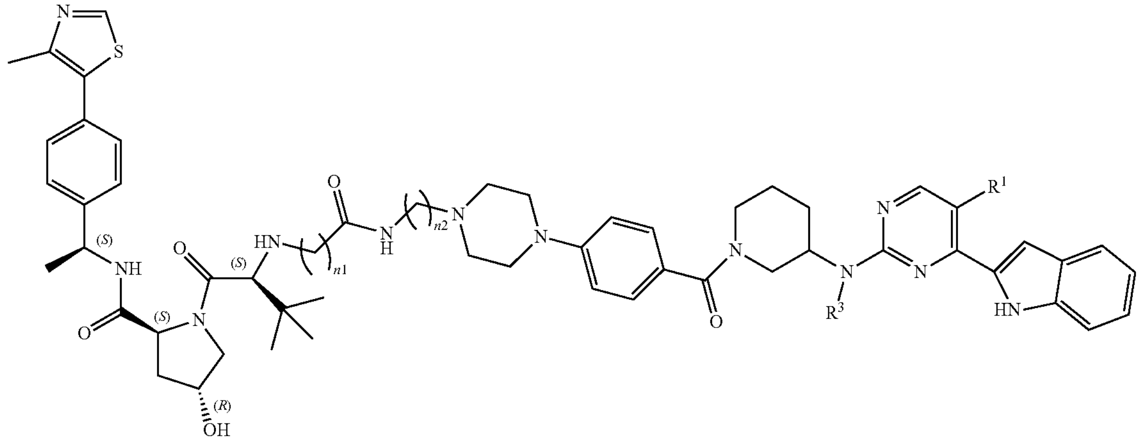
,

-continued

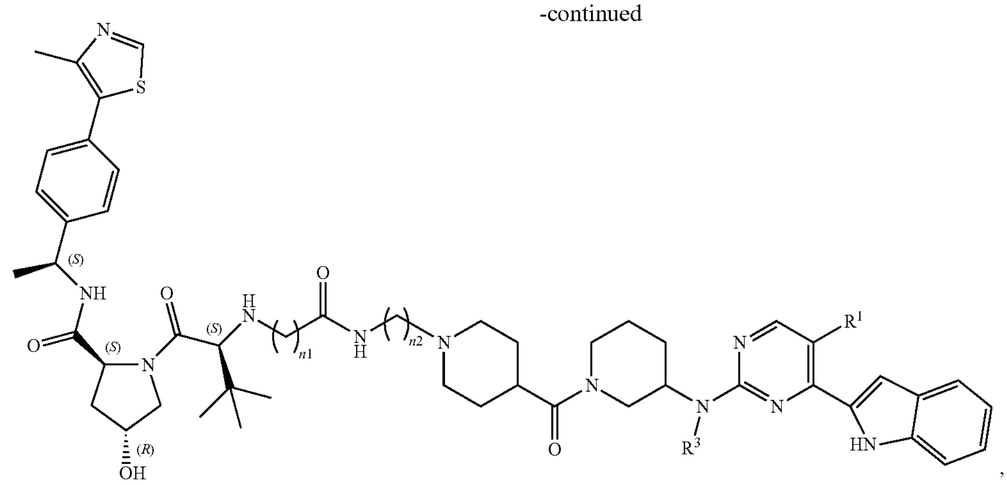

or a pharmaceutically acceptable salt, co-crystal, tautomer, stereoisomer, solvate, hydrate, polymorph, isotopically enriched derivative, or prodrug thereof.

In certain embodiments, the compound of Formula (I) is of the formula:

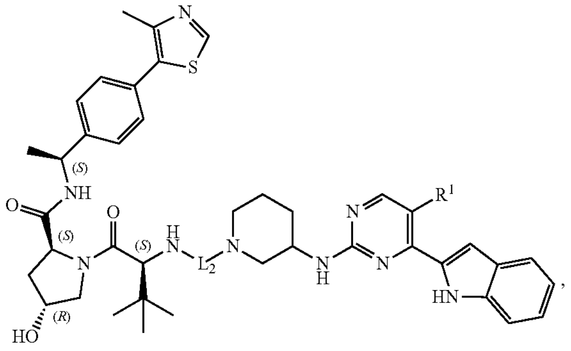

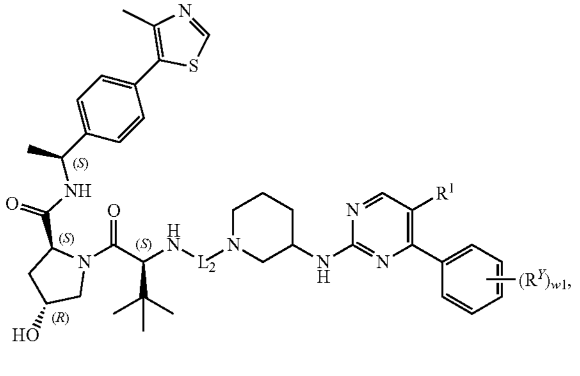

-continued

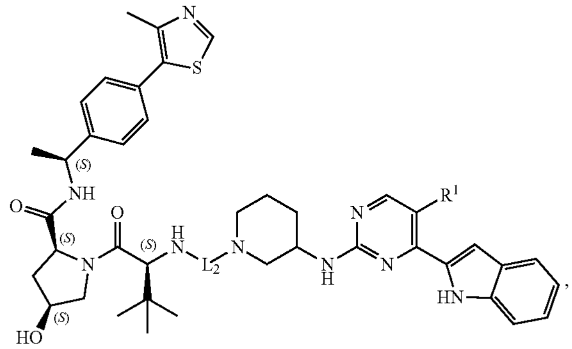

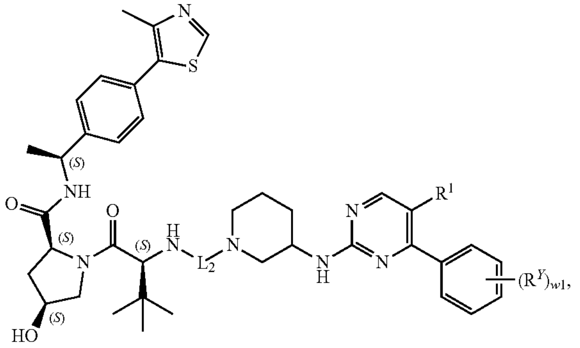

or a pharmaceutically acceptable salt, co-crystal, tautomer, stereoisomer, solvate, hydrate, polymorph, isotopically enriched derivative, or prodrug thereof;

wherein L2 is of the formula:

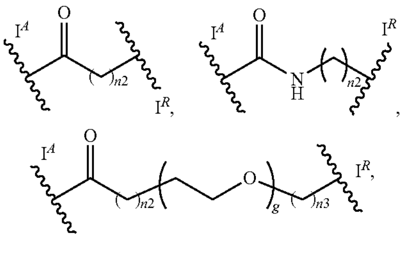

-continued
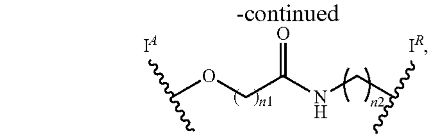
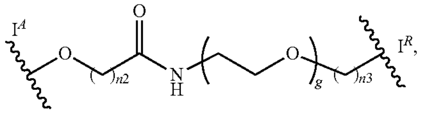
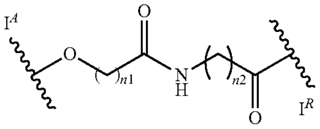
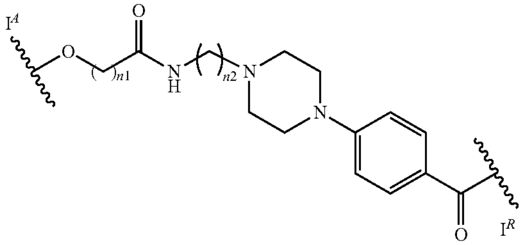
, or
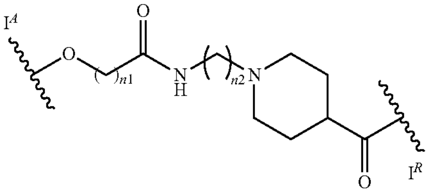
.
-continued
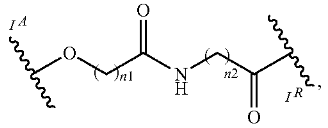
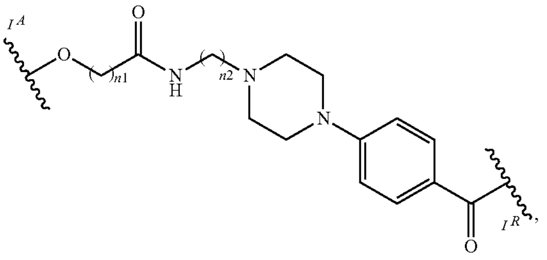
, or
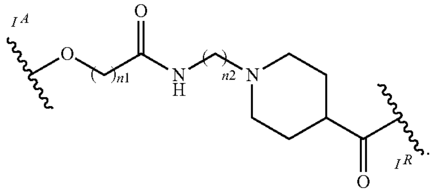
In certain embodiments, the compound of Formula (I) is of the formula:
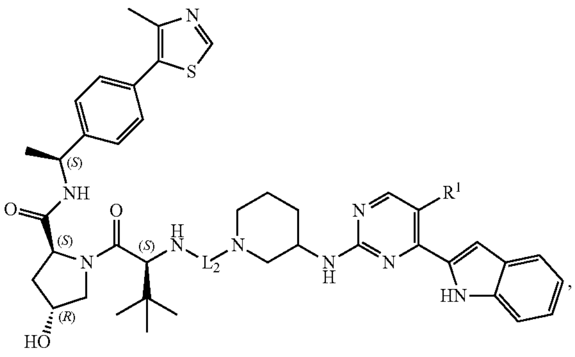
or a pharmaceutically acceptable salt, co-crystal, tautomer, stereoisomer, solvate, hydrate, polymorph, isotopically enriched derivative, or prodrug thereof;
wherein L2 is of the formula:
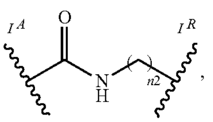
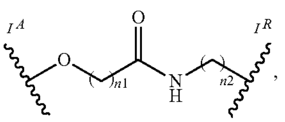
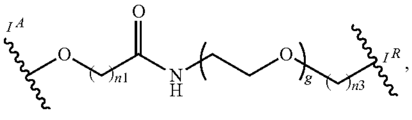
In certain embodiments, the compound of Formula (I) is of the formula:
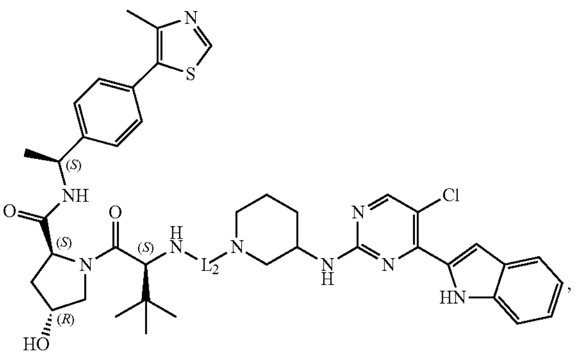
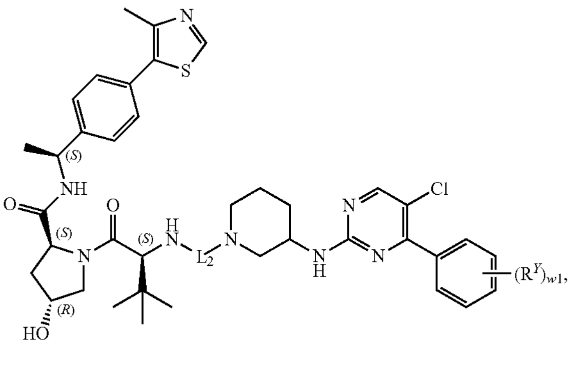

-continued

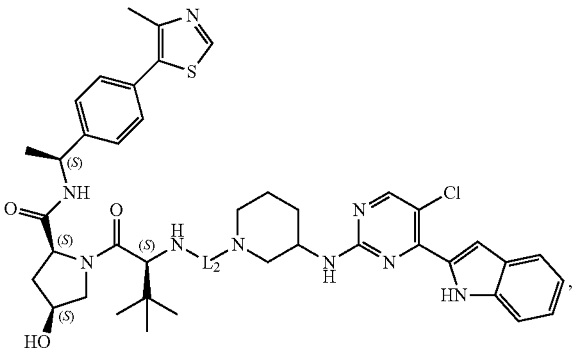

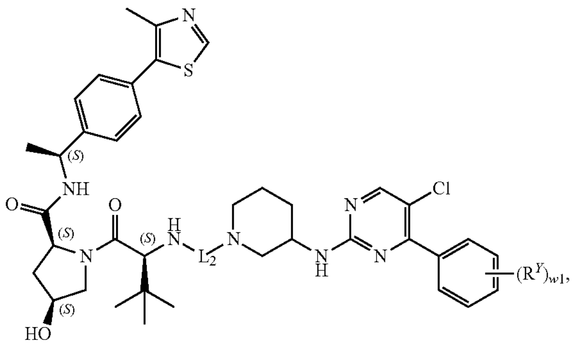

or a pharmaceutically acceptable salt, co-crystal, tautomer, stereoisomer, solvate, hydrate, polymorph, isotopically enriched derivative, or prodrug thereof.

In certain embodiments, the compound of Formula (I) is of the formula:

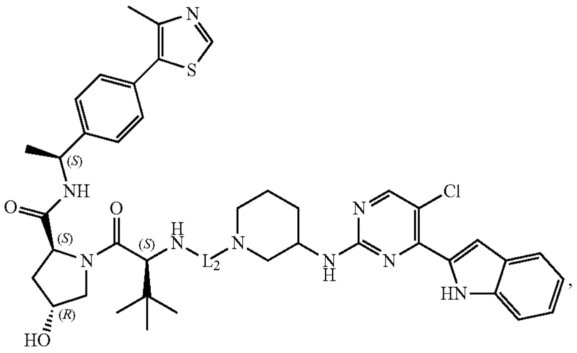

or a pharmaceutically acceptable salt, co-crystal, tautomer, stereoisomer, solvate, hydrate, polymorph, isotopically enriched derivative, or prodrug thereof.

In certain embodiments, the compound of Formula (I) is of the formula:

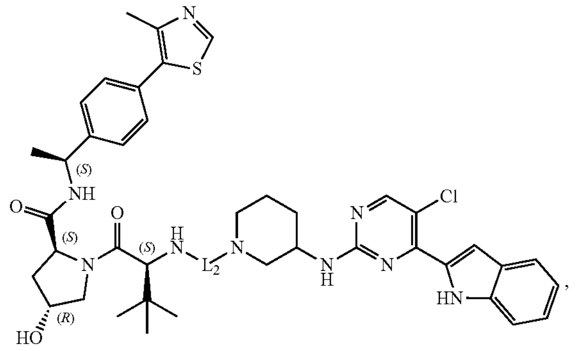

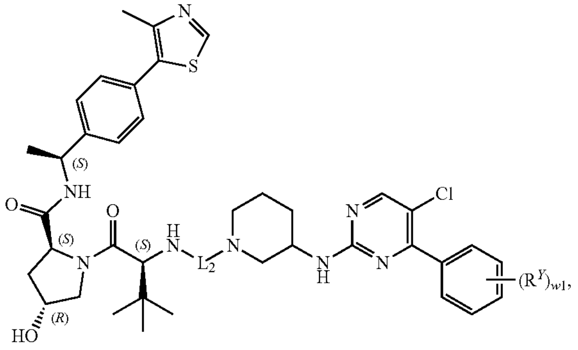

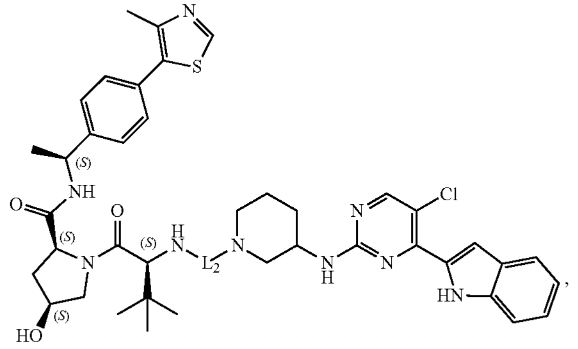

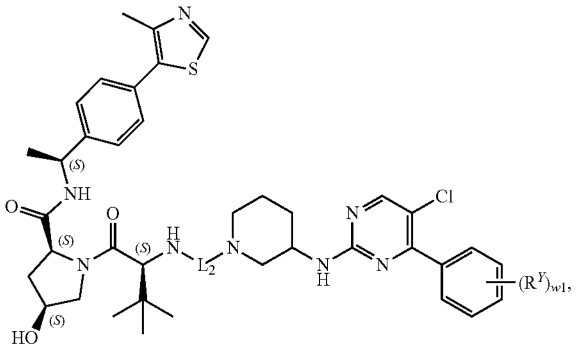

or a pharmaceutically acceptable salt, co-crystal, tautomer, stereoisomer, solvate, hydrate, polymorph, isotopically enriched derivative, or prodrug thereof, wherein L2 is of the formula:
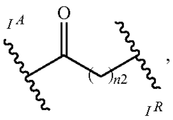,
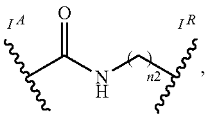,
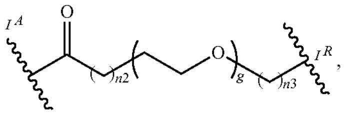,
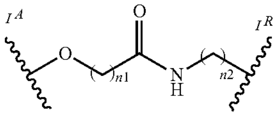,
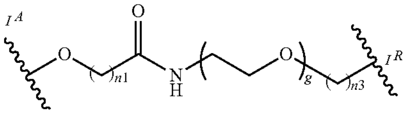,
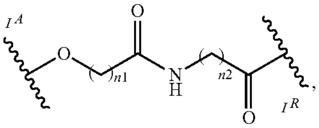,
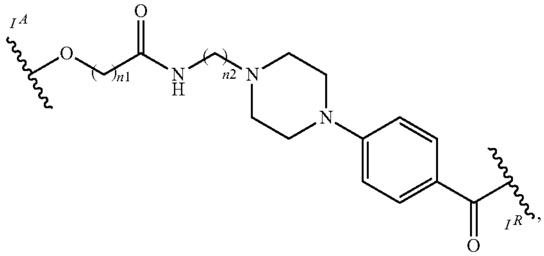, or
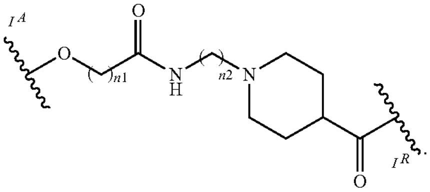.
In certain embodiments, the compound of Formula (I) is of the formula:
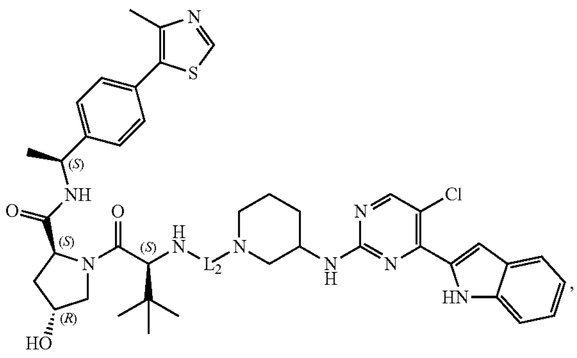,
or a pharmaceutically acceptable salt, co-crystal, tautomer, stereoisomer, solvate, hydrate, polymorph, isotopically enriched derivative, or prodrug thereof,
wherein L2 is of the formula:
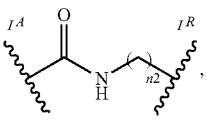,
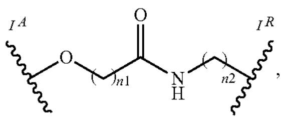,
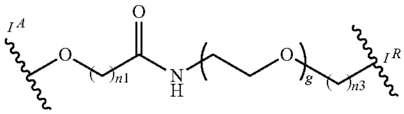,
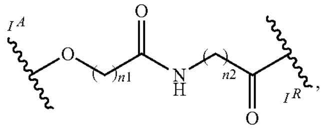,
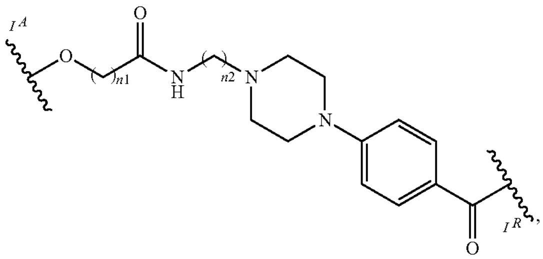, or
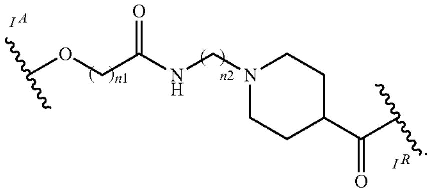.
In certain embodiments, the compound of Formula (I) is of the formula:
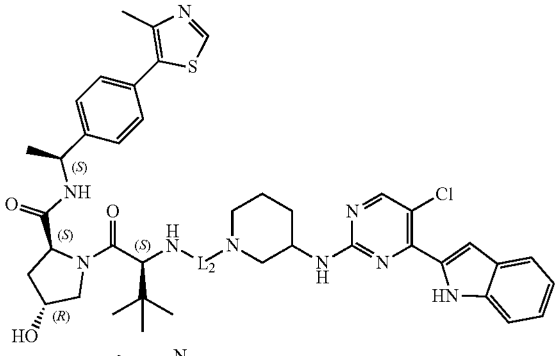,
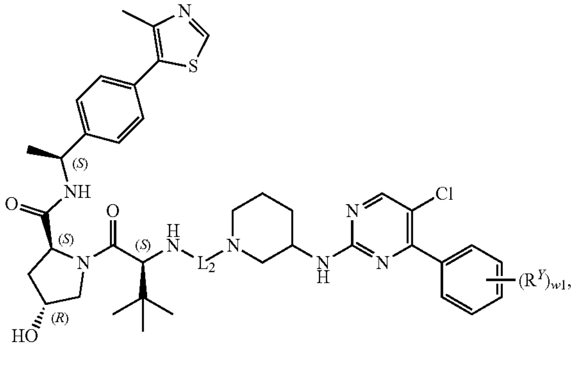

-continued

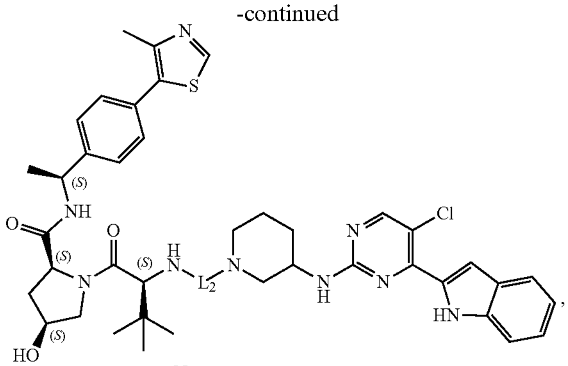

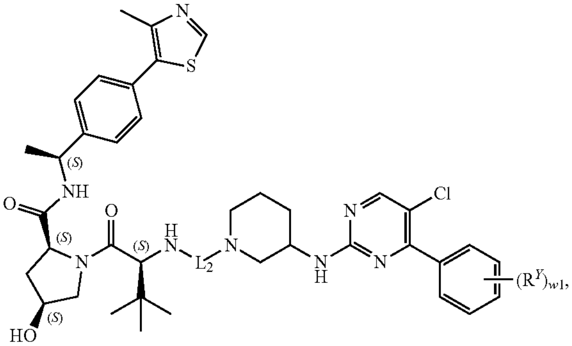

or a pharmaceutically acceptable salt, co-crystal, tautomer, stereoisomer, solvate, hydrate, polymorph, isotopically enriched derivative, or prodrug thereof, wherein L2 is of the formula:

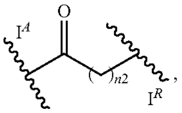, 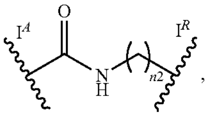,

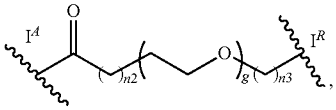,

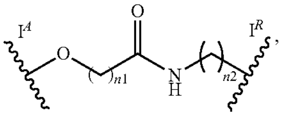,

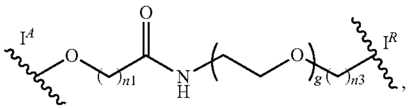,

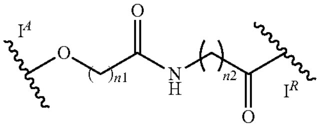,

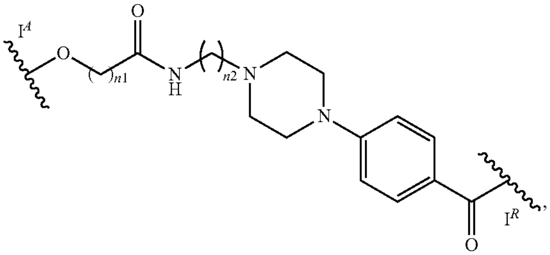, or

-continued

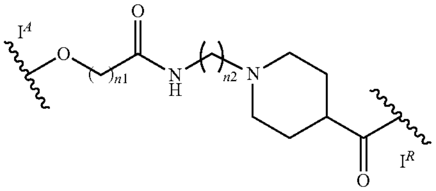;

n1 is 1; n2 is 0, 1, 2, 3, 4, 5, 6, 7, 8, 9, or 10; n3 is 1 or 2; and g is 2 or 3.

In certain embodiments, the compound of Formula (I) is of the formula:

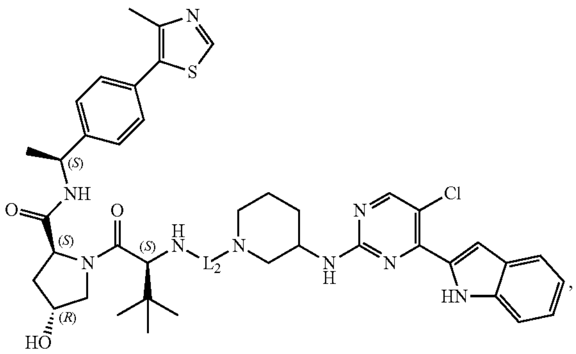, or a pharmaceutically acceptable salt, co-crystal, tautomer, stereoisomer, solvate, hydrate, polymorph, isotopically enriched derivative, or prodrug thereof, wherein L2 is of the formula:

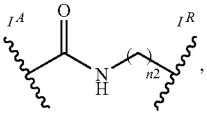, 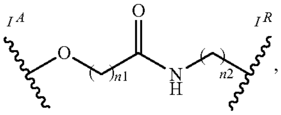,

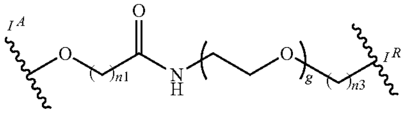,

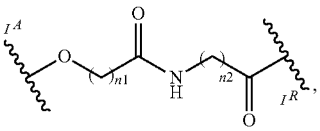,

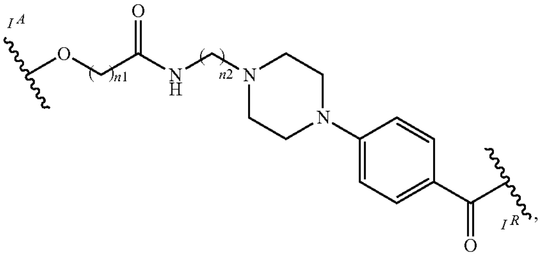, or

-continued
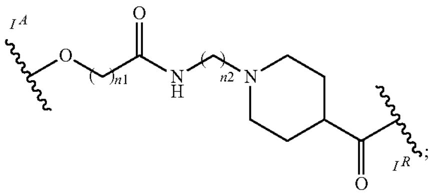
n1 is 1; n2 is 3, 4, 5, 6, 7, or 8; n3 is 1 or 2; and g is 2 or 3.
In certain embodiments, the compound of Formula (I) is of the formula:
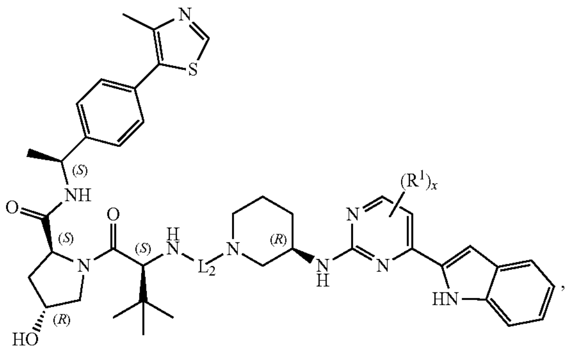
,
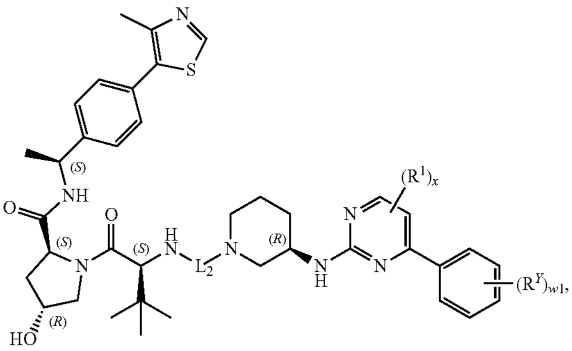
,
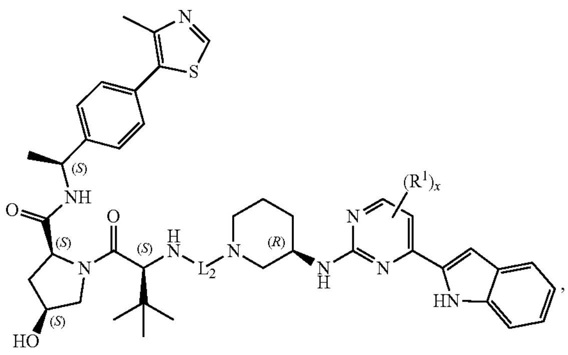
,
-continued
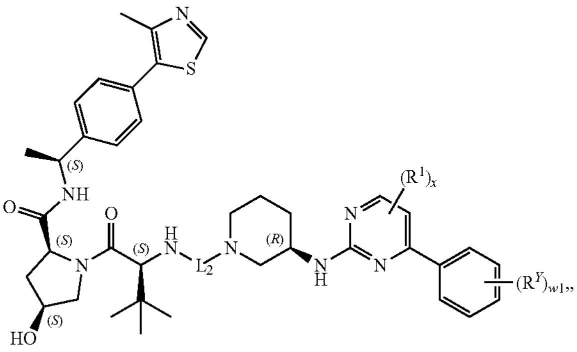
,
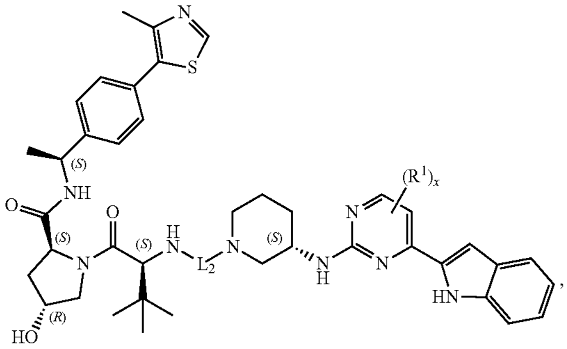
,
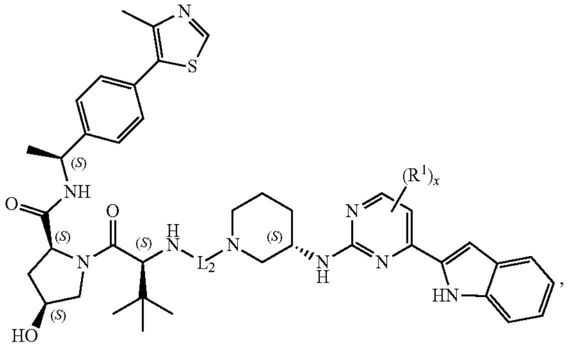
,
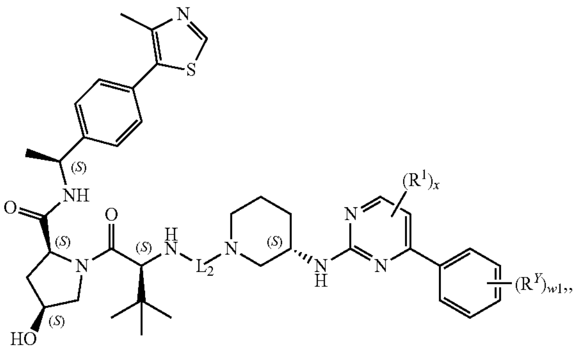
,
or a pharmaceutically acceptable salt, co-crystal, tautomer, stereoisomer, solvate, hydrate, polymorph, isotopically enriched derivative, or prodrug thereof.

In certain embodiments, the compound of Formula (I) is of the formula:
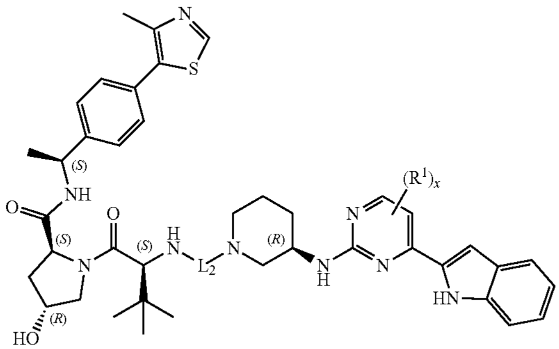
,
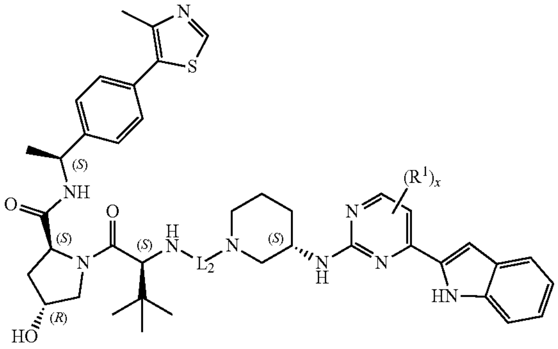
,
or a pharmaceutically acceptable salt, co-crystal, tautomer, stereoisomer, solvate, hydrate, polymorph, isotopically enriched derivative, or prodrug thereof.
In certain embodiments, the compound of Formula (I) is of the formula:
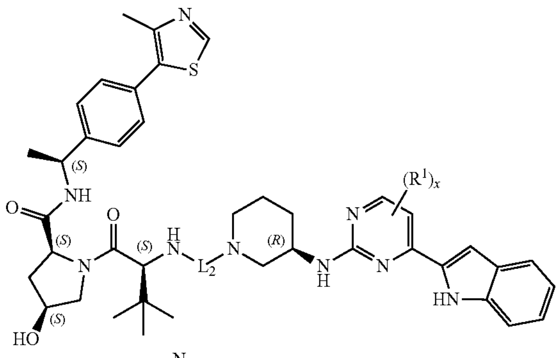
,
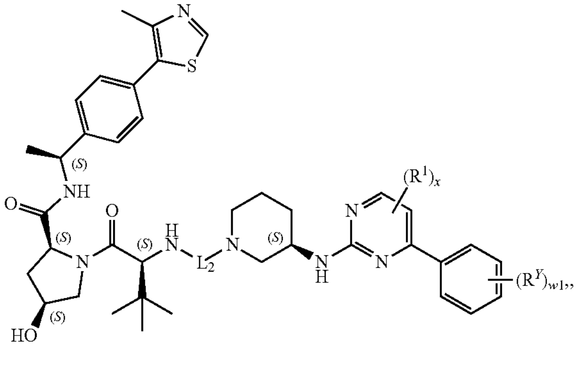
,
-continued
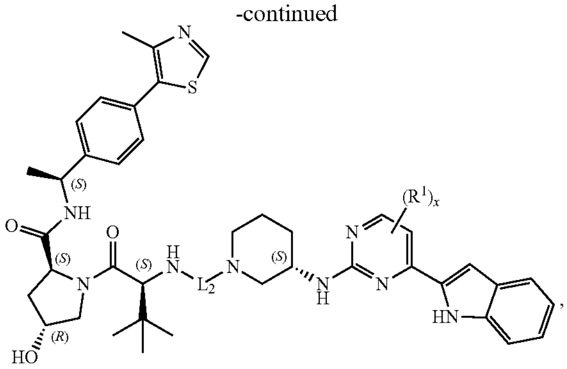
,
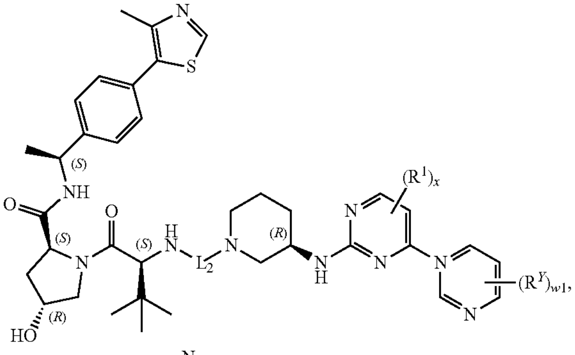
,
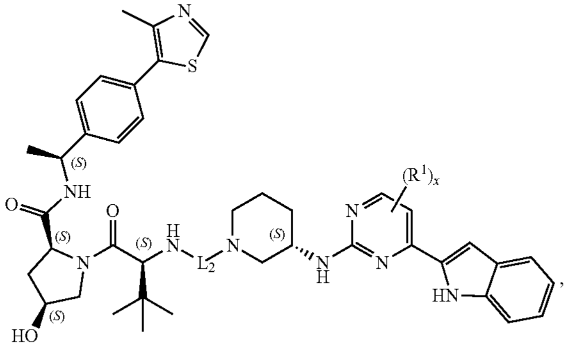
,
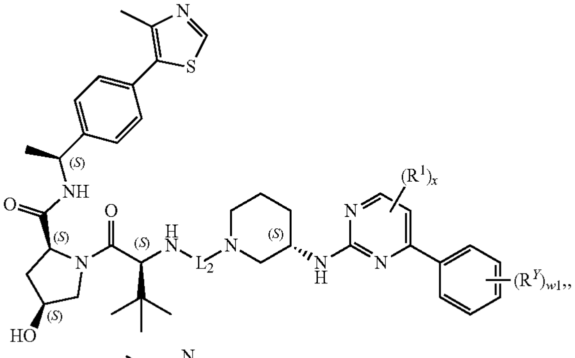
,
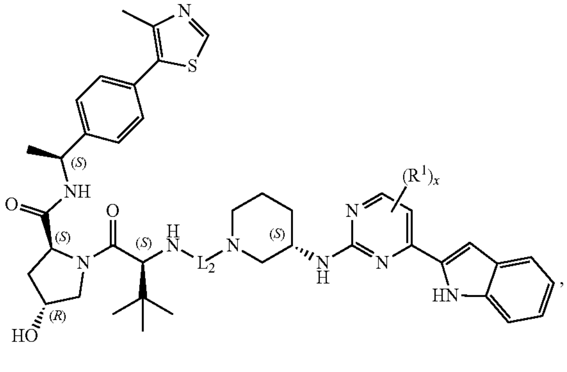
, -continued

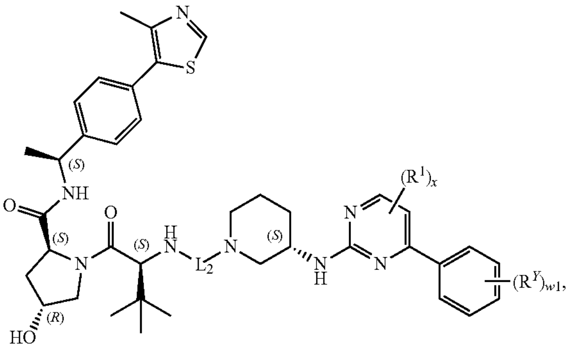

or a pharmaceutically acceptable salt, co-crystal, tautomer, stereoisomer, solvate, hydrate, polymorph, isotopically enriched derivative, or prodrug thereof, wherein $R^1$ is halogen or optionally substituted $C_{1-6}$ alkyl; and L2 is of the formula:

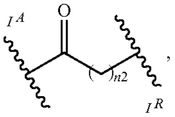
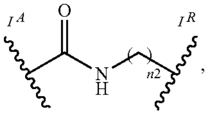
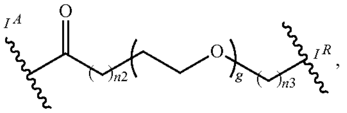
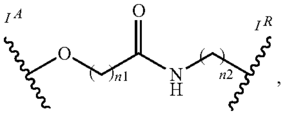
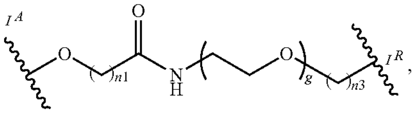
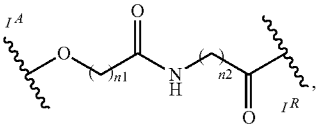
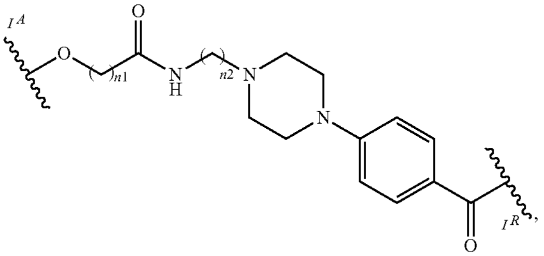
or
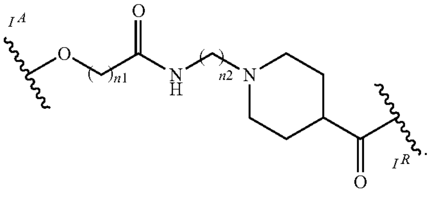

In certain embodiments, the compound of Formula (I) is of the formula:

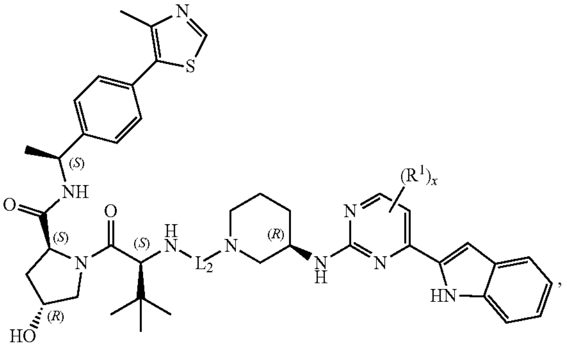
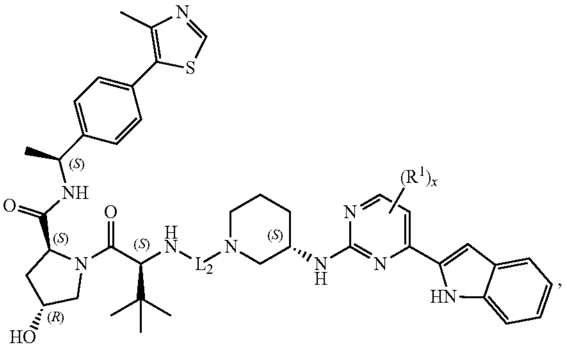

or a pharmaceutically acceptable salt, co-crystal, tautomer, stereoisomer, solvate, hydrate, polymorph, isotopically enriched derivative, or prodrug thereof, wherein $R^1$ is halogen or optionally substituted $C_{1-6}$ alkyl; and L2 is of the formula:

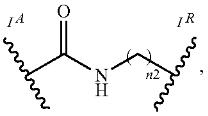
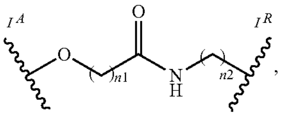
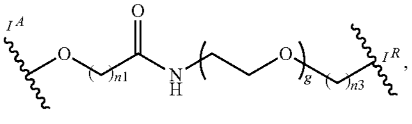
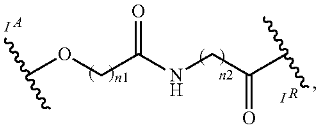
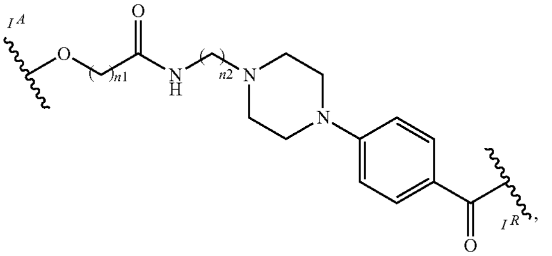
or

-continued
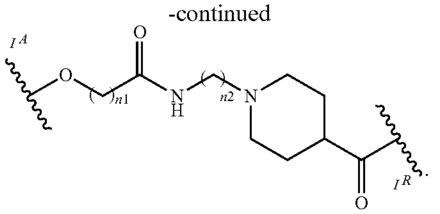
In certain embodiments, the compound of Formula (I) is of the formula:
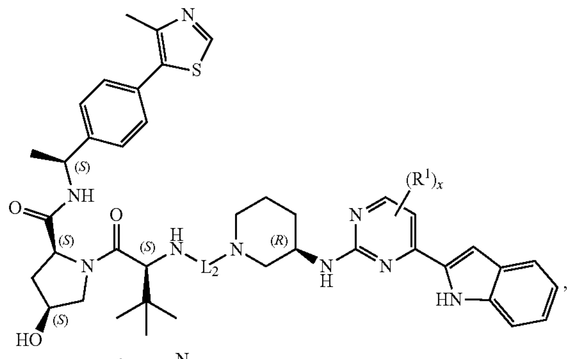
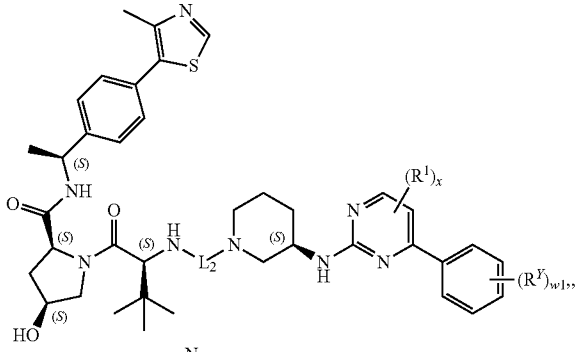
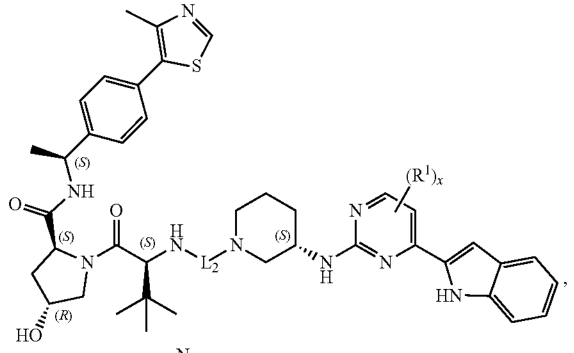
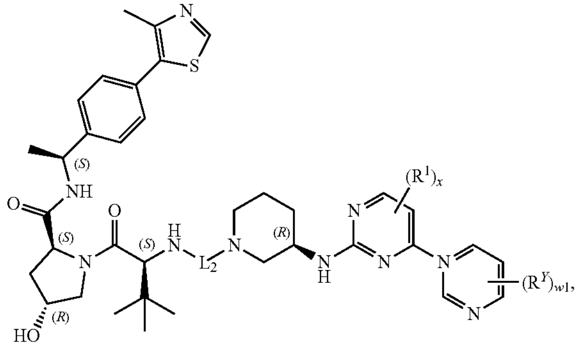
-continued
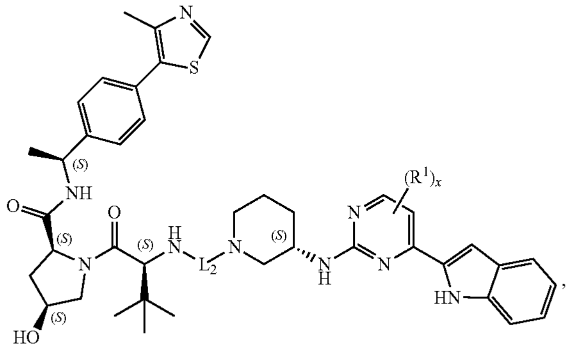
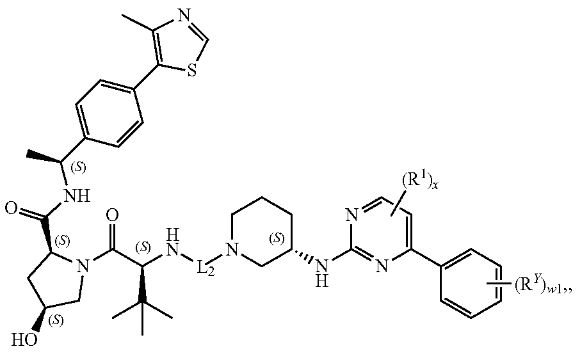
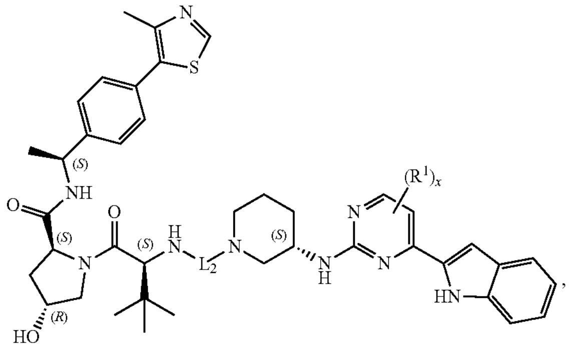
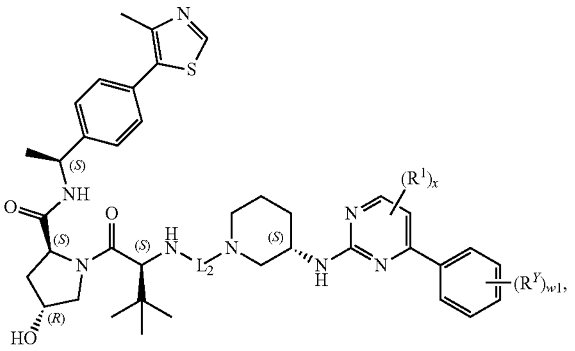
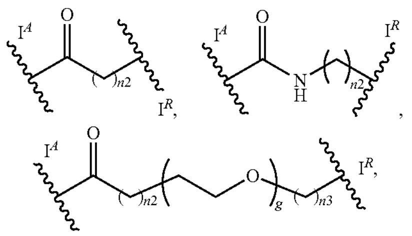

-continued

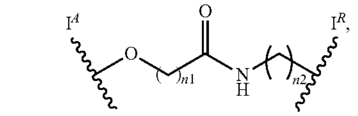

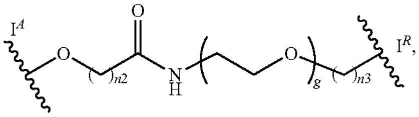

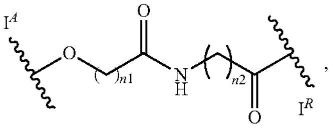

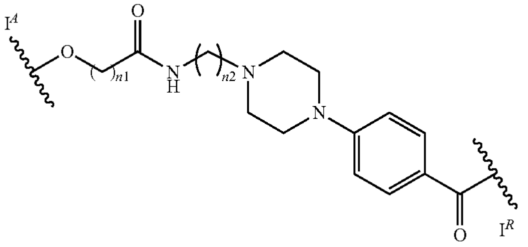

, or

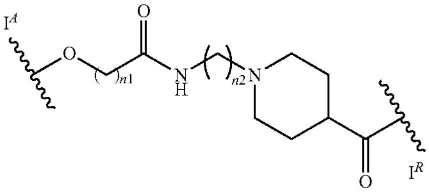

;

n1 is 1; n2 is 0, 1, 2, 3, 4, 5, 6, 7, 8, 9, or 10; n3 is 1 or 2; and g is 2 or 3.

In certain embodiments, the compound of Formula (I) is of the formula:

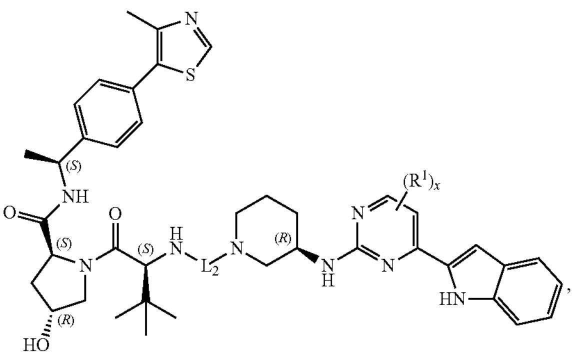

,

-continued

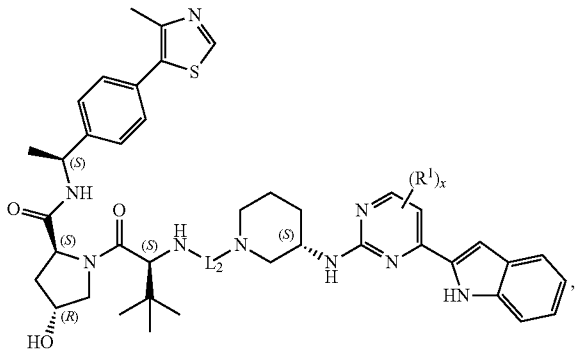

, or a pharmaceutically acceptable salt, co-crystal, tautomer, stereoisomer, solvate, hydrate, polymorph, isotopically enriched derivative, or prodrug thereof, wherein $R^1$ is halogen or optionally substituted $C_{1-6}$ alkyl; and L2 is of the formula:

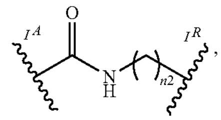

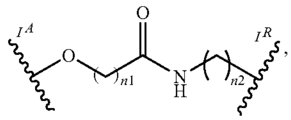

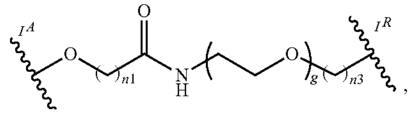

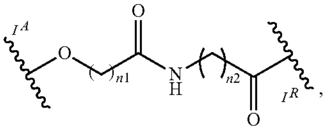

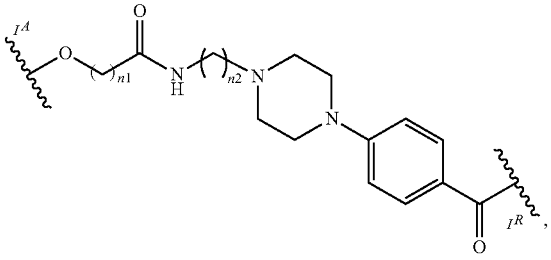

, or

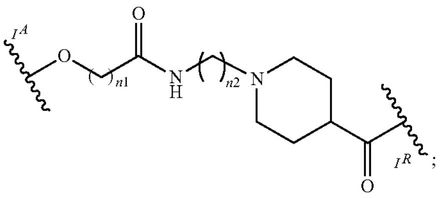

;

n1 is 1; n2 is 3, 4, 5, 6, 7, or 8; n3 is 1 or 2; and g is 2 or 3.

In certain embodiments, the compound of Formula (I) is of the formula:
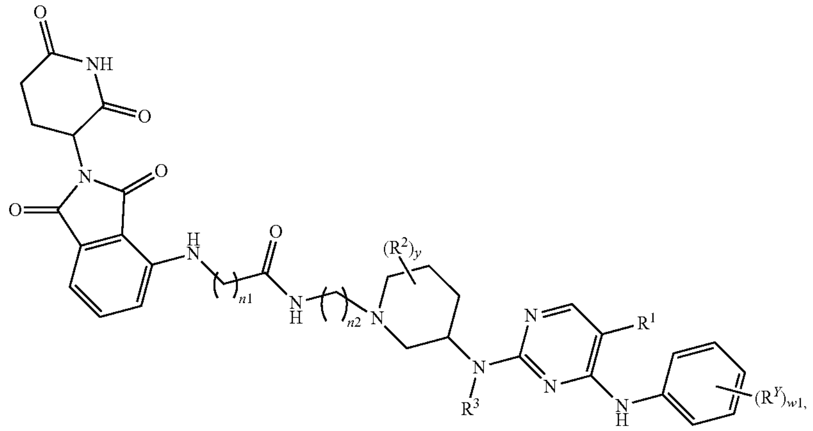
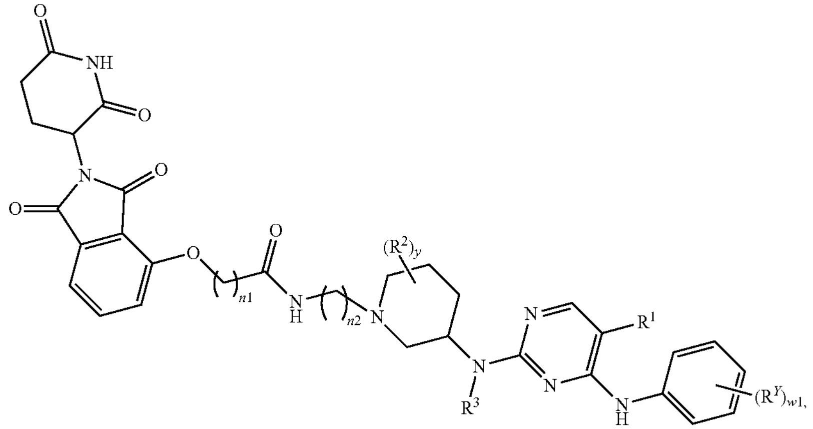
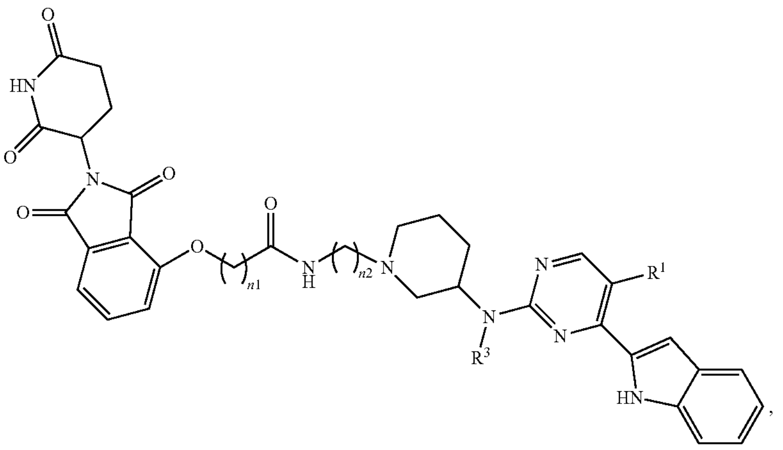

-continued
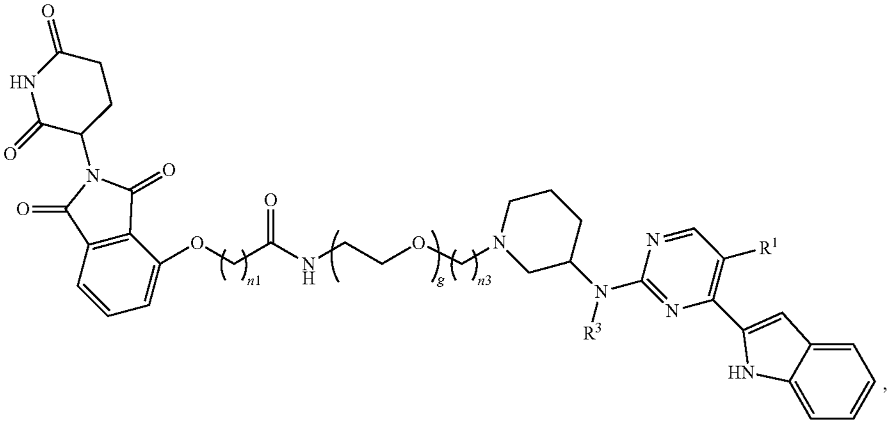
,
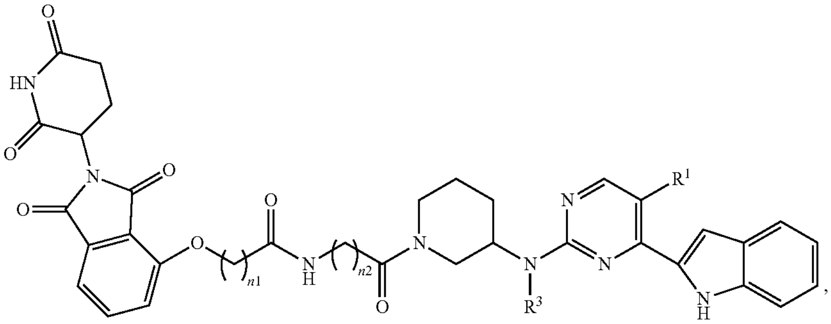
,
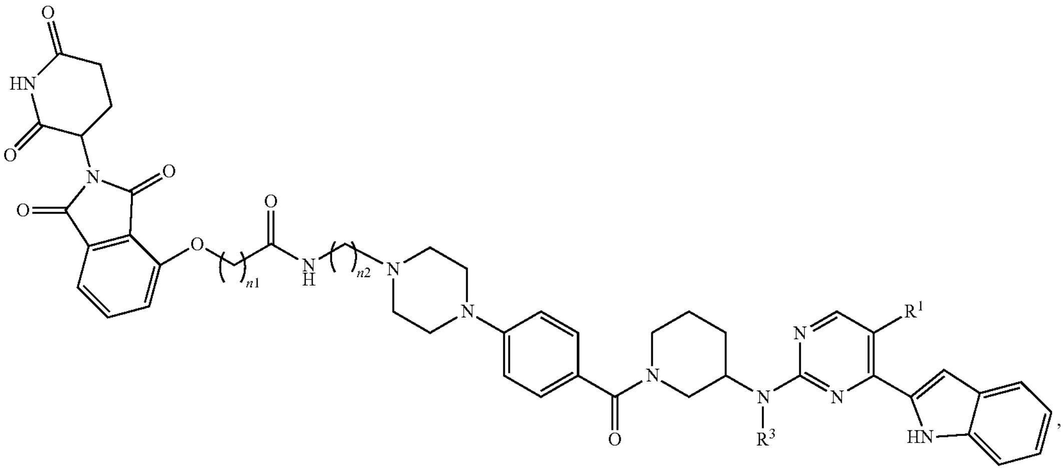
,
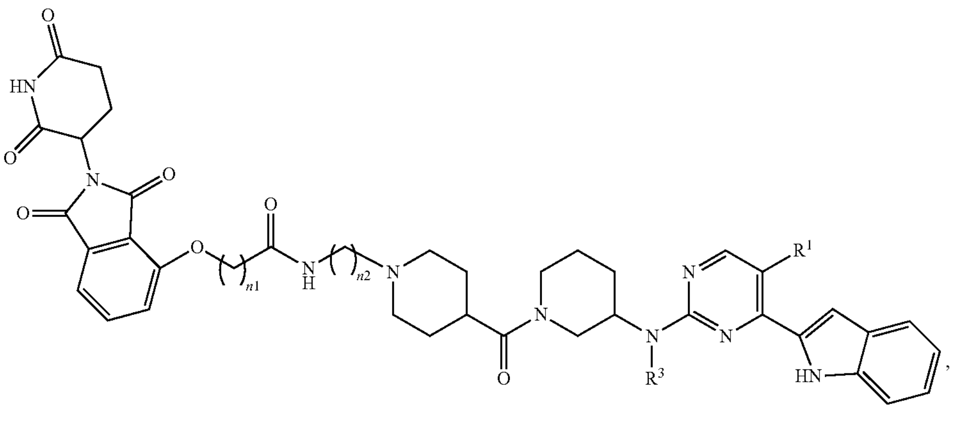
,

-continued
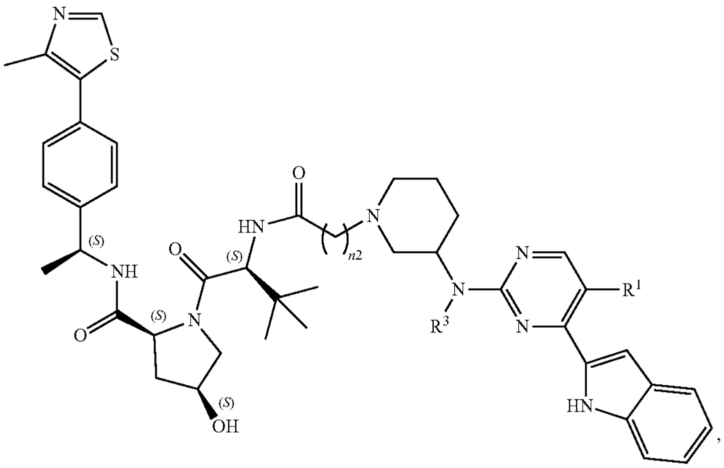
,
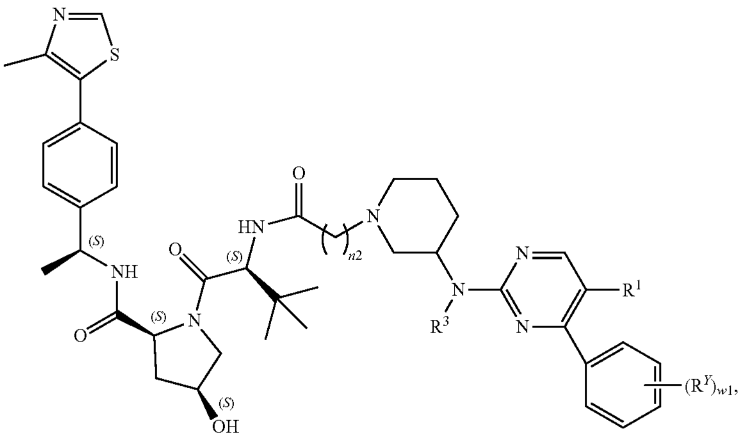
,
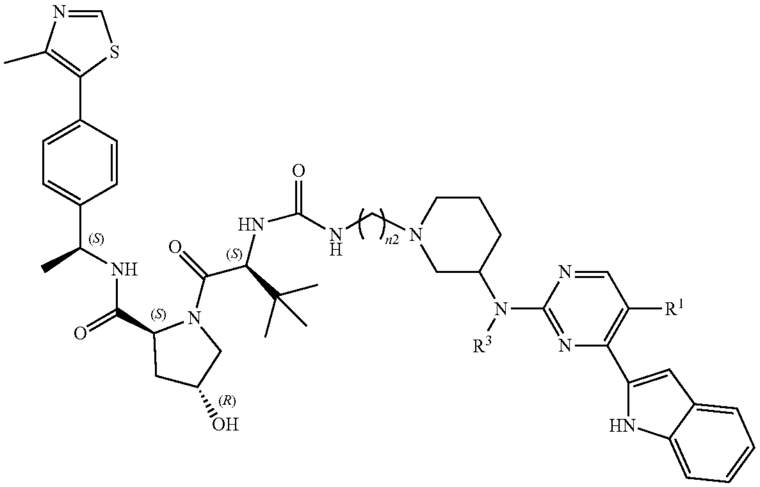

-continued
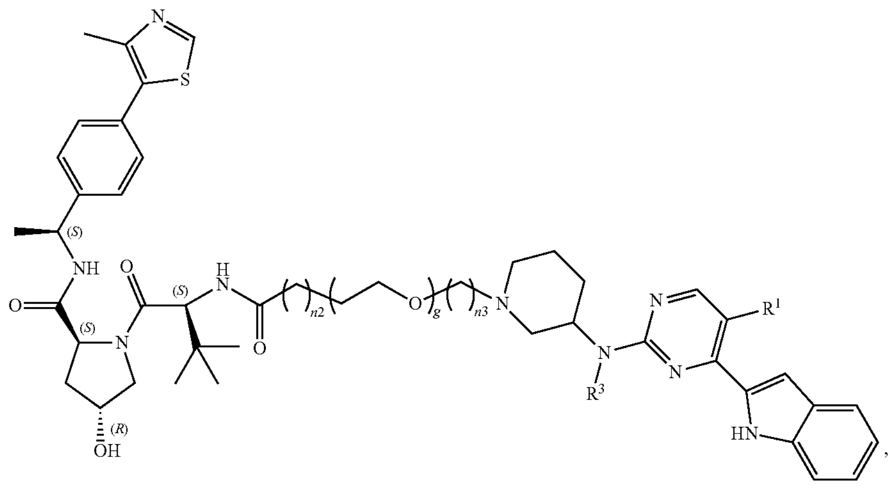
,
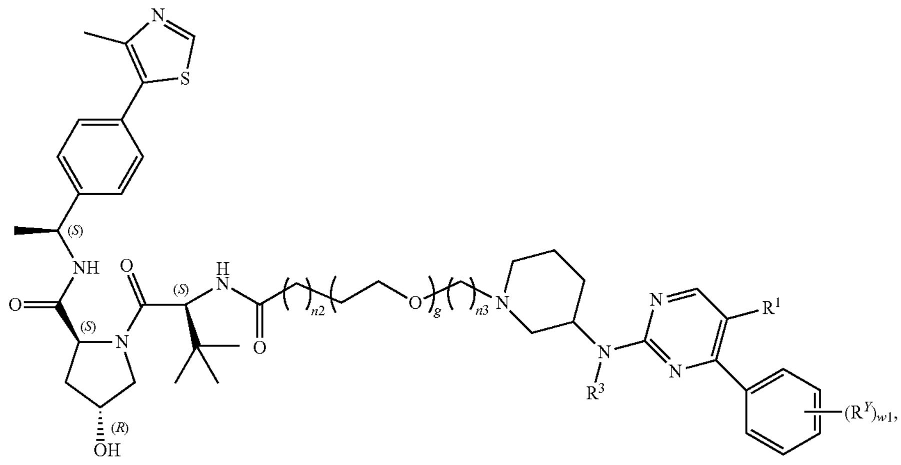
,
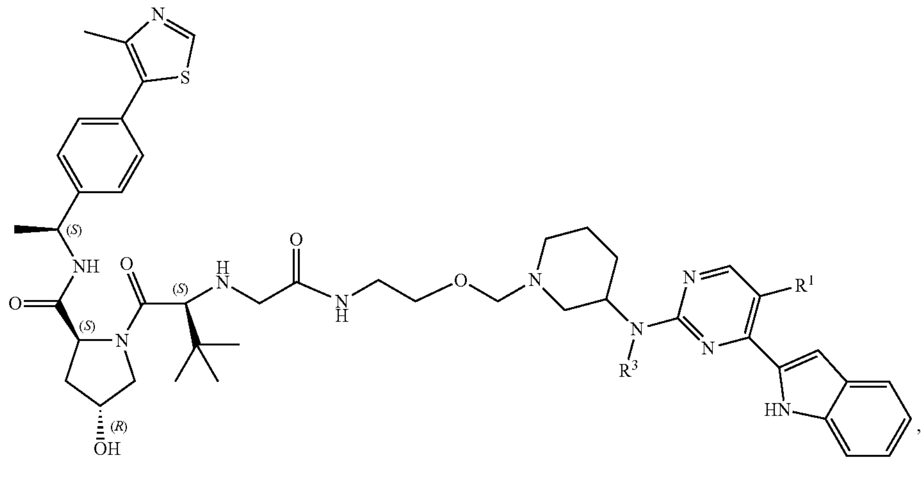
,

-continued
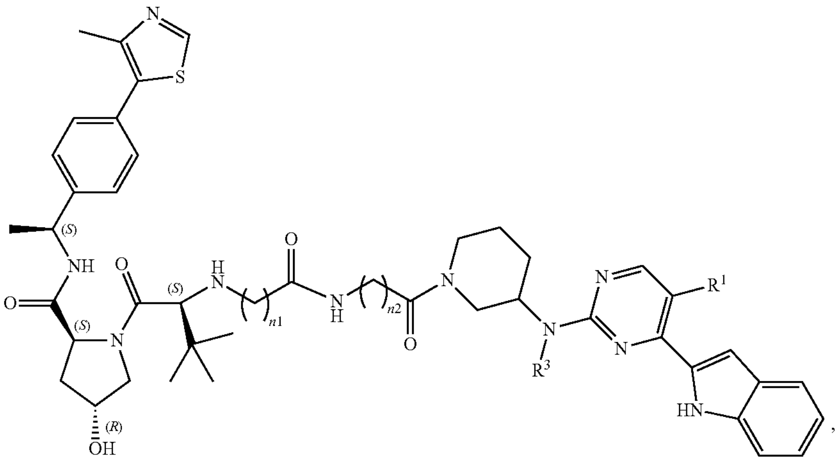
,
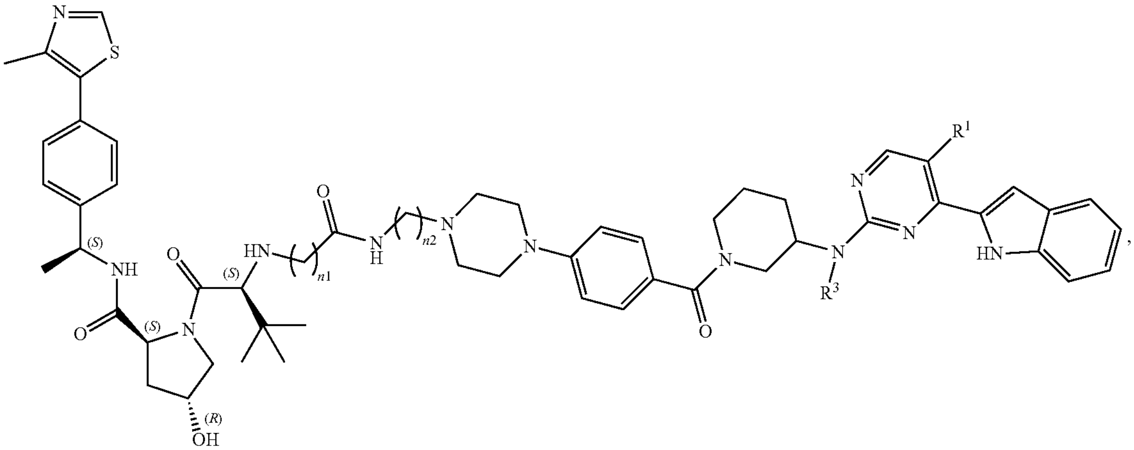
,
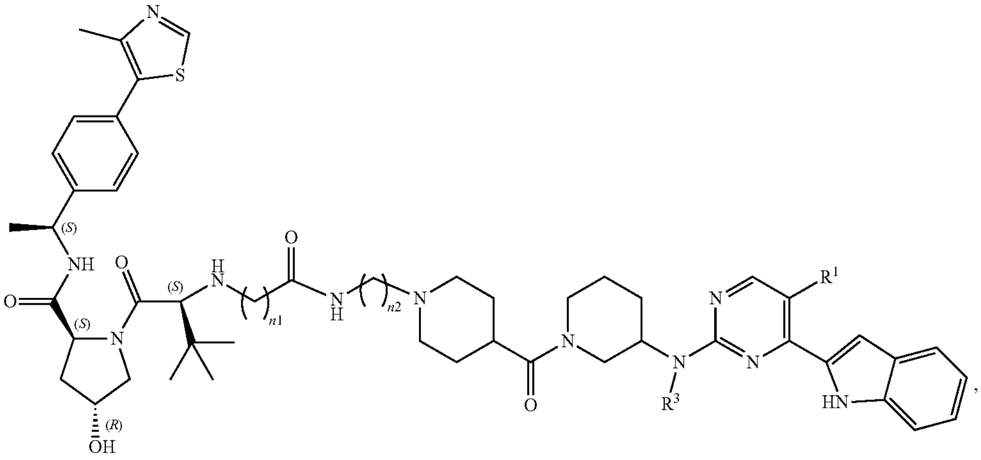
,

-continued
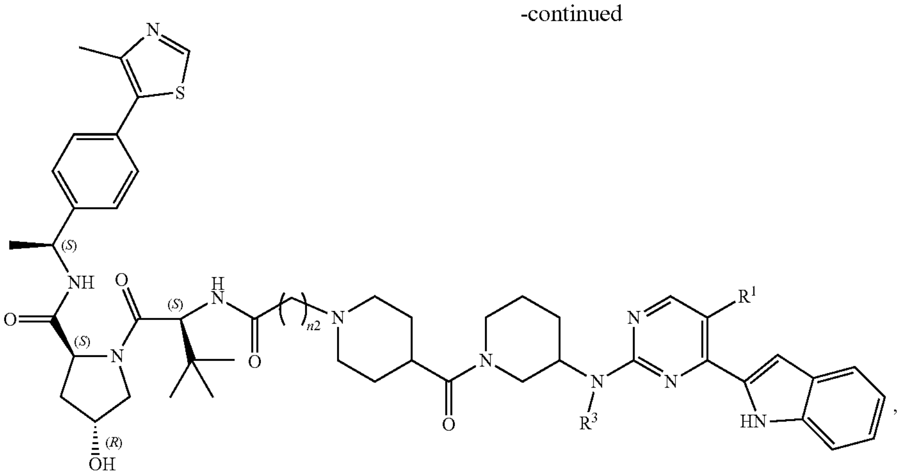
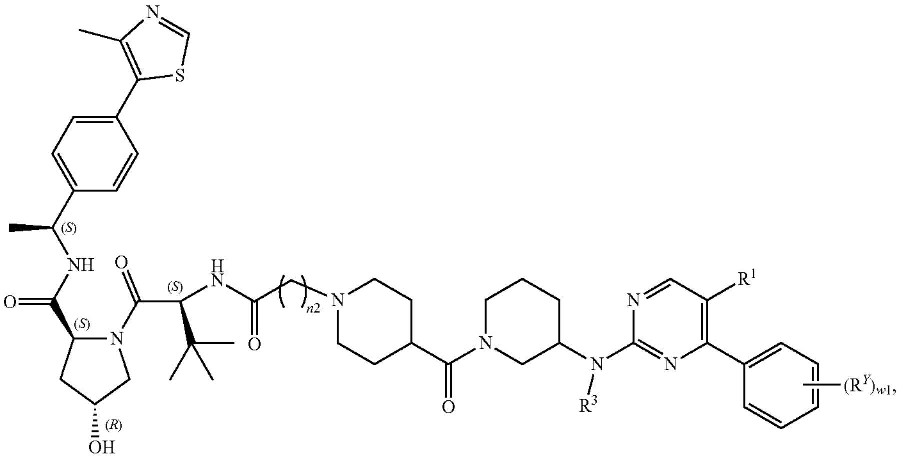
or a pharmaceutically acceptable salt, co-crystal, tautomer, stereoisomer, solvate, hydrate, polymorph, isotopically enriched derivative, or prodrug thereof, wherein each of $R^1$, $R^3$, n1; n2; n3; and g are as described herein.
In certain embodiments, the compound of Formula (I) is of the formula:
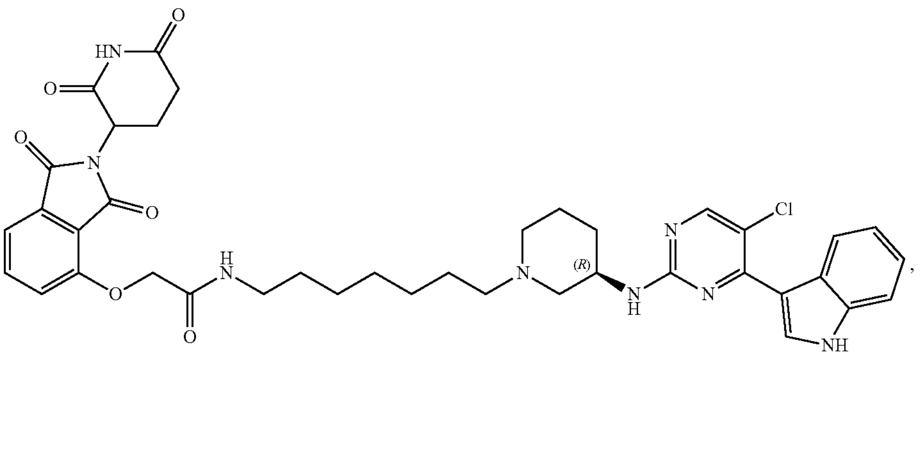

-continued
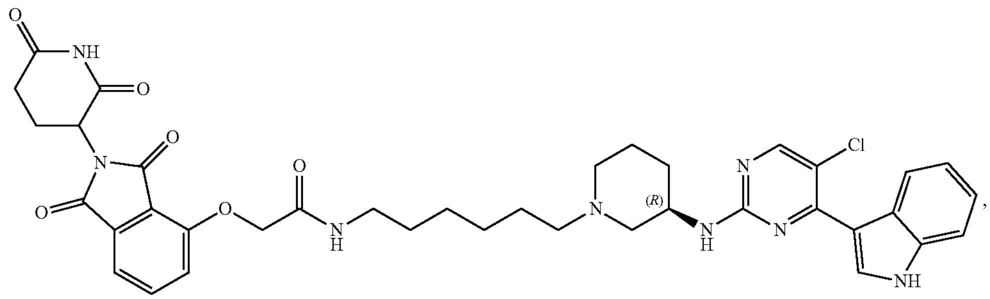,
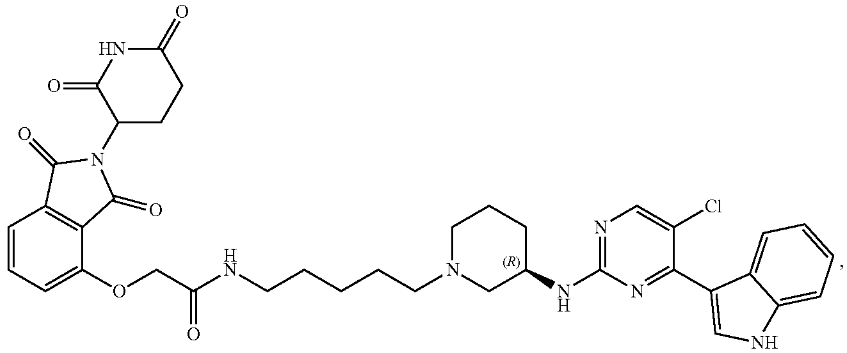,
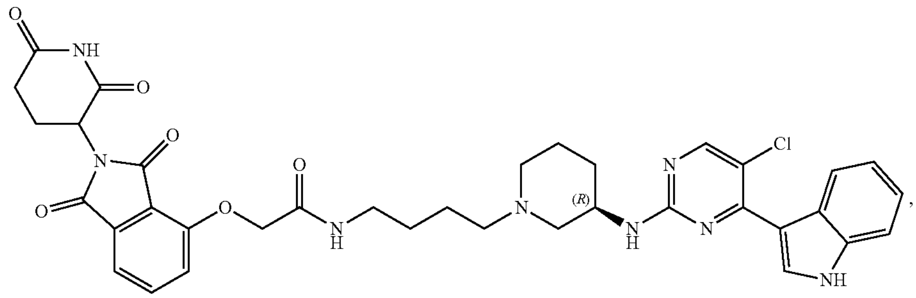,
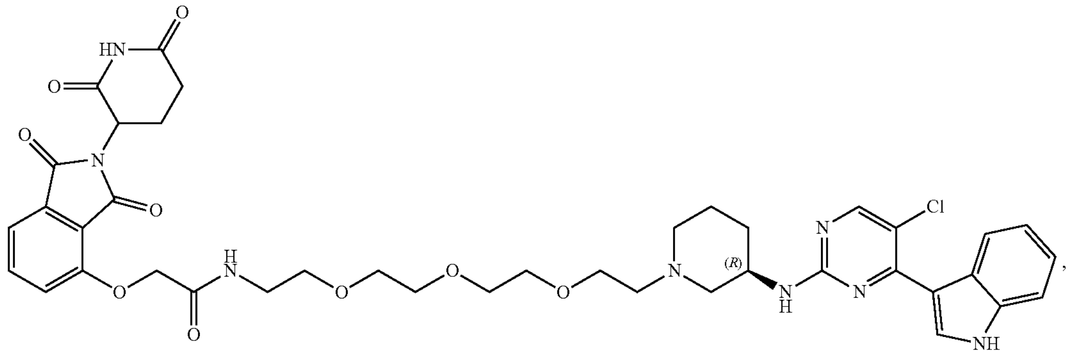,
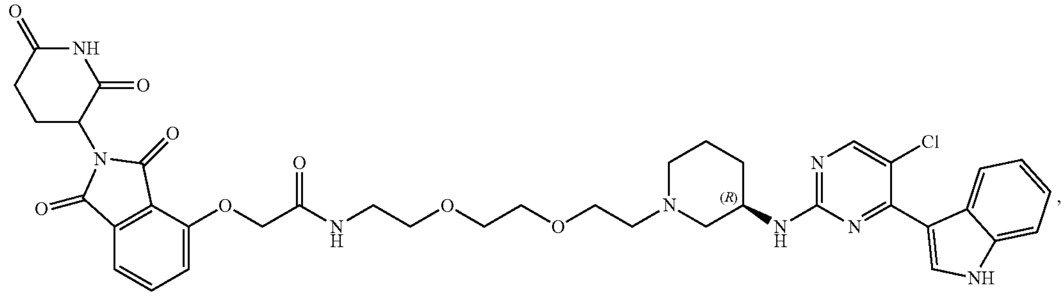,

-continued
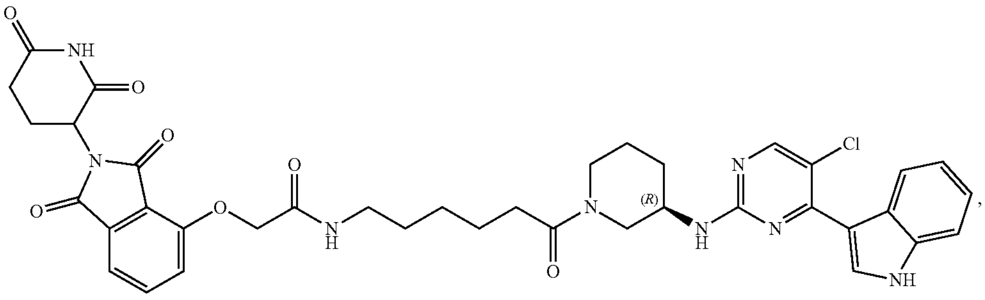
,
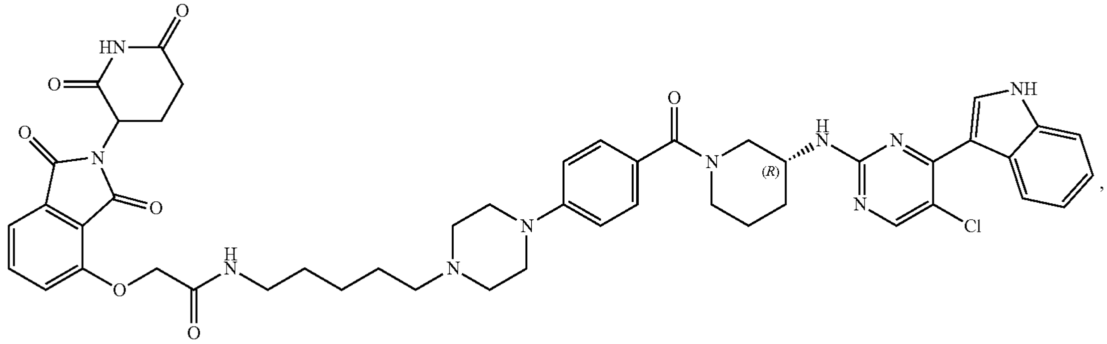
,
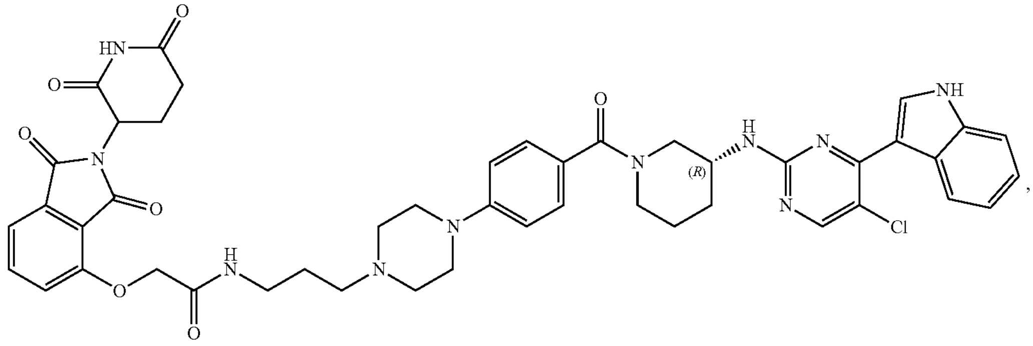
,
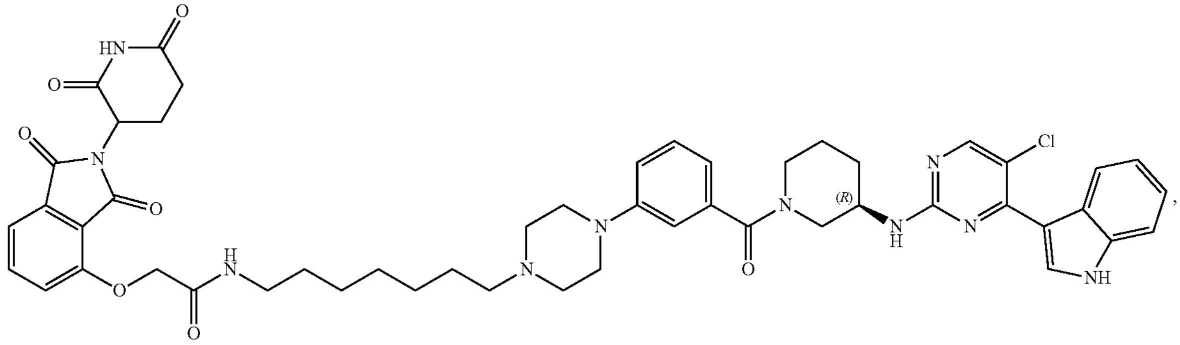
,
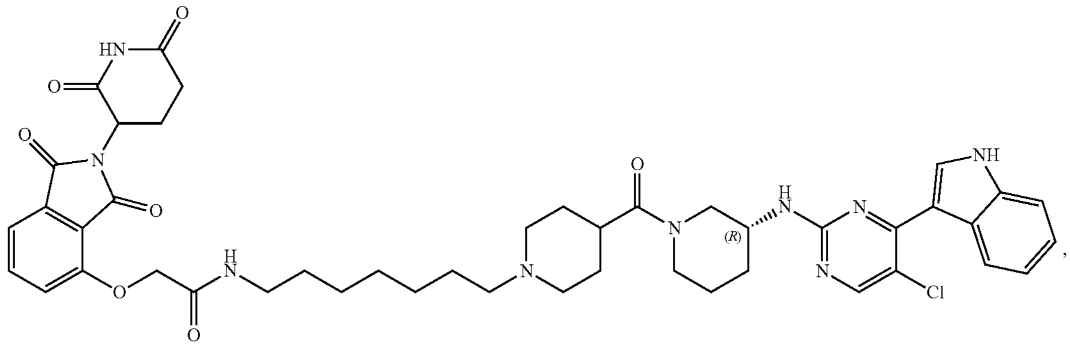
, -continued
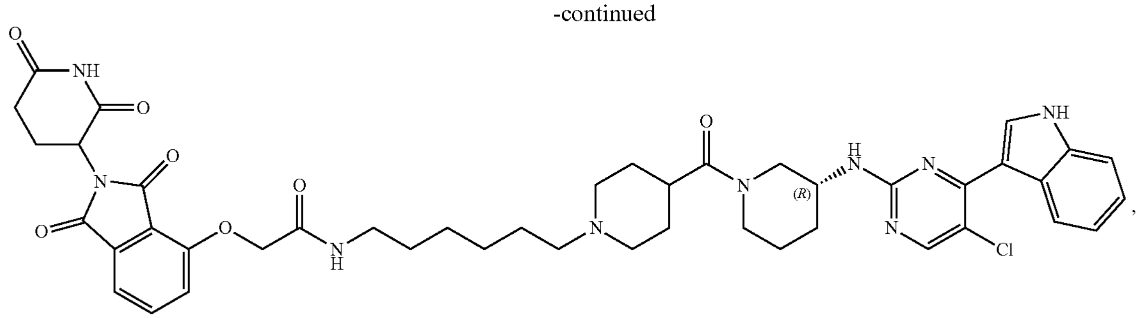
,
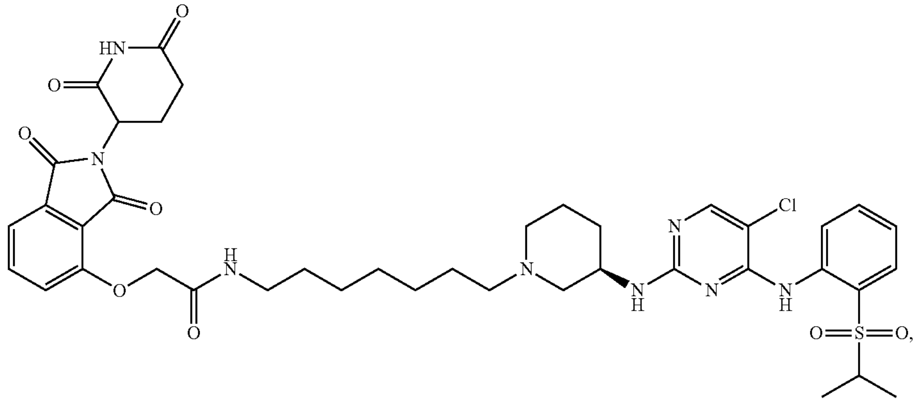
,
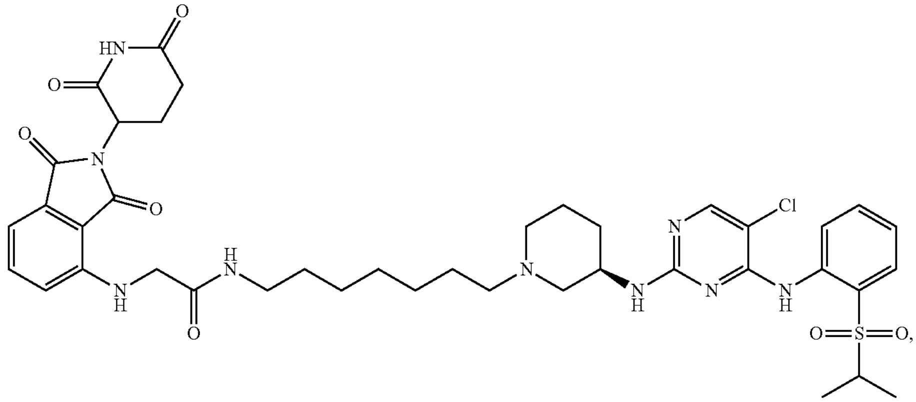
,
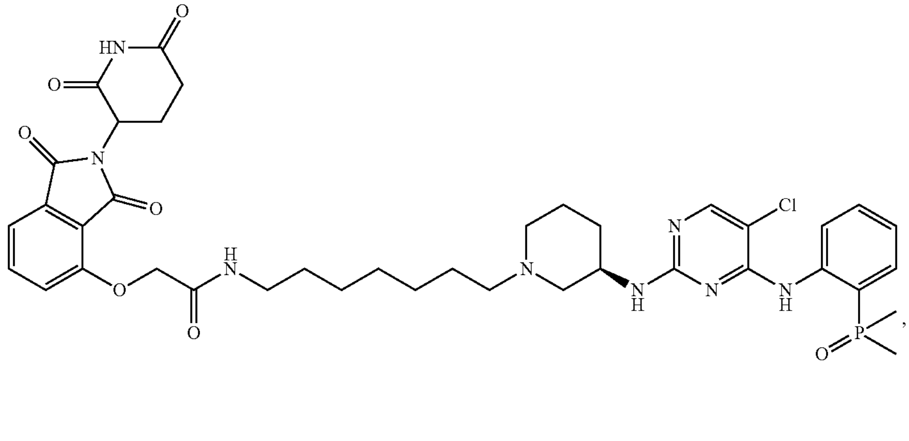
, -continued
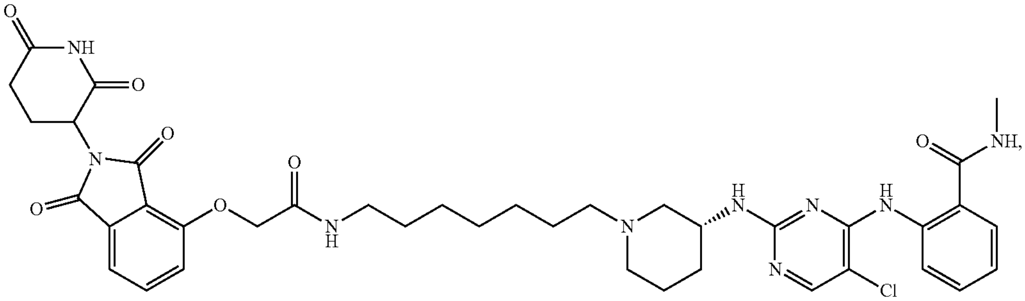
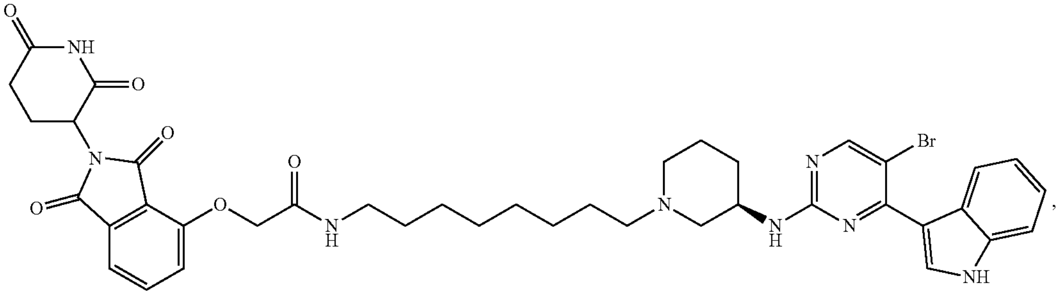
,
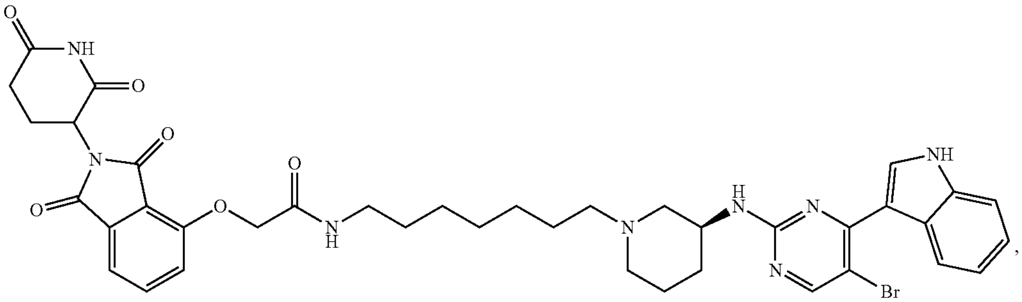
,
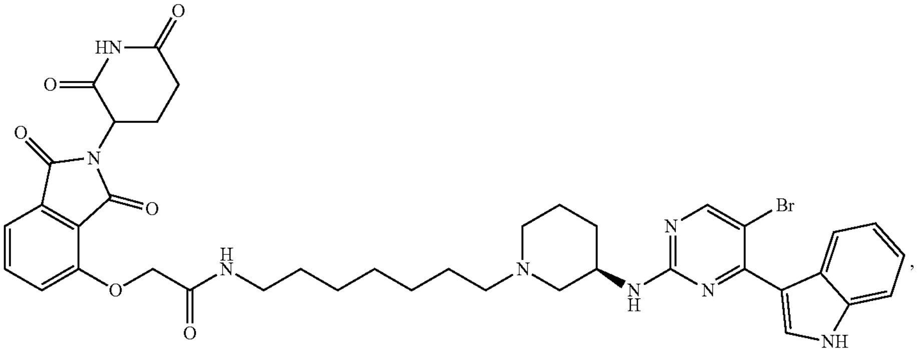
,
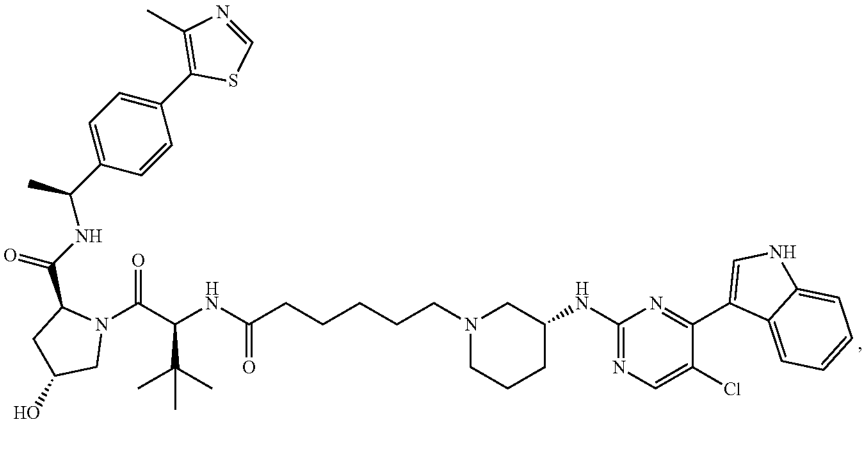
, or a pharmaceutically acceptable salt, co-crystal, tautomer, stereoisomer, solvate, hydrate, polymorph, isotopically enriched derivative, or prodrug thereof.
In certain embodiments, the compound of Formula (I) is of the formula:
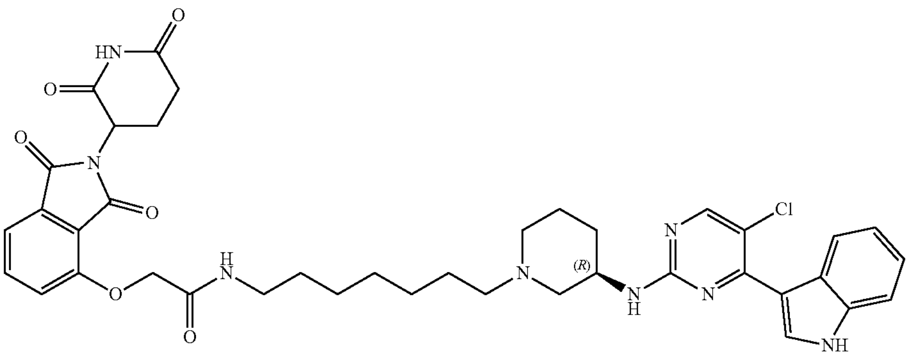
,
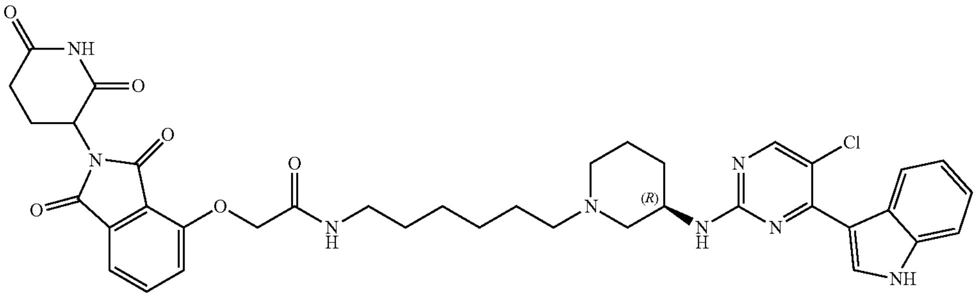
,
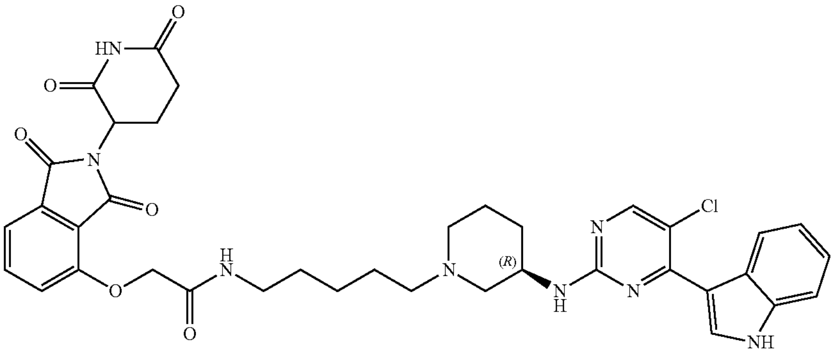
,
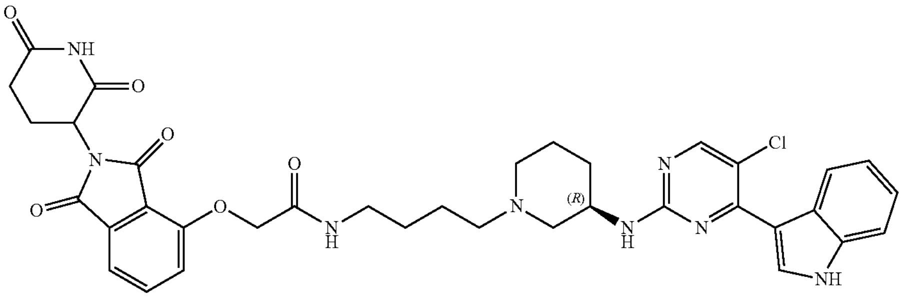
, -continued
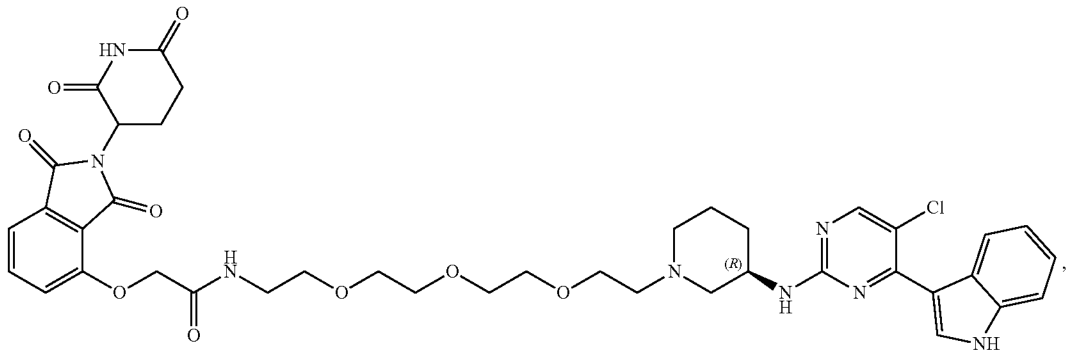
,
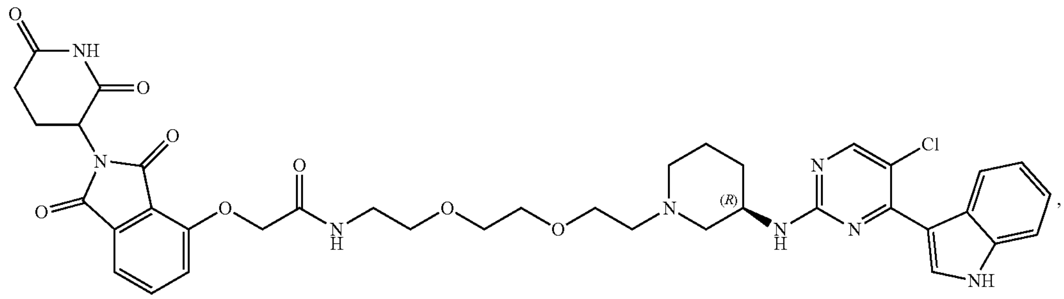
,
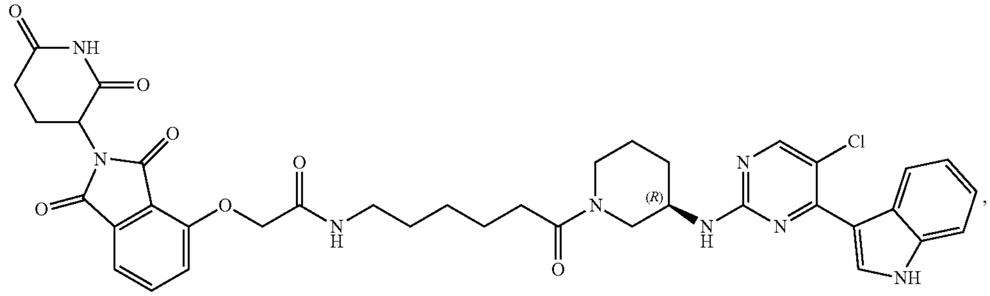
,
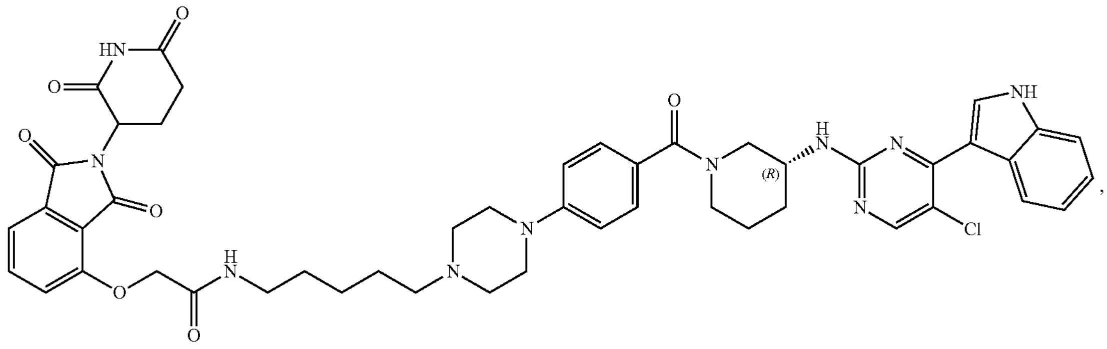
,
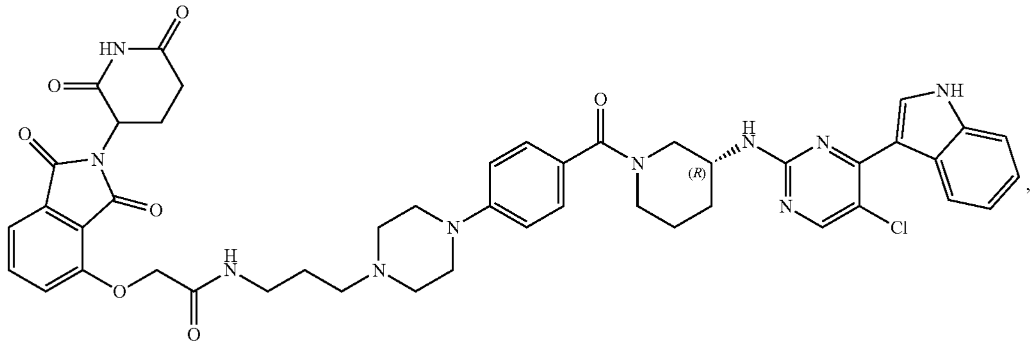
, -continued
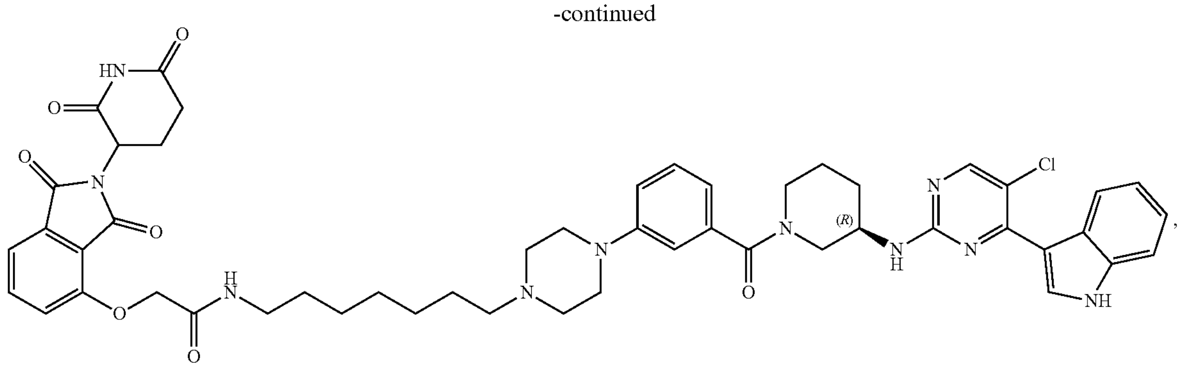
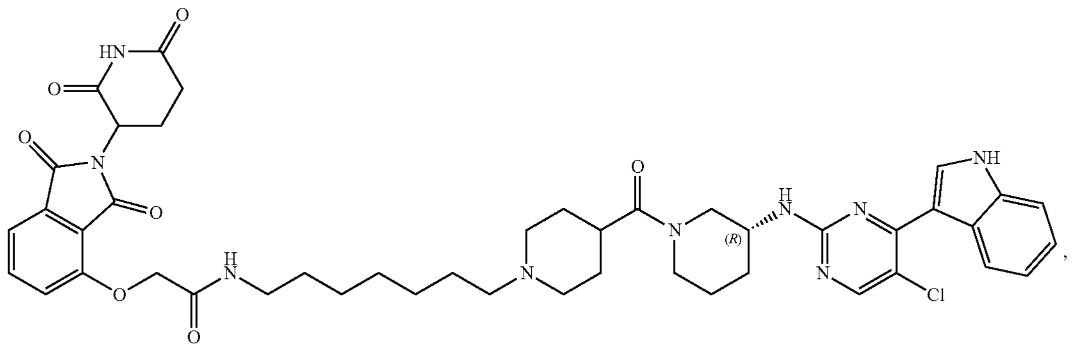
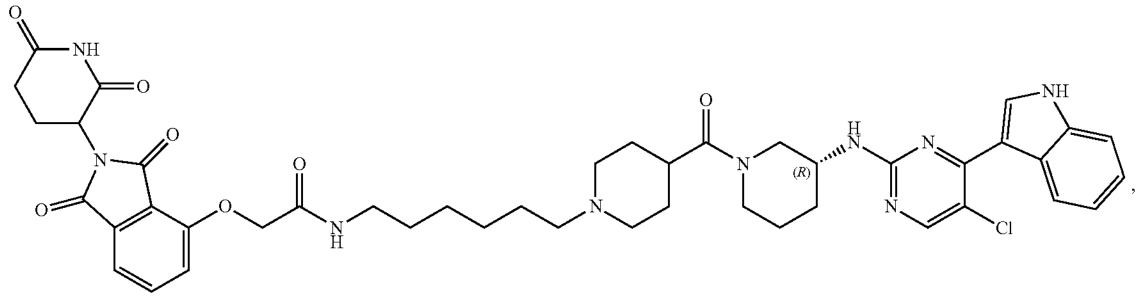
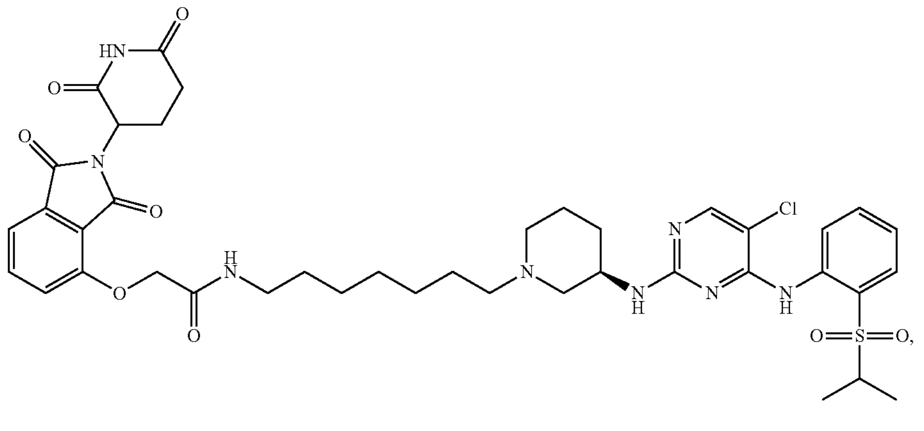

-continued
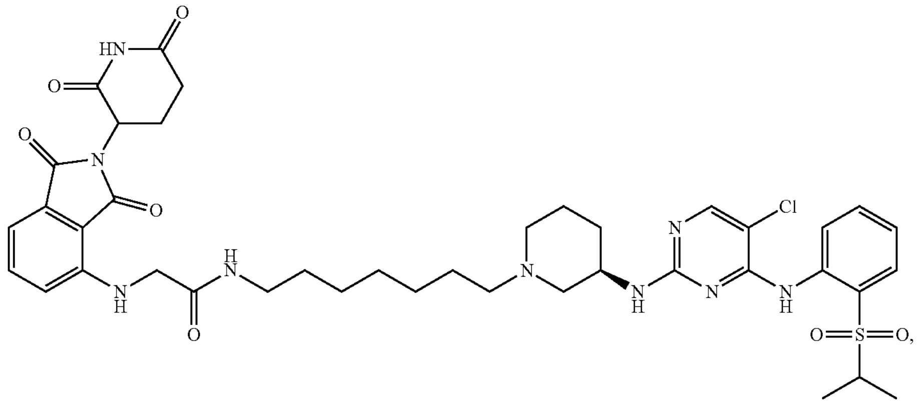
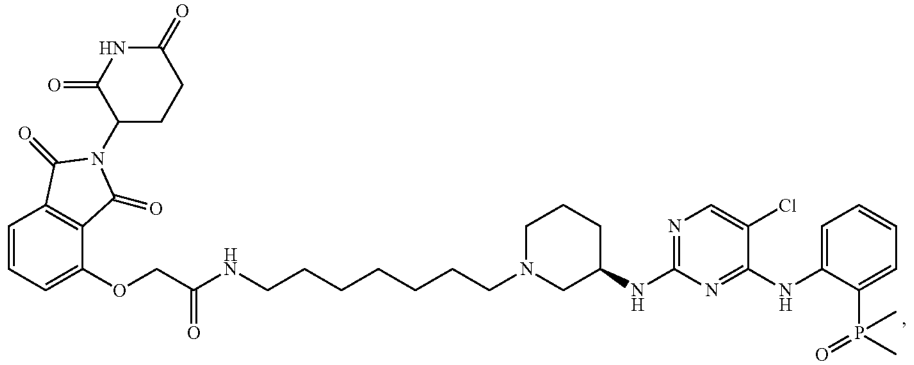
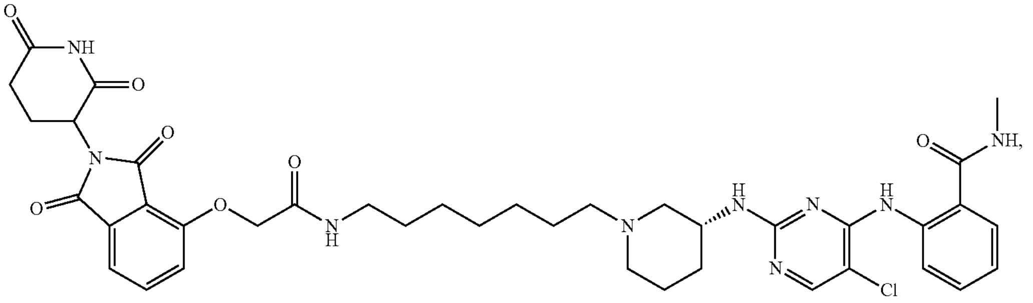
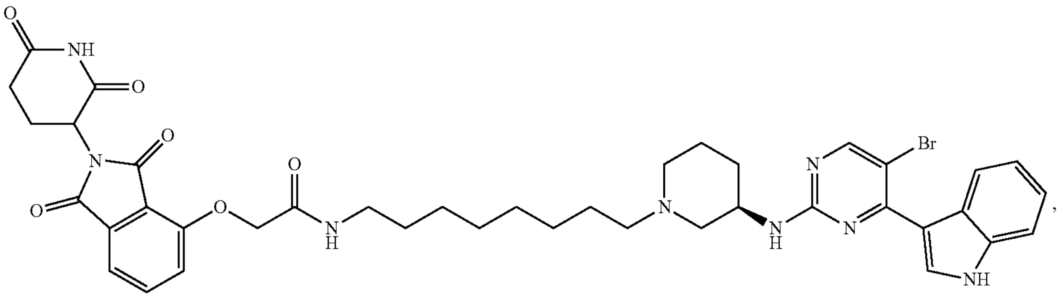
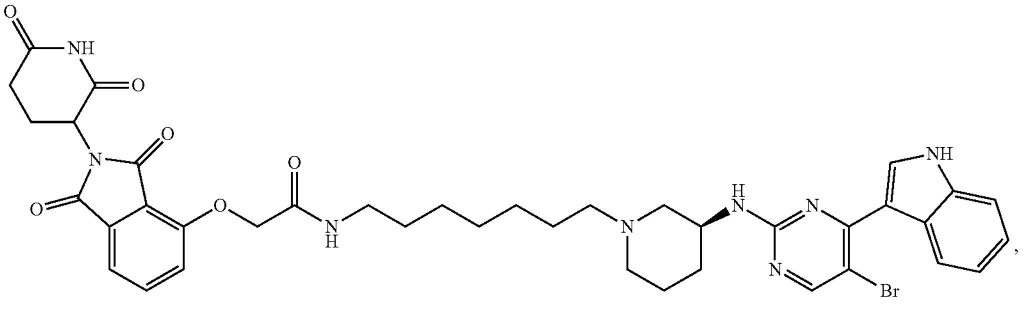

-continued
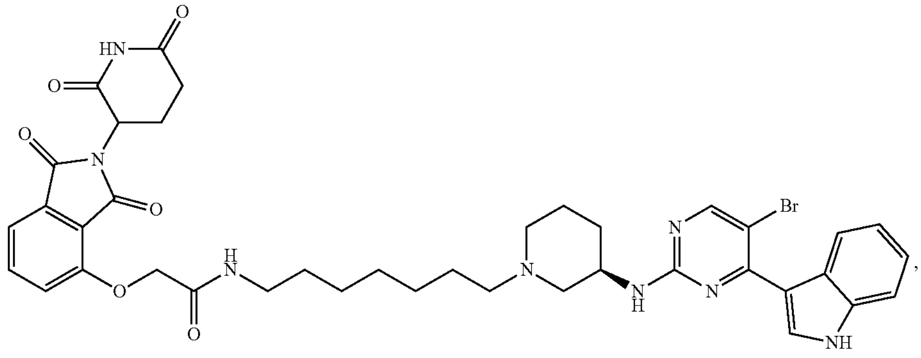
,
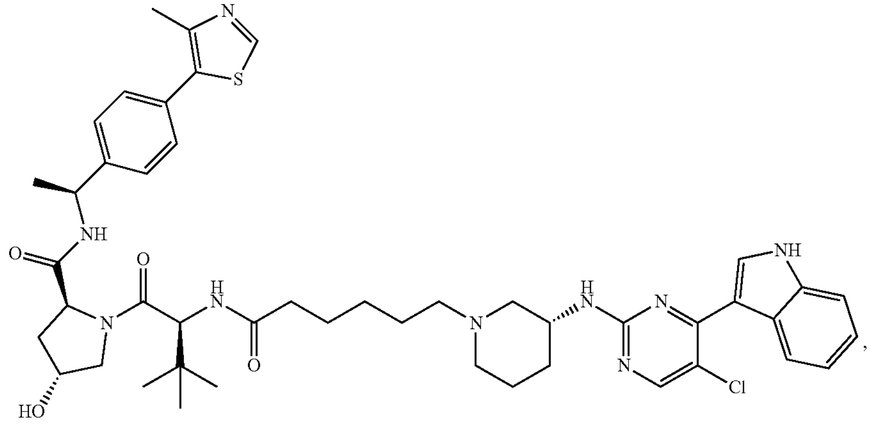 [SMILES: Cc1ncsc1-c1ccc([C@H](C)NC(=O)[C@@H]2C[C@@H](O)CN2C(=O)[C@@H](NC(=O)CCCCCN2CCC[C@@H](Nc3ncc(Cl)c(-c4c[nH]c5ccccc45)n3)C2)C(C)(C)C)cc1]
,
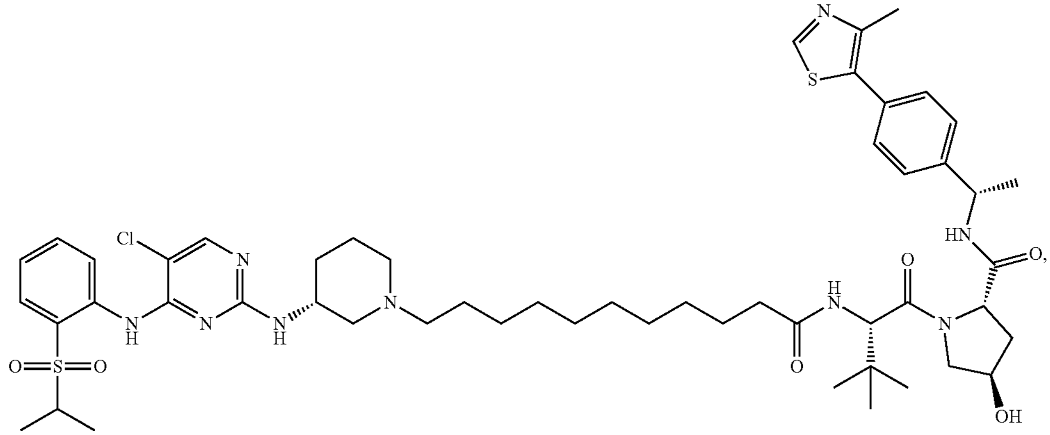
,
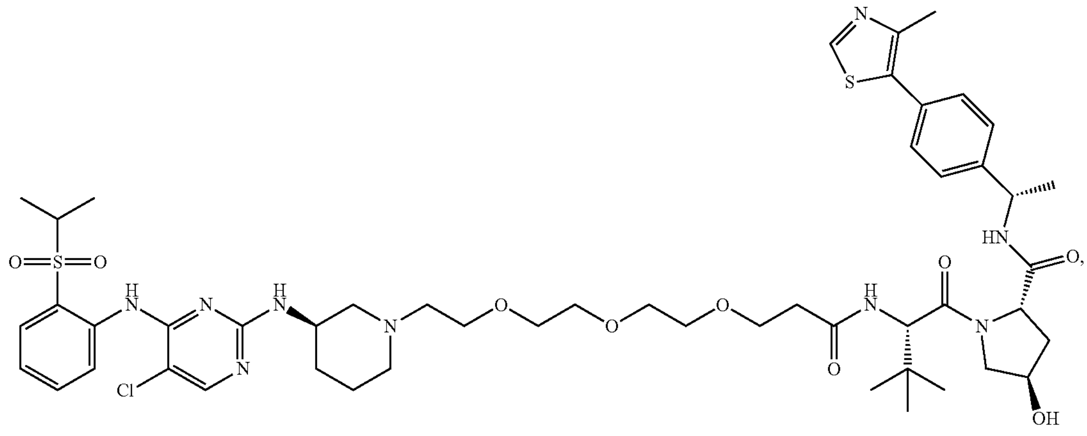
,

-continued

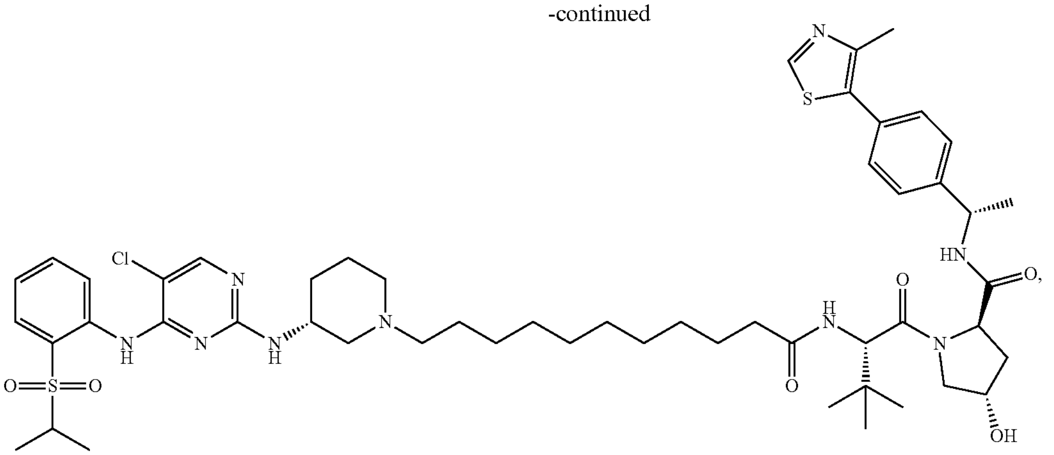

or a pharmaceutically acceptable salt, co-crystal, tautomer, stereoisomer, solvate, hydrate, polymorph, isotopically enriched derivative, or prodrug thereof.

In certain embodiments, the compound of Formula (I) is a compound provided in any one of the Examples below. In certain embodiments, the compound of Formula (I) is a compound provided in Table 1.

In certain embodiments, a compound described herein is a compound of Formula (I), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (I), or a pharmaceutically acceptable salt thereof.

In some embodiments, the compound of Formula (I) selectively binds CDK12 over another protein. In some embodiments, the compound of Formula (I) selectively binds a specific CDK (e.g., CDK9 and/or CDK12) over another CDK. In some embodiments, the compound of Formula (I) selectively binds CDK12 over another CDK. In some embodiments, the compound of Formula (I) selectively binds CDK12 over CDK13. In some embodiments, the compound of Formula (I) selectively binds CDK9 over another protein. In some embodiments, the compound of Formula (I) selectively binds CDK9 over another CDK. In some embodiments, the compound of Formula (I) selectively binds CDK9 and/or CDK12 over other CDK's (e.g., CDK2, CDK4, CDK13, CDK14, CDK15, CDK16, CDK17, CDK18). In certain embodiments, the selectivity is between about 2-fold and about 5-fold. In certain embodiments, the selectivity is between about 5-fold and about 10-fold. In certain embodiments, the selectivity is between about 10-fold and about 20-fold. In certain embodiments, the selectivity is between about 20-fold and about 50-fold. In certain embodiments, the selectivity is between about 50-fold and about 100-fold. In certain embodiments, the selectivity is between about 100-fold and about 200-fold. In certain embodiments, the selectivity is between about 200-fold and about 500-fold. In certain embodiments, the selectivity is between about 500-fold and about 1000-fold. In certain embodiments, the selectivity is at least about 1000-fold.

In some embodiments, the compound of Formula (I) leads to the selective degradation of CDK12 over other proteins in the proteome. In some embodiments, the compound of Formula (I) leads to the selective degradation of CDK12 over other kinases. In some embodiments, the compound of Formula (I) leads to the selective degradation of CDK12 over other CDK's. In some embodiments, the compound of Formula (I) leads to the selective degradation of CDK12 over CDK13. In some embodiments, the compound of Formula (I) induces selective degradation of CDK12 over other kinases. In some embodiments, the compound of Formula (I) induces selective degradation of CDK12 over other CDK's. In some embodiments, the compound of Formula (I) leads to the selective degradation of CDK12 over CDK13. In some embodiments, the compound of Formula (I) induces the selective degradation of CDK12 over CDK13. In some embodiments, the compound of Formula (I) leads to the selective degradation of CDK9 over other proteins in the proteome. In some embodiments, the compound of Formula (I) leads to the selective degradation of CDK9 over other kinases. In some embodiments, the compound of Formula (I) leads to the selective degradation of CDK9 over other CDK's. In certain embodiments, the selectivity is between about 2-fold and about 5-fold. In certain embodiments, the selectivity is between about 5-fold and about 10-fold. In certain embodiments, the selectivity is between about 10-fold and about 20-fold. In certain embodiments, the selectivity is between about 20-fold and about 50-fold. In certain embodiments, the selectivity is between about 50-fold and about 100-fold. In certain embodiments, the selectivity is between about 100-fold and about 200-fold. In certain embodiments, the selectivity is between about 200-fold and about 500-fold. In certain embodiments, the selectivity is between about 500-fold and about 1000-fold. In certain embodiments, the selectivity is at least about 1000-fold.

In some embodiments, the compound of Formula (I) selectively binds E3 ligase over another protein. In certain embodiments, the selectivity is between about 2-fold and about 5-fold. In certain embodiments, the selectivity is between about 5-fold and about 10-fold. In certain embodiments, the selectivity is between about 10-fold and about 20-fold. In certain embodiments, the selectivity is between about 20-fold and about 50-fold. In certain embodiments, the selectivity is between about 50-fold and about 100-fold. In certain embodiments, the selectivity is between about 100-fold and about 200-fold. In certain embodiments, the selectivity is between about 200-fold and about 500-fold. In certain embodiments, the selectivity is between about 500-fold and about 1000-fold. In certain embodiments, the selectivity is at least about 1000-fold.

In certain embodiments, the compound of Formula (I) induces the degradation of up to 10%, up to 15%, up to 20%, up to 25%, up to 30%, up to 35%, up to 40%, up to 45%, up to 50%, up to 55%, up to 60%, up to 65%, up to 70%, up to 75%, up to 80%, up to 85%, up to 90%, up to 95%, up to 99%, or up to 100% of the target kinase at a concentration of 100,000 nM or less, 50,000 nM or less, 20,000 nM or less, 10,000 nM or less, 5,000 nM or less, 3,500 nM or less, 2,500 nM or less, 1,000 nM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 4 nM or less, 3 nM or less, 2 nM or less, or 1 nM or less. In certain embodiments, the compound of Formula (I) induces the degradation of up to 10%, up to 15%, up to 20%, up to 25%, up to 30%, up to 35%, up to 40%, up to 45%, up to 50%, up to 55%, up to 60%, up to 65%, up to 70%, up to 75%, up to 80%, up to 85%, up to 90%, up to 95%, up to 99%, or up to 100% of the target CDK at a concentration of 100,000 nM or less, 50,000 nM or less, 20,000 nM or less, 10,000 nM or less, 5,000 nM or less, 3,500 nM or less, 2,500 nM or less, 1,000 nM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 4 nM or less, 3 nM or less, 2 nM or less, or 1 nM or less. In certain embodiments, the compound of Formula (I) induces the degradation of up to 10%, up to 15%, up to 20%, up to 25%, up to 30%, up to 35%, up to 40%, up to 45%, up to 50%, up to 55%, up to 60%, up to 65%, up to 70%, up to 75%, up to 80%, up to 85%, up to 90%, up to 95%, up to 99%, or up to 100% of the target protein CDK9 and/or CDK12 at a concentration of 100,000 nM or less, 50,000 nM or less, 20,000 nM or less, 10,000 nM or less, 5,000 nM or less, 3,500 nM or less, 2,500 nM or less, 1,000 nM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 4 nM or less, 3 nM or less, 2 nM or less, or 1 nM or less.

In certain embodiments, the compound of Formula (I) increases the rate of degradation of the target kinase up to 10%, up to 15%, up to 20%, up to 25%, up to 30%, up to 35%, up to 40%, up to 45%, up to 50%, up to 55%, up to 60%, up to 65%, up to 70%, up to 75%, up to 80%, up to 85%, up to 90%, up to 95%, up to 99%, or up to 100% at a concentration of 100,000 nM or less, 50,000 nM or less, 20,000 nM or less, 10,000 nM or less, 5,000 nM or less, 3,500 nM or less, 2,500 nM or less, 1,000 nM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 4 nM or less, 3 nM or less, 2 nM or less, or 1 nM or less. In certain embodiments, the compound of Formula (I) increases the rate of degradation of the target CDK up to 10%, up to 15%, up to 20%, up to 25%, up to 30%, up to 35%, up to 40%, up to 45%, up to 50%, up to 55%, up to 60%, up to 65%, up to 70%, up to 75%, up to 80%, up to 85%, up to 90%, up to 95%, up to 99%, or up to 100% at a concentration of 100,000 nM or less, 50,000 nM or less, 20,000 nM or less, 10,000 nM or less, 5,000 nM or less, 3,500 nM or less, 2,500 nM or less, 1,000 nM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 4 nM or less, 3 nM or less, 2 nM or less, or 1 nM or less. In certain embodiments, the compound of Formula (I) increases the rate of degradation of the target protein CDK9 and/or CDK12 up to 10%, up to 15%, up to 20%, up to 25%, up to 30%, up to 35%, up to 40%, up to 45%, up to 50%, up to 55%, up to 60%, up to 65%, up to 70%, up to 75%, up to 80%, up to 85%, up to 90%, up to 95%, up to 99%, or up to 100% at a concentration of 100,000 nM or less, 50,000 nM or less, 20,000 nM or less, 10,000 nM or less, 5,000 nM or less, 3,500 nM or less, 2,500 nM or less, 1,000 nM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 4 nM or less, 3 nM or less, 2 nM or less, or 1 nM or less.

Pharmaceutical Compositions, Kits, and Administration

The present disclosure provides pharmaceutical compositions comprising a compound of Formula (I), or a pharmaceutically acceptable salt, co-crystal, tautomer, stereoisomer, solvate, hydrate, polymorph, isotopically enriched derivative, or prodrug thereof, and optionally a pharmaceutically acceptable excipient. In certain embodiments, the pharmaceutical composition described herein comprises a compound of Formula (I), or a pharmaceutically acceptable salt thereof, and a pharmaceutically acceptable excipient.

In certain embodiments, the compound of Formula (I) is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating a disease (e.g., a proliferative disease (e.g., ovarian cancer, breast cancer, or prostate cancer)) in a subject in need thereof. In certain embodiments, the effective amount is an amount effective for preventing a disease (e.g., a proliferative disease (e.g., ovarian cancer, breast cancer, or prostate cancer)) in a subject in need thereof. In certain embodiments, the effective amount is an amount effective for treating cancer in a subject in need thereof. In certain embodiments, the effective amount is an amount effective for preventing cancer in a subject in need thereof. In certain embodiments, the effective amount is an amount effective for reducing the risk of developing a disease (e.g., proliferative disease (e.g., ovarian cancer, breast cancer, or prostate cancer)) in a subject in need thereof.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the effective amount is an amount effective for inducing the degradation of at least about 10%, at least about 15%, at least about 20%, at least about 25%, at least about 30%, at least about 35%, at least about 40%, at least about 42%, at least about 45%, at least about 50%, at least about 55%, at least about 60%, at least about 65%, at least about 70%, at least about 75%, at least about 80%, at least about 85%, at least about 90%, at least about 95%, at least about 98%, or at least about 99% of the target kinase in a cell. In certain embodiments, the effective amount is an amount effective for inducing the degradation of at least about 10%, at least about 15%, at least about 20%, at least about 25%, at least about 30%, at least about 35%, at least about 40%, at least about 42%, at least about 45%, at least about 50%, at least about 55%, at least about 60%, at least about 65%, at least about 70%, at least about 75%, at least about 80%, at least about 85%, at least about 90%, at least about 95%, at least about 98%, or at least about 99% of the target CDK in a cell. In certain embodiments, the effective amount is an amount effective for inducing the degradation of at least about 10%, at least about 15%, at least about 20%, at least about 25%, at least about 30%, at least about 35%, at least about 40%, at least about 42%, at least about 45%, at least about 50%, at least about 55%, at least about 60%, at least about 65%, at least about 70%, at least about 75%, at least about 80%, at least about 85%, at least about 90%, at least about 95%, at least about 98%, or at least about 99% of the target protein CDK9 and/or CDK12 in a cell. In certain embodiments, the effective amount is an amount effective for inducing the degradation of the target protein CDK9 and/or CDK12 in a cell by a range between a percentage described in this paragraph and another percentage described in this paragraph, inclusive.

The present disclosure provides pharmaceutical compositions comprising a compound that interacts with a E3 ubiquitin ligase (e.g., cereblon) and the target kinase (e.g., CDK) for use in treating a disease (e.g., a proliferative disease (e.g., ovarian cancer, breast cancer, or prostate cancer)) in a subject in need thereof. The present disclosure provides pharmaceutical compositions comprising a compound that interacts with a E3 ubiquitin ligase (e.g., cereblon) and the target protein CDK9 and/or CDK12 for use in treating a disease (e.g., a proliferative disease (e.g., ovarian cancer, breast cancer, or prostate cancer)) in a subject in need thereof. In certain embodiments, the composition is for use in treating cancer. In certain embodiments, the composition is for use in treating ovarian cancer, breast cancer, or prostate cancer. In certain embodiments, the composition is for use in treating ovarian cancer. In certain embodiments, the composition is for use in treating breast cancer. In certain embodiments, the composition is for use in treating prostate cancer.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly (vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum®), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus (DMDM Hydantoin, Iodopropynyl Butylcarbamate), Phenonip® (phenoxyethanol, methylparaben, ethylparaben, propylparaben, butylparaben, and isobutylparaben), methylparaben, Germall® 115 (imidazolidinyl urea), Germaben® II (diazolidinyl urea, methylparaben, propylparaben, and propylene glycol), Neolone® (methylisothiazolinone and phenoxyethanol), Kathon® (methylchloroisothiazolinone and methylisothiazolinone), and Euxyl® (phenoxyethanol and ethylhexylglycerin).

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, chamomile, canola, caraway, carnauba, castor, cinnamon, cocoa butter, coconut, cod liver, coffee, corn, cotton seed, emu, *Eucalyptus*, evening primrose, fish, flaxseed, geraniol, gourd, grape seed, hazel nut, hyssop, isopropyl myristate, jojoba, kukui nut, lavandin, lavender, lemon, *Litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, buccal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the biological sample, tissue, or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the biological sample, tissue, or cell is one dose per day. In certain embodiments, the frequency of administering the multiple doses to the subject or applying the multiple doses to the biological sample, tissue, or cell is two doses per day. In certain embodiments, the frequency of administering the multiple doses to the subject or applying the multiple doses to the biological sample, tissue, or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, biological sample, tissue, or cell. In certain embodiments, the duration between the first dose and last dose of the multiple doses is three months, six months, or one year. In certain embodiments, the duration between the first dose and last dose of the multiple doses is the lifetime of the subject, biological sample, tissue, or cell. In certain embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in inducing the degradation of a target protein, and/or in reducing the risk to develop a disease in a subject in need thereof), improve bioavailability, improve their ability to cross the blood-brain barrier, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a compound described herein and an additional pharmaceutical agent exhibit a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease (e.g., ovarian cancer, breast cancer, or prostate cancer)). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, cytotoxic chemotherapeutic agents, epigenetic modifiers, glucocorticoids, immunotherapeutic agents, anti-proliferative agents, anti-cancer agents, cytotoxic agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, and a combination thereof. In certain embodiments, the additional pharmaceutical agent is an anti-proliferative agent (e.g., anti-cancer agent). In certain embodiments, the additional pharmaceutical agent is abiraterone acetate (e.g., ZYTIGA®), ABVD, ABVE, ABVE-PC, AC, AC-T, ADE, ado-trastuzumab emtansine (e.g., KADCYLA®), afatinib dimaleate (e.g., GILOTRIF®), aldesleukin (e.g., PROLEUKIN®), alemtuzumab (e.g., CAMPATH®), anastrozole (e.g., ARIMIDEX®), arsenic trioxide (e.g., TRISENOX®), asparaginase *Erwinia chrysanthemi* (e.g., ERWINAZE®), axitinib (e.g., INLYTA®), azacitidine (e.g., MYLOSAR®, VIDAZA®), BEACOPP, belinostat (e.g., BELEODAQ®), bendamustine hydrochloride (e.g., TREANDA®), BEP, bevacizumab (e.g., AVASTIN®), bicalutamide (e.g., CASODEX®), bleomycin (e.g., BLENOXANE®), blinatumomab (e.g., BLINCYTO®), bortezomib (e.g., VELCADE®), bosutinib (e.g., BOSU- LIF®), brentuximab vedotin (e.g., ADCETRIS®), busulfan (e.g., BUSULFEX®, MYLERAN®), cabazitaxel (e.g., JEVTANA®), cabozantinib-s-malate (e.g., COMETRIQ®), CAF, capecitabine (e.g., XELODA®), CAPOX™, carboplatin (e.g., PARAPLAT®, PARAPLATIN®), carboplatin-taxol, carfilzomib (e.g., KYPROLIS®), carmustine (e.g., BECENUM®, BICNU®, CARMUBRIS®), carmustine implant (e.g., GLIADEL WAFER®, GLIADEL®), ceritinib (e.g., ZYKADIA®), cetuximab (e.g., ERBITUX®), chlorambucil (e.g., AMBOCHLORIN®, AMBOCLORIN®, LEUKERAN®, LINFOLIZIN®), chlorambucil-prednisone, CHOP, cisplatin (e.g., PLATINOL®, PLATINOL-AQ®), clofarabine (e.g., CLOFAREX®, CLOLAR®), CMF, COPP, COPP-ABV, crizotinib (e.g., XALKORI®), CVP, cyclophosphamide (e.g., CLAFEN®, CYTOXAN®, NEOSAR®), cytarabine (e.g., CYTOSAR-U®, TARABINE PFS®), dabrafenib (e.g., TAFINLAR®), dacarbazine (e.g., DTIC-DOME®), dactinomycin (e.g., COSMEGEN®), dasatinib (e.g., SPRYCEL®), daunorubicin hydrochloride (e.g., CERUBIDINE®), decitabine (e.g., DACOGEN®), degarelix, denileukin diftitox (e.g., ONTAK®), denosumab (e.g., PROLIA®, XGEVA®), Dinutuximab (e.g., UNITUXIN®), docetaxel (e.g., TAXOTERE®), doxorubicin hydrochloride (e.g., ADRIAMYCIN PFS®, ADRIAMYCIN RDF®), doxorubicin hydrochloride liposome (e.g., DOXIL®, DOX-SL®, EVACET®, LIPODOX®), enzalutamide (e.g., XTANDI®), epirubicin hydrochloride (e.g., ELLENCE®), EPOCH™, erlotinib hydrochloride (e.g., TARCEVA®), etoposide (e.g., TOPOSAR®, VEPESID®), etoposide phosphate (e.g., ETOPOPHOS®), everolimus (e.g., AFINITOR DISPERZ®, AFINITOR®), exemestane (e.g., AROMASIN®), FEC, fludarabine phosphate (e.g., FLUDARA®), fluorouracil (e.g., ADRUCIL®, EFUDEX®, FLUOROPLEX®), FOLFIRI, FOLFIRI-BEVACIZUMAB, FOLFIRI-CETUXIMAB, FOLFIRINOX, FOLFOX, FU-LV, fulvestrant (e.g., FASLODEX®), gefitinib (e.g., IRESSA®), gemcitabine hydrochloride (e.g., GEMZAR®), gemcitabine-cisplatin, gemcitabine-oxaliplatin, goserelin acetate (e.g., ZOLADEX®), Hyper-CVAD, ibritumomab tiuxetan (e.g., ZEVALIN®), ibrutinib (e.g., IMBRUVICA®), ICE, idelalisib (e.g., ZYDELIG®), ifosfamide (e.g., CYFOS®, IFEX®, IFOSFAMIDUM®), imatinib mesylate (e.g., GLEEVEC®), imiquimod (e.g., ALDARA®), ipilimumab (e.g., YERVOY®), irinotecan hydrochloride (e.g., CAMPTOSAR®), ixabepilone (e.g., IXEMPRA®), lanreotide acetate (e.g., SOMATULINE DEPOT®), lapatinib ditosylate (e.g., TYKERB®), lenalidomide (e.g., REVLIMID®), lenvatinib (e.g., LENVIMA®), letrozole (e.g., FEMARA®), leucovorin calcium (e.g., WELLCOVORIN®), leuprolide acetate (e.g., LUPRON DEPOT®, LUPRON DEPOT®-3 MONTH, LUPRON DEPOT®-4 MONTH, LUPRON DEPOT®-PED, LUPRON®, VIADUR®), liposomal cytarabine (e.g., DEPOCYT®), lomustine (e.g., CEENU®), mechlorethamine hydrochloride (e.g., MUSTARGEN®), megestrol acetate (e.g., MEGACE®), mercaptopurine (e.g., PURINETHOL®, PURIXAN®), methotrexate (e.g., ABITREXATE®, FOLEX PFS®, FOLEX®, METHOTREXATE LPF®, MEXATE®, MEXATE-AQ®), mitomycin c (e.g., MITOZYTREX®, MUTAMYCIN®), mitoxantrone hydrochloride, MOPP, nelarabine (e.g., ARRANON®), nilotinib (e.g., TASIGNA®), nivolumab (e.g., OPDIVO®), obinutuzumab (e.g., GAZYVA®), OEPA, ofatumumab (e.g., ARZERRA®), OFF, olaparib (e.g., LYNPARZA®), omacetaxine mepesuccinate (e.g., SYNRIBO®), OPPA, oxaliplatin (e.g., ELOXATIN®), paclitaxel (e.g., TAXOL®), paclitaxel albumin-stabilized nanoparticle formulation (e.g., ABRAXANE®), PAD, palbociclib (e.g., IBRANCE®), pamidronate disodium (e.g., AREDIA®), panitumumab (e.g., VECTIBIX®), panobinostat (e.g., FARYDAK®), pazopanib hydrochloride (e.g., VOTRIENT®), pegaspargase (e.g., ONCASPAR®), peginterferon alfa-2b (e.g., PEG-INTRON®), peginterferon alfa-2b (e.g., SYLATRON®), pembrolizumab (e.g., KEYTRUDA®), pemetrexed disodium (e.g., ALIMTA®), pertuzumab (e.g., PERJETA®), plerixafor (e.g., MOZOBIL®), pomalidomide (e.g., POMALYST®), ponatinib hydrochloride (e.g., ICLUSIG®), pralatrexate (e.g., FOLOTYN®), prednisone, procarbazine hydrochloride (e.g., MATULANE®), radium 223 dichloride (e.g., XOFIGO®), raloxifene hydrochloride (e.g., EVISTA, KEOXIFENE®), ramucirumab (e.g., CYRAMZA®), R—CHOP, recombinant HPV bivalent vaccine (e.g., CERVARIX®), recombinant human papillomavirus (e.g., HPV) nonavalent vaccine (e.g., GARDASIL 9®), recombinant human papillomavirus (e.g., HPV) quadrivalent vaccine (e.g., GARDASIL®), recombinant interferon alfa-2b (e.g., INTRON A), regorafenib (e.g., STIVARGA®), rituximab (e.g., RITUXAN®), romidepsin (e.g., ISTODAX®), ruxolitinib phosphate (e.g., JAKAFI®), siltuximab (e.g., SYLVANT®), sipuleucel-t (e.g., PROVENGE®), sorafenib tosylate (e.g., NEXAVAR®), STANFORD V, sunitinib malate (e.g., SUTENT®), TAC, tamoxifen citrate (e.g., NOLVADEX®, NOVALDEX®), temozolomide (e.g., METHAZOLASTONE, TEMODAR®), temsirolimus (e.g., TORISEL®), thalidomide (e.g., SYNOVIR®, THALOMID®), thiotepa, topotecan hydrochloride (e.g., HYCAMTIN®), toremifene (e.g., FARESTON®), tositumomab and iodine I 131 tositumomab (e.g., BEXXAR®), TPF, trametinib (e.g., MEKINIST®), trastuzumab (e.g., HERCEPTIN®), VAMP, vandetanib (e.g., CAPRELSA®), VEIP, vemurafenib (e.g., ZELBORAF®), vinblastine sulfate (e.g., VELBAN®, VELSAR®), vincristine sulfate (e.g., VINCASAR PFS®), vincristine sulfate liposome (e.g., MARQIBO®), vinorelbine tartrate (e.g., NAVELBINE®), vismodegib (e.g., ERIVEDGE®), vorinostat (e.g., ZOLINZA®), XELIRI, XELOX, ziv-aflibercept (e.g., ZALTRAP®), or zoledronic acid (e.g., ZOMETA®). In certain embodiments, the additional pharmaceutical agent is ENMD-2076, PCI-32765, AC220, dovitinib lactate (e.g., TKI258, CHIR-258), BIBW 2992 (e.g., TOVOK™), SGX523, PF-04217903, PF-02341066, PF-299804, BMS-777607, ABT-869, MP470, BIBF 1120 (e.g., VARGATEF®), AP24534, JNJ-26483327, MGCD265, DCC-2036, BMS-690154, CEP-11981, tivozanib (e.g., AV-951), OSI-930, MM-121, XL-184, XL-647, and/or XL228), proteasome inhibitors (e.g., bortezomib (e.g., Velcade®)), mTOR inhibitors (e.g., rapamycin, temsirolimus (e.g., CCI-779), everolimus (e.g., RAD-001), ridaforolimus, AP23573 (e.g., Ariad®), AZD8055 (AstraZeneca®), BEZ235 (Novartis®), BGT226 (Norvartis®), XL765 (Sanofi Aventis®), PF-4691502 (Pfizer®), GDC0980 (Genetech®), SF1126 (Semafoe®), and OSI-027 (OSI), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin,, aminopterin, and hexamethyl melamine, or a combination thereof. In certain embodiments, the additional pharmaceutical agent is a cytotoxic chemotherapy (e.g., cytotoxic chemotherapeutic agent (e.g., gemcitabine, cytarabine, daunorubicin, doxorubicin, vincristine, 1-asparaginase, cyclophosphamide, or etoposide)). Exemplary chemotherapeutic agents also include anthracycline antibiotics, actinomycin D, plicamycin, puromycin, gramicidin D, paclitaxel, colchicine, cytochalasin B, emetine, maytansine, amsacrine, cisplatin, carboplatin, mitomycin, altretamine, cyclophosphamide, lomustine, and carmustine. In certain embodiments, the additional pharmaceutical agent is an epigenetic modifier, such as azacitidine or romidepsin. In certain embodiments, the additional pharmaceutical agent is ruxolitinib, BBT594, CHZ868, CYT387, or BMS911543. In certain embodiments, the additional pharmaceutical agent is an inhibitor of a tyrosine kinase. In some embodiments, the additional pharmaceutical agent is a topoisomerase inhibitor, a MCL1 inhibitor, a BCL-2 inhibitor, a BCL-XL inhibitor, a BRD4 inhibitor, a BRCA1 inhibitor, BRCA2 inhibitor, HER1 inhibitor, HER2 inhibitor, a CDK9 inhibitor, a Jumonji histone demethylase inhibitor, or a DNA damage inducer. In some embodiments, the additional pharmaceutical agent is etoposide, obatoclax, navitoclax, JQ1, 4-(((5'-chloro-2'-(((1R,4R)-4-(((R)-1-methoxypropan-2-yl) amino) cyclohexyl) amino)-[2,4'-bipyridin]-6-yl) amino) methyl) tetrahydro-2H-pyran-4-carbonitrile, JIB04, or cisplatin. In certain embodiments, the additional pharmaceutical agent is a binder or inhibitor of a kinase (e.g., CDK). In certain embodiments, the additional pharmaceutical agent is an antibody or a fragment thereof (e.g., monoclonal antibody). In certain embodiments, the additional pharmaceutical agent is a tyrosine kinase inhibitor. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and *vinca* alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the additional pharmaceutical agent is a glucocorticoid (e.g., cortisol, cortisone, prednisone, methylprednisolone, dexamethasone, betamethasone, triamcinolone, fludrocortisone acetate, or deoxycorticosterone acetate). In certain embodiments, the additional therapy is an immunotherapy (e.g., an immunotherapeutic monoclonal antibody). In certain embodiments, the additional pharmaceutical agent is an immunomodulator. In certain embodiments, the additional pharmaceutical agent is an immune checkpoint inhibitor. In certain embodiments, the additional pharmaceutical agent is a programmed cell death 1 protein (PD-1) inhibitor. In certain embodiments, the additional pharmaceutical agent is a programmed cell death 1 protein ligand 1 (PD-L1) inhibitor. In certain embodiments, the additional pharmaceutical agent is a cytotoxic T-lymphocyte-associated protein 4 (CTLA-4) inhibitor. In certain embodiments, the additional pharmaceutical agent is a T-cell immunoglobulin domain and mucin domain 3 (TIM3) inhibitor, lymphocyte activation gene-3 (LAG3) inhibitor, V-set domain-containing T-cell activation inhibitor 1 (VTCN1 or B7-H4) inhibitor, cluster of differentiation 276 (CD276 or B7-H3) inhibitor, B and T lymphocyte attenuator (BTLA) inhibitor, galectin-9 (GAL9) inhibitor, checkpoint kinase 1 (Chk1) inhibitor, adenosine A2A receptor (A2AR) inhibitor, indoleamine 2,3-dioxygenase (IDO) inhibitor, killer-cell immunoglobulin-like receptor (KIR) inhibitor, or V-domain Ig suppressor of T cell activation (VISTA) inhibitor. In certain embodiments, the PD-1 inhibitor is nivolumab, pidilizumab, pembrolizumab, MEDI-0680, REGN2810, or AMP-224. In certain embodiments, the PD-L1 inhibitor is atezolizumab, durvalumab, BMS-936559, avelumab, or CA-170. In certain embodiments, the CTLA-4 inhibitor is ipilimumab or tremelimumab. In certain embodiments, the additional pharmaceutical agent is an aromatase inhibitor. In certain embodiments, the additional pharmaceutical agent is an PI3K inhibitor. In certain embodiments, the additional pharmaceutical agent is an mTOR inhibitor. In certain embodiments, the additional pharmaceutical agent is an endocrine therapy. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy. In certain embodiments, the compounds described herein or pharmaceutical compositions can be administered in combination with chemotherapy. In certain embodiments, the compounds described herein or pharmaceutical compositions can be administered in combination with immunotherapy. In certain embodiments, the compounds described herein or pharmaceutical compositions can be administered in combination with chemotherapy or immunotherapy.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease (e.g., proliferative disease (e.g., ovarian cancer, breast cancer, or prostate cancer)) in a subject in need thereof. In certain embodiments, the kits are useful for preventing a disease (e.g., proliferative disease (e.g., ovarian cancer, breast cancer, or prostate cancer)) in a subject in need thereof.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., proliferative disease (e.g., ovarian cancer, breast cancer, or prostate cancer)) in a subject in need thereof. In certain embodiments, the kits and instructions provide for preventing a disease (e.g., proliferative disease (e.g., ovarian cancer, breast cancer, or prostate cancer)) in a subject in need thereof. In certain embodiments, the kits and instructions provide for inducing the degradation of target (e.g., kinase (e.g., CDK (e.g., CDK9, CDK12))) in a subject, biological sample, tissue, or cell. A kit described herein may include one or more additional pharmaceutical agents described herein as a separate composition.

Methods of Treatment and Uses

The compounds described herein are capable of binding (e.g., reversibly binding or irreversibly binding) an E3 ubiquitin ligase (e.g., Cereblon) and the target protein (e.g., kinase (e.g., CDK (e.g., CDK9 and/or CDK12))) and inducing the degradation of the target protein (e.g., kinase (e.g., CDK (e.g., CDK9 and/or CDK12))). The present disclosure thus also provides methods of inducing the degradation of the target protein (e.g., kinase (e.g., CDK (e.g., CDK9 and/or CDK12))) in a subject, biological sample, tissue, or cell. The compounds described herein are capable of binding (e.g., reversibly binding or irreversibly binding) an E3 ubiquitin ligase (e.g., Cereblon) and the target protein (e.g., CDK9 and/or CDK12) and inducing the degradation of the target protein CDK9 and/or CDK12. The present disclosure thus also provides methods of inducing the degradation of the target protein (e.g., kinase (e.g., CDK (e.g., CDK9 and/or CDK12))) in a subject, biological sample, tissue, or cell. The present disclosure thus also provides methods of inducing the degradation of the target protein (e.g., CDK9 and/or CDK12) in a subject, biological sample, tissue, or cell. The present disclosure further provides methods of inducing apoptosis in a cell in a cell, tissue, biological sample, or subject. The present disclosure further provides methods for the treatment of diseases, such as proliferative diseases in a subject in need thereof.

In certain embodiments, the application provides a method of binding an ubiquitin receptor E3 ubiquitin ligase (e.g., Cereblon) and promoting the degradation of the target protein (e.g., kinase (e.g., CDK (e.g., CDK9 and/or CDK12))). In certain embodiments, the application provides a method of binding an ubiquitin receptor E3 ubiquitin ligase (e.g., Cereblon) and promoting the degradation of the target protein CDK9 and/or CDK12. In another aspect, the present disclosure provides methods of inducing the degradation of the target protein (e.g., kinase (e.g., CDK (e.g., CDK9 and/or CDK12))) in a subject in need thereof, the methods comprise administering to the subject an effective amount of a compound or pharmaceutical composition described herein. In another aspect, the present disclosure provides methods of inducing the degradation of the target protein CDK9 and/or CDK12 in a subject in need thereof, the methods comprise administering to the subject an effective amount of a compound or pharmaceutical composition described herein. In another aspect, the present disclosure provides methods of inducing the degradation of the target protein (e.g., kinase (e.g., CDK (e.g., CDK9 and/or CDK12))) in a biological sample, tissue, or cell, the methods comprise contacting the biological sample, tissue, or cell with an effective amount of a compound or pharmaceutical composition described herein. In another aspect, the present disclosure provides methods of inducing the degradation of the target protein CDK9 and/or CDK12 in a biological sample, tissue, or cell, the methods comprise contacting the biological sample, tissue, or cell with an effective amount of a compound or pharmaceutical composition described herein.

In another aspect, the present disclosure provides methods of inducing apoptosis in a cell in a biological sample, tissue, or cell, the methods comprise contacting the biological sample, tissue, or cell with an effective amount of a compound or pharmaceutical composition described herein.

In certain embodiments, the application provides a method of binding an E3 ubiquitin ligase (e.g., Cereblon) and the target protein (e.g., kinase (e.g., CDK (e.g., CDK9 and/or CDK12))) and selectively inducing the degradation of the target protein (e.g., kinase (e.g., CDK (e.g., CDK9 and/or CDK12))).

Use of a bifunctional compound that binds an E3 ubiquitin ligase (e.g., Cereblon) and the target protein (e.g., kinase (e.g., CDK (e.g., CDK9 and/or CDK12))) provides a strategy for treating diseases associated with (e.g., kinase (e.g., CDK (e.g., CDK9 and/or CDK12))) (e.g. proliferative diseases), as research tools for studying the role of CDK9 and/or CDK12 in the cell, or as research tools for studying diseases associated with (e.g., kinase (e.g., CDK (e.g., CDK9 and/or CDK12))) (e.g. proliferative diseases).

The present disclosure also provides a compound of Formula (I), or a pharmaceutically acceptable salt, co-crystal, tautomer, stereoisomer, solvate, hydrate, polymorph, isotopically enriched derivative, or prodrug, or composition thereof, for use in the treatment of diseases, such as proliferative diseases, in a subject in need thereof.

The present disclosure also provides uses of a compound of Formula (I), or a pharmaceutically acceptable salt, co-crystal, tautomer, stereoisomer, solvate, hydrate, polymorph, isotopically enriched derivative, or prodrug, or composition thereof, in the manufacture of a medicament for the treatment of diseases, such as proliferative diseases, in a subject in need thereof.

In certain embodiments, the methods of the disclosure comprise administering to the subject an effective amount of a compound of Formula (I), or a pharmaceutically acceptable salt, co-crystal, tautomer, stereoisomer, solvate, hydrate, polymorph, isotopically enriched derivative, or prodrug, or composition thereof. In some embodiments, the effective amount is a therapeutically effective amount. In some embodiments, the effective amount is a prophylactically effective amount.

In certain embodiments, the subject being treated is an animal. The animal may be of either sex and may be at any stage of development. In certain embodiments, the subject is a mammal. In certain embodiments, the subject being treated is a human. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal.

Certain methods described herein may comprise administering one or more additional pharmaceutical agent(s) in combination with the compounds described herein. The additional pharmaceutical agent(s) may be administered at the same time as the compound of Formula (I), or at different times than the compound of Formula (I). For example, the compound of Formula (I) and any additional pharmaceutical agent(s) may be on the same dosing schedule or different dosing schedules. All or some doses of the compound of Formula (I) may be administered before all or some doses of an additional pharmaceutical agent, after all or some does an additional pharmaceutical agent, within a dosing schedule of an additional pharmaceutical agent, or a combination thereof. The timing of administration of the compound of Formula (I) and additional pharmaceutical agents may be different for different additional pharmaceutical agents.

In certain embodiments, the additional pharmaceutical agent comprises an agent useful in the treatment of diseases, such as proliferative diseases, in a subject in need thereof. In certain embodiments, the additional pharmaceutical agent is useful in the treatment of a proliferative disease. In certain embodiments, the additional pharmaceutical agent is useful in the treatment of an inflammatory disease. In certain embodiments, the additional pharmaceutical agent is useful in the treatment of proliferative diseases.

In another aspect, the present disclosure provides methods for inducing the degradation of a target protein (e.g., kinase (e.g., CDK (e.g., CDK9 and/or CDK12))), the method comprising administering to the subject a compound of Formula (I), or a pharmaceutically acceptable salt, co-crystal, tautomer, stereoisomer, solvate, hydrate, polymorph, isotopically enriched derivative, or prodrug, or composition thereof.

In another aspect, the present disclosure provides methods for binding an E3 ubiquitin ligase and promoting the degradation and/or ubiquitination of a target protein (e.g., kinase (e.g., CDK (e.g., CDK9 and/or CDK12))), the method comprising administering to the subject a compound of Formula (I), or a pharmaceutically acceptable salt, co-crystal, tautomer, stereoisomer, solvate, hydrate, polymorph, isotopically enriched derivative, or prodrug, or composition thereof.

All types of biological samples described herein or known in the art are contemplated as being within the scope of the invention. In certain embodiments, the disease (e.g., proliferative disease (e.g., ovarian cancer, breast cancer, or prostate cancer)) to be treated or prevented using the compounds described herein is cancer. All types of cancers disclosed herein or known in the art are contemplated as being within the scope of the invention. In certain embodiments, the proliferative disease is cancer. In certain embodiments, the cancer is ovarian cancer. In certain embodiments, the cancer is breast cancer. In certain embodiments, the cancer is recurring breast cancer. In certain embodiments, the cancer is mutant breast cancer. In certain embodiments, the cancer is HER2+ breast cancer. In certain embodiments, the cancer is HER2− breast cancer. In certain embodiments, the cancer is triple-negative breast cancer (TNBC). In certain embodiments, the cancer is prostate cancer. In certain embodiments, the cancer is colon cancer.

In still another aspect, the present disclosure provides the pharmaceutical compositions described herein for use in binding an E3 ubiquitin ligase and CDK9 and/or CDK12 and promoting the degradation of a target protein (e.g., kinase (e.g., CDK (e.g., CDK9 and/or CDK12))); inducing apoptosis in a cell in a subject, biological sample, tissue, or cell; and treating and/or preventing proliferative diseases.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

The compounds provided herein can be prepared from readily available starting materials using the following general methods and procedures or methods known in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Example 1. Synthetic Preparation of Exemplary Compounds of Formula (I)

Compounds of Formula (I) may be prepared using the synthetic schemes and procedures described in detail below.

Synthesis of N-(7-((R)-3-((5-chloro-4-(1H-indol-3-yl)pyrimidin-2-yl)amino)piperidin-1-yl)heptyl)-2-((2-(2,6-dioxopiperidin-3-yl)-1,3-dioxoisoindolin-4-yl)oxy)acetamide (BSJ-04-023)

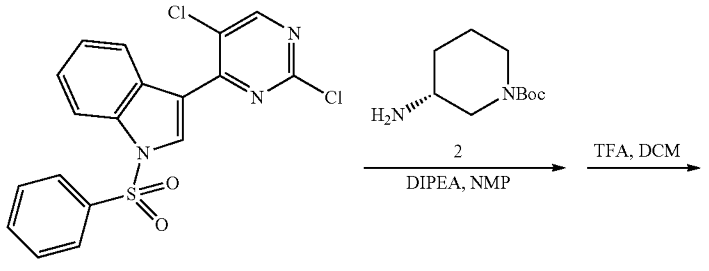

7

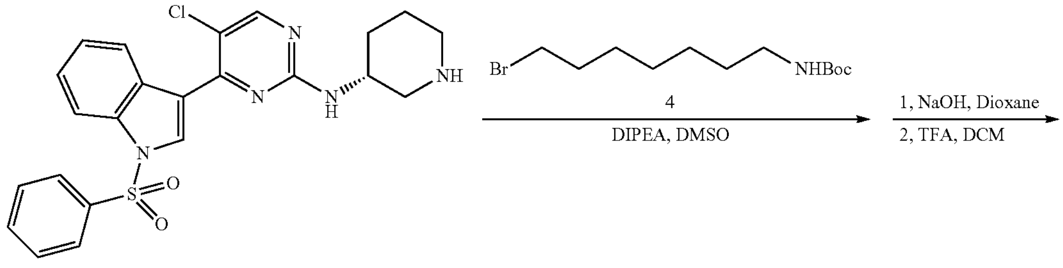

8

-continued

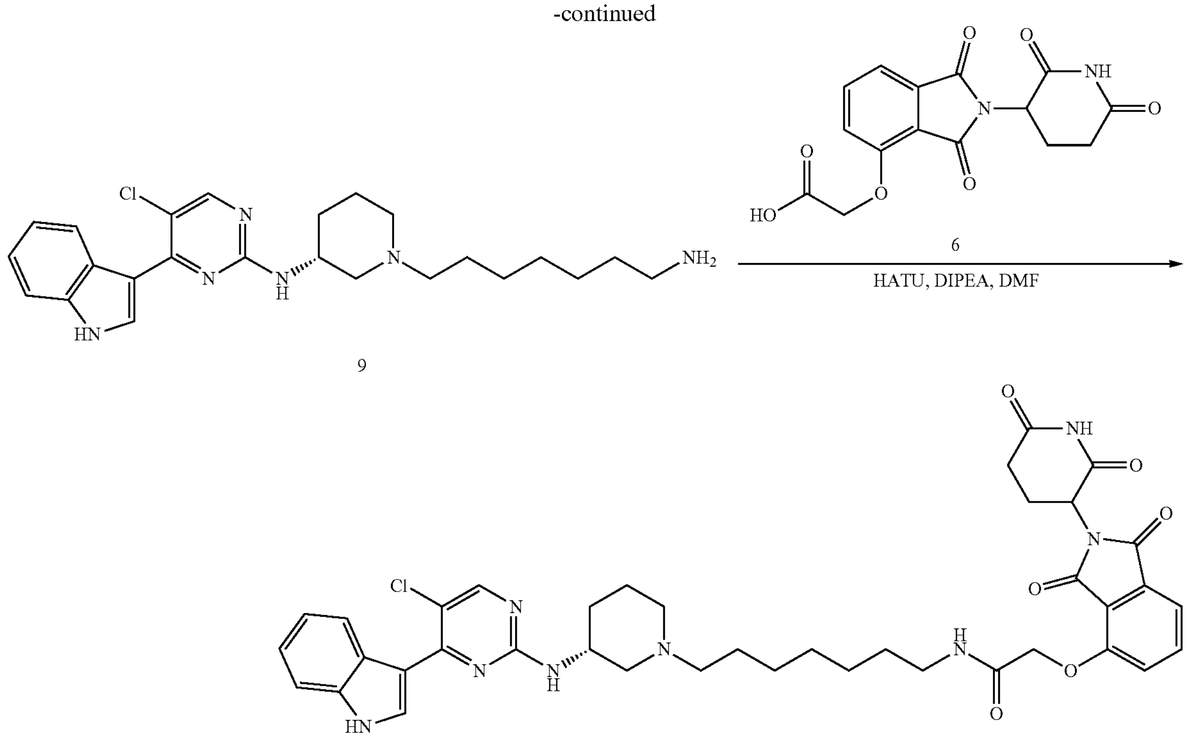

9

BSJ-04-023

(R)-5-chloro-4-(1-(phenylsulfonyl)-1H-indol-3-yl)-N-(piperidin-3-yl)pyrimidin-2-amine (8)

To a solution of 3-(2,5-dichloropyrimidin-4-yl)-1-(phenylsulfonyl)-1H-indole (7) (404 mg, 1.0 mmol) in 5 mL of NMP was added tert-butyl (R)-3-aminopiperidine-1-carboxylate (300 mg, 1.5 mmol) and DIPEA (0.52 mL, 3.0 mmol). The reaction mixture was heated to 125° C. and kept stirring overnight. The mixture was then warmed to room temperature, extracted with 100 mL of Ethyl Acetate (EA) and 50 mL of water. The organic layer was washed with 50 mL of Saturated $Na_2CO_3$ and 50 mL of brine, dried over anhydrous $Na_2SO_4$, and evaporated to give a yellowish residue which was directly dissolved into 2.5 mL of DCM, followed by slow addition of 2.5 mL of TFA at ice-bath. The mixture was warmed to room temperature and stirred for 0.5 h. The solvent was then evaporated, and the residue was purified by reverse phase HPLC (5-95% MeOH in $H_2O$) to give 8 (TFA salt) as a yellow solid (407 mg, 87% in two steps). LC-MS: m/z 468 [M+1]. $^1H$ NMR (500 MHz, DMSO-$d_6$) δ 8.61 (s, 1H), 8.53-8.47 (m, 1H), 8.45-8.19 (m, 1H), 8.09 (d, J=7.8 Hz, 2H), 8.05-7.96 (m, 1H), 7.88-7.69 (m, 2H), 7.66-7.58 (m, 2H), 7.51-7.32 (m, 2H), 4.19 (br, 1H), 3.38-3.27 (m, 1H), 3.16 (d, J=1.5 Hz, 1H), 3.15-3.07 (m, 1H), 2.82 (q, J=11.0 Hz, 2H), 2.00 (br, 1H), 1.87 (br, 1H), 1.73 (br, 1H), 1.54 (br, 1H). $^{13}C$ NMR (126 MHz, DMSO) δ 159.49, 159.39, 158.13, 136.42, 135.18, 133.69, 130.11, 129.61, 129.58, 128.82, 128.73, 128.44, 127.06, 125.63, 124.41, 117.07, 115.17, 115.12, 112.92, 46.17, 44.96, 42.85, 28.18, 20.33.

(R)—N-(1-(7-aminoheptyl)piperidin-3-yl)-5-chloro-4-(1H-indol-3-yl)pyrimidin-2-amine (9)

To a solution of 8 (103 mg, 0.22 mmol) in DMSO (2 mL) was added tert-butyl (7-bromoheptyl)carbamate (4) (129 mg, 0.44 mmol) and DIPEA (0.115 mL, 0.66 mmol). The mixture was heated to 80° C. and kept stirring for 24 h. The mixture was then cooled down to room temperature, extracted, dried, filtered and concentrated to give a Boc-protected intermediate which was then dissolved into 2 mL of dioxane, followed by addition of 1 mL of 1N NaOH solution, and stirred at room temperature for 4 h. The reaction mixture was extracted with DCM, dried over anhydrous $Na_2SO_4$, and evaporated to give a brown residue, LC-MS: m/z 541 [M+1]. The residue was dissolved in 2 mL of DCM, then 2 mL of TFA was added at ice-bath. The resulting mixture was then warmed to room temperature and stirred for 0.5 h. Then, the solvent was evaporated and the residue was purified by reverse phase HPLC (5-95% MeOH in $H_2O$) to give 9 (TFA salt) as a light yellow solid (56.3 mg, 58% in three steps). LC-MS: m/z 441 [M+1].

N-(7-((R)-3-((5-chloro-4-(1H-indol-3-yl)pyrimidin-2-yl)amino)piperidin-1-yl)heptyl)-2-((2-(2,6-dioxopiperidin-3-yl)-1,3-dioxoisoindolin-4-yl)oxy) acetamide (BSJ-04-023)

To a solution of 9 (18.6 mg, 0.0422 mmol) in 2 mL of DMF was added 6 (14 mg, 0.0422 mmol), HATU (33 mg, 0.0844 mmol) and DIPEA (37 μL, 0.211 mmol). The resulting mixture was stirred for 1 h at room temperature, then evaporated the solvent and purified by reverse phase HPLC (5-95% MeOH in $H_2O$) to give BSJ-04-023 (TFA salt) as a light-yellow solid (30.7 mg, 83%). LC-MS: m/z 756 [M+1]. $^1H$ NMR (500 MHz, DMSO-$d_6$) δ 11.90 (d, J=3.3 Hz, 1H), 11.12 (s, 1H), 9.42 (s, 1H), 8.54-8.41 (m, 1H), 8.38-8.26 (m, 1H), 7.93 (q, J=5.8 Hz, 1H), 7.85-7.73 (m, 1H), 7.50 (d, J=7.3 Hz, 3H), 7.43-7.32 (m, 1H), 7.27-7.09 (m, 2H), 5.11 (dd, J=12.8, 5.4 Hz, 1H), 4.76 (d, J=3.3 Hz, 2H), 3.19-2.97 (m, 5H), 2.97-2.67 (m, 3H), 2.65-2.51 (m, 2H), 2.15-1.95

(m, 4H), 1.70-1.51 (m, 2H), 1.49-1.36 (m, 3H), 1.34-1.10 (m, 8H). $^{13}C$ NMR (126 MHz, DMSO) δ 172.80, 169.89, 166.73, 166.66, 165.54, 159.39, 158.27, 157.99, 155.04, 136.94, 136.07, 133.04, 131.11, 131.05, 126.21, 122.45, 120.75, 120.42, 116.83, 116.10, 113.84, 111.95, 67.68, 56.19, 48.81, 38.24, 30.95, 28.90, 28.09, 26.00, 25.93, 23.21, 22.00.

Synthesis of N-(6-((R)-3-((5-chloro-4-(1H-indol-3-yl)pyrimidin-2-yl)amino)piperidin-1-yl)hexyl)-2-((2-(2,6-dioxopiperidin-3-yl)-1,3-dioxoisoindolin-4-yl)oxy)acetamide (I-2, BSJ-04-078)

I-2 was synthesized with similar procedures as I-1 from 3 (21.1 mg, 0.045 mmol), tert-butyl (4-bromohexyl)carbamate (12.6 mg, 0.045 mmol) and 6 (10 mg, 0.03 mmol). I-2 was obtained as an off-white solid (14.7 mg, 44% in 4 steps). LC-MS: m/z 741 [M+1]. $^1H$ NMR (500 MHz, DMSO-$d_6$) δ 11.90 (t, J=3.3 Hz, 1H), 11.12 (s, 1H), 9.43 (s, 1H), 8.48 (t, J=2.9 Hz, 1H), 8.39-8.28 (m, 1H), 8.03-7.90 (m, 1H), 7.85-7.75 (m, 1H), 7.55-7.48 (m, 3H), 7.42-7.37 (m, 1H), 7.23 (t, J=7.5 Hz, 1H), 7.17 (t, J=7.5 Hz, 1H), 5.15-5.07 (m, 1H), 4.76 (d, J=3.6 Hz, 2H), 3.20-2.98 (m, 5H), 2.96-2.70 (m, 3H), 2.64-2.53 (m, 2H), 2.15-1.71 (m, 4H), 1.71-1.37 (m, 5H), 1.35-1.03 (m, 6H).

Synthesis of N-(5-((R)-3-((5-chloro-4-(1H-indol-3-yl)pyrimidin-2-yl)amino)piperidin-1-yl)pentyl)-2-((2-(2,6-dioxopiperidin-3-yl)-1,3-dioxoisoindolin-4-yl)oxy)acetamide (I-3, BSJ-04-079)

I-3 was synthesized with similar procedures as I-1 from 3 (21.1 mg, 0.045 mmol), tert-butyl (5-bromopentyl)carbamate (11.9 mg, 0.045 mmol) and 6 (10 mg, 0.03 mmol). I-3 was obtained as an off-white solid (14.4 mg, 44% in 4 steps). LC-MS: m/z 727 [M+1]. $^1H$ NMR (500 MHz, DMSO-$d_6$) δ 11.89 (d, J=3.2 Hz, 1H), 11.12 (s, 1H), 9.44 (s, 1H), 8.48 (t, J=3.1 Hz, 1H), 8.31 (s, 1H), 8.02-7.91 (m, 1H), 7.85-7.75 (m, 1H), 7.50 (d, J=7.5 Hz, 3H), 7.42-7.36 (m, 1H), 7.26-7.21 (m, 1H), 7.20-7.12 (m, 1H), 5.11 (dd, J=12.8, 5.4 Hz, 1H), 4.76 (d, J=4.7 Hz, 2H), 3.22-2.99 (m, 6H), 2.95-2.71 (m, 4H), 2.65-2.53 (m, 2H), 2.15-1.94 (m, 3H), 1.72-1.57 (m, 2H), 1.55-1.37 (m, 3H), 1.34-1.13 (m, 4H).

Synthesis of N-(4-((R)-3-((5-chloro-4-(1H-indol-3-yl)pyrimidin-2-yl)amino)piperidin-1-yl)butyl)-2-((2-(2,6-dioxopiperidin-3-yl)-1,3-dioxoisoindolin-4-yl)oxy)acetamide (I-4, BSJ-04-080)

I-4 was synthesized with similar procedures as I-1 from 3 (21.1 mg, 0.045 mmol), tert-butyl (4-bromobutyl)carbamate (11.4 mg, 0.045 mmol) and 6 (10 mg, 0.03 mmol). I-4 was obtained as an off-white solid (15.1 mg, 47% in 4 steps). LC-MS: m/z 713 [M+1]. $^1H$ NMR (500 MHz, DMSO-$d_6$) δ 11.90 (d, J=3.2 Hz, 1H), 11.12 (s, 1H), 9.50 (s, 1H), 8.48 (t, J=2.7 Hz, 1H), 8.32 (d, J=12.8 Hz, 1H), 8.03 (t, J=5.8 Hz, 1H), 7.85-7.74 (m, 1H), 7.50 (q, J=6.7 Hz, 3H), 7.43-7.35 (m, 1H), 7.26-7.21 (m, 1H), 7.20-7.13 (m, 1H), 5.15-5.05 (m, 1H), 4.77 (d, J=7.8 Hz, 2H), 3.67-3.27 (m, 2H), 3.23-3.07 (m, 5H), 2.96-2.69 (m, 3H), 2.64-2.52 (m, 2H), 2.09-1.93 (m, 3H), 1.92-1.59 (m, 4H), 1.56-1.39 (m, 3H).

Synthesis of N-(2-(2-(2-(2-((R)-3-((5-chloro-4-(1H-indol-3-yl)pyrimidin-2-yl)amino)piperidin-1-yl)ethoxy)ethoxy)ethoxy)ethyl)-2-((2-(2,6-dioxopiperidin-3-yl)-1,3-dioxoisoindolin-4-yl)oxy)acetamide (I-5, BSJ-04-026)

I-5 was synthesized with similar procedures as I-1 from 3 (21.1 mg, 0.045 mmol), tert-butyl (2-(2-(2-(2-bromoethoxy)ethoxy)ethoxy)ethyl)carbamate (16.0 mg, 0.045 mmol) and 6 (10 mg, 0.03 mmol). I-5 was obtained as an off-white solid (16.5 mg, 45% in 4 steps). LC-MS: m/z 817 [M+1]. $^1H$ NMR (500 MHz, DMSO-$d_6$) δ 11.90 (d, J=4.2 Hz, 1H), 11.13 (s, 1H), 9.63 (s, 1H), 8.48 (d, J=2.9 Hz, 1H), 8.32 (s, 1H), 7.97 (t, J=5.7 Hz, 1H), 7.90-7.76 (m, 1H), 7.68-7.45 (m, 3H), 7.38 (dd, J=8.6, 2.2 Hz, 1H), 7.30-7.14 (m, 2H), 5.15-5.07 (m, 1H), 4.77 (s, 2H), 4.46-4.12 (br, 2H), 3.84-3.65 (m, 4H), 3.43-3.18 (m, 10H), 3.00-2.71 (m, 4H), 2.66-2.52 (m, 2H), 2.19-1.73 (m, 6H).

Synthesis of N-(2-(2-(2-((R)-3-((5-chloro-4-(1H-indol-3-yl)pyrimidin-2-yl)amino)piperidin-1-yl)ethoxy)ethoxy)ethyl)-2-((2-(2,6-dioxopiperidin-3-yl)-1,3-dioxoisoindolin-4-yl)oxy)acetamide (I-6, BSJ-04-098)

I-6 was synthesized with similar procedures as I-1 from 3 (21.1 mg, 0.045 mmol), tert-butyl (2-(2-(2-bromoethoxy)ethoxy)ethyl)carbamate (14.0 mg, 0.045 mmol) and 6 (10 mg, 0.03 mmol). I-6 was obtained as an off-white solid (16.7 mg, 48% in 4 steps). LC-MS: m/z 772 [M+1]. $^1H$ NMR (500 MHz, DMSO-$d_6$) δ 11.89 (d, J=3.3 Hz, 1H), 11.12 (s, 1H), 9.63 (s, 1H), 8.48 (dd, J=5.2, 3.0 Hz, 1H), 8.32 (d, J=15.6 Hz, 1H), 8.03-7.90 (m, 1H), 7.85-7.75 (m, 1H), 7.49 (dd, J=7.4, 2.2 Hz, 3H), 7.38 (dd, J=9.4, 3.9 Hz, 1H), 7.27-7.10 (m, 2H), 5.11 (dd, J=12.9, 5.4 Hz, 1H), 4.76 (d, J=4.3 Hz, 2H), 3.81-3.64 (m, 3H), 3.63-3.50 (m, 4H), 3.44 (d, J=5.8 Hz, 2H), 3.41-3.22 (m, 6H), 2.99-2.73 (m, 3H), 2.65-2.53 (m, 1H), 2.13-1.92 (m, 3H), 1.92-1.73 (m, 2H).

N-(2-(2-(3-((R)-3-((5-chloro-4-(1H-indol-3-yl)pyrimidin-2-yl)amino)piperidin-1-yl)-3-oxopropoxy)ethoxy)ethyl)-2-((2-(2,6-dioxopiperidin-3-yl)-1,3-dioxoisoindolin-4-yl)oxy)acetamide (I-7, BSJ-04-099)

I-7 was synthesized with similar procedures as I-1. LC-MS: m/z 801 [M+1].

Synthesis of N-(6-((R)-3-((5-chloro-4-(1H-indol-3-yl)pyrimidin-2-yl)amino)piperidin-1-yl)-6-oxohexyl)-2-((2-(2,6-dioxopiperidin-3-yl)-1,3-dioxoisoindolin-4-yl)oxy)acetamide (I-8, BSJ-04-071)

I-8 was synthesized with similar procedures as I-1. LC-MS: m/z 756 [M+1]. $^1H$ NMR (500 MHz, DMSO-$d_6$) δ 11.85 (s, 1H), 11.11 (d, J=2.6 Hz, 1H), 8.49-8.41 (m, 1H), 8.27 (d, J=3.7 Hz, 1H), 7.98-7.91 (m, 1H), 7.84-7.71 (m, 1H), 7.52-7.43 (m, 2H), 7.41-7.34 (m, 2H), 7.33-7.03 (m, 3H), 5.15-5.06 (m, 1H), 4.75 (d, J=3.6 Hz, 2H), 4.53-3.88 (m, 4H), 3.21-3.10 (m, 1H), 3.08-2.96 (m, 2H), 2.95-2.83 (m, 2H), 2.83-2.69 (m, 1H), 2.65-2.53 (m, 2H), 2.43-2.21 (m, 1H), 2.14-1.90 (m, 3H), 1.86-1.72 (m, 1H), 1.69-0.90 (m, 9H).

N-(5-(4-(4-((R)-3-((5-chloro-4-(1H-indol-3-yl)pyrimidin-2-yl)amino)piperidine-1-carbonyl)phenyl)piperazin-1-yl)pentyl)-2-((2-(2,6-dioxopiperidin-3-yl)-1,3-dioxoisoindolin-4-yl)oxy)acetamide (I-9, BSJ-04-077)

I-9 was synthesized with similar procedures as I-1. LC-MS: m/z 915 [M+1].

N-(3-(4-(4-((R)-3-((5-chloro-4-(1H-indol-3-yl)pyrimidin-2-yl)amino)piperidine-1-carbonyl)phenyl)piperazin-1-yl)propyl)-2-((2-(2,6-dioxopiperidin-3-yl)-1,3-dioxoisoindolin-4-yl)oxy)acetamide (I-10, BSJ-04-076)

I-10 was synthesized with similar procedures as I-1. LC-MS: m/z 887 [M+1].

N-(7-(4-(3-((R)-3-((5-chloro-4-(1H-indol-3-yl)pyrimidin-2-yl)amino)piperidine-1-carbonyl)phenyl)piperazin-1-yl)heptyl)-2-((2-(2,6-dioxopiperidin-3-yl)-1,3-dioxoisoindolin-4-yl)oxy)acetamide (I-11, BSJ-04-100)

I-11 was synthesized with similar procedures as I-1. LC-MS: m/z 943 [M+1].

N-(7-(4-((R)-3-((5-chloro-4-(1H-indol-3-yl)pyrimidin-2-yl)amino)piperidine-1-carbonyl)piperidin-1-yl)heptyl)-2-((2-(2,6-dioxopiperidin-3-yl)-1,3-dioxoisoindolin-4-yl)oxy)acetamide (I-12, BSJ-04-086)

I-12 was synthesized with similar procedures as I-10. LC-MS: m/z 866 [M+1].

N-(7-(4-((R)-3-((5-chloro-4-(1H-indol-3-yl)pyrimidin-2-yl)amino)piperidine-1-carbonyl)piperidin-1-yl)heptyl)-2-((2-(2,6-dioxopiperidin-3-yl)-1,3-dioxoisoindolin-4-yl)oxy)acetamide (I-13, BSJ-04-089)

I-13 was synthesized with similar procedures as I-10. LC-MS: m/z 852 [M+1].

Synthesis of N-(7-((R)-3-((5-chloro-4-((2-(isopropylsulfonyl)phenyl)amino)pyrimidin-2-yl)amino)piperidin-1-yl)heptyl)-2-((2-(2,6-dioxopiperidin-3-yl)-1,3-dioxoisoindolin-4-yl)oxy)acetamide (I-14; BSJ-04-116)

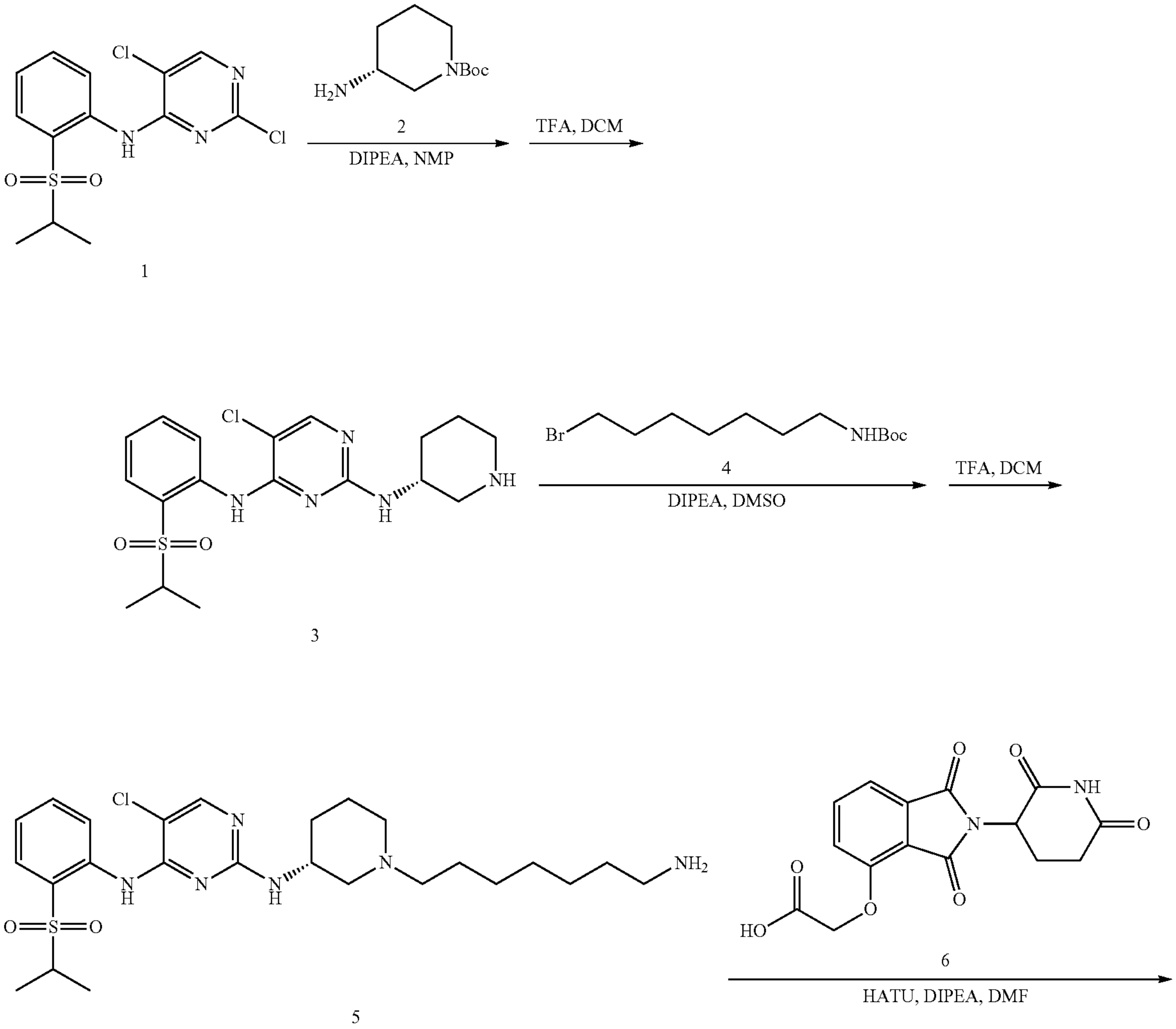

-continued

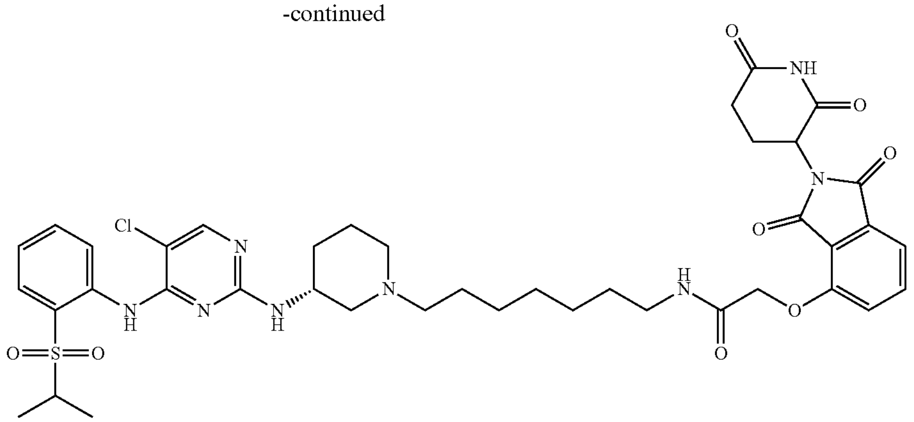

BSJ-04-116

(R)-5-chloro-$N_4$-(2-(isopropylsulfonyl)phenyl)-$N_2$-(piperidin-3-yl)pyrimidine-2,4-diamine (3)

To a solution of 2,5-dichloro-N-(2-(isopropylsulfonyl)phenyl)pyrimidin-4-amine 1 (345 mg, 1.0 mmol) in 5 mL of NMP was added tert-butyl (R)-3-aminopiperidine-1-carboxylate (300 mg, 1.5 mmol) and DIPEA (0.52 mL, 3.0 mmol). The reaction mixture was heated to 125° C. and kept stirring overnight. The mixture was then warmed to room temperature, extracted with 100 mL of Ethyl Acetate (EA) and 50 mL of water. The organic layer was washed with 50 mL of Saturated $Na_2CO_3$ and 50 mL of brine, dried over anhydrous $Na_2SO_4$, and evaporated to give a yellowish residue which was directly dissolved into 2.5 mL of DCM, followed by slow addition of 2.5 mL of TFA at ice-bath. The mixture was warmed to room temperature and stirred for 0.5 h. The solvent was then evaporated, and the residue was purified by reverse phase HPLC (5-95% MeOH in $H_2O$) to give 3 (TFA salt) as a yellow solid (368 mg, 90% in two steps). LC-MS: m/z 410 (M+1). $^1$H NMR (500 MHz, DMSO-$d_6$) δ 9.54 (s, 1H), 8.81 (br, 2H), 8.29-8.10 (m, 1H), 7.92-7.82 (m, 1H), 7.78 (s, 1H), 7.37 (s, 1H), 4.03 (br, 1H), 3.50-3.40 (m, 1H), 3.39-3.28 (br, 1H), 3.23-3.13 (m, 1H), 2.90-2.74 (m, 3H), 1.97 (s, 1H), 1.93-1.82 (m, 1H), 1.72-1.61 (m, 1H), 1.55 (d, J=36.1 Hz, 1H), 1.18 (d, J=2.1 Hz, 3H), 1.16 (d, J=2.1 Hz, 3H). $^{13}$C NMR (126 MHz, DMSO) δ 158.77, 158.49, 158.20, 154.97, 154.70, 153.93, 138.10, 135.07, 131.01, 123.37, 116.95, 114.62, 54.92, 46.26, 45.08, 43.03, 28.07, 20.55, 14.87, 14.83.

(R)—$N_2$-(1-(7-aminoheptyl)piperidin-3-yl)-5-chloro-$N_4$-(2-(isopropylsulfonyl)phenyl)pyrimidine-2,4-diamine (5)

To a solution of 3 (90 mg, 0.22 mmol) in DMSO (2 mL) was added tert-butyl (7-bromoheptyl)carbamate (4) (129 mg, 0.44 mmol) and DIPEA (0.115 mL, 0.66 mmol). The mixture was heated to 80° C. and kept stirring for 24 h. The mixture was then cooled down to room temperature, extracted, dried, filtered and concentrated to give a light brown residue which was then dissolved into 1 mL of DCM, followed by slow addition of 1 mL of TFA at ice bath. The mixture was then warmed to room temperature and evaporated after 0.5 h. The residue was purified by reverse phase HPLC (5-95% MeOH in $H_2O$) to give 5 (TFA salt) as a light grey solid (115 mg, 65% in two steps). LC-MS: m/z 523 [M+1].

N-(7-((R)-3-((5-chloro-4-((2-(isopropylsulfonyl)phenyl)amino)pyrimidin-2-yl)amino)piperidin-1-yl)heptyl)-2-((2-(2,6-dioxopiperidin-3-yl)-1,3-dioxoisoindolin-4-yl)oxy)acetamide (I-14; BSJ-04-116)

To a solution of 5 (22 mg, 0.0422 mmol) in 2 mL of DMF was added 6 (14 mg, 0.0422 mmol), HATU (33 mg, 0.0844 mmol) and DIPEA (37 μL, 0.211 mmol). The resulting mixture was stirred for 1 h at room temperature, then evaporated the solvent and purified by reverse phase HPLC (5-95% MeOH in $H_2O$) to give I-14; BSJ-04-116 (TFA salt) as an off-white solid (30.7 mg, 87%). LC-MS: m/z 838 [M+1]. $^1$H NMR (500 MHz, DMSO-$d_6$) δ 11.12 (s, 1H), 9.52 (s, 1H), 9.41 (s, 1H), 8.63 (br, 1H), 8.19 (d, J=11.9 Hz, 1H), 7.93 (t, J=6.2 Hz, 1H), 7.87-7.71 (m, 3H), 7.50 (d, J=7.3 Hz, 1H), 7.43-7.26 (m, 3H), 5.11 (dd, J=12.9, 5.4 Hz, 1H), 4.76 (s, 2H), 3.49-3.31 (m, 3H), 3.20-3.11 (m, 2H), 3.10-2.97 (m, 2H), 2.95-2.77 (m, 2H), 2.75-2.53 (m, 2H), 2.10-2.00 (m, 2H), 2.00-1.88 (m, 2H), 1.86-1.53 (m, 3H), 1.52-1.36 (m, 4H), 1.33-1.20 (m, 6H), 1.20-1.11 (m, 6H). $^{13}$C NMR (126 MHz, DMSO) δ 172.81, 169.89, 166.73, 166.66, 165.55, 158.31, 158.03, 155.04, 154.95, 136.96, 135.06, 133.04, 131.05, 120.43, 116.84, 116.12, 67.69, 56.16, 54.98, 48.82, 38.24, 30.95, 28.89, 28.08, 26.01, 25.91, 25.87, 23.19, 22.00, 14.92, 14.85, 14.81.

Synthesis of (2S,4R)-1-((S)-14-(tert-butyl)-1-((R)-3-((5-chloro-4-((2-(isopropylsulfonyl)phenyl)amino)pyrimidin-2-yl)amino)piperidin-1-yl)-12-oxo-3,6,9-trioxa-13-azapentadecan-15-oyl)-4-hydroxy-N—((S)-1-(4-(4-methylthiazol-5-yl)phenyl)ethyl)pyrrolidine-2-carboxamide (I-15; BSJ-05-063)

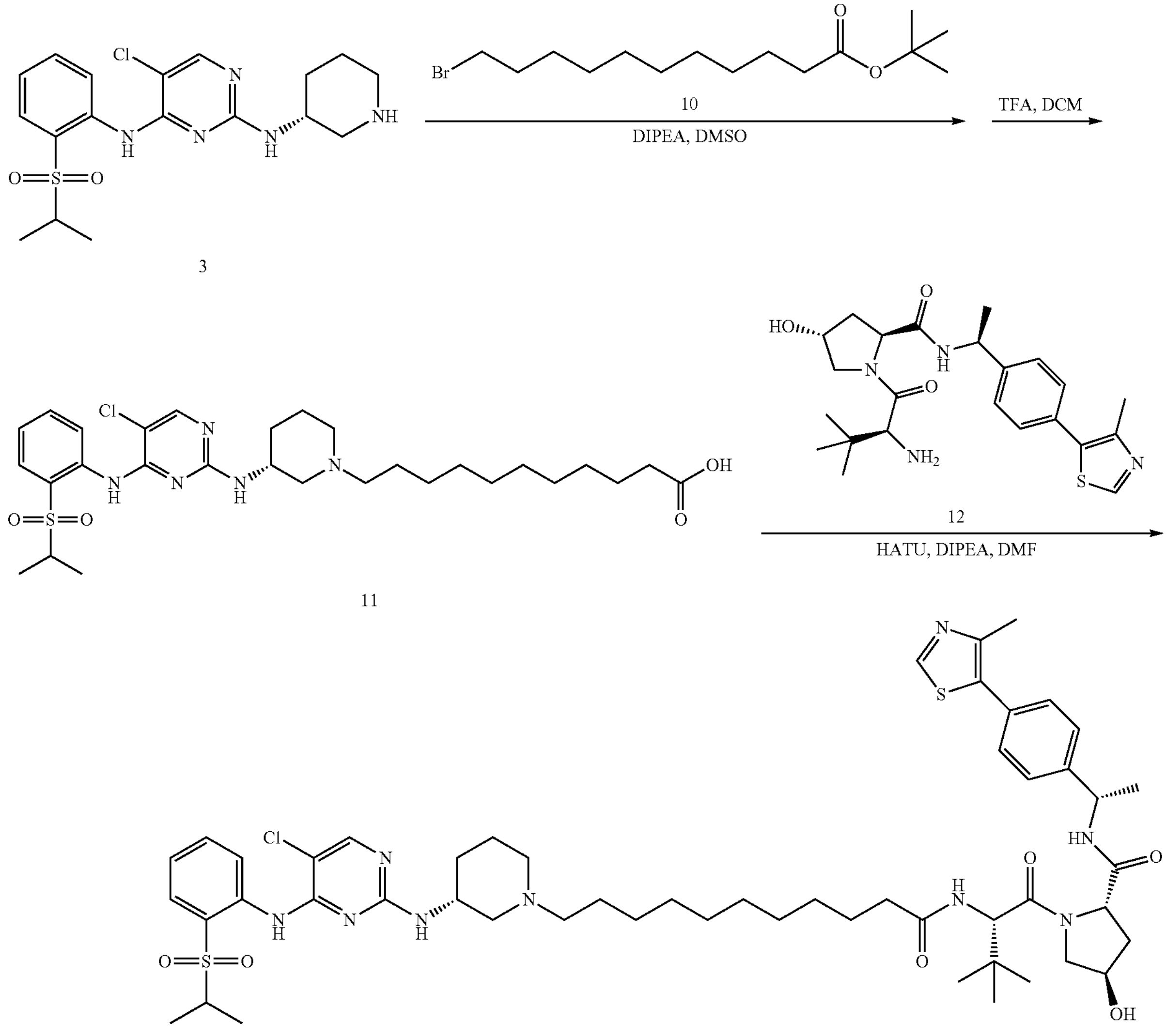

BSJ-5-063

((R)-11-(3-((5-chloro-4-((2-(isopropylsulfonyl)phenyl)amino)pyrimidin-2-yl)amino)piperidin-1-yl)undecanoic Acid (11)

To a solution of 3 (90 mg, 0.22 mmol) in DMSO (2 mL) was added tert-butyl 11-bromoundecanoate (11) (150 mg, 0.44 mmol) and DIPEA (0.115 mL, 0.66 mmol). The mixture was heated to 80° C. and kept stirring for 24 hours. The mixture was then cooled down to room temperature, extracted, dried, filtered and concentrated to give a light brown residue which was then dissolved into 1 mL of DCM, followed by slow addition of 1 mL of TFA at ice bath. The mixture was then warmed to room temperature and evaporated after 0.5 hours. The residue was purified by reverse phase HPLC (5-95% MeOH in $H_2O$) to give 11 (TFA salt) as a light-yellow oil (94 mg, 70% in two steps). LC-MS: m/z 594 [M+1].

(Synthesis of (2S,4R)-1-((S)-2-(11-((R)-3-((5-chloro-4-((2-(isopropylsulfonyl)phenyl)amino)pyrimidin-2-yl)amino)piperidin-1-yl)undecanamido)-3,3-dimethylbutanoyl)-4-hydroxy-N—((S)-1-(4-(4-methylthiazol-5-yl)phenyl)ethyl)pyrrolidine-2-carboxamide (I-15, BSJ-05-063)

To a solution of 11 (26 mg, 0.0422 mmol) in 2 mL of DMF was added 12 (19 mg, 0.0422 mmol), HATU (33 mg, 0.0844 mmol) and DIPEA (37 µL, 0.211 mmol). The resulting mixture was stirred for 1 hour at room temperature, then evaporated the solvent and purified by reverse phase HPLC (5-95% MeOH in $H_2O$) to give BSJ-06-63 (TFA salt) as an off-white solid (33 mg, 75%). LC-MS: m/z 1020 [M+1].

(2S,4R)-1-((S)-14-(tert-butyl)-1-((R)-3-((5-chloro-4-((2-(isopropylsulfonyl)phenyl)amino)pyrimidin-2-yl)amino)piperidin-1-yl)-12-oxo-3,6,9-trioxa-13-aza-pentadecan-15-oyl)-4-hydroxy-N—((S)-1-(4-(4-methylthiazol-5-yl)phenyl)ethyl)pyrrolidine-2-carboxamide (I-16; BSJ-05-064)

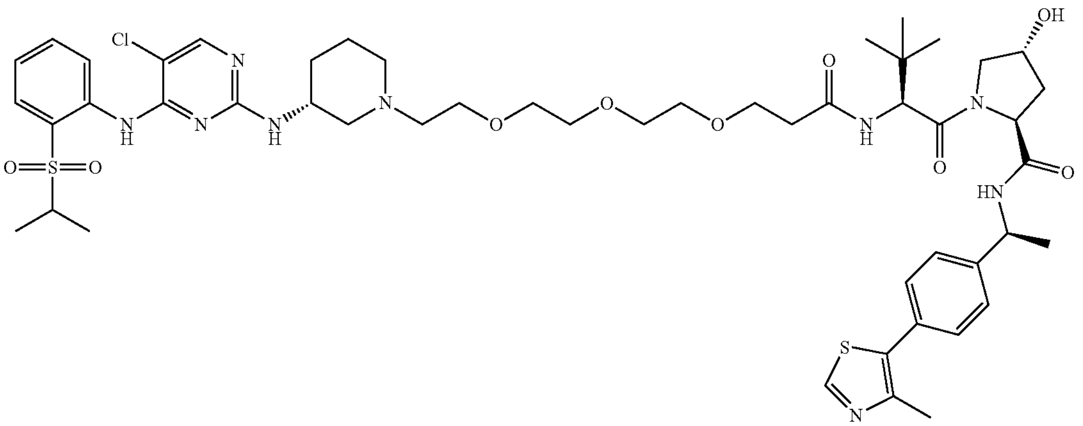 [SMILES: Cc1ncsc1-c1ccc([C@H](C)NC(=O)[C@@H]2C[C@@H](O)CN2C(=O)[C@@H](NC(=O)CCOCCOCCOCCN2CCC[C@@H](Nc3ncc(Cl)c(Nc4ccccc4S(=O)(=O)C(C)C)n3)C2)C(C)(C)C)cc1]

Compound I-16 (BSJ-05-064) was synthesized with similar procedures as for the synthesis of compound I-16 (BSJ-05-064) from 3 (47.4 mg, 0.0844 mmol), tert-butyl 3-(2-(2-(2-bromoethoxy)ethoxy)ethoxy)propanoate (30 mg, 0.0844 mmol) and 12 (23.3 mg, 0.0844 mmol). Compound I-16 (BSJ-05-064) was obtained as a yellow solid (20.6 mg, 24% in 4 steps). LC-MS: m/z 1041 [M+1].

(2R,4S)-1-((S)-2-(11-((R)-3-((5-chloro-4-((2-(isopropylsulfonyl)phenyl)amino)pyrimidin-2-yl)amino)piperidin-1-yl)undecanamido)-3,3-dimethylbutanoyl)-4-hydroxy-N—((S)-1-(4-(4-methylthiazol-5-yl)phenyl)ethyl)pyrrolidine-2-carboxamide (I-17; ZXH-7-091)

Compound I-17 was a negative control of compound I-15. It was synthesized using similar procedures as for compound I-15. LC-MS: m/z 1020 [M+1].

Example 2. CDK12 Biology Assays

Cyclin-dependent kinase 12 and 13 (CDK12/13) are elongation regulators of RNA polymerase II-mediated transcription through kinase function of phosphorylation on the C-terminal repeat domain (CTD) of RNA polymerase II. CDK12 plays a critical role in mediating genome stability and its deletion impairs the expression of several critical regulators of genome stability. Mutations of CDK12 have been identified in variety of tumors including ovary, breast, and prostate. Previous CDK12 inhibitors including, for example, covalent THZ531 (see above for chemical structure), as well as others, are not selective and potent inhibition of CDK13 is also observed.

The presently disclosed novel bifunctional compounds conjugate CDK12 inhibitors with E3 ligase ligands to induce CDK12 protein degradation (see Brief Description of the Drawings, and Table 1 below for chemical structures of exemplary CDK inhibitors). CDK12 degradation activity of exemplary compounds is shown in Table 1.

Assays for the degradation of CDK12 by exemplary compounds of Formula (I) were conducted. The results for the assays for the degradation of CDK12 by exemplary CDK12 degrader compounds depicted in Table 1 are shown in FIGS. 1-3. Table 1 also shows the CDK12 degradation activity of exemplary CDK12 inhibitor compounds 1-13 depicted in Table 1 below, wherein "+++" indicates a greater than 90% degradation, "++" indicates 80% degradation and "+" indicates 60% degradation of CDK12 at 100 nM. "N/A" indicates that the activity is undetectable at up to 500 nM via Western blotting.

TABLE 1
Exemplary CDK12 Degrader Compounds
| Compound | Structure | CDK12 degradation activity |
| --- | --- | --- |
| I-1 (BSJ-04-023) | 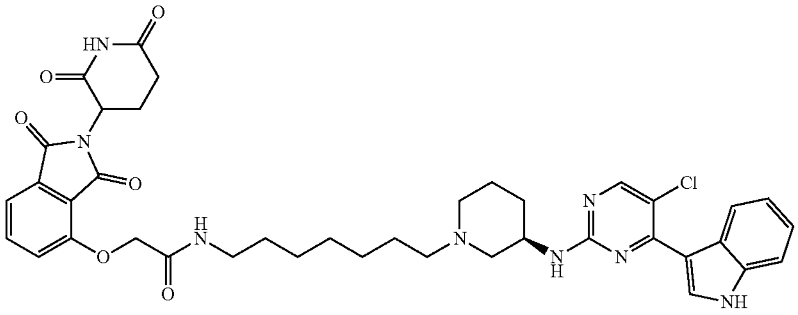 [SMILES: O=C(COc1cccc2c1C(=O)N(C1CCC(=O)NC1=O)C2=O)NCCCCCCCN1CCC[C@@H](Nc2ncc(Cl)c(-c3c[nH]c4ccccc34)n2)C1] | +++ |
| I-2 (BSJ-04-078) | 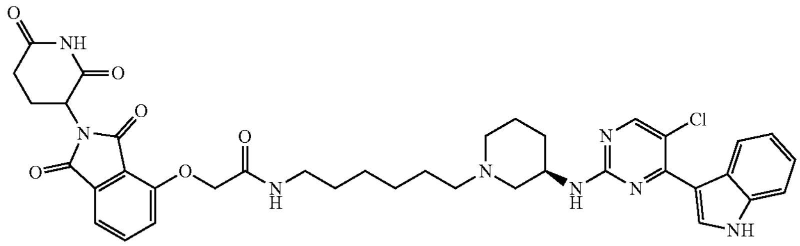 [SMILES: O=C(COc1cccc2c1C(=O)N(C1CCC(=O)NC1=O)C2=O)NCCCCCCN1CCC[C@@H](Nc2ncc(Cl)c(-c3c[nH]c4ccccc34)n2)C1] | ++ |
| 1-3 (BSJ-04-079) | 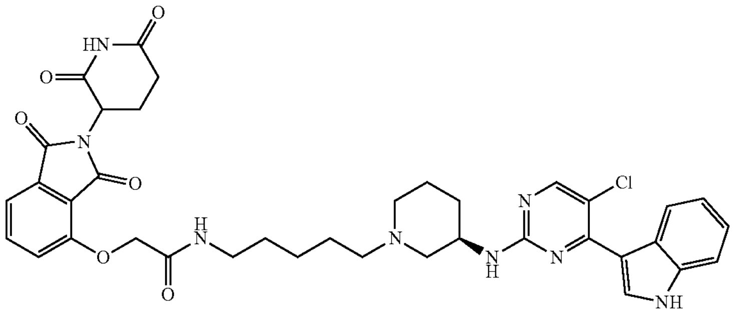 [SMILES: O=C(COc1cccc2c1C(=O)N(C1CCC(=O)NC1=O)C2=O)NCCCCCN1CCC[C@@H](Nc2ncc(Cl)c(-c3c[nH]c4ccccc34)n2)C1] | N/A |
| 1-4 (BSJ-04-080) | 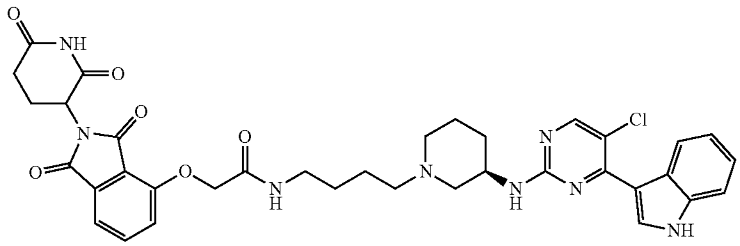 [SMILES: O=C(COc1cccc2c1C(=O)N(C1CCC(=O)NC1=O)C2=O)NCCCCN1CCC[C@@H](Nc2ncc(Cl)c(-c3c[nH]c4ccccc34)n2)C1] | N/A |
| 1-5 (BSJ-04-026) | 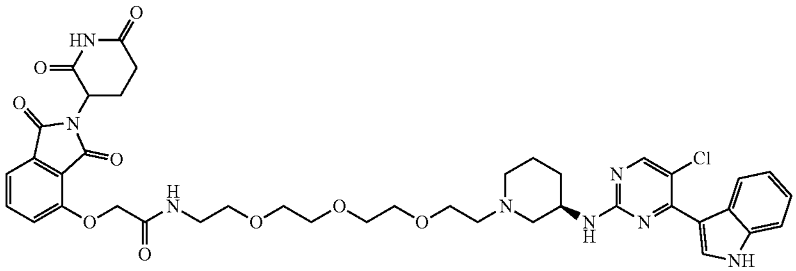 [SMILES: O=C(COc1cccc2c1C(=O)N(C1CCC(=O)NC1=O)C2=O)NCCOCCOCCOCCN1CCC[C@@H](Nc2ncc(Cl)c(-c3c[nH]c4ccccc34)n2)C1] | ++ |

TABLE 1-continued
Exemplary CDK12 Degrader Compounds
| Compound | Structure | CDK12 degradation activity |
|---|---|---|
| 1-6 (BSJ-04-026) (BSJ-04-098) | 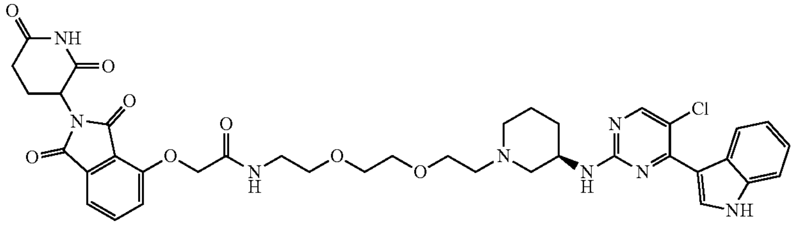 [SMILES: O=C(COc1cccc2c1C(=O)N(C1CCC(=O)NC1=O)C2=O)NCCOCCOCCN1CCC[C@@H](Nc2ncc(Cl)c(-c3c[nH]c4ccccc34)n2)C1] | N/A |
| 1-7 (BSJ-04-099) | 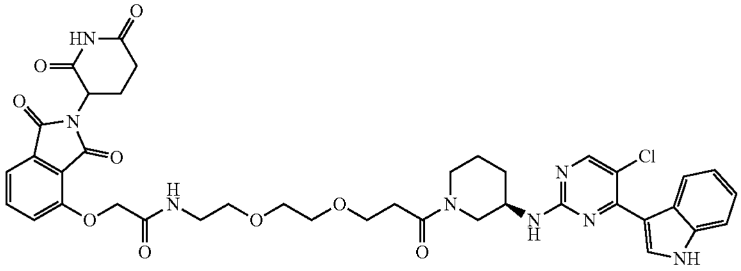 [SMILES: O=C(COc1cccc2c1C(=O)N(C1CCC(=O)NC1=O)C2=O)NCCOCCOCCC(=O)N1CCC[C@@H](Nc2ncc(Cl)c(-c3c[nH]c4ccccc34)n2)C1] | N/A |
| 1-8 (BSJ-04-071) | 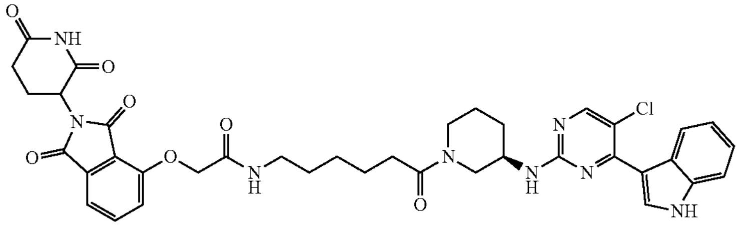 | N/A |
| 1-9 (BSJ-04-77) | 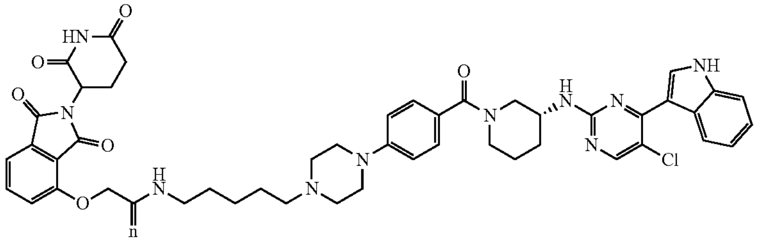 | ++ |
| 1-10 (BSJ-04-076) | 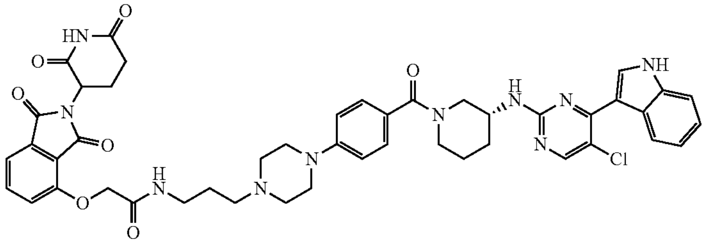 [SMILES: O=C(COc1cccc2c1C(=O)N(C1CCC(=O)NC1=O)C2=O)NCCCN1CCN(c2ccc(C(=O)N3CCC[C@@H](Nc4ncc(Cl)c(-c5c[nH]c6ccccc56)n4)C3)cc2)CC1] | + |
| I-11 (BSJ-04-100) | 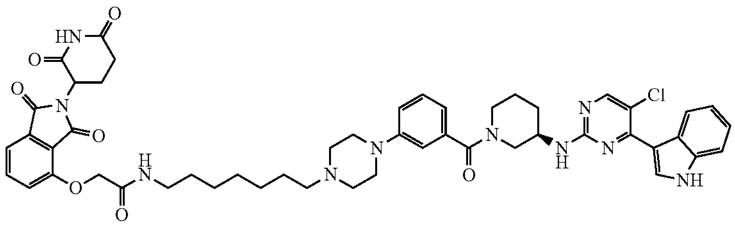 [SMILES: O=C(COc1cccc2c1C(=O)N(C1CCC(=O)NC1=O)C2=O)NCCCCCCCN1CCN(c2cccc(C(=O)N3CCC[C@@H](Nc4ncc(Cl)c(-c5c[nH]c6ccccc56)n4)C3)c2)CC1] | N/A |

TABLE 1-continued
| Exemplary CDK12 Degrader Compounds | | |
|---|---|---|
| Compound | Structure | CDK12 degradation activity |
| 1-12 (BSJ-04-086) | 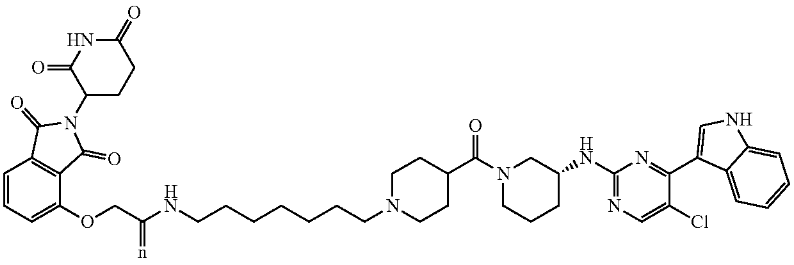 | ++ |
| 1-13 (BSJ-04-089) | 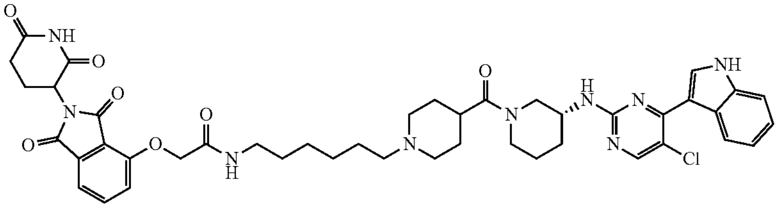 [SMILES: O=C(COc1cccc2c1C(=O)N(C1CCC(=O)NC1=O)C2=O)NCCCCCCN1CCC(C(=O)N2CCC[C@@H](Nc3ncc(Cl)c(-c4c[nH]c5ccccc45)n3)C2)CC1] | ++ |
| 1-14 (BSJ-04-116) | 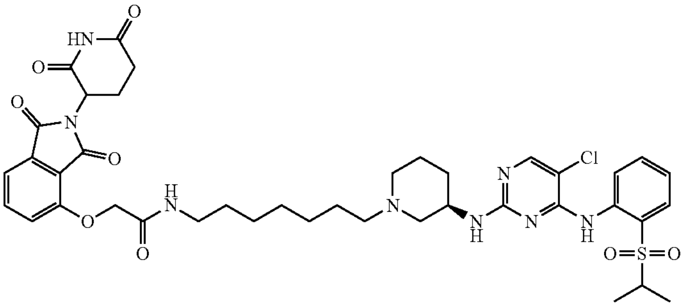 [SMILES: CC(C)S(=O)(=O)c1ccccc1Nc1nc(N[C@@H]2CCCN(CCCCCCCNC(=O)COc3cccc4c3C(=O)N(C3CCC(=O)NC3=O)C4=O)C2)ncc1Cl] | +++ |
| 1-15 (BSJ-05-063) | 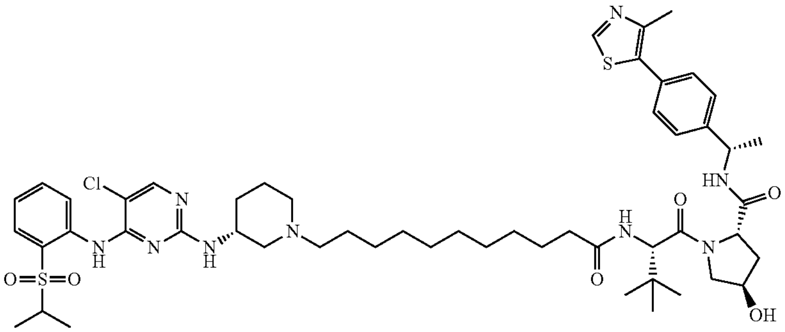 [SMILES: Cc1ncsc1-c1ccc([C@H](C)NC(=O)[C@@H]2C[C@@H](O)CN2C(=O)[C@@H](NC(=O)CCCCCCCCCCN2CCC[C@@H](Nc3ncc(Cl)c(Nc4ccccc4S(=O)(=O)C(C)C)n3)C2)C(C)(C)C)cc1] | +++ |
| 1-16 (BSJ-05-064) | 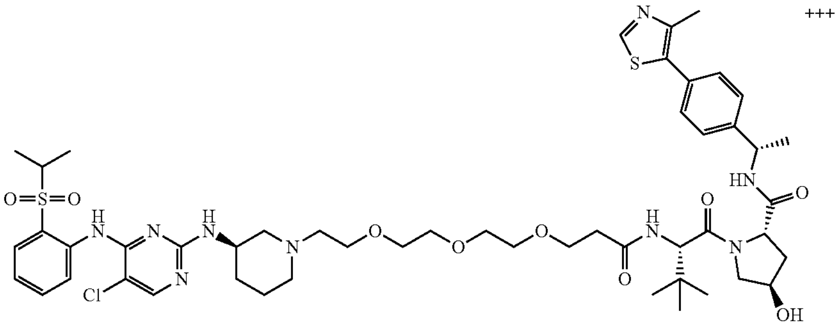 | +++ |

TABLE 1-continued

| Exemplary CDK12 Degrader Compounds | | |
|---|---|---|
| Compound | Structure | CDK12 degradation activity |
| 1-17 (ZXH-7-091) | 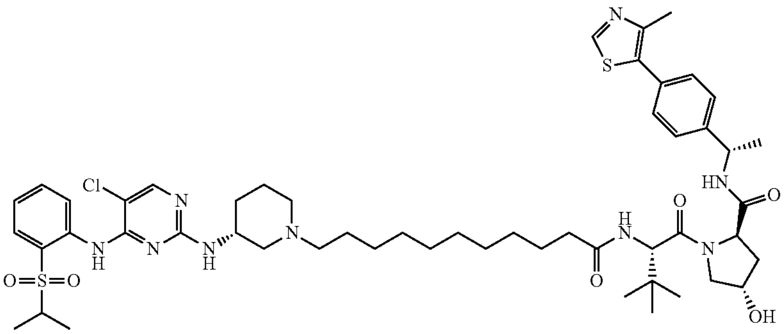 [SMILES: Cc1ncsc1-c1ccc([C@H](C)NC(=O)[C@H]2C[C@H](O)CN2C(=O)[C@@H](NC(=O)CCCCCCCCCCN2CCC[C@@H](Nc3ncc(Cl)c(Nc4ccccc4S(=O)(=O)C(C)C)n3)C2)C(C)(C)C)cc1] | N/A |

Example 3. Pharmacokinetic Studies of Exemplary Compounds

Standard pharmacokinetic parameters were determined by administration of exemplary compound BSJ-05-063 to male C57Bl/6 mice, and conducting standard pharmacokinetic studies. A single 2 mg/kg intravenous (IV) injection of compound BSJ-05-063 solution in May 5, 1990 DMSO/Cremophor EL® (oxirane, propane-1,2,3-triol)/water was delivered, and the pharmacokinetic parameters were evaluated. The plasma concentrations of BSJ-05-063 were reported at each of the 8 time points (5 minutes, 15 minutes, 30 minutes, 1 hours, 2 hours, 4 hours, 6 hours, and 8 hours post-dosing) are the average values from 3 test animals (male C57Bl/6 mice). The results for the pharmacokinetic studies for exemplary compound BSJ-05-063 are shown in Table 2 below.

TABLE 2

Average pharmacokinetic parameters for exemplary compound BSJ-05-063 (IV administration).

| $T_{1/2}$ hr | $T_{max}$ hr | $C_{max}$ ng/mL | $C_{max}$ μM | $AUC_{last}$ min * ng/mL | $AUC_{last}$ μM · hr | $AUC_{INF\_obs}$ min * ng/mL | AUC % Extrap | $Cl_{\_obs}$ mL/min/kg | $MRT_{INF\_obs}$ hr | $Vss_{\_obs}$ L/kg |
|---|---|---|---|---|---|---|---|---|---|---|
| 2.21 | 0.08 | 4573 | 4.49 | 343429 | 5.61 | 368545 | 6.27 | 6.04 | 2.41 | 0.84 |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects described herein, is/are referred to as comprising particular elements and/or features, certain embodiments described herein or aspects described herein consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments described herein, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment described herein can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A compound of Formula (I):

(I)

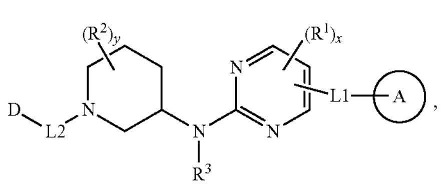

or a pharmaceutically acceptable salt, co-crystal, tautomer, stereoisomer, solvate, hydrate, polymorph, isotopically enriched derivative, or prodrug thereof, wherein:

each instance of $R^1$ is independently halogen, acyl, alkyl, alkenyl, alkynyl, carbocyclyl, heterocyclyl, aryl, heteroaryl, —CN, —$OR^{D1}$, —$N(R^{D1a})_2$, or —$SR^{D1}$, wherein $R^{D1}$ is hydrogen, acyl, alkyl, alkenyl, alkynyl, carbocyclyl, heterocyclyl, aryl, or heteroaryl;

wherein each occurrence of $R^{D1a}$ is hydrogen, acyl, alkyl, alkenyl, alkynyl, carbocyclyl, heterocyclyl, aryl, or heteroaryl; or two instances of $R^{D1a}$ are taken together with their intervening atoms to form a heteroaryl ring;

each instance of $R^2$ is independently halogen, acyl, alkyl, alkenyl, alkynyl, carbocyclyl, heterocyclyl, aryl, heteroaryl, —CN, —$OR^{D1}$, —$N(R^{D1a})_2$, or —$SR^{D1}$;

$R^3$ is hydrogen, acyl, alkyl, alkenyl, alkynyl, carbocyclyl, heterocyclyl, aryl, or heteroaryl;

Ring A is of formula:

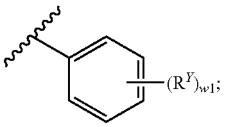

$R^Y$ is —$SO_2R^{Y1}$, —$P(=O)(R^{Y2})^2$, or —$C(=O)N(R^{y3})=_2$;

$R^{Y1}$ is $C_1$-$C_6$ alkyl;

each instance of $R^{Y2}$ is $C_1$-$C_6$ alkyl;

each instance of $R^{y3}$ is independently hydrogen or alkyl;

w1 is 1;

x is 0 or 1;

y is 0 or 1;

L1 is —$NR^A$—; wherein $R^A$ is hydrogen;

L2 is an unsubstituted $C_{1-24}$ hydrocarbon chain, optionally wherein one or more chain atoms of the hydrocarbon chain are independently replaced with —C(=O)—, —O—, or —$NR^b$—, wherein $R^b$ is hydrogen, or

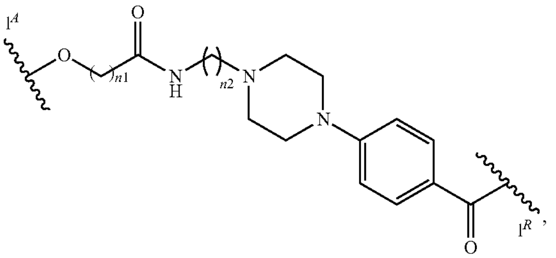

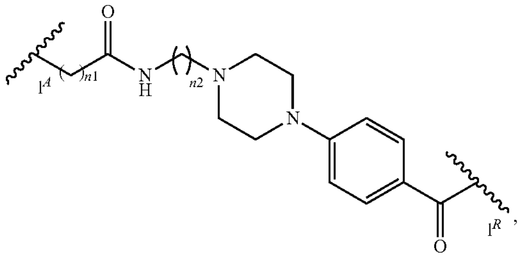

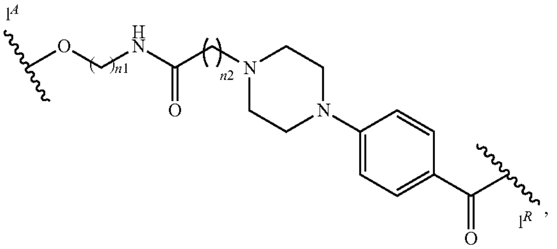

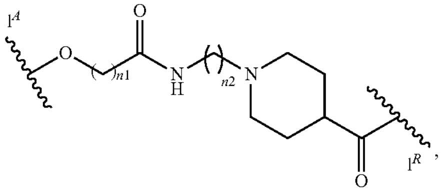

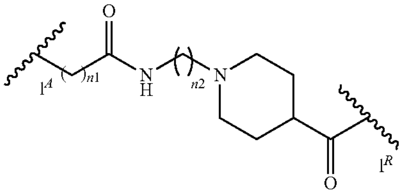

or

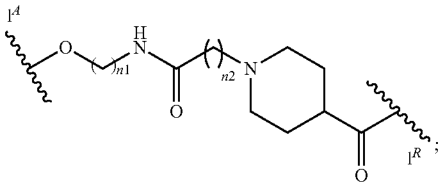

$l^A$ indicates the point of attachment to D, and $l^R$ indicates the point of attachment to the moiety of formula

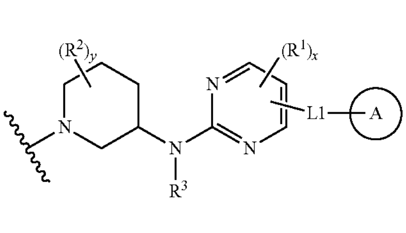

;

n1 is 1, 2, 3, 4, 5, or 6;

n2 is 0, 1, 2, 3, 4, 5, 6, 7, 8, 9, or 10; and

D is of the formula:

(IA)

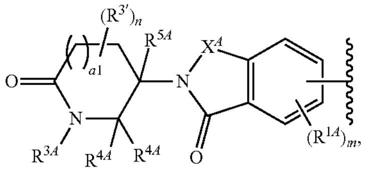

wherein:

$X^A$ is C(O) or $C(R^{3A})_2$;

$R^{1A}$ is halogen, —OH, $C_1$-$C_6$ alkyl, or $C_1$-$C_6$ alkoxy;

each $R^{3A}$ is independently H or $C_1$-$C_3$ alkyl;

$R^{3'}$ is $C_1$-$C_3$ alkyl;

each $R^{4A}$ is independently H or $C_1$-$C_3$ alkyl; or two $R^{4A}$, together with the carbon atom to which they are attached, form C(O);

$R^{5A}$ is H, $C_1$-$C_3$ alkyl, or halogen;

m is 0 or 1;

n is 0 or 1; and a1 is 0 or 1, or

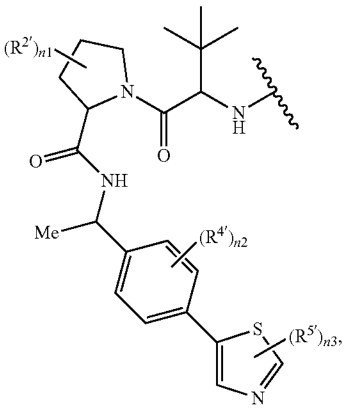

wherein:

$R^{2'}$ is halogen, —OH, $C_1$-$C_6$ alkyl, or $C_1$-$C_6$ alkoxy;

$R^{4'}$ is halogen, —OH, $C_1$-$C_6$ alkyl, or $C_1$-$C_6$ alkoxy;

$R^{5'}$ is halogen, —OH, $C_1$-$C_6$ alkyl, or $C_1$-$C_6$ alkoxy;

n1 is 0 or 1;

n2 is 0 or 1; and n3 is 0 or 1.

2. The compound of claim 1, wherein the compound is of formula:

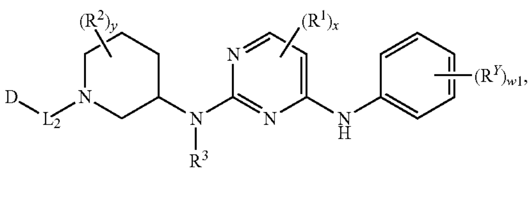

or a pharmaceutically acceptable salt, co-crystal, tautomer, stereoisomer, solvate, hydrate, polymorph, isotopically enriched derivative, or prodrug thereof, wherein at least one instance of $R^Y$ is $-SO_2R^{Y1}$ wherein $R^{Y1}$ is $C_1$-$C_6$ alkyl, $-C(=O)N(R^{y3})_2$ wherein each instance of $R^{y3}$ is independently hydrogen or alkyl, or $-P(=O)(R^{Y2})_2$ wherein each instance of $R^{Y2}$ is $C_1$-$C_6$ alkyl.

3. The compound of claim 1, or a pharmaceutically acceptable salt, co-crystal, tautomer, stereoisomer, solvate, hydrate, polymorph, isotopically enriched derivative, or prodrug thereof, wherein D is of the formula:

(IA)

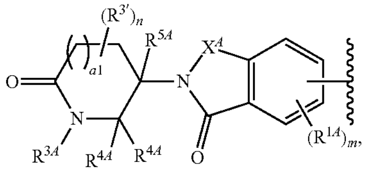

wherein:

$X^A$ is C(O) or $C(R^{3A})_2$;

each $R^{3A}$ is H;

two $R^{4A}$, together with the carbon atom to which they are attached, form C(O);

$R^{5A}$ is H;

m is 0;

n is 0; and a1 is 1.

4. The compound of claim 1, or a pharmaceutically acceptable salt, co-crystal, tautomer, stereoisomer, solvate, hydrate, polymorph, isotopically enriched derivative, or prodrug thereof, wherein D is of the formula:

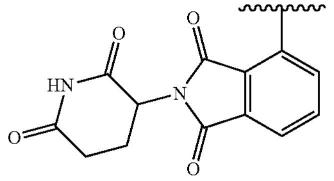

or

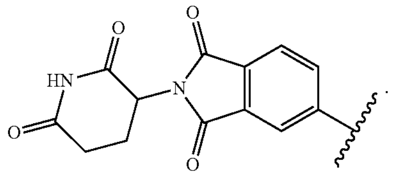

5. The compound of claim 1, or a pharmaceutically acceptable salt, co-crystal, tautomer, stereoisomer, solvate, hydrate, polymorph, isotopically enriched derivative, or prodrug thereof, wherein D is of the formula:

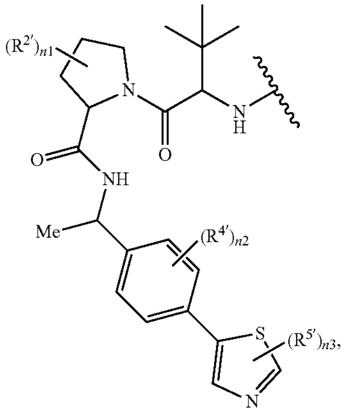

wherein:

$R^{2'}$ is —OH;

$R^{5'}$ is $C_1$-$C_6$ alkyl;

n1 is 1;

n2 is 0; and n3 is 1.

6. The compound of claim 1, or a pharmaceutically acceptable salt, co-crystal, tautomer, stereoisomer, solvate, hydrate, polymorph, isotopically enriched derivative, or prodrug thereof, wherein D is of the formula:

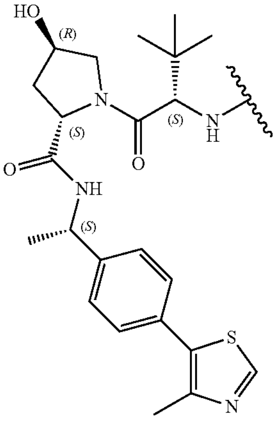

or

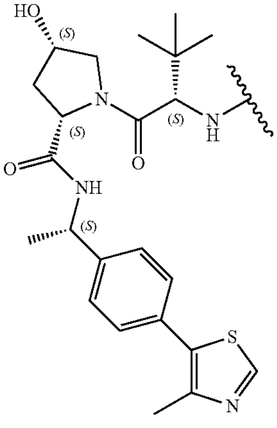

.

7. The compound of claim 1, wherein the compound is of formula:

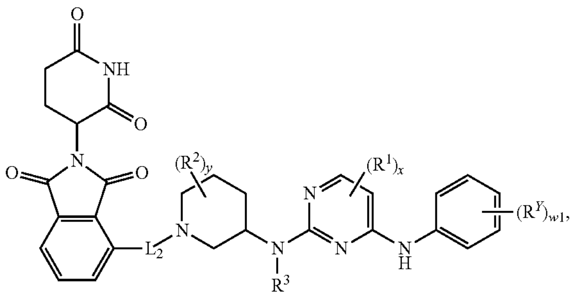

or a pharmaceutically acceptable salt, co-crystal, tautomer, stereoisomer, solvate, hydrate, polymorph, isotopically enriched derivative, or prodrug thereof, wherein at least one instance of $R^1$ is halogen, optionally substituted $C_{1-6}$ alkyl, —$CF_3$, or —CN.

8. The compound of claim 1, or a pharmaceutically acceptable salt, co-crystal, tautomer, stereoisomer, solvate, hydrate, polymorph, isotopically enriched derivative, or prodrug thereof, wherein L2 is:

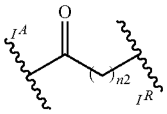,
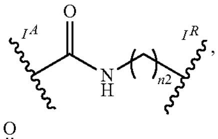,
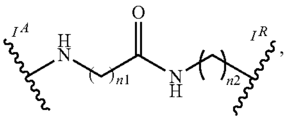,
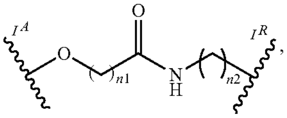,
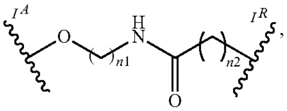,
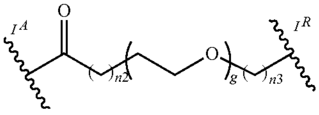,
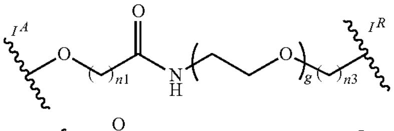,
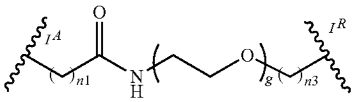,
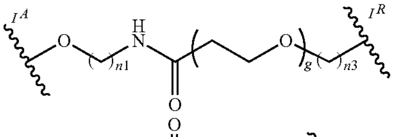,
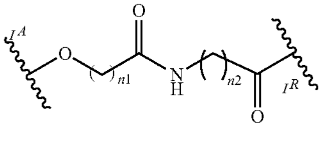, -continued

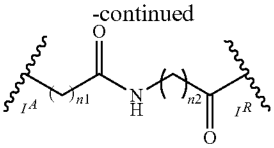,
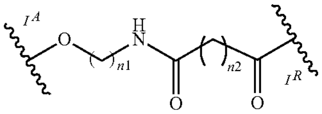,
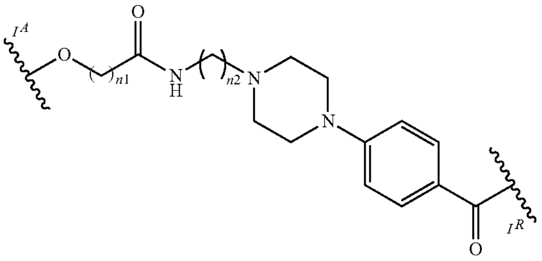,
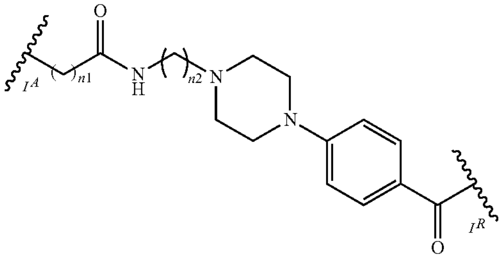,
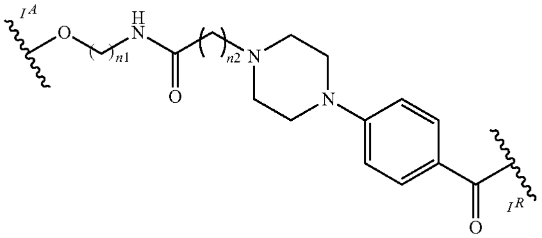,
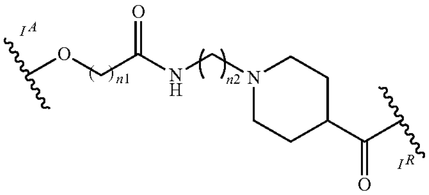,
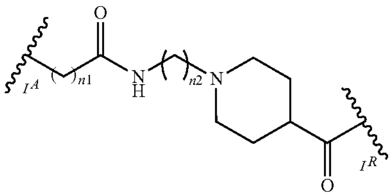

or

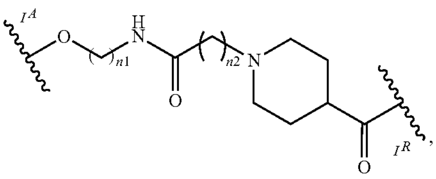, $l^A$ indicates the point of attachment to D, and/R indicates the point of attachment to the moiety of formula
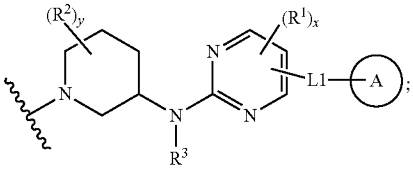
n1 is 1, 2, 3, 4, 5, or 6;
n2 is 0, 1, 2, 3, 4, 5, 6, 7, 8, 9, or 10;
n3 is 1, 2, 3, 4, 5, or 6; and
g is 1, 2, 3, 4, 5, or 6.
9. The compound of claim 1, or a pharmaceutically acceptable salt, co-crystal, tautomer, stereoisomer, solvate, hydrate, polymorph, isotopically enriched derivative, or prodrug thereof, wherein L2 is of the formula:
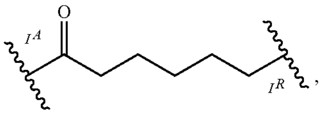
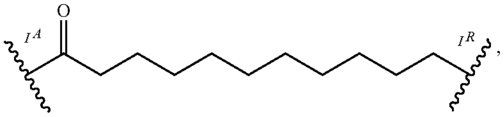
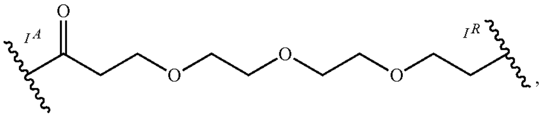
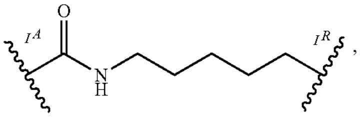
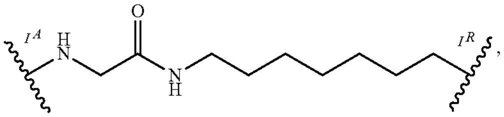
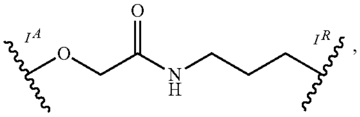
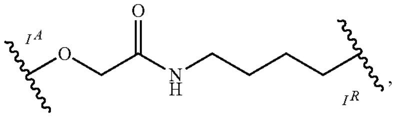
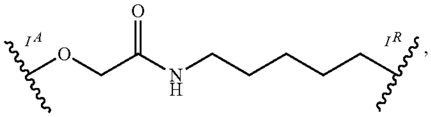
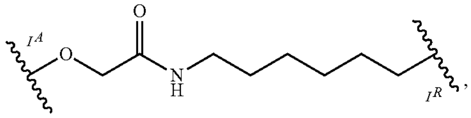
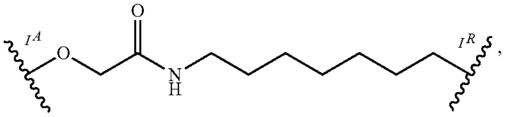
-continued
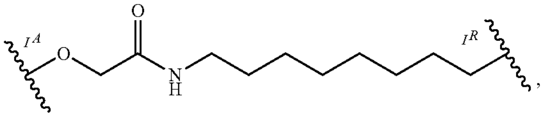
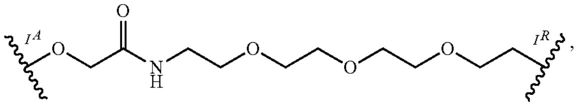
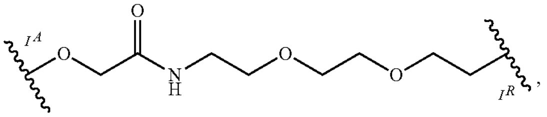
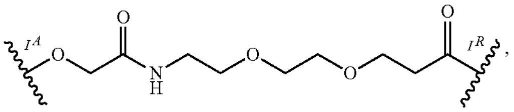
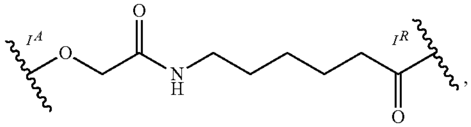
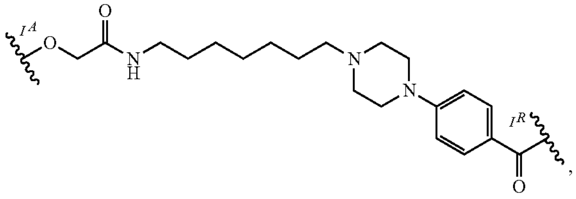
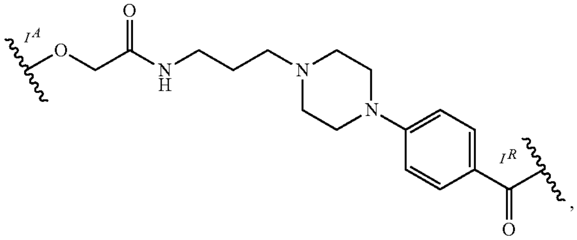
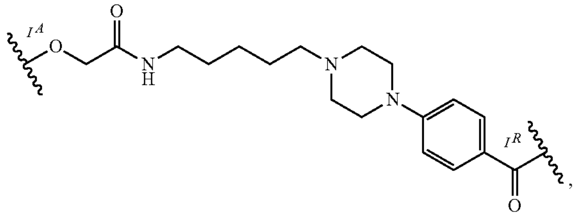
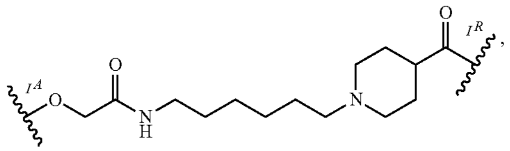
or
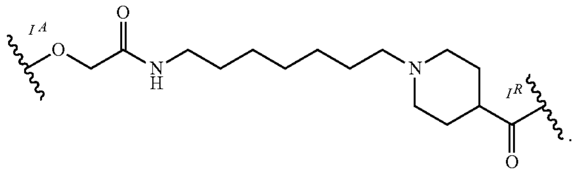

10. The compound of claim 1, wherein the compound is of the formula:
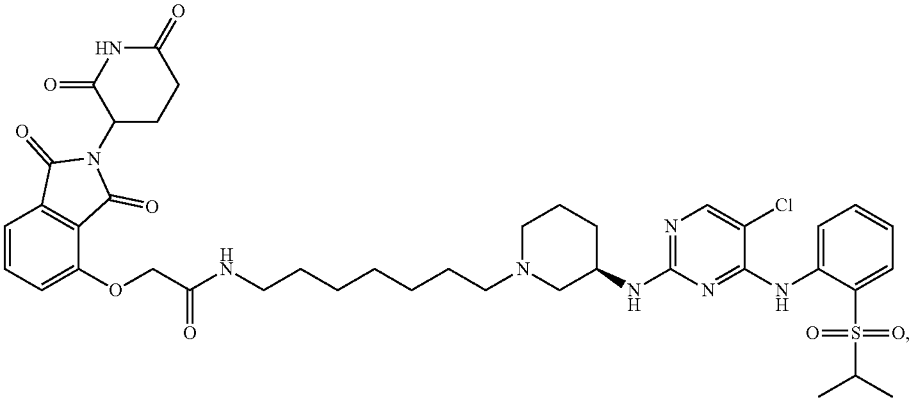
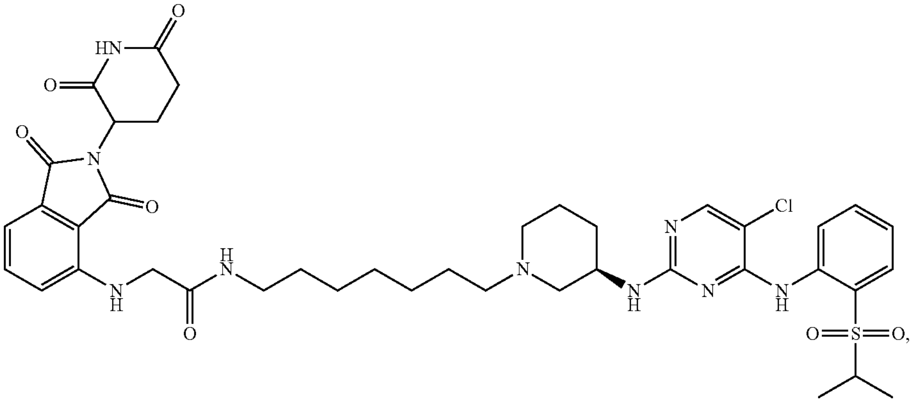
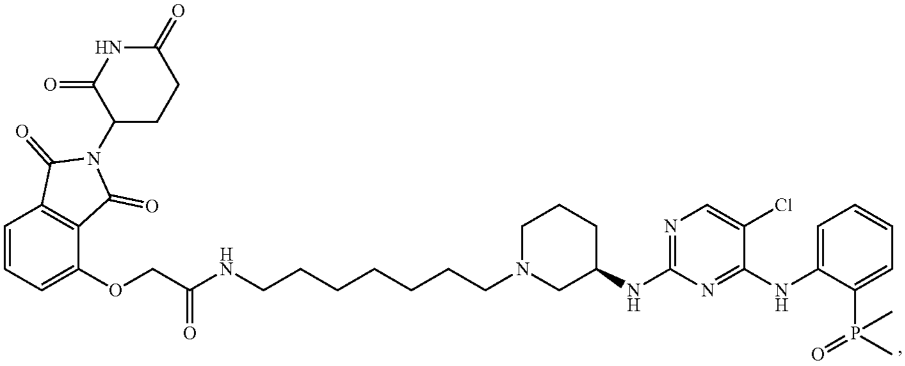
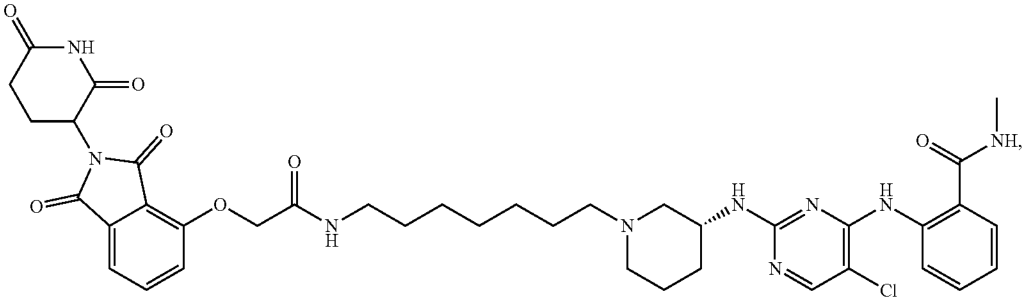

-continued
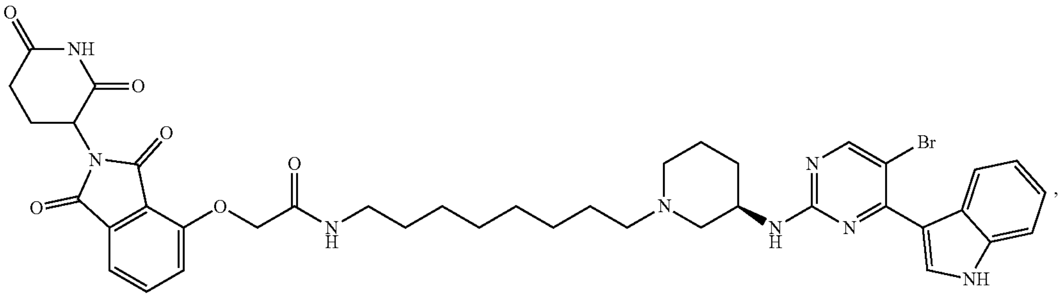
,
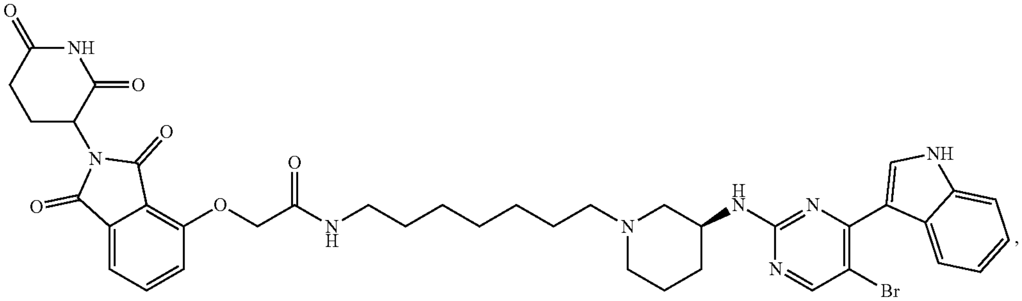
,
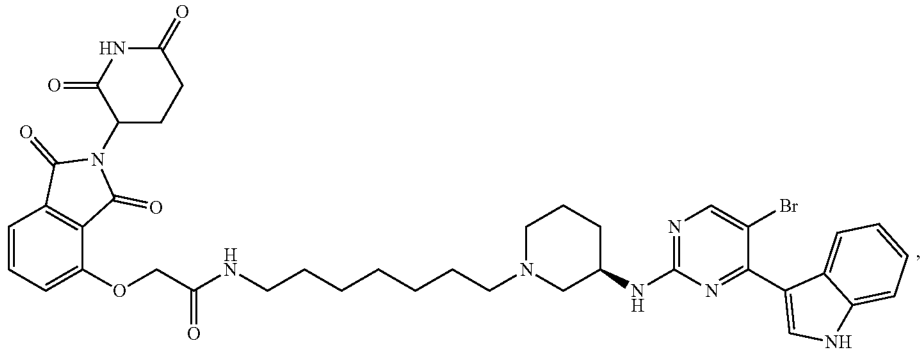
,
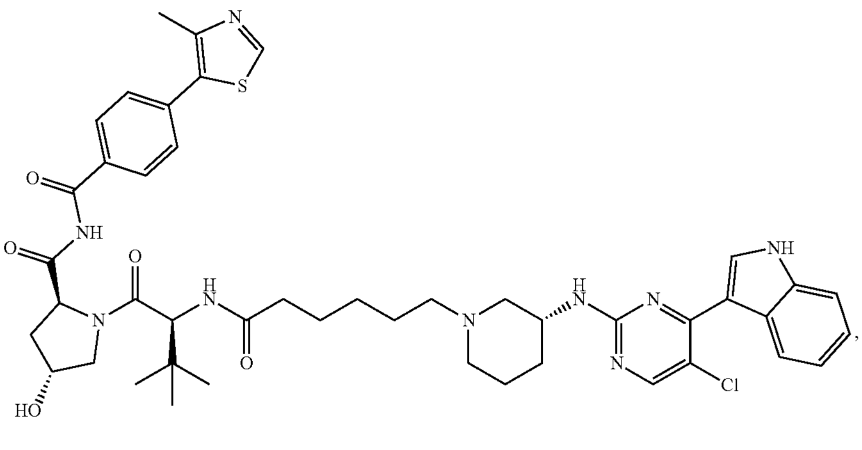
,

-continued

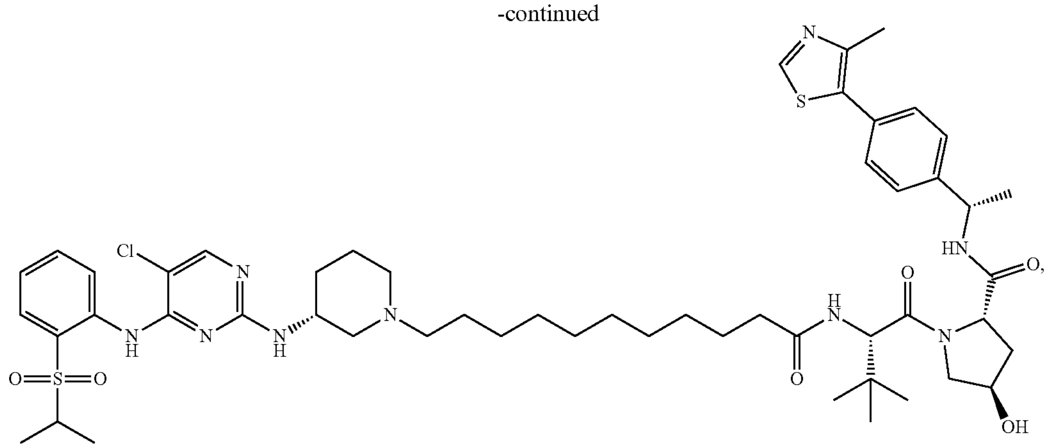

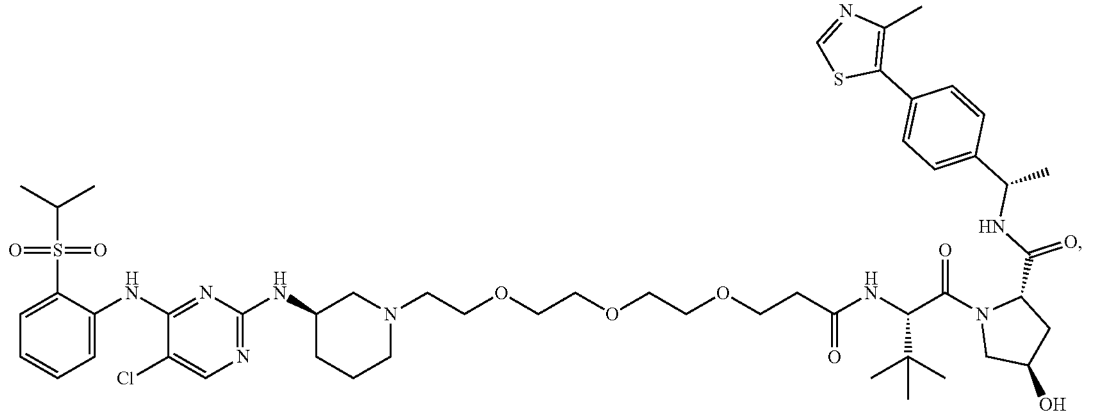

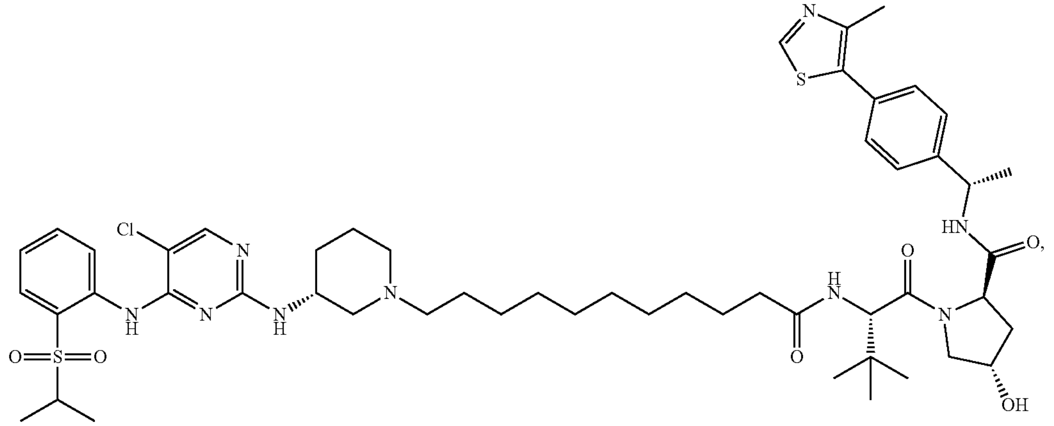

or a pharmaceutically acceptable salt, co-crystal, tautomer, stereoisomer, solvate, hydrate, polymorph, isotopically enriched derivative, or prodrug thereof.

11. A pharmaceutical composition comprising a compound of claim 1, or a pharmaceutically acceptable salt, co-crystal, tautomer, stereoisomer, solvate, hydrate, polymorph, isotopically enriched derivative, or prodrug thereof, and optionally a pharmaceutically acceptable excipient, wherein $R^{3A}$ is H when D is of formula IA.

12. A method of inducing the degradation of CDK9 and/or CDK12 in a cell, tissue, or biological sample, the method comprising:

contacting the cell, tissue, or biological sample with a therapeutically effective amount of a compound of claim 1, or a pharmaceutically acceptable salt, co-crystal, tautomer, stereoisomer, solvate, hydrate, polymorph, isotopically enriched derivative, or prodrug thereof, wherein $R^{3A}$ is H when D is of formula IA.

* * * * *